(12) United States Patent
Cameron et al.

(10) Patent No.: US 6,498,172 B1
(45) Date of Patent: Dec. 24, 2002

(54) PROSTAGLANDIN AGONISTS AND THEIR USE TO TREAT BONE DISORDERS

(75) Inventors: Kimberly O. Cameron, East Lyme, CT (US); Bruce A. Lefker, Gales Ferry, CT (US); Robert L. Rosati, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/367,970

(22) PCT Filed: Oct. 5, 1998

(86) PCT No.: PCT/IB98/01540

§ 371 (c)(1),
(2), (4) Date: Aug. 20, 1999

(87) PCT Pub. No.: WO99/19300

PCT Pub. Date: Apr. 22, 1999

Related U.S. Application Data

(60) Provisional application No. 60/061,727, filed on Oct. 10, 1997.

(51) Int. Cl.[7] .................... A61P 19/08; A61K 31/44; A61K 31/495; A61K 31/505; C07D 213/70
(52) U.S. Cl. .................. 514/347; 514/231.5; 514/242; 514/252.1; 514/255.05; 514/266.24; 514/269; 514/335; 514/336; 514/337; 514/338; 514/339; 514/341; 514/342; 514/343; 514/357; 514/362; 514/364; 514/365; 514/369; 514/380; 514/397; 514/398; 514/399; 514/406; 514/422; 514/445; 514/448; 514/452; 514/466; 514/469; 514/539; 514/562; 544/146; 544/182; 544/285; 544/383; 544/335; 544/336; 544/405; 546/261; 546/269.7; 546/275.1; 546/275.4; 546/276.1; 546/277.4; 546/278.4; 546/280.4; 546/282.4; 546/283.4; 546/283.7; 546/284.1; 546/284.7; 546/293; 546/335; 548/126; 548/185; 548/187; 548/204
(58) Field of Search .................. 514/255.05, 269, 514/335, 336, 337, 338, 339, 341, 342, 343, 347; 544/333, 405; 546/261, 269.7, 275.1, 275.4, 276.1, 277.4, 278.4, 280.4, 282.4, 283.4, 283.7, 284.1, 284.7, 293

(56) References Cited

U.S. PATENT DOCUMENTS

| | | | |
|---|---|---|---|
| 3,442,890 A | 5/1969 | Larsen et al. | 260/239 |
| 3,528,961 A | 9/1970 | Miles et al. | 260/162 |
| 3,780,095 A | 12/1973 | Klemme et al. | 260/518 A |
| 3,987,091 A | 10/1976 | Cragoe, Jr. et al. | 260/490 |
| 3,991,106 A | 11/1976 | Cragoe, Jr. et al. | 260/519 |
| 4,033,996 A | 7/1977 | Cragoe, Jr. et al. | 260/490 |
| 4,055,596 A | 10/1977 | Cragoe, Jr. et al. | 260/534 |
| 4,097,601 A | 6/1978 | Schaaf | 424/269 |
| 4,112,236 A | 9/1978 | Bicking et al. | 560/12 |
| 4,175,203 A | 11/1979 | Cragoe, Jr. et al. | 560/55 |
| 4,243,678 A | 1/1981 | Krastinat | 424/319 |
| 4,386,031 A | 5/1983 | Hilboll et al. | 260/404 |
| 4,443,477 A | 4/1984 | Witte et al. | 424/319 |
| 4,761,430 A | 8/1988 | Choay et al. | 514/562 |
| 4,911,888 A | 3/1990 | Fikentscher et al. | 422/16 |

FOREIGN PATENT DOCUMENTS

| | | | |
|---|---|---|---|
| EP | 0608847 | 12/1996 | C07C/311/13 |
| FR | 0897566 | 12/1983 | |
| GB | 1478281 | 6/1977 | C07C/59/00 |
| GB | 1479156 | 7/1977 | C07C/59/00 |
| GB | 2233644 | 1/1991 | |
| JP | 5019756 | 3/1975 | |
| WO | WO9731640 | 9/1997 | A61K/31/557 |
| WO | WO9828264 | 7/1998 | C07C/311/06 |

OTHER PUBLICATIONS

Sartori, E. et al., *Eur. J. Med. Chem*, "Synthesis and Activities of New Arylsulfonamido Thromboxane $A_2$ Receptor Antagonists", p 625–632 (1993).

Partial Transmation of Citation 6, Japanese Patent Laid-–Open Publication No. Sho 50–19756, 1975.

The Merck Index, Twelfth Edition, Merck & Co., Inc., NJ, pp. 43, 583, 1394, 1548 (1996).

John B. Bicking et al., Journal of Medicinal Chemistry, vol. 21, No. 10, 1978, pp. 1011–1018.

James H. Jones et al., Journal of Medicinal Chemistry, vol. 20, No. 10, 1977, pp. 1299–1304.

John H. Billman et al., J. Org. Chem, 26; 1961; 1437–1440.

Bolander, et al, 38th Annual Meeting, Orthopedic Research Society, 1992.

*Primary Examiner*—Brenda Coleman
(74) *Attorney, Agent, or Firm*—Peter C. Richardson; Gregg C. Benson; Todd M. Crissey

(57) ABSTRACT

This invention relates to prostaglandin agonists, methods of using such prostaglandin agonists, pharmaceutical compositions containing such prostaglandin agonists and kits containing such prostaglandin agonists. The prostaglandin agonists are useful for the treatment of bone disorders including osteoporosis.

12 Claims, No Drawings

PROSTAGLANDIN AGONISTS AND THEIR USE TO TREAT BONE DISORDERS

CROSS-REFERENCE TO RELATED APPLICATIONS

This application is the national stage of International Patent Application No. PCT/IB98/01540, filed Oct. 5, 1998, which is a continuation of U.S. Provisional Application No. 60/061,727, filed Oct. 10, 1997 (now abandoned).

BACKGROUND OF INVENTION

This invention relates to prostaglandin agonists, pharmaceutical compositions containing such agonists and the use of such agonists to prevent bone loss or restore or augment bone mass and to enhance bone healing including the treatment of conditions which present with low bone mass and/or bone defects in vertebrates, and particularly mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk osteoporosis, and the problem is therefore predicted to increase significantly with the aging of the population. Worldwide fracture incidence is forecasted to increase three-fold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone back to young adult levels in the established osteoporotic skeleton. Furthermore, long-term estrogen therapy, has been implicated in a variety of disorders including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporosis skeleton.

U.S. Pat. No. 4,112,236 discloses certain interphenylene 8-aza-9-dioxothia-11,12-secoprostaglandins for the treatment of patients with renal impairment.

Certain prostaglandin agonists are disclosed in GB 1478281, GB1479156 and U.S. Pat. Nos. 4,175,203, 4,055, 596, 4,175,203, 3,987,091 and 3,991,106 as being useful as, for example, renal vasodilators.

U.S. Pat. No. 4,033,996 discloses certain 8-aza-9-oxo(and dixox)-thia-11,12-secoprostanglandins which are useful as renal vasodilators, for the prevention of thrombus formation, to induce growth hormone release, and as regulators of the immune response.

French patent no. 897,566 discloses certain amino acid derivatives for the treatment of neurological, mental or cardiovascular disease.

J. Org. Chem. 26; 1961; 1437 discloses N-acetyl-N-benzyl-p-aminophenylmercaptoacetic acid.

U.S. Pat. No. 4,761,430 discloses certain arylbenzenesulfonamide compounds as lipid-lowering agents.

U.S. Pat. No. 4,443,477 discloses certain sulphonamidophenylcarboxylic acids as lipid lowering agents.

U.S. Pat. No. 3,528,961 discloses certain $\epsilon$-caprolactam derivatives as dyes.

U.S. Pat. No. 3,780,095 discloses certain acylated anilinocarboxylic acids as choleretics.

U.S. Pat. No. 4,243,678 discloses certain acylhydrocarbylaminoalkanoic acids as having utility in the treatment of gastric ulcers, as sebaceous gland excretion inhibitors and for combatting skin inflammation.

U.S. Pat. No. 4,386,031 discloses certain N-benzoyl-$\omega$-anilinoalkanecarboxylic acids as antiallergic agents, thrombotic aggregation inhibitors, antiinflammatory agents and lipid-lowering agents.

In addition to osteoporosis, approximately, 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

Estrogens have been shown (Bolander et al., 38th Annual Meeting Orthopedic Research Society, 1992) to improve the quality of the healing of appendicular fractures. Therefore, estrogen replacement therapy might appear to be a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. The need exists for a therapy which would be beneficial to patients who have suffered debilitating bone fractures and which would increase patient compliance.

Although there are a variety of osteoporosis therapies, there is a continuing need and a continuing search in this field of art for alternative osteoporosis therapies. In addition, there is a need for bone fracture healing therapies. Also, there is need for a therapy which can promote bone re-growth into skeletal areas where defects exist such as defects caused or produced by, for example, tumors in bone. Further, their is a need for therapy which can promotes bone re-growth into skeletal areas where bone grafts are indicated.

SUMMARY OF THE INVENTION

This invention is directed to compounds having the Formula I

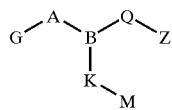

Formula I prodrugs thereof, and the pharmaceutical acceptable salts of said compounds and prodrugs, wherein A is $SO_2$ or CO;

G is Ar, $Ar^1$-V-$Ar^2$, Ar-($C_1$–$C_6$)alkylene, Ar-CONH-($C_1$–$C_6$)alkylene, $R^1R^2$-amino, oxy($C_1$–$C_6$)alkylene, amino substituted with Ar, or amino substituted with Ar($C_1$–$C_4$)alkylene and $R^{11}$, wherein $R^{11}$ is H or ($C_1$–$C_8$)alkyl, $R^1$ and $R^2$ may be taken separately and are independently selected from H and ($C_1$–$C_8$)alkyl, or $R^1$ and $R^2$ are taken together with the nitrogen atom of the amino group to form a five- or six-membered azacycloalkyl, said azacycloalkyl optionally containing an oxygen atom and optionally mono-, di- or tri-substituted independently with up to two oxo, hydroxy, ($C_1$–$C_4$)alkyl, fluoro or chloro;

B is N or CH;

Q is

-($C_2$–$C_6$)alkylene-W-($C_1$–$C_3$)alkylene-, said alkylenes each optionally substituted with up to four substitutes independently selected from fluoro or ($C_1$–$C_4$) alkyl, -($C_4$–$C_8$)alkylene-, said alkylene optionally substituted with up to four substituents independently selected from fluoro or ($C_1$–$C_4$)alkyl, -X-($C_1$–$C_5$)alkylene-, said alkylene optionally substituted with up to four substituents independently selected from fluoro or ($C_1$–$C_4$)alkyl, -($C_1$–$C_5$)alkylene-X-, said alkylene optionally substituted with up to four substituents independently selected fluoro or ($C_1$–$C_4$)alkyl, -($C_1$–$C_3$)alkylene-X-($C_1$–$C_3$)alkylene, said alkylenes each optionally substituted with up to four substituents independently selected from fluoro or ($C_1$–$C_4$)alkyl, -($C_2$–$C_4$)alkylene-W-X-($C_0$–$C_3$)-alkylene-, said alkylenes each optionally substituted with up to four substituents each independently selected from fluoro or ($C_1$–$C_4$) alkyl, -($C_0$–$C_4$)alkylene-X-W-($C_1$–$C_3$)alkylene-, said alkylenes each optionally substituted with up to four substituents each independently selected from fluoro or ($C_1$–$C_4$) alkyl, -($C_2$–$C_5$)alkylene-W-X-W-($C_1$–$C_3$)alkylene-, wherein the two occurrences of W are independent of each other, said alkylenes each optionally substituted with up to four substituents each independently selected from fluoro or ($C_1$–$C_4$)alkyl, -($C_1$–$C_4$)alkylene-ethenylene-($C_1$–$C_4$)alkylene-, said alkylenes and said ethenylene each optionally substituted with up to four substituents each independently selected from fluoro or ($C_1$–$C_4$)alkyl, -($C_1$–$C_4$)alkylene-ethenylene-($C_0$–$C_2$)alkylene-X-($C_0$–$C_5$)alkylene-, said alkylenes and said ethenylene each optionally substituted with up to four substituents each independently selected from fluoro or ($C_1$–$C_4$) alkyl, -($C_1$–$C_4$)alkylene-ethenylene-($C_0$–$C_2$)alkylene-X-W-($C_1$–$C_3$)alkylene-, said alkylenes and said ethenylene optionally each substituted with up to four substitutes each independently selected from fluoro is ($C_1$–$C_4$) alkyl, -($C_1$–$C_4$)alkylene-ethynylene-($C_1$–$C_4$)alkylene-, said alkylenes and said ethynylene each optionally substituted with up to four substituents each independently selected from fluoro or ($C_1$–$C_4$)alkyl, or -($C_1$–$C_4$)alkylene-ethynylene-X-($C_0$–$C_3$)alkylene-, said alkylenes and said ethynylene each optionally substituted with up to four substituents each independently selected from fluoro or ($C_1$–$C_4$)alkyl;

Z is carboxyl, ($C_1$–$C_6$)alkoxycarbonyl, tetrazolyl, 1,2,4-oxadiazolyl, 5-oxo-1,2,4-oxadiazolyl, 5-oxo-1,2,4-thiadiazolyl, ($C_1$–$C_4$)alkylsulfonylcarbamoyl or phenylsulfonylcarbamoyl;

K is a bond, ($C_1$–$C_9$)alkylene, thio($C_1$–$C_4$)alkylene, ($C_1$–$C_4$)alkylenethio($C_1$–$C_4$)alkylene, ($C_1$–$C_4$)alkyleneoxy($C_1$–$C_4$)alkylene or oxy($C_1$–$C_4$)alkylene, said ($C_1$–$C_9$)alkylene optionally mono-unsaturated and wherein, when K is not a bond, K is optionally mono-, di- or tri-substituted independently with chloro, fluoro, hydroxy or methyl;

M is —$Ar^3$, —$Ar^4$-$V^1$-$Ar^5$, —$Ar^4$-S—$Ar^5$, —$Ar^4$-SO—$Ar^5$, —$Ar^4$-$SO_2$-$Ar^5$ or —$Ar^4$-O—$Ar^5$;

Ar is a partially saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, or a tricyclic ring consisting of three fused independently partially saturated, fully saturated or fully unsaturated five or six membered rings, optionally having one to four heteroatoms selected independently from nitrogen, sulfur and oxygen, said partially or fully saturated ring, bicyclic ring or tricyclic ring optionally having one or two oxo groups substituted on carbon or one or two oxo groups substituted on sulfur; or Ar is a fully saturated five to seven membered ring having one or two heteroatoms selected independently from oxygen, sulfur and nitrogen;

$Ar^1$ and $Ar^2$ are each independently a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, or a tricyclic ring consisting of three fused independently partially saturated, fully saturated or fully unsaturated five or six membered rings, optionally having one to four heteroatoms selected independently from nitrogen, sulfur and oxygen, said partially or fully saturated ring, bicyclic ring or tricyclic ring optionally having one or two oxo groups substituted on carbon or one or two oxo groups substituted on sulfur;

said Ar, $Ar^1$ and $Ar^2$ moieties are optionally substituted on carbon or nitrogen, on one ring if the moiety is monocyclic, on one or both rings if the moiety is bicyclic, or one, two or three rings if the moiety is tricyclic, with up to three substituents per moiety independently selected from $R^3$, $R^4$ and $R^5$ wherein $R^3$, $R^4$ and $R^5$ are independently hydroxy, nitro, halo, carboxy, ($C_1$–$C_7$)alkoxy, ($C_1$–$C_4$)alkoxy($C_1$–$C_4$)alkyl, ($C_1$–$C_4$)alkoxycarbonyl, ($C_1$–$C_7$)alkyl, ($C_2$–$C_7$)

alkenyl, $(C_2-C_7)$alkynyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, hydroxysulfonyl, aminocarbonylamino or mono-N-, di-N,N-, di-N,N'- or tri-N,N,N'-$(C_1-C_4)$alkyl substituted aminocarbonylamino, sulfonamido, $(C_1-C_4)$alkylsulfonamido, amino, mono-N or di-N,N-$(C_1-C_4)$alkylamino, carbamoyl, mono-N- or di-N,N-$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N or di-N,N-$(C_1-C_4)$alkylaminosulfinyl;

$Ar^3$, $Ar^4$ and $Ar^5$ are each independently a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, or a tricyclic ring consisting of three fused independently partially saturated, fully saturated or fully unsaturated five or six membered rings, optionally having one to four heteroatoms selected independently from nitrogen, sulfur and oxygen, said partially or fully saturated ring, bicyclic ring or tricyclic ring optionally having one or two oxo groups substituted on carbon or one or two oxo groups substituted on sulfur;

said $Ar^3$, $Ar^4$ and $Ar^5$ moieties are optionally substituted on carbon or nitrogen, on one ring if the moiety is monocyclic, on one or both rings if the moiety is bicyclic, or on one, two or three rings if the moiety is tricyclic, with up to three substituents per moiety independently selected from $R^{31}$, $R^{41}$ and $R^{51}$ wherein $R^{31}$, $R^{41}$ and $R^{51}$ are independently hydroxy, nitro, halo, carboxy, $(C_1-C_7)$alkoxy, $(C_1-C_4)$alkoxy$(C_1-C_4)$alkyl, $(C_1-C_4)$alkoxycarbonyl, $(C_1-C_7)$alkyl, $(C_2-C_7)$alkenyl, $(C_2-C_7)$alkynyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, hydroxysulfonyl, aminocarbonylamino or mono-N-, di-N,N-, di-N,N'- or tri-N,N,N'-$(C_1-C_4)$alkyl substituted aminocarbonylamino, sulfonamide, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N- or di-N,N-$(C_1-C_4)$alkylaminosulfinyl;

W is oxy, thio, sulfino, sulfonyl, aminosulfonyl-, mono-N-$(C_1-C_4)$alkyleneaminosulfonyl-, sulfonylamino, N-$(C_1-C_4)$alkylenesulfonylamino, craboxamido, N-$(C_1-C_4)$alkylenecarboxamido, carboxamidooxy, N-$(C_1-C_4)$alkylenecarboxamidooxy, carbamoyl, -mono-N-$(C_1-C_4)$alkylenecarbamoyl, carbamoyloxy, or -mono-N-$(C_1-C_4)$alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, di- or tri-substituted independently with halo, $(C_1-C_3)$alkyl, trifluoromethyl, trifluoromethyloxy, difluoromethyloxy, hydroxyl, $(C_1-C_4)$alkoxy, or carbamoyl;

$R^1$, $R^2$, $R^3$, $R^4$, $R^5$, $R^{11}$, $R^{31}$, $R^{41}$ and $R^{51}$, when containing an alkyl, alkylene, alkenylene or alkynylene moiety, are optionally mono-, di- or tri-substituted on carbon independently with halo or hydroxy; and V and $V^1$ are each independently a bond, thio$(C_1-C_4)$alkylene, $(C_1-C_4)$alkylenethio, $(C_1-C_4)$alkyleneoxy, oxy$(C_1-C_4)$alkylene or $(C_1-C_3)$alkylene optionally mono- or di-substituted independently with hydroxy or fluoro;

with the provisos that:
a. when K is $(C_2-C_4)$alkylene and M is $Ar^3$ and $Ar^3$ is cyclopent-1-yl, cyclohex-1-yl, cyclohept-1-yl or cyclooct-1-yl then said $(C_5-C_8)$cycloalkyl substituents are not substituted at the one position with hydroxy; and
b. when K is a bond; G is phenyl, phenylmethyl, substituted phenyl or substituted phenylmethyl; Q is $(C_3-C_8)$alkylene; and M is $Ar^3$ or $Ar^4$-$Ar^5$, then A is sulfonyl.

A preferred group of compounds, designated the A Group, comprises those compounds having the formula I as shown above, prodrugs thereof and pharmaceutically acceptable salts of said compounds and said prodrugs, wherein B is N; Z is carboxyl, $(C_1-C_6)$alkoxycarbonyl or tetrazolyl; Ar is phenyl, furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 2H-pyrrolyl, 3H-pyrrolyl, pyrrolyl, 2-pyrrolinyl, 3-pyrrolinyl, pyrrolidinyl, 1,3-dioxolanyl, 2H-imidazolyl, 2-imidazolinyl, imidazolidinyl, 2-pyrazolinyl, pyrazolidinyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 2H-pyranyl, 4H-pyranyl, pyridyl, piperindyl, 1,4-dioxanyl, morpholinyl, 1,4-dithianyl, thiomorpholinyl, piperazinyl, 1,3,5-triazinyl, 1,2,4-triazinyl, azepinyl, oxepinyl, thiepinyl, cyclopentenyl, cyclohexenyl, benzo(b)thienyl, benzoxazolyl, benzimidazolyl, benzthiazolyl, qunioliny, isoquinolinyl, phthalazinyl, quinazolinyl, quinoxalinyl, naphthyl, tetralinyl, decalinyl, 2H-1-benzopyranyl and 1,4-benzodioxan; $Ar^1$, $Ar^2$, $Ar^3$, $Ar^4$ and $Ar^5$ are each independently cyclopentyl, cyclohexyl, cycloheptyl, cyclooctyl, phenyl, furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 2H-pyrrolyl, 3H-pyrrolyl, pyrrolyl, 2-pyrrolinyl, 3-pyrrolinyl, pyrrolidinyl, 1,3-dioxolanyl, 2H-imidazolyl, 2-imidazolinyl, imidazolidinyl, 2-pyrazolinyl, pyrazolidinyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 2H-pyranyl, 4H-pyranyl, pyridyl, piperidinyl, 1,4-dioxanyl, morpholinyl, 1,4-dithianyl, thiomorpholinylpiperazinyl, 1,3,5-triazinyl, 1,2,4-triazinyl, azepinyl, oxepinyl, thiepinyl, 1,2,4-diazepinyl, cyclopentenyl, cyclohexenyl, cycloheptenyl, cyclooctenyl, cyclooctadienyl, indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4H-quinolizinyl, quinolinyl, isoquinolinyl, cinnolinyl, phthalazinyl, quinazolinyl, qunioxalinyl, 1,8-naphthyridinyl, pteridinyl, indenyl, isoindenyl, naphthyl, tetralinyl, decalinyl, 2H-1-benzopyranyl, 1,4-benzodioxan, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl; and X is tetrahydrofuranyl, phenyl, thiazolyl, thienyl, pyridyl, pyrrazolyl, furanyl or pyrimidyl, wherein X is optionally mono-, di- or tri-substituted independently with chloro, fluoro, methoxy, difluoromethoxy, trifluoromethoxy, trifluoromethyl or methyl; and wherein each of said Ar, $Ar^1$ and $Ar^2$ groups are optionally substituted on carbon or nitrogen with up to three substituents independently selected from $R^3$, $R^4$ and $R^5$; each of said Ar, $Ar^1$ and $Ar^2$ groups are optionally substituted independently on carbon or sulfur with one or two oxo groups; each of said $Ar^3$, $Ar^4$ and $Ar^5$ groups are optionally substituted on carbon or nitrogen independently with up to three $R^{31}$, $R^{41}$ and $R^{51}$ groups and each of said $Ar^3$, $Ar^4$ and $Ar^5$ groups are optionally substituted independently on carbon or sulfur with one or two oxo groups.

A group of compounds within the A Group, designated the B Group, comprises those compounds, prodrugs thereof and pharmaceutically acceptable salts of said compounds and said prodrugs, wherein A is CO; G is oxy($C_1$–$C_6$)alkylene; Q is -($C_2$–$C_6$)alkylene-O-($C_1$–$C_3$)alkylene-, -($C_4$–$C_8$)alkylene-, said -($C_4$–$C_8$)alkylene- optionally substituted with up to four substituents independently selected from fluoro or ($C_1$–$C_4$)alkyl, -X-($C_2$–$C_5$)alkylene-, -($C_1$–$C_5$)alkylene-X-, -($C_1$–$C_3$)alkylene-X-($C_1$–$C_3$)alkylene-, -($C_2$–$C_4$)alkylene-O-X-($C_0$–$C_3$)alkylene-, or -($C_0$–$C_4$)alkylene-X-O-($C_1$–$C_3$)alkylene; and X is phenyl, thienyl, furanyl or thiazolyl, wherein X is optionally mono-, di- or tri-substituted with chloro, fluoro, methoxy, difluoromethoxy, trifluoromethoxy, trifluoromethyl or methyl.

Another group of compounds which is preferred within the A Group, designated the C Group, comprises those compounds, prodrugs thereof and pharmaceutically acceptable salts of said compounds and said prodrugs, wherein A is CO; G is Ar; Q is -($C_2$–$C_6$)alkylene-O-($C_1$–$C_3$)alkylene-, -($C_4$–$C_8$)alkylene-, said -($C_4$–$C_8$)alkylene- optionally substituted with up to substituents independently selected from fluoro or ($C_1$–$C_4$)alkyl, -X-($C_2$–$C_5$)alkylene-, -($C_1$–$C_5$)alkylene-X-, -($C_1$–$C_3$)alkylene-X-($C_1$–$C_3$)alkylene-, -($C_2$–$C_4$)alkylene-O-X-($C_0$–$C_3$)alkylene-, or -($C_0$–$C_4$)alkylene-X-O-($C_1$–$C_3$)alkylene-; and X is phenyl, thienyl, furanyl or thiazolyl, wherein X is optionally mono-, di or tri-substituted with chloro, fluoro, methoxy, difluoromethoxy, trifluoromethoxy, trifluoromethyl or methyl.

Another group of compounds which is preferred within the A Group, designated the D Group, comprises those compounds, prodrugs thereof and pharmaceutically acceptable salts of said compounds and said prodrugs, wherein A is CO, G is $R^1R^2$-amino or amino substituted with Ar, or amino substituted with Ar($C_1$–$C_4$)alkylene and $R^{11}$, wherein $R^{11}$ is H; Q is -($C_2$–$C_6$)alkylene-O-($C_1$–$C_3$)alkylene-, -($C_4$–$C_8$)alkylene-, said -($C_4$–$C_8$)alkylene- optionally substituted with up to four substituents independently selected from fluoro or ($C_1$–$C_4$)alkyl, -X-($C_2$–$C_5$)alkylene-, -($C_1$–$C_5$)alkylene-X-, -($C_1$–$C_3$)alkylene-X-($C_1$–$C_3$)alkylene-, -($C_2$–$C_4$)alkylene-O-X-($C_0$–$C_3$)alkylene-, or -($C_0$–$C_4$)alkylene-X-O-($C_1$–$C_3$)alkylene-; and X is phenyl, thienyl, furanyl or thiazolyl, wherein X is optionally mono-, di- or tri-substituted with chloro, fluoro, methoxy, difluoromethoxy, trifluoromethoxy, trifluoromethyl or methyl; and wherein $R^1$ and $R^2$ may be taken separately and are independently selected from H and ($C_1$–$C_8$)alkyl, or $R^1$ and $R^2$ are taken together to form a five- or six-membered azacycloalkyl, said axazcycloalkyl optionally containing an oxygen atom.

Another group of compounds which is preferred within the G Group, designated the E Group, comprises those compounds, prodrugs thereof and pharmaceutically acceptable salts of said compounds and said prodrugs, wherein A is $SO_2$; G is $R^1R^2$-amino, or amino substituted with Ar and $R^{11}$; Q is -($C_2$–$C_6$)alkylene-O-($C_1$–$C_3$)alkylene-, -($C_4$–$C_8$)alkylene-, said -($C_4$–$C_8$)alkylene- optionally substituted with up to four substituents independently selected from fluoro or ($C_1$–$C_4$)alkyl, —X-($C_2$–$C_5$)alkylene-, -($C_1$–$C_5$)alkylene-X-, -($C_1$–$C_3$)alkylene-X-($C_1$–$C_3$)alkylene-, -($C_2$–$C_4$)alkylene-)-O-X-($C_0$–$C_3$)alkylene-, or -($C_0$–$C_4$)alkylene-X-O-($C_1$–$C_3$)alkylene; and X phenyl, thienyl, furanyl or thiazolyl, wherein X is optionally mono-, di- or tri-substituted with chloro, fluoro, methoxy, difluoromethoxy, trifluoromethoxy, trifluoromethyl or methyl; and wherein $R^1$ and $R^2$ may be taken separately and are independently selected from H and ($C_1$–$C_8$)alkyl, or $R^1$ and $R^2$ are taken together to form a five- or six-membered azacycloalkyl, said azacycloalkyl optionally containing an oxygen atom.

Another group of compounds which is preferred within the A Group, designated the F Group, comprises those compounds, prodrugs thereof and pharmaceutically acceptable salts of said compounds and said prodrugs, wherein A is $SO_2$; G is Ar, Ar($C_1$–$C_2$)alkylene or $Ar^1$-V-$Ar^2$; Q is -($C_2$–$C_6$)alkylene-O-($C_1$–$C_3$)alkylene-, -($C_4$–$C_8$)alkylene-, said -($C_4$–$C_8$)alkylene- optionally substituted with up to four substituents independently selected from fluoro or ($C_1$–$C_4$)alkyl, -X-($C_2$–$C_5$)alkylene-, -($C_1$–$C_5$)alkylene-X-, -($C_1$–$C_3$)alkylene-X-($C_1$–$C_3$)alkylene-, -($C_2$–$C_4$)alkylene-O-X-($C_0$–$C_3$)alkylene-, or -($C_0$–$C_4$)alkylene-X-O-($C_1$–$C_3$)alkylene; and X is phenyl, pyrimidyl, pyridyl, thienyl, tetrahydrofuranyl, furanyl or thiazolyl, wherein X is optionally mono-, di- or tri-substituted with chloro, fluoro, methoxy, difluoromethoxy, trifluoromethoxy, trifluoromethyl or methyl.

A particularly preferred group of compounds within the F Group, designated the FA Group, comprises those compounds, prodrugs thereof and pharmaceutically acceptable salts of said compounds and said prodrugs, wherein G is Ar or Ar-($C_1$–$C_2$)-alkylene; Ar is phenyl, furyl, thienyl, pyrrolyl, oxazolyl, thiazolyl, imidazolyl, pyrazolyl, isoxazolyl, pyridyl, pyridazinyl, pyrimidinyl, pyrazinyl, isothiazolyl, 1,2,3-triazolyl, 1,2,4-triazolyl or 1,3,4-thiadiazolyl wherein each of said Ar groups is optionally substituted on carbon or nitrogen with $R^1$, $R^2$ or $R^3$; $Ar^4$ is cyclopentyl, cyclohexyl, cycloheptyl, cyclooctyl, phenyl, furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, pyrrolidinyl, 1,2,3-triazolyl, 1,2,4-triazolyl, pyranyl, thiomorpholinyl, piperazinyl, 1,3,5-triazinyl, 1,2,4-triazinyl, 1,2,3-trazinyl, azepinyl, oxepinyl or thiepinyl wherein each of said $Ar^4$ groups is optionally mono- di- or tri-substituted on carbon on nitrogen with $R^{31}$, $R^{41}$ or $R^{51}$; $Ar^5$ is cyclopentyl, cyclohexyl, cycloheptyl, cyclooctyl, phenyl, furyl, thienyl, pyrrolyl, oxazolyl, thiazolyl, imidazolyl, pyrazolyl, isoxazolyl, isothiazolyl, pyridyl, pyridazinyl, primidinyl, pyrazinyl, pyrrolidinyl, 1,2, 3-triazolyl, 1,2,4-triazolyl, pyranyl, 1,4-dioxanyl, thiomorpholinyl, piperazinyl, 1,3,5-triazinyl, 1,2,4-triazinyl, 1,2,3-triazinyl, azepinyl, oxepinyl or thiepinyl wherein each of said $Ar^5$ groups is optionally mono- di- or tri-substituted on carbon or nitrogen with $R^{31}$, $R^{41}$ or $R^{51}$; Q is -($C_5$–$C_7$)-alkylene-, -($C_1$–$C_2$)-alkylene-X-($C_1$–$C_2$)-alkylene-, -($C_1$–$C_2$)-X-O-($C_1$–$C_2$)-alkylene-, -($C_2$–$C_4$)-alkylene-thienyl-, -($C_2$–$C_4$)-alkylene-furanyl- or -($C_2$–$C_4$)-alkylene-thiazolyl-; X is phenyl, pyridyl, pyrimidyl or thienyl; and said X groups are optionally mono-, di- or tri-substituted with chloro, fluoro, methoxy, difluoromethoxy, trifluoromethoxy, trifluoromethoxy or methyl; said -($C_2$–$C_4$)-alkylene-furanyl- and -($C_2$–$C_4$)-alkylene-thienyl- having a 2,5-substitution pattern, e.g.,

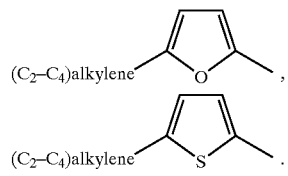

A preferred group of compounds within the FA Group, designated the FB Group, comprises those compounds, prodrugs thereof and pharmaceutically acceptable salts of said compounds and said prodrugs, wherein K is methylene, M is $Ar^4$-$Ar^5$, $Ar^4$-O-$Ar^5$ or $Ar^4$-S-$Ar^5$ and Ar is phenyl, pyridyl, pyrazolyl, imidazolyl, pyrimidyl, thienyl or thiazolyl, wherein Ar is optionally mono-, di- or tri-substituted on carbon or nitrogen with $R^3$, $R^4$ or $R^5$.

A preferred group of compounds within the FB Group, designated the FC Group, comprises those compounds, prodrugs thereof and pharmaceutically acceptable salts of said compounds and said prodrugs, wherein M is $Ar^4$-$Ar^5$; Ar is phenyl, pyridyl or imidazolyl; $Ar^4$ is phenyl, furanyl or pyridyl; and $Ar^5$ is cyclopentyl, cyclohexyl, cycloheptyl, phenyl, pyridyl, imidazolyl, pyrimidyl, thienyl, pyridazinyl, pyrazinyl, imidazolyl, pyrazolyl or thiazolyl, wherein Ar, $Ar^4$ and $Ar^5$ are optionally mono, -di- or tri-substituted on carbon or nitrogen independently with chloro, fluoro, methyl, methoxy, difluoromethoxy, trifluoromethyl or trifluoromethoxy.

An especially preferred group of compounds within the FC Group, designated the FD Group, comprises those compounds, prodrugs thereof and pharmaceutically acceptable salts of said compounds and said prodrugs, wherein Q is -($C_5$–$C_7$)alkylene-.

Another especially preferred group of compounds within the FC Group, designated the FE Group, comprises those compounds, prodrugs thereof and pharmaceutically acceptable salts of said compounds and said prodrugs, wherein Q is $CH_2$-X-$CH_2$- and X is metaphenylene optionally mono- or di- substituted with chloro, fluoro, methoxy, difluoromethoxy, trifluoromethoxy, trifluoromethyl or methyl.

A preferred group of compounds within the FE Group are those compounds, and pharmaceutically acceptable salts and prodrugs thereof, selected from (3-(((pyridine-3-sulfonyl)-(4-pyrimidin-5-yl-benzyl)-amino)-methyl)-phenyl)-acetic acid; (3-(((5-phenyl-furan-2-ylmethyl)-(pyridine-3-sulfonyl)-amino)-methyl)-phenyl)-acetic acid; (3-(((pyridine-3-sulfonyl)-(4-pyrimidin-2-yl-benzyl)-amino)-methyl)-phenyl)-acetic acid; (3-(((pyridine-3-sulfonyl)-(4-thiazol-2-yl-benzyl)-amino)-methyl)-phenyl)-acetic acid; and (3-(((4-pyrazin-2-yl-benzyl)-(pyridine-3-sulfonyl)-amino)-methyl)-phenyl)-acetic acid.

An especially preferred compound within the FE Group is the compound wherein Ar is pyrid-3-yl; Z is carboxy; M is $Ar^4$-$Ar^5$ wherein $Ar^4$ is a furanyl ring and $Ar^5$ is phenyl wherein said phenyl moiety is substituted at the 5-position of said furanyl ring; and Q is —$CH_2$-X-$CH_2$- wherein X is metaphenylene.

Another especially preferred compound within the FE Group is the compound wherein Ar is pyrid-3-yl; Z is carboxy; M is $Ar^4$-$Ar^5$ wherein $Ar^4$ is phenyl and $Ar^5$ is pyrimid-2-yl and said pyrimid-2-yl moiety is substituted at the 4-position of said phenyl ring; and Q is -$CH_2$-X-$CH_2$- wherein X is metaphenylene.

Yet another especially preferred compound within the FE Group is the compound wherein Ar is pyrid-3-yl; Z is carboxy; M is $Ar^4$-$Ar^5$ wherein $Ar^4$ is phenyl and $Ar^5$ is thiazol-2-yl and said thiazol-2-yl moiety is substituted at the 4-position of said phenyl ring; and Q is -$CH_2$-X-$CH_2$- wherein X is metaphenylene.

Yet another especially preferred compound within the FE Group is the compound wherein Ar is pyrid-3-yl; Z is carboxy; M is $Ar^4$-$Ar^5$ wherein $Ar^4$ is phenyl and $Ar^5$ is pyrimid-5-yl and said pyrimid-5-yl moiety is substituted at the 4-position of said phenyl ring; and Q is -$CH_2$-X-$CH_2$- wherein X is metaphenylene.

Yet another especially preferred compound within the FE Group is the compound wherein Ar is pyrid-3-yl; Z is carboxy; M is $Ar^4$-$Ar^5$ wherein $Ar^4$ is phenyl and $Ar^5$ is pyrazin-2-yl and said pyrazin-2-yl is substituted at the 4-position of said phenyl ring; and Q is —$CH_2$-X—$CH_2$- wherein X is metaphenylene.

A preferred group of compounds within the FC Group, designated the G Group, comprises those compounds, prodrugs thereof and pharmaceutically acceptable salts of said compounds and said prodrugs, wherein Q is -($C_2$–$C_4$)-alkylene-thienyl-, -($C_2$–$C_4$)-alkylene-furanyl- or -($C_2$–$C_4$)-alkylene-thiazolyl-.

An especially preferred compound within the G Group is 5-(3-((pyridine-3-sulfonyl)-(4-thiazol-2-yl-benzyl)-amino)-propyl)-thiophene-2-carboxylic acid.

An especially preferred compound within the G Group is the compound, prodrugs thereof and pharmaceutically acceptable salts of said compounds and said prodrugs, wherein Q is n-propylenyl; X is thienyl; Z is carboxy; Ar is 3-pyridyl; $Ar^4$ is phenyl; and $Ar^5$ is 2-thiazolyl; said 2-thiazolyl being substituted at the 4-position of said phenyl.

Another especially preferred group of compounds within the FC Group, designated the H Group, comprises those compounds, prodrugs thereof and pharmaceutically acceptable salts of said compounds and said prodrugs, wherein Q is -$CH_2$-X-O-$CH_2$-; $Ar^4$ is phenyl or pyridyl; said phenyl and pyridyl are optionally substituted with chloro, fluoro, methoxy, difluoromethoxy, trifluoromethoxy, trifluoromethyl and methyl; and X is metaphenylene.

A preferred group of compounds within the H Group are (3-(((4-cyclohexyl-benzyl)-(pyridine-3-sulfonyl)-amino)-methyl)-phenoxy)-acetic acid; (3-(((pyridine-3-sulfonyl)-(4- pyridin-2-yl-benzyl)-amino)-methyl)-phenoxy)-acetic acid; (3-(((pyridine-3-sulfonyl)-(4-pyridin-3-yl-benzyl)-amino)-methyl)-phenoxy)-acetic acid; (3-(((pyridine-3-sulfonyl)-(4-pyridin-4-yl-benzyl)-amino)-methyl)-phenoxy)-acetic acid; and (3-(((pyridine-3-sulfonyl)-(4-thiazol-2-yl-benzyl)-amino)-methyl)-phenoxy)-acetic acid.

An especially preferred compound within the H Group is the compound, prodrugs thereof and pharmaceutically acceptable salts of said compounds and said prodrugs, wherein Ar is pyrid-3-yl; Z is carboxy; $Ar^4$ is phenyl; $Ar^5$ is cyclohexyl; and said cyclohexyl moiety is substituted at the 4-position of said phenyl ring.

Another especially preferred compound within the H Group is the compound wherein Ar is pyrid-3-yl; Z is carboxy; $Ar^4$ is phenyl; $Ar^5$ is thiazol-2-yl; and said thiazol-2-yl moiety is substituted at the 4-position of said phenyl ring.

Yet another especially preferred compound within the H Group is the compound wherein Ar is pyrid-3-yl; Z is carboxy; $Ar^4$ is phenyl; $Ar^5$ is 2-pyridyl; and said 2-pyridyl moiety is substituted at the 4-position of said phenyl ring.

Yet another especially preferred compound within the H Group is the compound wherein Ar is pyrid-3-yl; Z is carboxy; $Ar^4$ is phenyl; $Ar^5$ is 3-pyridyl; and said 3-pyridyl moiety is substituted at the 4-position of said phenyl ring.

Yet another especially preferred compound within the H Group is the compound wherein Ar is pyrid-3-yl; Z is carboxy; $Ar^4$ is phenyl; $Ar^5$ is 4-pyridyl; and said 4-pyridyl moiety is substituted at the 4-position of said phenyl ring.

A preferred group of compounds within the FA Group, designated the I Group, comprises those compounds, prodrugs thereof and pharmaceutically acceptable salts of said compounds and said prodrugs, wherein K is methylene, G is Ar; Ar is phenyl, pyridazinyl, pyrazolyl, pyrazinyl, pyridyl, imidazolyl, pyrimidyl, thienyl or thiazolyl, Ar is optionally mono-, di- or tri-substituted with $R^3$, $R^4$ or $R^5$, and M is $Ar^3$, wherein said $Ar^3$ is cyclopentyl, cyclohexyl, phenyl, thienyl, pyridazinyl, pyrimidinyl, pyrazinyl, indolyl, benzofuryl, benzo(b)thienyl, benzoxazolyl, benzthiazolyl, quinolinyl, isoquinolinyl, naphthyl, tetralinyl, 2H-1-benzopyranyl or 1,4-benzodioxan and is optionally mono-, di- or tri-substituted with $R^{31}$, chloro, fluoro, methyl, methoxy, difluoromethoxy, trifluoromethyl or trifluoromethoxy.

An especially preferred group of compounds within the I Group are (3-(((dihydro-benzo[1,4]dioxin-6-ylmethyl)-(pyridine-3-sulfonyl)-amino)-methyl)-phenyl)-acetic acid; and (3-((benzofuran-2-ylmethyl-(pyridine-3-sulfonyl)-amino)-methyl)-phenyl)-acetic acid.

An especially preferred compound within the I Group is the compound, prodrugs thereof and pharmaceutically acceptable salts of said compound and prodrugs, wherein Ar is pyrid-3-yl; Z is carboxy; M is 6-(1,4-benzodioxan); and Q is -$CH_2$-X-$CH_2$- wherein X is metaphenylene.

Another especially preferred compound within the I Group is the compound wherein Ar is pyrid-3-yl; Z is carboxy; M is 2-benzofuryl; and Q is -$CH_2$-X-$CH_2$- wherein X is metaphenylene.

Another especially preferred group of compounds within the I Group, designated the J Group, comprises those compounds, prodrugs thereof and pharmaceutically acceptable salts of said compounds and said prodrugs, wherein Ar is phenyl, pyridyl or imidazolyl, said phenyl, pyridyl and imidazolyl optionally substituted independently with chloro, fluoro, methyl, methoxy, difluoromethoxy, trifluoromethyl or trifluoromethoxy; $Ar^3$ is phenyl substituted with $R^{31}$, wherein $R^{31}$ is ($C_1$–$C_7$)alkyl, mono-N- or di-N, N-($C_1$–$C_4$) alkylamine, or ($C_1$–$C_5$)alkoxy, said ($C_1$–$C_7$)alkyl or ($C_1$–$C_5$) alkoxy optionally mono-, di- or tri-substituted independently with hydroxy or fluoro; and $Ar^3$ is further optionally mono- or di-substituted with chloro, fluoro, methyl, methoxy, difluoromethoxy, trifluoromethoxy or trifluoromethyl.

A preferred group of compounds within the J Group, designated the K Group, comprises those compounds, prodrugs thereof and pharmaceutically acceptable salts of said components and said prodrugs, wherein Q is -($C_5$–$C_7$) alkylene-.

Another preferred group of compounds within the J Group, designated the L Group, comprises those compounds, prodrugs thereof and pharmaceutically acceptable salts of said compounds and said prodrugs, wherein Q is -$CH_2$-X-$CH_2$- and X is phenyl optionally mono-, di- or tri-substituted with chloro, fluoro, methoxy, difluoromethoxy, trifluoromethoxy, trifluoromethyl or methyl.

An especially preferred group of compounds within the L Group are (3-(((4-butyl-benzyl)-(pyridine-3-sulfonyl)-amino)-methyl)-phenyl)-acetic acid; (3-((benzenesulfonyl-(4-butyl-benzyl)-amino)-methyl)-phenyl)-acetic acid; (3-(((4-butyl-benzyl)-(1-methyl-1H-imidazole-4-sulfonyl)-amino)-methyl)-phenyl)-acetic acid; and (3-(((4-dimethylamino-benzyl)-(pyridine-3-sulfonyl)-amino)-methyl)-phenyl)-acetic acid.

An especially preferred compound within the L Group is the compound, prodrugs thereof and pharmaceutically acceptable salts of said compounds and said prodrugs, wherein Ar is pyrid-3-yl; Z is carboxy; M is phenyl substituted at the 4-position with n-butyl; and Q is -$CH_2$-X-$CH_2$- wherein X is metaphenylene.

Another especially preferred compound within the L Group is the compound, prodrugs thereof and pharmaceutically acceptable salts of said compounds and said prodrugs, wherein Ar is phenyl; Z is carboxy; M is phenyl substituted at the 4-position with n-butyl; and Q is -$CH_2$-X-$CH_2$- wherein X is metaphenylene.

Yet another especially preferred compound within the L Group is the compound, prodrugs thereof and pharmaceutically acceptable salts of said compounds and said prodrugs, wherein Ar is 4-(1-methyl-imidazolyl); Z is carboxy M is phenyl substituted at the 4-position with n-butyl; and Q is -$CH_2$-X-$CH_2$- wherein X is metaphenylene.

Yet another especially preferred compound with the L Group is the compounds, prodrugs thereof and pharmaceutically acceptable salts of said compounds and said prodrugs, wherein Ar is pyrid-3-yl; Z is carboxy; M is phenyl substituted at the 4-position with dimethylamino, and Q is -$CH_2$-X-$CH_2$- wherein X is metaphenylene.

Another preferred group of compounds will the J Group comprises those compounds, prodrugs thereof and pharmaceutically acceptable salts of said compounds and said prodrugs, wherein Q is -($C_2$–$C_4$)alkylene-thienyl, -($C_2$–$C_4$) alkylene-furanyl or -($C_2$–$CH_4$)alkylene-thiazolyl.

A preferred group of compounds within the J Group, designated the M Group, comprises those compounds, prodrugs thereof and pharmaceutically acceptable salts of said compounds and said prodrugs, wherein Q is ($C_1$–$C_2$)-X-O-($C_1$–$C_2$)alkylene- and X is metaphenylene, said X being optionally mono-, di- or tri-substituted with chloro, fluoro, methoxy, difluoromethoxy, trifluoromethoxy, trifluoromethoxy or methyl.

An especially preferred group of compounds with the M Group are (3-(((4-dimethylamino-benzyl)-(pyridine-3-sulfonyl)-amino)methyl-phenoxy)-acetic acid and (3-(((4-tert-butyl-benzyl)-(pyridine-3-sulfonyl)-amino)-methyl)-phenoxy)-acetic acid.

An especially preferred compound within the M Group is the compound, prodrugs thereof and pharmaceutically acceptable salts of said compounds and said prodrugs, wherein Ar is pyrid-3-yl; Z is carboxyl; M is phenyl substituted at the 4-position with dimethylamino: and Q is -CH$_2$-X-O-CH$_2$- wherein X is metaphenylene.

Another especially preferred compound within the M Group is the compound, prodrugs thereof and pharmaceutically acceptable salts of said compounds and said prodrugs, wherein Ar is pyrid-3-yl; Z is carboxy; M is phenyl substituted at the 4-position with tert-butyl; and Q is -CH$_2$-X-O-CH$_2$- wherein X is metaphenylene.

Another preferred group of compounds within the FA Group, designated the N Group, comprises those compounds, prodrugs thereof and pharmaceutically acceptable salts of said compounds and said prodrugs, wherein G is Ar; K is (C$_2$–C$_4$) alkylene or n-propenylene; Ar is phenyl, pyrazolyl, pyridazinyl, pyrazinyl, pyridinyl, imidazolyl, pyrimidyl thienyl or thiazolyl, wherein Ar is optionally mono-, di-or tri-substituted with R$^3$, R$^4$ or R$^5$; and Ms is Ar$^3$, optionally mono-, di- or tri-substituted with chloro, fluro, methyl, mtehoxy, difluoromethoxy, trifluoromethoxy and trifluoromethyl.

An especially preferred compound within the N Group is trans-(3-(((3-3,5-dichloro-phenyl)-allyl)-(pyridine-3-sulfonyl)-amino)-methyl)-phenyl)-acetic acid.

An especially preferred compound within the N Group is the compound, prodrugs thereof and pharmaceutically acceptable salts of said compounds and said prodrugs, wherein K is trans-n-propenylene, said M group being attached to the 1-position of the n-propenylene and said N atom being attached to 3-position of the n-propenylene; Ar is pyrid-3-yl; M is phenyl 3,5-disubstituted with chloro; Z is carboxy; and Q is CH$_2$-X-CH$_2$- wherein X is metaphenylene.

A preferred group of compounds within the N Group, designated the O Group, comprises those compounds, prodrugs thereof and pharmaceutically acceptable salts of said compounds and said prodrugs, wherein Ar$^3$ is phenyl optionally substituted with chloro, fluoro, methyl, methoxy, difluoromethoxy, trifluoromethoxy and trifluoromethyl.

A preferred group of compounds within the O Group, designated the P Group, comprises those compounds, prodrugs thereof and pharmaceutically acceptable salts of said compounds and said prodrugs, wherein Q is -(C$_5$–C$_7$) alkylene-.

Another group of compounds within the O Group, designated the Q Group, comprises those compounds, prodrugs thereof and pharmaceutically acceptable salts of said compounds and said prodrugs, wherein Q is -CH$_2$-X-CH$_2$- and X is metaphenylene.

Yet another group of compounds within the O Group, designated the R Group, comprises those compounds, prodrugs thereof and pharmaceutically acceptable salts of said compounds and said prodrugs, wherein Q is -(C$_2$–C$_4$) alkylene-X- and X is furanyl, thienyl or thiazolyl.

Yet another preferred group of compounds within the O Group, designated the S Group, comprises these compounds, prodrugs thereof and pharmaceutically acceptable salts of said compounds and said prodrugs, wherein Q is -(C$_1$–C$_2$)-X-O-(C$_1$–C$_2$)alkylene- and X is metaphenylene.

Another preferred group of compounds within the FA Group, designated the T Group, comprises those compounds, prodrugs thereof and pharmaceutically acceptable salts of said compounds and said prodrugs, wherein G is Ar; K is thioethylene or oxyethylene, Ar is phenyl, pyrazolyl, pyridazinyl, pyrazinyl, pyridyl, imidazolyl, pyrimidyl, thienyl or thiazolyl, wherein Ar is optionally substituted with up to three R$^3$, R$^4$ or R$^5$; and M is Ar$^3$, optionally mono-, di- or tri-substituted with chloro, fluoro, methyl, difluoromethoxy, trifluoromethoxy or trifluoromethyl.

A preferred group of compounds within the T Group, designated the U Group, comprises those compounds, prodrugs thereof and pharmaceutically acceptable salts of said compounds and said prodrugs, wherein A$^3$ is phenyl.

A preferred group of compounds within the U Group, designated the V Group, comprises those compounds, prodrugs thereof and pharmaceutically acceptable salts of said compounds and said prodrugs, wherein Q is -(C$_5$–C$_7$) alkylene-.

Another preferred group of compounds within the U Group, designated the W Group, comprises those compounds, prodrugs thereof and pharmaceutically acceptable salts of said compounds and said prodrugs, wherein Q is -CH$_2$-X-CH$_2$- and X is metaphenylene.

Another preferred group of compounds with the U Group, designated the Y Group, comprises those compounds, prodrugs thereof and pharmaceutically acceptable salts of said compounds and said prodrugs, wherein Q is -(C$_2$–C$_4$) alkylene-X- and X is furanyl, thienyl or thiazolyl Another preferred group of compounds within the U Group, designated the Y Group, comprises those compounds, prodrugs thereof and pharmaceutically acceptable salts of said compounds and said prodrugs, wherein Q is -(C$_1$–C$_2$)-X-O-(C$_1$–C$_2$)alkylene- and X is metaphenylene.

An especially preferred compound with the Y Group is (3-(((2-(3,5-dichloro-phenoxy)-ethyl)-(pyridine-3-sulfonyl)-amino)methyl)-phenoxy)-acetic acid.

An especially preferred compound within the Y Group is the compound, prodrugs thereof and pharmaceutically acceptable salts of said compounds and said prodrugs, wherein K is ethylenyloxy; said M group being attached to the oxygen atom of the ethylenloxy group and said N atom being attached to the 2-position of the ethylenyloxy group; Ar is pyrid-3-yl; M is phenyl 3,5-disubstituted with chloro; Z is carboxy and Q is -CH$_2$-X-O-CH$_2$- wherein X is a second phenyl ring and said CH$_2$ and OCH$_2$ substituents are situated in a meta substitution pattern on said second phenyl ring.

Another preferred group of compounds, designated the Z Group, comprises those compounds of Formula I, prodrugs thereof and pharmaceutically acceptable salts of said compounds and said prodrugs, wherein B is CH.

A preferred group of compounds within the Z Group comprises those compounds, prodrugs thereof and pharmaceutically acceptable salts of said compounds and said prodrugs, wherein A is CO; G is Ar, K is methylenyl, propylenyl, propenylenyl or oxyethylenyl; M is Ar$^3$ or Ar$^4$-Ar$^5$; Ar$^3$ is phenyl or pyridyl; Ar$^4$ is phenyl, thienyl, pyridyl or furanyl; Ar$^5$ is (C$_5$–C$_7$) cycloalkyl, phenyl, pyridyl, imidazolyl, pyrimidyl, thienyl, pyridazinyl, pyrazinyl, imidazolyl, pyrazolyl or thiazolyl; Ar is phenyl, pyrazolyl, pyrazinyl, pyridyl, imidazolyl, pyrimidyl, thienyl or thiazolyl, wherein Ar, Ar$^3$, Ar$^4$ and Ar$^5$ are optionally substituted independently with up to three chloro, fluoro, methyl, difluoromethoxy, trifluoromethoxy or trifluoromethyl.

Another especially preferred group of compounds within the Z Group comprises those compounds, prodrugs thereof and pharmaceutically acceptable salts of said compounds and said prodrugs, wherein A is CO; G is Ar, K is methylenyl, propylenyl, propenylenyl or oxyethylenyl; M is Ar$^3$ or Ar$^4$-Ar$^5$; Ar$^3$ is phenyl or pyridyl; Ar$^4$ is phenyl, thienyl, pyridyl or furanyl; $Ar^5$ is ($C_5$–$C_7$) cycloalkyl, phenyl, pyridyl, imidazolyl, pyrimidyl, thienyl, pyridazinyl, pyrazinyl, imidazolyl, pyrazolyl or thiazolyl; Ar is phenyl, pyrazolyl, pyridazinyl, pyrazinyl, pyridyl, imidazolyl, pyrimidyl, thienyl or thiazolyl, wherein Ar, $Ar^3$, $Ar^4$ and $Ar^5$ are optionally substituted independently with up to three chloro, fluoro, methyl, difluoromethoxy, trifluoromethoxy or trifluoromethyl.

This invention is also directed to methods for treating vertebrates, e.g., a mammal, having a condition which presents with low bone mass comprising administering to said vertebrate, e.g., a mammal, having a condition which presents with low bone mass a therapeutically effective amount of a compound of Formula I, a prodrug thereof of a pharmaceutically acceptable salt of said compound or said prodrug. Preferably post-menopausal women and men over the age of 80 are treated. Also included are individuals regardless of age who have significantly reduced bone mass, i.e., greater than or equal to 1.5 standard deviations below young normal levels.

Yet another aspect of this invention is directed to methods for treating osteoporosis, bone fractures, osteotomy, bone loss associated with periodontitis, or prosthetic ingrowth in a vertebrate, e.g., a mammal (including a human being), comprising administering to said vertebrate, e.g., a mammal suffering from osteoporosis, bone fracture, osteotomy, bone loss associated with periodontitis, or prosthetic ingrowth an osteoporosis, bone fracture, osteotomy, bone loss associated with periodontitis, or prosthetic ingrowth treating amount of a Formula I compound, a prodrug thereof or a pharmaceutically acceptable salt of said compound or said prodrug.

Yet another aspect of this invention is directed to methods for treating osteoporosis in a vertebrate, e.g., a mammal (including a human being), comprising administering to said vertebrate, e.g., a mammal suffering from osteoporosis an osteoporosis treating amount of a Formula I compound, a prodrug thereof or a pharmaceutically acceptable salt of said compound or said prodrug.

Yet another aspect of this invention is directed to methods for treating osteotomy in a vertebrate, e.g., a mammal (including a human being), comprising administering to said vertebrate, e.g. a mammal having undergone an osteotomy a bone restoration treating amount of a Formula I compound, a prodrug thereof or a pharmaceutically acceptable salt of said compound or said prodrug, wherein a bone restoration treating amount is an amount of said Formula I compound, prodrug thereof or pharmaceutically acceptable salt of said compound or said prodrug sufficient to restore bone in areas containing bone defects due to said osteotomy. In one aspect the Formula I compound, prodrug thereof or pharmaceutically acceptable salt thereof is applied locally to a site of osteotomy.

Yet another aspect of this invention is directed to methods for treating alveolar or mandibular bone loss in a vertebrate, e.g., a mammal (including a human being), comprising administering to said vertebrate, e.g., a mammal suffering from an alveolar bone or mandibular loss, an alveolar or mandibular bone loss treating amount of a Formula I compound, a prodrug thereof or a pharmaceutically acceptable salt of said compound or said prodrug.

Yet another aspect of this invention is directed to methods for treating bone loss associated with periodontitis in a vertebrate, e.g., a mammal (including a human being), comprising administering to said vertebrate, e.g., mammal suffering from bone loss associated with periodontitis, a bone loss associated with periodontitis treating amount of a Formula I compound, a prodrug thereof or a pharmaceutically acceptable salt of said compound or said prodrug.

Yet another aspect of this invention is directed to methods for treating childhood idiopathic bone loss is a child comprising administering to a child suffering from childhood idiopathic bone loss a childhood idiopathic bone loss treating amount of a Formula I compound, a prodrug thereof or a pharmaceutically acceptable salt of said compound or said prodrug.

Yet another aspect of this invention is directed to methods for treating "secondary osteoporosis," which includes gluococorticoid-induced osteoporosis, hyperthyroidism-induced osteoporosis, immobilization-induced osteoporosis, heparin-induced osteoporosis or immunosuppressive-induced osteoporosis in a vertebrate, e.g., a mammal (including a human being), by administering to said vertebrate, e.g., a mammal suffering from "secondary osteoporosis," a "secondary osteoporosis" treating amount of a Formula I compound, a prodrug thereof or a pharmaceutically acceptable salt of said compound or said prodrug.

Yet another aspect of this invention is directed to methods for treating glucocorticoid-induced osteoporosis in a vertebrate, e.g., a mammal (including a human being), comprising administering to said vertebrate, e.g., a mammal suffering from gluocorticoid-induced osteoporosis, a glucocorticoid-induced osteoporosis treating amount of a Formula I compound, a prodrug thereof or a pharmaceutically acceptable salt of said compound or said prodrug.

Yet another aspect of this invention is directed to methods for treating hyperthyrodism-induced osteoporosis in a vertebrate, e.g., a mammal (including a human being), comprising administering to said vertebrate, e.g., a mammal suffering from hyperthyroidism-induced osteoporosis a hyperthyroidism-induced osteoporosis treating amount of a Formula I compound, a prodrug thereof or a pharmaceutically acceptable salt of said compound or said prodrug.

Yet another aspect of this invention is directed to methods for treating immobilization-induced osteoporosis in a vertebrate, e.g., a mammal (including a human being), comprising administering to said vertebrate, e.g., a mammal suffering from immobilization-induced osteoporosis, an immobilization-induced osteoporosis treating amount of a Formula I compound, a prodrug thereof or a pharmaceutically acceptable salt of said compound or said prodrug.

Yet another aspect of this invention is directed to methods for treating heparin-induced osteoporosis in a vertebrate, e.g., a mammal (including a human being), comprising administering to said vertebrate, e.g., a mammal suffering from heparin-induced osteoporosis, a heparin-induced osteoporosis treating amount of a Formula I compound, a prodrug thereof or a pharmaceutically acceptable salt of said compound or said prodrug.

Yet another aspect of this invention is directed to methods for treating immunosuppressive-induced osteoporosis in a vertebrate, e.g., a mammal (including a human being), comprising administering to said vertebrate, e.g., a mammal suffering from immunosuppressive-induced osteoporosis, an immunosuppressive-induced osteoporosis treating amount of a Formula I compound, a prodrug thereof or a pharmaceutically acceptable salt of said compound or said prodrug.

Yet another aspect of this invention is directed to methods for treating a bone fracture in a vertebrate, e.g., a mammal (including a human being), comprising administering to said vertebrate, e.g., a mammal suffering from a bone fracture, a bone fracture treating amount of a Formula I compound, a prodrug thereof or a pharmaceutically acceptable salt of said compound or said prodrug. In one aspect of this invention for treating a bone fracture the Formula I compound, prodrug thereof or pharmaceutically acceptable salt of said compound or said prodrug is applied locally to the site of bone fracture. In another aspect of this invention the Formula I compound, prodrug thereof or pharmaceutically acceptable salt of said compound or said prodrug is administered systemically.

Yet another aspect of this invention is directed to methods for enhancing bone healing following focal reconstruction, maxillary reconstruction or mandibular reconstruction in a vertebrate, e.g., a mammal (including a human being), comprising administering to said vertebrate, e.g., a mammal which has undergone facial reconstruction, maxillary reconstruction or mandibular reconstruction, a bone enhancing amount of a Formula 1 compound, a prodrug thereof or a pharmaceutically acceptable salt of said compound or said prodrug. In one aspect of this method a Formula 1 compound, prodrug thereof or pharmaceutically acceptable salt of said compound or said prodrug is applied locally to the site of bone reconstruction.

Yet another aspect of this invention is directed to methods for treating prosthetic ingrowth in a vertebrate, such as promoting bone ingrowth into a bone prothesis in, e.g., a mammal (including a human being), comprising administering to said vertebrate, e.g., a mammal suffering from prosthetic ingrowth, a prosthetic ingrowth treating amount of a Formula 1 compound, a prodrug thereof or a pharmaceutically acceptable salt of said compound or said prodrug.

Yet another aspect of this invention is directed to methods for inducing vertebral synostosis in a vertebrate, e.g., a mammal (including a human being), comprising administering to said vertebrate, e.g., a mammal undergoing surgery for vertebral synostosis, a therapeutically effective amount of a Formula 1 compound, a prodrug thereof or a pharmaceutically acceptable salt of said compound or said prodrug.

Yet another aspect of this invention is directed to methods for enhancing long bone extension in a vertebrate, e.g., a mammal (including a human being), comprising administering to said vertebrate, e.g., a mammal suffering from an insufficiently sized long bone, a long bone enhancing amount of a Formula 1 compound, a prodrug thereof or a pharmaceutically acceptable salt of said compound or said prodrug.

Yet another aspect of this invention is directed to methods for strengthening a bone graft i a vertebrate, e.g., a mammal (including a human being), comprising administering to said vertebrate, e.g., a mammal in receipt of a bone graft, a bone graft strengthening amount of a Formula 1 compound, a prodrug thereof or a pharmaceutically acceptable salt of said compound or said prodrug. Additionally, a compound of Formula 1 a prodrug thereof or a pharmaceutically acceptable salt of said compound or said prodrug can be used as an alternative to bone graft surgery. In one aspect of this method of Formula 1 compound, prodrug thereof or pharmaceutically acceptable salt of said compound or said prodrug is applied locally to the site of the bone graft. In another aspect of this method a Formula 1 compound, prodrug thereof or pharmaceutically acceptable salt of said compound or said prodrug is applied directly to the bone by injection or direct application to the bone surface.

A preferred dosage is about 0.001 to 100 mg/kg/day of a Formula 1 compound, a prodrug thereof or a pharmaceutically acceptable salt of said compound or said prodrug. An especially preferred dosage is about 0.01 to 10 mg/kg/day of a Formula 1 compound, a prodrug thereof or a pharmaceutically acceptable salt of said compound or said prodrug.

This invention is also directed to pharmaceutical compositions which comprise a therapeutically effective amount of a compound of Formula 1, a prodrug thereof or a pharmaceutically acceptable salt of said compound or said prodrug and a pharmaceutically acceptable carrier or diluent.

This invention is also directed to pharmaceutical compositions for the augmentation of bone mass which comprise a bone mass augmenting amount of a compound of Formula 1, a prodrug thereof or a pharmaceutically acceptable salt of said compound or said prodrug and a pharmaceutically acceptable carrier or diluent.

This invention is also directed to pharmaceutical compositions for the treatment of a condition which presents with low bone mass in a vertebrate, e.g., a mammal (including a human being), which comprise a low bone mass condition treating amount of a compound of Formula 1, a prodrug thereof or a pharmaceutically acceptable salt of said compound or said prodrug and a pharmaceutically acceptable carrier or diluent.

This invention is also directed to pharmaceutical compositions for the local or systemic treatment of osteoporosis, bone fractures, osteotomy, bone loss associated with periodontitis, or prosthetic ingrowth in a vertebrate, e.g., a mammal (including a human being), which comprises a therapeutically effective amount of a compound of Formula 1, a prodrug thereof or a pharmaceutically acceptable salt of said compound or said prodrug and a pharmaceutically acceptable carrier or diluent.

This invention is also directed to pharmaceutical compositions for the treatment of "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a vertebrate, e.g., a mammal (including a human being), which compositions comprise a "secondary osteoporosis" treating amount of a compound of Formula 1, a prodrug thereof or a pharmaceutically acceptable salt of said compound or said prodrug and a pharmaceutically acceptable carrier or diluent.

This invention is also directed to pharmaceutical compositions for the treatment of osteoporosis in a vertebrate, e.g., a mammal (including a human being), which comprise an osteoporosis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for enhancing bone fracture healing in a vertebrate, e.g., a mammal (including a human being), which comprise a bone fracture treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of osteotomy in a vertebrate, e.g., a mammal (including a human being), comprising administering to said vertebrate, e.g. a mammal having undergone an osteotomy a bone restoration treating amount of a Formula 1 compound, a prodrug thereof or a pharmaceutically acceptable salt of said compound or said prodrug, wherein a bone restoration treating amount is an amount of said Formula 1 compound, prodrug thereof or pharmaceutically acceptable salt of said compound or said prodrug sufficient to restore bone in areas containing bone defects due to said osteotomy. In one aspect the Formula 1 compound, prodrug thereof or pharmaceutically acceptable salt thereof is applied locally to an osteotomy site.

This invention is also directed to pharmaceutical compositions for facilitating bone healing after an osteotomy in a vertebrate, e.g., a mammal (including a human being), comprising administering to said vertebrae, e.g., a mammal having undergone an osteotomy a bone healing amount of a Formula 1 compound, a prodrug thereof or a pharmaceutically acceptable salt of said compound or said prodrug. In one aspect the Formula 1 compound, prodrug thereof or pharmaceutically acceptable salt thereof is applied locally to an osteotomy site.

This invention is also directed to pharmaceutical compositions for the treatment of alveolar or mandibular bone loss in a vertebrate, e.g., a mammal (including a human being), which comprise an alveolar or mandibular bone loss treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of childhood idiopathic bone loss in a child which comprise a childhood idiopathic bone loss treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the augmentation of bone healing following facial reconstruction, maxillary reconstruction or mandibular reconstruction in a vertebrae, e.g., a mammal (including a human being), which comprise a bone healing amount of a compound of the formula 1, a prodrug thereof or a pharmaceutically acceptable salt of said compound or said prodrug and a pharmaceutically acceptable carrier or diluent.

This invention is also directed to pharmaceutical compositions for the treatment of bone loss associated with periodontitis in a vertebrate, e.g., a mammal (including a human being), which comprise a bone loss associated with periodontitis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of prosthetic ingrowth in a vertebrate, e.g., a mammal (including a human being), which comprise a prosthetic ingrowth treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for inducing vertebral synostosis or spinal fusion in a vertebrate, e.g., a mammal (including a human being), which comprise a therapeutically effective amount of a compound of the Formula 1, a prodrug thereof or a pharmaceutically acceptable salt of said compound or said prodrug and a pharmaceutically acceptable carrier or diluent.

This invention is also directed to pharmaceutical compositions for enhancing bone union in a long bone extension procedure in a vertebrate, e.g., a mammal (including a human being), which comprise a bone mass augmentation treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of glucocorticoid-induced osteoporosis in a vertebrate, e.g., a mammal (including a human being), which comprise a glucocorticoid-induced osteoporosis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of hyperthyroidism-induced osteoporosis in a vertebrate, e.g., a mammal (including a human being), which comprise a hyperthyroidism-induced osteoporosis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of immobilization-induced osteoporosis in a vertebrate, e.g., a mammal (including a human being), which comprise an immobilization-induced osteoporosis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of heparin-induced osteoporosis in a vertebrate, e.g., a mammal (including a human being) which comprise a heparin-induced osteoporosis treating amount of a compound of the Formula 1, a prodrug thereof or a pharmaceutically acceptable salt of said compound or said prodrug and a pharmaceutically acceptable carrier or diluent.

This invention is also directed to pharmaceutical compositions for the treatment of immunosuppressive-induced osteoporosis in a vertebrate, e.g., a mammal (including a human being) which comprise an immunosuppressive-induced osteoporosis treating amount of a compound of the Formula 1, a prodrug thereof or a pharmaceutically acceptable salt of said compound or said prodrug and a pharmaceutically acceptable carrier or diluent.

Yet another aspect of this invention is directed to combinations of the Formula 1 compounds, prodrugs thereof or pharmaceutically acceptable salts of said compounds or said prodrugs and other compounds as described below.

Yet another aspect of this invention is directed to pharmaceutical compositions comprising a compound of Formula 1, a prodrug thereof or a pharmaceutically acceptable salt of said compound or said prodrug and an anti-resorptive agent, a prodrug thereof or a pharmaceutically acceptable salt of said agent or said prodrug and for the use of such compositions for the treatment or prevention of conditions which present with low bone mass, including osteoporosis in a vertebrates, e.g., mammals (e.g., humans, particularly women) or the use of such compositions for other bone mass augmenting uses.

The combinations of this invention comprise a therapeutically effective amount of a first compound, said first compound being a Formula 1 compound, a prodrug thereof or a pharmaceutically acceptable salt of said compound or said prodrug; and a therapeutically effective amount of a second compound, said second compound being an anti-resorptive agent, a prodrug thereof or a pharmaceutically acceptable salt of said agent or said prodrug such as an estrogen agonist/antagonist or a bisphosphonate.

Another aspect of this invention is directed to methods for treating vertebrates, e.g., mammals which present with low bone mass comprising administering to said vertebrate, e.g., a mammal having a conduction which presents with low bone mass.

a. an amount of a first compound, said first compound being a Formula 1 compound, a prodrug thereof or a pharmaceutically acceptable salt of said compound or said prodrug; and b. an amount of a second compound, said second compound being an anti-resorptive agent, a prodrug thereof or a pharmaceutically acceptable salt of said agent or said prodrug such as an estrogen agonist/antagonist or a bisphosphonate.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the first compound is administered for a period of from about one week to about five years.

An especially preferred aspect of this method is wherein the first compound is administered for a period of from about one week to about three years.

Optionally the administration of the first compound is followed by administration of the second compound wherein the second compound is an estrogen agonist/antagonist for a period of from about three months to about three years without the administration of the first compound during the second period of from about three months to about three years.

Alternatively, the administration of the firs compound is followed by administration of the second compound wherein the second compound is an estrogen agonist/antagonist for a period greater than about three years without the administration of the first compound during the greater than about three year period.

Another aspect of this invention is a kit comprising:
a. an amount of a Formula 1 compound, a prodrug thereof or a pharmaceutically acceptable salt of said compound or said prodrug and a pharmaceutically acceptable carrier or diluent in a first unit dosage form;
b. an amount of an anti-resorptive agent, a prodrug thereof or a pharmaceutically acceptable salt of said agent or said prodrug such as an estrogen agonist/antagonist or a bisphosphonate and a pharmaceutically acceptable carrier or diluent in a second unit dosage form; and
c. container means for containing said first and second dosage forms.

Yet another aspect of this invention is directed to pharmaceutical compositions comprising a compound of Formula 1, a prodrug thereof or a pharmaceutically acceptable salt of said compound or said prodrug and another bone anabolic agent (although the other bone anabolic agent may be a different Formula 1 compound), a prodrug thereof or a pharmaceutically acceptable salt of said agent or said prodrug and for the use of such compositions for the treatment of conditions which present with low bone mass, including osteoporosis in a vertebrates, e.g., mammals (e.g., humans, particularly women), or the use of such compositions for other bone mass augmenting uses. Such compositions comprise a therapeutically effective amount of a first compound, said first compound being a Formula 1 compound, a prodrug thereof or a pharmaceutically acceptable salt of said compound or said prodrug; and a therapeutically effective amount of a second compound, said second compound being another bone anabolic agent, a prodrug thereof or a pharmaceutically acceptable salt of said agent or said prodrug.

Another aspect of this invention is directed to methods for treating vertebrates, e.g., mammals which present with low bone mass comprising administering to said vertebrate, e.g., a mammal having a condition which presents with low bone mass.

a. an amount of a first compound, said first compound being a Formula 1 compound, a prodrug thereof or a pharmaceutically acceptable salt or prodrug thereof; and b. an amount of a second compound, said second compound being another bone anabolic agent, a prodrug thereof or a pharmaceutically acceptable salt of said agent or said prodrug.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another aspect of this invention is a kit comprising:
a. an amount of a Formula 1 compound, a prodrug thereof or a pharmaceutically acceptable salt of said compound or said prodrug and a pharmaceutically acceptable carrier or diluent in a first unit dosage form;
b. an amount of a second compound, said second compound being another bone anabolic agent, a prodrug thereof or a pharmaceutically acceptable salt of said agent or said prodrug in a second unit dosage form; and
c. container means for containing said first and second dosage forms.

Where used in any of the above methods, kits and compositions, certain bone anabolic agents, estrogen agonists/antagonists and bisphosphonates are preferred or espectially preferred.

Preferred bone anabolic agents include IGF-1, prostaglandins, prostaglandin agonists/antagonists, sodium fluoride, parathyroid hormone (PTH), active fragments of parathyroid hormone, parathyroid hormone related peptides and active fragments and analogues of parathyroid hormone related peptides, growth hormones or growth hormone secretagogues and the pharmaceutically acceptable salts thereof.

Preferred estrogen agonists/antagonists include droloxifene, raloxifene, tamoxifen; 4-hydroxy-tamoxifen; toremifene; centchroman; levormeloxifene; idoxifene; 6-(4-hydroxy-phenyl)-5-(4-(2-piperidin-1-yl-ethoxy)-benzyl)-naphthalen-2-ol; (4-(2-(2-aza-bicyclo[2.2.1]hept-2-yl)-ethoxy)-phenyl)p(6-hydroxy-2-(4-hydroxy-phenyl)-benzo[b]thiophen-3-yl)-methanone;

3-(4-(1,2-diphenyl-but-1-enyl)-phenyl)-acrylic acid;

2-(4-methoxy-phenyl)-3-[4-(2-piperidin-1-yl-ethoxy)-phenoxy]-benzo[b]thiophen-6-ol;

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydro-naphthalene-2-ol;

cis-6-phenyl-5-(4-(2-pyrrolidin-1-yl-ethoxy)-phenyl)-5,6,7,8-tetrahydro-naphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline and the pharmaceutically acceptable salts thereof.

Especially preferred estrogen agonists/antagonists include droloxifene;

3-(4-(1,2-diphenyl-but-1-enyl)-phenyl)-acrylic acid;
2-(4-methoxy-phenyl)-3-[4-(2-piperidin-1-yl-ethoxy)-phenoxy]-benzo[b]thiophen-6-ol;
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol;
cis-6-phenyl-5-(4-(2-pyrrolidin-1-yl-ethoxy)-phenyl)-5,6,7,8-tetrahydro-naphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol;
1-(4'-pyrrolidinolethoxyphenyl)-2-phenyl-6-hydroxy-1,2,3,4-tetrahydroisoquinoline; and the pharmaceutically acceptable salts thereof.

Preferred bisphosphonates include, tiludronic acid, alendronic acid, zoledronic acid, ibandronic acid, risedronic acid, etidronic acid, clodronic acid, and pamidronic acid and their pharmaceutically acceptable salts.

It will be recognized that prodrugs and pharmaceutically acceptable salts may be formed from the compounds used as the second compounds in the combinations of this invention. All of such prodrugs and pharmaceutically acceptable salts so formed are within the scope of this invention. Particularly preferred salt forms include droxloxifene citrate, raloxifene hydrochloride, tamoxifen citrate and toremifene citrate.

The phrase "condition(s) which presents will low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, post-osteotomy and childhood idiopathic bone loss. The phrase "condition(s) which presents with low bone mass" also includes long term complications of osteoporosis such as curvature of the spine, loss of height and prosthetic surgery.

The phrase "condition(s) which presents with low bone mass" also refers to a vertebrate, e.g., a mammal known to have a significantly higher than average chance of developing such diseases as are described above including osteoporosis (e.g., post-menopausal women, men over the age of 60).

Other bone mass augmenting or enhancing uses include bone restoration, increasing the bone fracture healing rate, replacing bone graft surgery entirely, enhancing the rate of successful bone grafts, bone healing following facial reconstruction or maxillary reconstruction or mandibular reconstruction, prosthetic ingrowth, vertebral synostosis or long bone extension.

The compounds and compositions of this invention may also be used in conjunction with orthopedic devices such as spinal fusion cages, spinal fusion hardware, internal and external bone fixation devices, screws and pins.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic), palliative and curative treatment.

By "pharmaceutically acceptable" it is meant the carrier, diluent, excipients, and/or salt must be compatible with the other ingredients of the Formulation, and not deleterious to the recipient thereof.

The expression "prodrug" refers to compounds that are drug precursors which, following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula 1 compounds include but are not limited to substituents wherein the Z moiety is independently carboxyl and the free hydrogen is replaced by $(C_1-C_4)$alkyl, $(C_2-C_7)$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy) ethyl having from 5 to 8 carbon atoms, N-(alkoxycarbonyl) aminomethyl having from 3 to 9 carbon atoms, 1-(N-(alkoxycarbonyl) amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as b-dimethylaminoethyl), carbamoyl-$(C_1-C_2)$ alkyl, N,N-di $(C_1-C_2)$ alkylcarbamoyl-$(C_1-C_2)$alkyl and piperidino-, pyrrolidino- or morpholino$(C_2-C_3)$ alkyl.

Exemplary five to six membered aromatic rings optionally having one or two heteroatoms selected independently from oxygen, nitrogen and sulfur (i.e., X rings) are phenyl, furyl, thienyl, pyrrolyl, oxazolyl, thiazolyl, imidazolyl, pyrazolyl, isoxazolyl, isothiazolyl, pyridyl, pyridiazinyl, pyrimidinyl and pyrazinyl.

Exemplary partially saturated, fully saturated or fully unsaturated vive to eight membered rings optionally having one to four heteroatoms selected independently from oxygen, sulfur and nitrogen (i.e., Ar, $Ar^1$ and $Ar^2$) are cyclopentyl, cyclohexyl, cycloheptyl, cyclooctyl and phenyl. Further exemplary five membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, osoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused independently partially saturated, fully saturated or fully unsaturated five and/or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, 1,4-benzodioxan, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

Exemplary tricyclic rings consisting of three fused independently partially saturated, fully saturated or fully unsaturated five and/or six membered rings, taken independently, optionally having one to four heteroatoms selected independently from nitrogen, sulfur and oxygen are indacenyl, biphenylenyl, acenaphthylenyl, fluorenyl, phenalenyl, phenanthrenyl, anthracenyl, naphthothienyl, thianthrenyl, xanthenyl, phenoxathiinyl, carbazolyl, carbolinyl, phenanthridinyl, acridinyl, perimidinyl, phenanthrolinyl, phenazinyl, phenothiazinyl and phenoxazinyl. It will be understood that the fully saturated and all partially unsaturated forms of these rings are within the scope of this invention. Further, it will be understood that nitrogen may be substituted as the heteroatom at any position, including a bridgehead position, in the heterocyclic rings. Further still, it will be understood that sulfur and oxygen may be substituted as the heteroatom at any non-bridgehead position within the heterocyclic rings.

By alkylene is meant saturated hydrocarbon (straight chain or branched) wherein a hydrogen atom is removed from each of the terminal carbons. Exemplary of such groups (assuming the designated length encompases the particular example) are methylene, ethylene, propylene, butylene, pentylene, hexylene and heptylene.

By alkenylene is meant a hydrocarbon containing monounsaturation in the form of one double bond wherein said hydrocarbon is straight chain or branched and wherein a hydrogen atom is removed from each of the terminal carbons. Exemplary of such groups (assuming the designated length encompasses the particular example) are ethenylene (or vinylene), propenylene, butenylene, pentenylene, hexenylene and heptenylene.

By alkynylene is meant a hydrocarbon containing di-unsaturation in the form of one triple bond wherein said hydrocarbon is straight chain or branched and wherein a hydrogen atom is removed from each of the terminal carbons. Exemplary of such groups (assuming the designated length encompasses the particular example) are ethynylene, propynylene, butynylene, pentynylene, hexynylene and heptynylene.

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopenyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and oxtoxy.

As used herein, the term mono-N- or di-N,N-$(C_1-C_x)$ alkyl . . . refers to the $(C_1-CV_x)$ alkyl moiety taken independently when it is di-N,N-$(C_1-C_x)$alkyl . . . (x refers to integers and is taken independently when two $(C_1-C_x)$alkyl groups are present, e.g., methylenethylamino is within the scope of di-N,N-$(C_1-C_x)$alkyl).

Unless otherwise stated the "M" moieties defined above are optionally substituted (e.g., the mere listing of a substituent such as $R^1$ in a subgenus or dependent claim does not mean that M is always substituted with the $R^1$ moiety unless it is stated that the M moiety is substituted with $R^1$). However, in the compounds of Formula 1, when K is a bond and M is phenyl, said phenyl group is substituted with one to three substituents. Additionally, in the compounds of Formula 1, when Ar or $Ar^1$ is a fully saturated five to eight membered ring, said ring is unsubstituted.

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular sterochemical or geometric configuration, giving rise to stereoisomers such as enantiomers and diastereomers; and configurational isomers such as cis and trans olefins and cis and trans substitution patterns on saturated alicyclic rings. All such isomers and mixtures thereof are included in this invention.

Hydrates and solvates of the compounds of this invention are also included.

DTT means dithiothreitol. DMSO means dimethyl sulfoxide. EDTA means ethylenediamine tetraacetic acid.

The methods and compounds of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

This invention is also directed to methods for treating glaucoma in a mammal suffering from glaucoma comprising administering to said mammal a therapeutically effective amount of a compound of claim 1, a prodrug thereof or a pharmaceutically acceptable salt of said compound or said prodrug.

This invention is also directed to methods for treating ocular hypertension in a mammal suffering from ocular hypertension comprising administering to said mammal a therapeutically effective amount of a compound of claim 1, a prodrug thereof or a pharmaceutically acceptable salt of said compound or said prodrug.

DETAILED DESCRIPTION OF THE INVENTION

In general the compounds of this invention can be made by processes which include processes known in the chemical arts, particularly in light of the description contained herein. Certain processes for the manufacture of the compounds of this invention are provided as further features of the invention and are illustrated by the following reaction schemes. Other processes are described in the experimental section.

Some substituents (e.g., carboxyl) may best be prepared through conversion of another functional group (e.g., carboxyl substituents may be prepared through conversion of, e.g., hydroxyl or carboxaldehyde) at a point later in the synthetic sequence.

Compounds of Formula 1 wherein B is nitrogen may be prepared using methods described in SCHEMES 1–5. These methods include (a) sequential alkylation of a sulfonamide or amide with two appropriate alkylating agents, generally alkyl halides or alkyl sulfonates; (b) alkylation of a sulfonamide or amide with an alkyl halide or alkyl sulfonate; or (c) reductive amination of an aldehyde followed by reaction with an acylating agent such as an acyl chloride, a chloroformate, an isocyanate or a chlorocarbonyl amide; or a sulfonylating agent such as a sulfonyl chloride. When performing sequential alkylation, one of the alkylating agents will contain a Q–Z portion, where the Z portion is suitably protected if necessary, and the other alkylating agent will contain a K–M portion, where any functional groups requiring protection are suitably protected. The order of the alkylation, i.e., whether the alkylating agent containing the Q–Z portion is added first or second, will depend upon the reactivity of the electrophilic side chain. When performing a reductive amination, the Q–Z portion may be attached to either the amine reagent or the aldehyde reagent depending upon the ease of preparation of the reagent and the reactivity of the reagents in the reductive amination reaction. The reductive amination is followed by acylation or sulfonylation with an appropriate acylating agent or sulfonyl chloride and, if desired the product is hydrolysed. The starting materials, including amines, aldehydes and alkylating agents, are prepared using methods well known to those skilled in the art. Certain preferred methods for their preparation are described herein.

For example, compounds of Formula 1 where B is N are prepared of the methods set forth in SCHEMES 1 and 2 below. In general, the sequences involve sequential alkylation of an appropriate sulfonamide of Formula 1 or amide of Formula 1 with two appropriate alkyl halides or alkyl sulfonates. SCHEMES 1 and 2 differ only in the order of addition of the two alkylating agents. The alkylation order is typically chosen depending on the reactivity of the electrophilic side-chain. It is generally preferable to react the less reactive electrophilic side chain first. This reduces the amount of dialkylation which occurs in that first alkylation step, thereby resulting in a greater yield of monoalkylated material to be carried on to the next alkylation. In SCHEMES 1 and 2, one of the alkylating agents contains a carboxylic acid or a carboxylic acid isostere, suitably protected with an appropriate protecting group, if necessary. Further, in SCHEMES 1 and 2, the carboxylic acid precursor of Formula 3 is a carboxylic acid ester where R is a suitable carboxylic acid protecting group. Generally, the protecting group is either a straight chain lower alkyl, preferably methyl or ethyl, or a tert-butyl or phenyl group. Other acid isosteres can be employed by appropriately modifying SCHEMES 1 and 2 of methods well known to those skilled in the art (e.g., see SCHEME 6 which sets forth the preparation of a tetrazole). Typical alkylating agents are primary, secondary, benzylic or allylic halides and sulfonates and are preferably alkyl bromides or alkyl iodides.

The Formula 1 sulfonamide or amide is converted to its anion with a strong base such as sodium hydride, lithium diisopropylamide, lithium bis(trimethylsilyl)amide, potassium (bis(trimethylsilyl)amide, potassium tert-butoxide, etc. in an aprotic solvent such as dimethylformamide, tetrahydrofuran or N,N-dimethylformamide/benzene at a temperature of about –78° C. to about 100° C. The resulting anion is alkylated with an appropriate alkyl halide of Formula 2 or 3 or an appropriate alkyl sulfonate of Formula 2 or 3, wherein X' is the halide or sulfonate portion of the alkylating agent, at a temperature of about 0° C. to about 100° C. to yield the corresponding mono-alkylated compound of Formula 4 or 5. In some cases, varying amounts of a side-product resulting from dialkylation of the amide or sulfonamide are obtained and can be removed using chromatographic techniques, preferably by flash chromatography (W. C. Still, M. Kahn, A. Mitra, J. Org. Chem. 43, 2923, 1978). After the first alkylation is complete, the compound of Formula 4 or 5 is converted to an anion using a suitable base such as sodium hydride, lithium bis(trimethylsilyl)amide, lithium diisopropylamide, potassium bis(trimethylsilyl)amide, potassium tert-butoxide, or potassium carbonate in an aprotic solvent such as N,N-dimethylformamide, tetrahydrofuran, N,N-dimethylformamide/benzene, or acetone at a temperature of about –78° C. to about 100° C. Alkylation of the anion with an appropriate second alkyl halide of 0Formula 3 or 2 or alkyl sulfonate of Formula 3 or 2 provides the corresponding dialkylated compound of Formula 6. When R is methyl or ethyl, the ester of Formula 6 is hydrolyzed to the corresponding carboxylic acid of Formula 1 with a dilute aqueous basic solution. This hydrolysis is preferably carried out using sodium or potassium hydroxide in aqueous methanol or ethanol, lithium hydroxide in aqueous alcoholic solvent or aqueous tetrahydrofuran at a temperature of about 0° C. to about 80° C. Alternatively, the hydrolysis may be carried out by using methods well known to those skilled in the art, for example, methods described in "Protecting Groups in Organic Synthesis," Second Edition, T. W. Greene and P. G. M. Wuts, John Wiley and Sons, Inc., 1991.

SCHEME 1

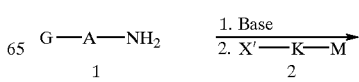

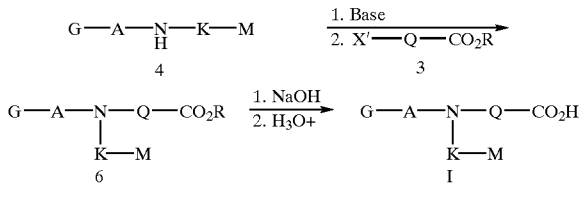

SCHEME 2

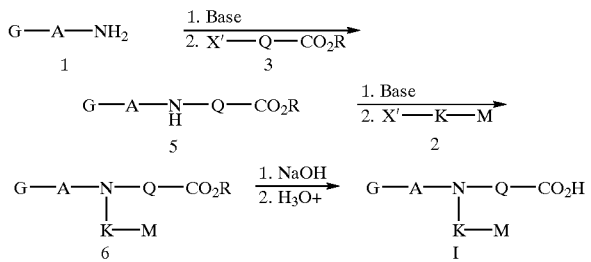

Compounds of Formula 1 wherein B is N are also prepared from amines as set forth in SCHEMES 3–4. Generally, the appropriate amine starting materials of Formulas 9 and 10 are commercially obtained or can be prepared using methods well known to those skilled in the art (see "The Chemistry of Amino, Nitroso and Nitro Compounds and their Derivatives," Ed. S. Patai, J. Wiley, N.Y., 1982). For example, the amine starting materials are prepared from the corresponding nitriles of Formulas 7 or 8. Said nitriles are available from commercial sources or can be prepared using methods well known to those skilled in the art (see Rappaport, "The Chemistry of the Cyano Group," Interscience, N.Y., 1970 or Patai and Rappaport, "The Chemistry of Functional Groups," pt. 2, Wiley, N.Y., 1983). The nitrile of Formula 7 or 8 is reduced with a reducing agent such as borane-tetrahydrofuran complex, borane-methyl sulfide complex or lithium aluminum hydride in an aprotic solvent such as tetrahydrofuran or diethyl ether at a temperature of about −78° C. to about 60° C. Alternatively, the nitrile is hydrogenated under a hydrogen atmosphere typically at 0 to 50 psi in the presence of Raney nickel or a platinum or palladium catalyst in a protic solvent such as methanol or ethanol at a temperature of about 0° C. to about 50° C. It may be desired to add an equivalent of an acid, such as hydrogen chloride, to accomplish the reduction. The amine of Formula 9 or 10 thus obtained is converted to the sulfonamide of Formula 11 or 12 by sulfonylation with a sulfonyl chloride or said amine is converted to an amide of Formula 11 or 12 by acylation with an appropriate acyl chloride. Both the sulfonylation reactions and the acylation reactions are generally carried out in the presence of a weak base such as triethylamine, pyridine, or 4-methylmorpholine in an aprotic solvent such as methylene chloride or diethyl ether at a temperature of about −20° C. to about 50° C. Alternatively, coupling of amines of Formulas 9 or 10 with carboxylic acids are conveniently carried out in an inert solvent such as dichloromethane or N,N-dimethylformamide by a coupling reagent such as 1-(3-dimethylaminopropyl)-3-ethylcarbodiimide hydrochloride (EDC) or 1,3-dicyclohexylcarbodiimide (DCC) in the presence of 1-hydroxybenzotriazole hydrate (HOBT) to generate compounds of Formulas 11 or 12. Where the amine is present as the hydrochloride or other salt, it is preferable to add one equivalent of a suitable base such as triethylamine to the reaction mixture. Alternatively, the coupling can be effected with a coupling reagent such as benzotriazol-1-yloxy-tris(dimethylamino)-phosphonium hexafluorophosphate (BOP) in an inert solvent such as methanol. Such coupling reactions are generally conducted at temperatures of about −30° C. to about 80° C., preferably 0° C. to about 25° C. For a discussion of other conditions used for coupling peptides see Houben-Weyl, Vol. XV, part II, E. Wunsch, Ed., George Theime Verlag, 1974, Stuttgart. Alkylation and if desired, deprotection, of the Formula 11 or 12 compound as described in SCHEMES 1 and 2 affords the corresponding acid Formula 13 and 14 compound. The compounds of Formulas 11 and 12 are alkylated in a manner analogous to the alkylation of the compounds of Formulas 1, 4 and 5 of SCHEMES 1 and 2 hereinabove. The alkylated products are deprotected, if necessary, to afford the compounds of Formulas 13 and 14.

The amines of Formulas 9 and 10 are also prepared via reduction of an appropriate amide of Formulas 15 and 16. This reduction is achieved using reagents such as a borane-tetrahydrofuran complex, a borane-methyl sulfide complex, or diisobutylaluminum hydride in an aprotic solvent such as tetrahydrofuran or diethyl ether at a temperature of about −78° C. to about 60° C.

The amines of Formulas 9 and 10 are also obtained from the corresponding nitro precursors by reduction of the nitro group using reducing reagents such as zinc/HCl, hydrogenation in the presence of Raney nickel, palladium, or platinum catalysts, and other reagents as described by P. N. Rylander in "Hydrogenation Methods," Academic Press, New York, 1985.

SCHEME 3

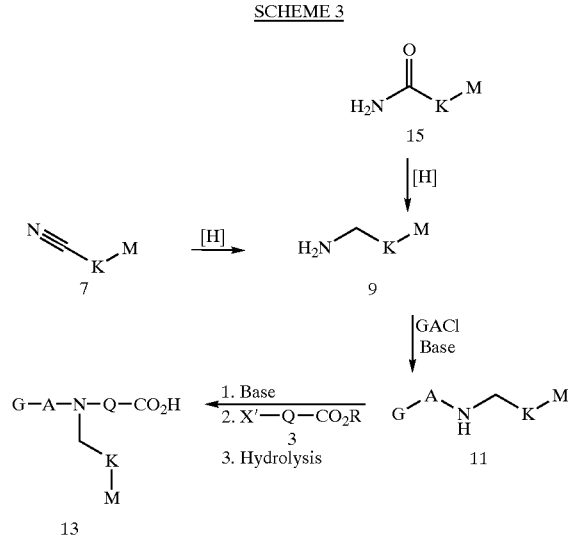

SCHEME 4

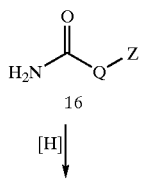

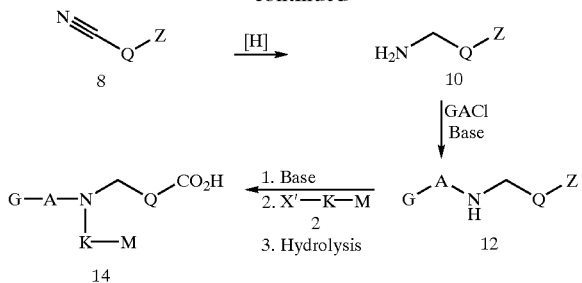

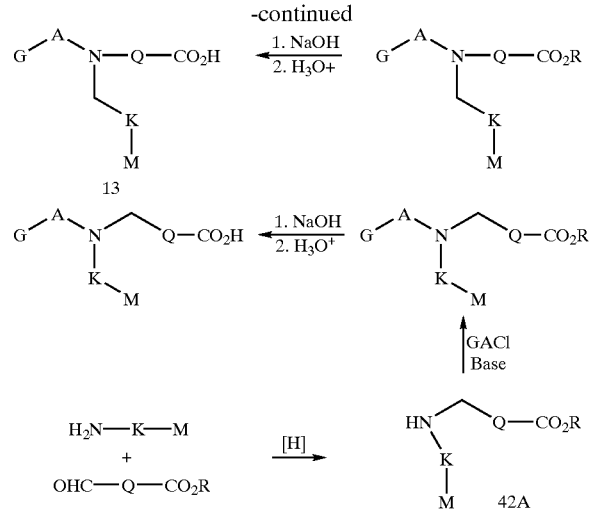

Amines and alkylating agents useful for the above syntheses are described and prepared as set forth in the section entitled PREPARATIONS below.

Alternatively, the compounds of Formula 1 wherein B is N are prepared by reductive amination of an aldehyde containing the appropriate suitably protected acidic functionality with an amine. This sequence is set forth in SCHEME 5. Alternatively, the amine may contain the appropriate suitably protected acidic functionality.

The reductive amination is typically carried out at a pH of between 6 and 8, using a reducing agent such as sodium cyanoborohydride or sodium triacetoxyborohydride. The reaction is normally performed in a protic solvent such as methanol or ethanol at temperatures of about −78° C. to about 40° C. (e.g., see A. Abdel-Magid, C. Maryanoff, K. Carson, Tetrahedron Lett. 39, 31, 5595–5598, 1990.) The reductive amination reaction may also be carried out using titanium isopropoxide and sodium cyanoborohydride (R. J. Mattson et al, J. Org. Chem. 1990, 55, 2552–4) or by preformation of the imine under dehydrating conditions followed by reduction. The resulting amine of Formulas 42 and 42A, is transformed to the desired amide or sulfonamide by coupling with an acid chloride, sulfonyl chloride, or carboxylic acid as set forth in SCHEMES 3 and 4. If desired, the amine intermediate of Formulas 42 or 42A may be converted to a urethane by treatment with a chloroformate or to a tetrasubstituted urea by treatment with a chlorocarbonyl amide. These reactions are performed in the presence of a weak base such as triethylamine, pyridine, or 4-methylmorpholine in an aprotic solvent such as methylene chloride or diethyl ether at a temperature of about −20° C. to about 50° C. Conversion of the amine of Formulas 42 or 42A to a trisubstituted urea is accomplished by treatment with an isocyanate in an aprotic solvent such as methylene chloride or diethyl ether at temperatures ranging between −20° C. and 50° C. (for example, see SCHEME 5A). In cases where the amine is present as the hydrochloride salt, it is preferable to add an equivalent of a suitable base such as triethylamine to the reaction. If desired, hydrolysis of the resulting sulfonamide or amide provides the corresponding acid.

SCHEME 5

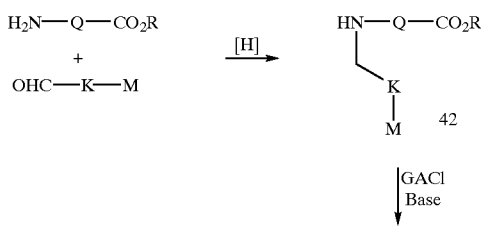

SCHEME 5A

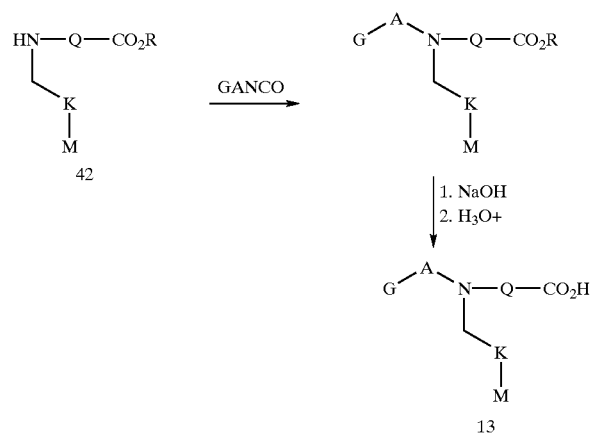

Aldehydes useful in the above SCHEME 5 are described and prepared as set forth in the section entitled PREPARATIONS below.

Compounds of Formula 1 where B is N and Z is tetrazolyl are prepared as set forth in SCHEME 6. A sulfonamide or amide of Formula 4 is alkylated with the appropriate alkyl halide or sulfonate (wherein X' is halide or sulfonate), preferably a primary, secondary, benzylic, or allylic alkyl bromide, iodide, or sulfonate, which contains a nitrile to provide a nitrile of Formula 59. This alkylation is achieved by treatment of the sulfonamide or amide of Formula 59 with a base such as sodium hydride, lithium bis(trimethylsilyl)amide, potassium bis(trimethylsilyl)amide, potassium tert-butoxide, or potassium carbonate in an aprotic solvent such as dimethylformamide, dimethylformamide/benzene, or acetone followed by reaction of the resulting anion with a suitable alkylating agent. Alkylation occurs at a temperature of about −78° C. to about 100° C. A preferred method for converting the resulting nitrile of Formula 59 to the tetrazole of Formula 60 is treatment of the alkylated nitrile with dibutyltin oxide and trimethylsilylazide, in refluxing toluene (S. J. Wittenberger and B. G. Donner, J. Org. Chem. 1993, 58, 4139–4141, 1993). For a review of alternative preparations of tetrazoles see R. N. Butler, Tetrazoles, In Comprehensive Heterocyclic Chemistry; Potts, K. T. Ed.; Pergamon Press: Oxford, 1984, Vol. 5, pp 791–838.

SCHEME 6

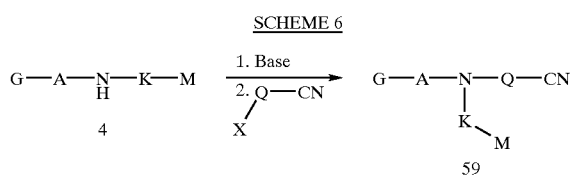

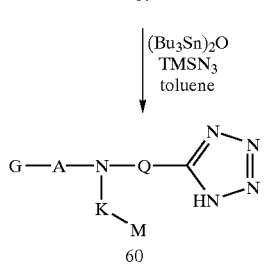

Alternatively, certain compounds of Formula I wherein B in N are prepared as set forth in SCHEME 7. Thus, esters of Formula 46 are prepared using the procedures described above in SCHEMES 1 and 2. Subsequent Heck coupling of this intermediate to an arylhalide (preferably an aryl bromide or aryl iodide), an aryl triflate, or a ring system which contains a vinyl bromide, iodide, or triflate is accomplished with a palladium catalyst, such as palladium acetate or tetrakis(triphenylphosphine)palladium(0) in the presence of a trialkylamine, such as triethylamine. In some cases, an additive such as a triarylphosphine or triarylarsene may be added to the reaction. The reaction is typically performed in an aprotic solvent such as dimethylformamide or acetonitrile at a temperature of about 0° C. to about 150° C. (see R. F. Heck in Comp. Org. Syn., Vol. 4, Ch. 4.3, p. 833 or Daves and Hallberg, Chem. Rev. 1989, 89, 1433). If desired, the compound of Formula 47 can be hydrolyzed to the corresponding acid. Alternatively, the compound of Formula 47 can be hydrogenated and, if desired, further hydrolyzed to the corresponding acid of Formula 49. Hydrogenation is preferably achieved under a hydrogen atmosphere typically at 0 to 50 psi in the presence of a palladium or platinum catalyst in an alcoholic solvent such as ethanol or methanol at a temperature of about 0° C. to about 50° C. In cases where M represents a partially saturated ring system, hydrogenation will generate a fully saturated ring system.

SCHEME 7

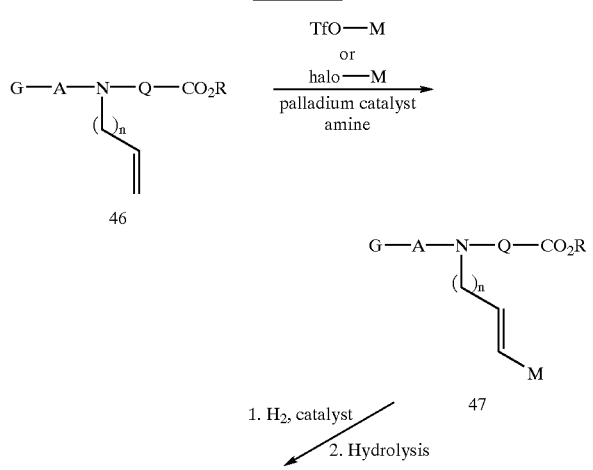

Alternatively, certain compounds of Formula I wherein B is N are prepared as described in SCHEME 8. Compounds of Formula 51 are prepared as described in SCHEMES 1 and 2 by alkylation of compounds of Formula 5 with an electrophile of Formula 2 which contains the appropriate functionality on the M ring. At least one of the substituents on the M ring must be suitable for subsequent conversion to an aldehyde. For example, electrophiles of Formula 2 containing a protected alcohol on the M ring may be alkylated and then deprotected and oxidized to the aldehyde, using reagents well known to those skilled in the art, to generate compounds of Formula 51. An alternative method is to alkylate with an electrophile of Formula 2 where M contains a vinyl group. After alkylation, oxidative cleavage of the double bond provides the desired aldehyde of Formula 51. The oxidative cleavage is accomplished by transforming the double bond to the 1,2-diol with catalytic osmium tetroxide and N-methylmorpholine followed by oxidative cleavage to the aldehyde using sodium periodate. Alternatively, oxidative cleavage via ozonolysis followed by reduction using reagents such as methyl sulfide, triphenylphosphine, zinc/acetic acid, or thiourea, generates the desired aldehyde of Formula 51. Addition of LMetal where LMetal is any organometallic reagent such as an organolithium or a Grignard reagent in an aprotic solvent such as diethyl ether or tetrahydrofuran at a temperature of about −78° C. to about 80° C., followed by hydrolysis of the ester as described above, provides the desired compound of Formula 50.

SCHEME 8

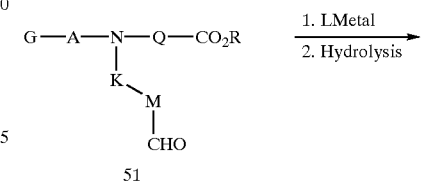

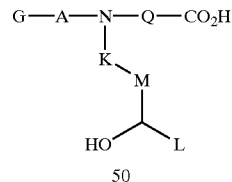

Alternatively, certain compounds of Formula I wherein B is N are prepared as described in SCHEME 9. The appropriate sulfonamide or amide of Formula 5 is alkylated using the conditions described in SCHEMES 1 and 2. The alkylating agent is an electrophile which contains an aromatic bromide or iodide or a ring system which contains a vinyl bromide or iodide (Ar$^1$) to provide compounds of Formula 53. Suzuki-type coupling of the compound of Formula 53 thus obtained with an aryl boronic acid (Ar$^2$) provides Formula 53a compounds. For a review of the Suzuki reaction see A. R. Martin and Y. Yang in Acta Chem. Scand. 1993, 47, 221. The coupling reaction is achieved using about two equivalents of a base, such as sodium carbonate, potassium carbonate, sodium hydroxide, thallium hydroxide or potassium phosphate, in the presence of a palladium catalyst, such as tetrakis(triphenylphosphine)palladium(0), palladium acetate, palladium chloride, tris (dibenzylideneacetone)dipalladium(0) or [1,4-bis (diphenylphosphine)butane]palladium(0). The reaction may be run in an aqueous alcoholic solvent such as methanol or ethanol; or in other aqueous solvents such as aqueous tetrahydrofuran, aqueous acetone, aqueous glycol dimethyl ether, or aqueous benzene at temperatures ranging from about 0° C. to about 120° C. When $Ar^1$ is a partially saturated ring, reduction to the ring to provide a saturated ring system may, if desired, be performed at this point. This transformation is achieved by hydrogenating the partially saturated ring in the presence of a catalyst such as palladium or platinum in an alcoholic solvent (ethanol or methanol) and/or ethyl acetate. Ester hydrolysis of compounds of Formulas 53 or 53a, if desired, provides the corresponding acid. The resulting acids may contain functional groups on either of the ring systems ($Ar^1$ or $Ar^2$) which can be modified using methods well known to those skilled in the art. Examples of such modifications are shown in SCHEME 10.

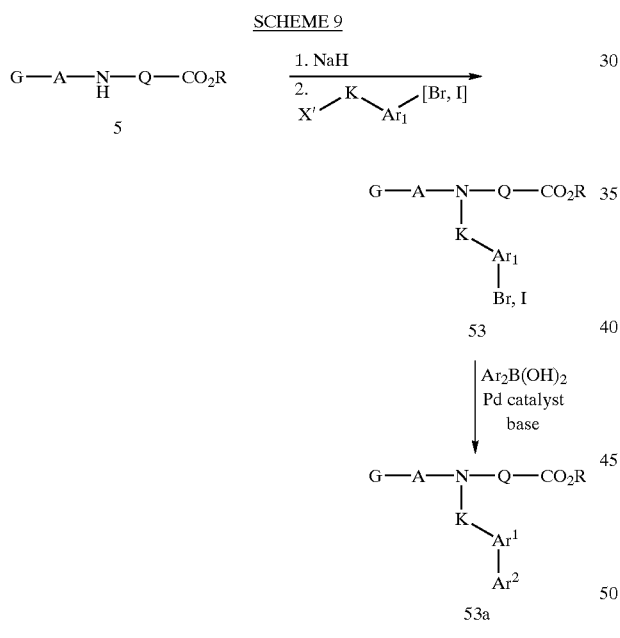

SCHEME 9

Compounds of Formula 54 which contain an aldehyde functional group are prepared using methods described in SCHEMES 8 and 9. Of SCHEME 10, treatment of a compound of Formula 54 with an appropriate organometallic reagent (LMetal), such as an organolithium or Grignard reagent, in an aprotic solvent such as diethyl ether or tetrahydrofuran at a temperature of about −78° C. to about 80° C., followed by hydrolysis of the ester, provides compounds of Formula 56. Alternatively, reduction of the aldehyde followed by hydrolysis provides Formula 55 compounds.

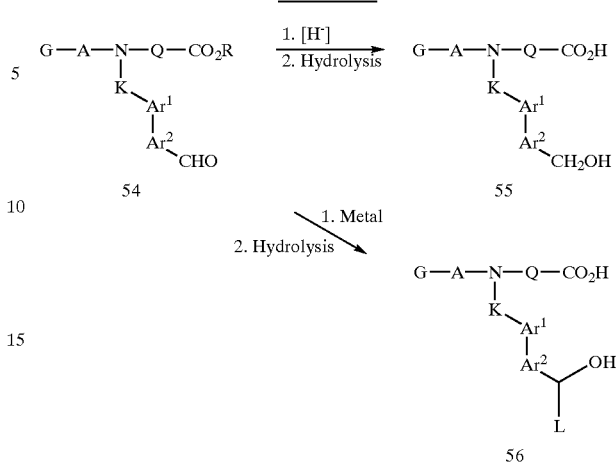

SCHEME 10

Alternatively, certain compounds of Formula I wherein B is N are prepared as described in SCHEME 11. The starting alcohols of Formula 58 are prepared of methods well known to persons skilled in the art, for example, by using methods described in SCHEMES 1 and 2. It will be recognized by a person of ordinary skill in the art that protecting groups may be required in the synthesis of certain of these alcohols. Intermediate 58 is coupled with a variety of aryl alcohols (M is as defined above) using Mitsonobu coupling conditions (for a review see O. Mitsonobu, Synthesis, 1, 1981). Typically the coupling is achieved by addition of a coupling agent such as triphenylphosphine and diethyl azodicarboxylate or diisopropyl azodicarboxylate in an inert solvent such as methylene chloride or tetrahydrofuran at a temperature of about 0° C. to about 80° C. If desired, subsequent hydrolysis yields the corresponding acid.

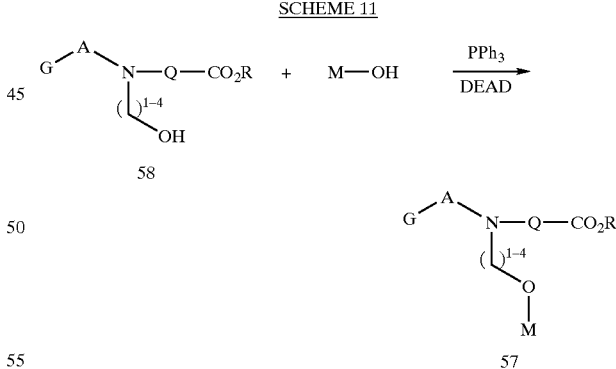

SCHEME 11

Alternatively, certain compounds of Formula I wherein B is N are prepared as described in SCHEME 12. A compound of Formula 102 is added to a compound of Formula 105 (wherein X is as defined above for the compound of Formula I) in the presence of a Lewis acid such as titanium tetrachloride or a mineral acid such as hydrochloric acid. If desired the ester of Formula 106 can be converted to the corresponding acid by hydrolysis or deprotection.

SCHEME 12

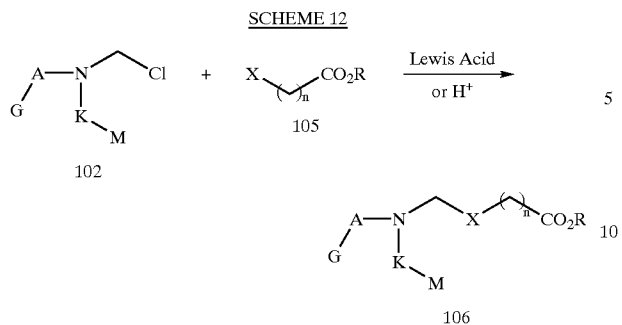

Alternatively, certain compounds of Formula I wherein B is N are prepared as described in SCHEME 13. Chloromethyl compounds of Formula 104 are treated with the appropriate substituted aromatic ring system, M, such as 4-ethoxybenzene or thiophene in the presence of a Lewis acid such as titanium tetrachloride or a mineral acid such as hydrochloric acid in an aprotic solvent such as chloroform at a temperature of about 0° C. to about 80° C. to yield compounds of Formula 107 which may subsequently be hydrolyzed or deprotected as described above to yield the corresponding carboxylic acids. Alternatively, chloromethyl compounds of Formula 104 can be treated with a Lewis acid such as titanium tetrachloride and an appropriately substituted vinyl silane in an aprotic solvent such as methylene chloride at a temperature of about −50° C. to about 50° C. to give compounds of Formula 108. If desired, the compounds of Formula 108 may subsequently be hydrolyzed or deprotected as described above to yield the corresponding acid. If desired, reduction of the double bond can be accomplished using conditions described in SCHEME 7.

SCHEME 13

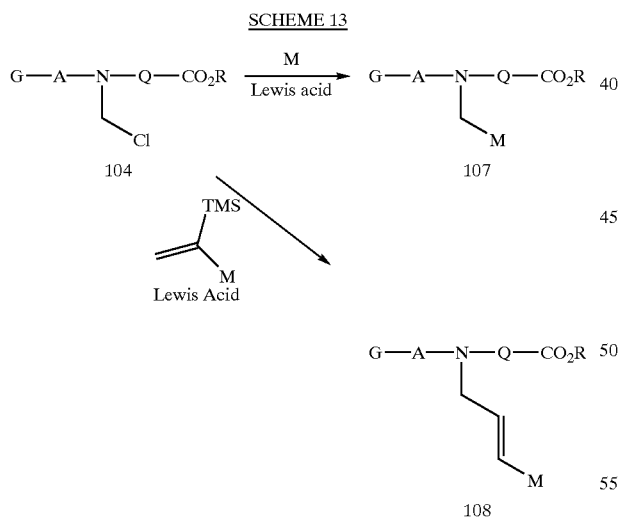

Alternatively, certain compounds of Formula I wherein B is N are prepared as described in SCHEME 14. Chloromethyl compounds of Formula 104 are treated with a Lewis acid such as titanium tetrachloride and an appropriately substituted allyl silane in an aprotic solvent such as chloroform at a temperature of about 0° C. to about 80° C. to give compounds of Formula 109 which may subsequently be hydrolyzed or deprotected as described above to afford the corresponding carboxylic acids.

SCHEME 14

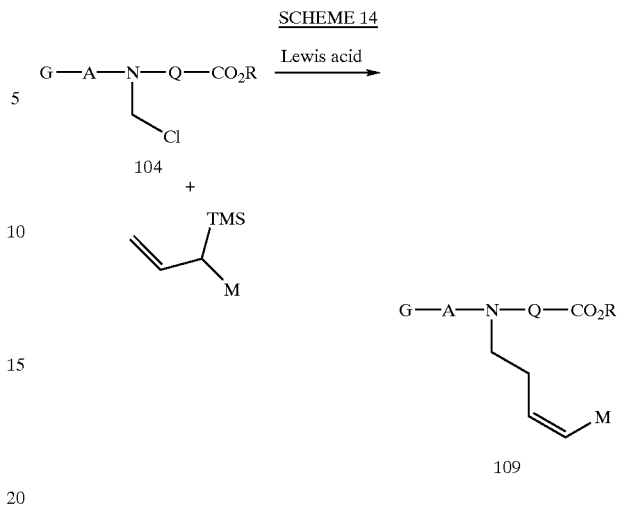

Alternatively, certain compounds of Formula I wherein B is N are prepared as described in SCHEME 15. Chloromethyl compounds of Formula 104 are treated with a sulfinic acid of Formula 111 in the presence of a base such as triethylamine in an aprotic solvent such as chloroform at a temperature of about −30° C. to about 50° C. to give compounds of Formula 112 which may subsequently be hydrolyzed or deprotected as described above to yield the corresponding acid.

SCHEME 15

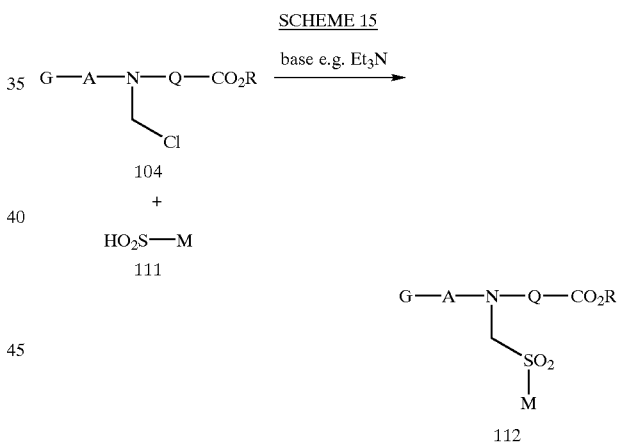

Formula I compounds wherein B is C(H) and Q, G, M and K are as described above in the Summary of the Invention can be prepared of SCHEME 16. Formula 113 beta-ketoesters are alkylated sequentially with Formula 114 compounds to form Formula 115 compounds followed by alkylation with Formula 116 compounds to give Formula 117 compounds (J. Med. Chem. 26, 1993, p335–41). Alkylations can be carried out in a suitable solvent such as DMF, THF, ether, or benzene using an appropriate base such as sodium hydride, LDA, or potassium carbonate at a temperature of about −78° C. to about 80° C. The resulting Formula 117 disubstituted keto esters are hydrolyzed and decarboxylated to give the corresponding Formula 118 compound by using an aqueous base such as sodium hydroxide to hydrolyze the ester, followed by an acidic quench such as with aqueous hydrochloric acid to effect decarboxylation.

SCHEME 16

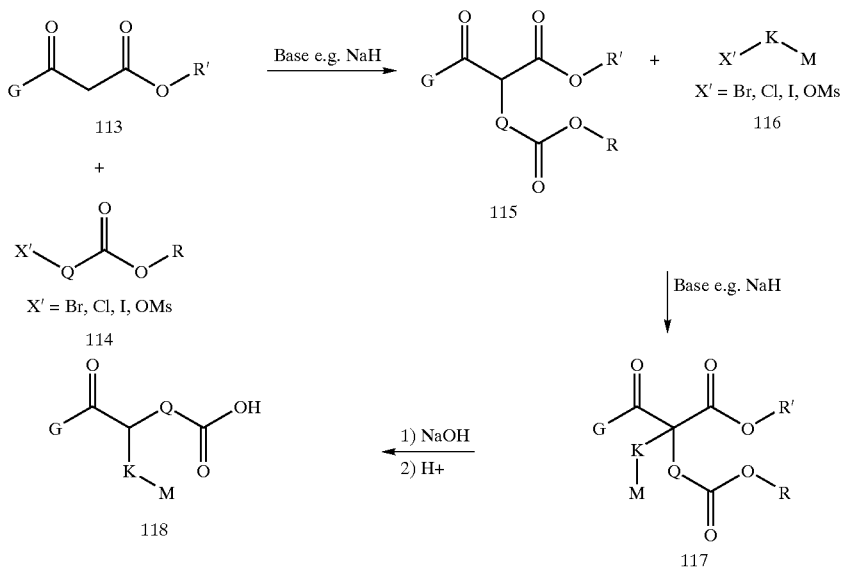

Alternatively, Formula I compounds wherein B is C(H) and G, Q, M and K are as described above in the Summary of the Invention may be prepared of SCHEME 17. Sequential alkylation of a malonate derivative of Formula 119 provides the Formula 121 dialkylated compound. Deprotection of the ester group by treatment with a strong acid such as TFA or HCl in ethanol at a temperature of about −20° C. to about 50° C. leads to the Formula 122 decarboxylated product. Conversion of the acid to an acid chloride using thionyl chloride or oxalyl chloride in an aprotic solvent at a temperature of about −78° C. to about 50° C. or to a Weinreb amide using methoxymethyl amine in the presence of a suitable coupling agent such as DCC or DEC in an aprotic solvent at a temperature of about −30° C. to about 50° C. provides Formula 123 compounds. Formula 123 compounds are suitable substrates for addition of various organometallic species, e.g., Grignard reagents and organo-cadmium reagents which, after hydrolysis of the terminal ester, provide the keto-acid compounds of Formula 118.

Alternatively, Formula 118 compounds can be prepared using methods described previously in Schemes 7–11 where one or both of the side chains are further functionalized after attachment to the alkanoyl fragment.

SCHEME 17

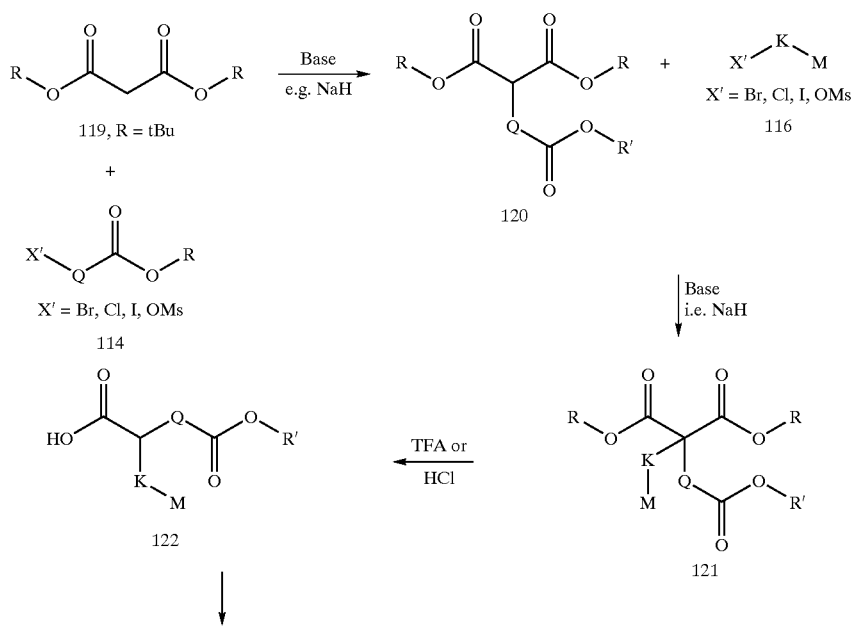

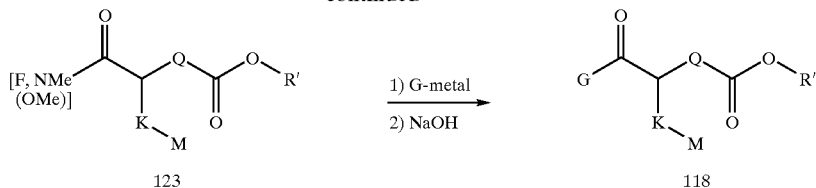

PREPARATIONS

Amines, Amides and Sulfonamides

Certain amides or sulfonamides described by Formulas 21, 22, and 23 wherein W and Z are as described above in the Summary of the Invention and X and M are aromatic or saturated ring systems are prepared as set forth in SCHEME 18. Alkynyl amides or sulfonamides of Formulas 25, 26 and 27 are prepared by coupling an alkynyl sulfonamide or alkynyl amide of Formula 24 to an aromatic or vinyl halide, preferably an aromatic or vinyl bromide or iodide wherein W and Z are as defined above and where X and M represent an aromatic ring or a partially saturated ring system. The coupling is typically accomplished in the presence of copper iodide, a palladium catalyst, such as palladium chloride, bis(triphenylphosphine)palladium dichloride, or tetrakis(triphenylphosphine)palladium(0), and an amine such as triethylamine, diisopropylamine, or butylamine in an aprotic solvent such as acetonitrile at a temperature of about 0° C. to about 100° C. The alkynes of Formulas 25, 26 and 27 are converted to the corresponding alkanes of Formulas 21, 22 or 23 via hydrogenation in the presence of a palladium or platinum catalyst in a solvent such as methanol, ethanol, and/or ethyl acetate at a temperature of about 0° C. to about 50° C. In the case where M represents a partially saturated ring system, hydrogenation will convert M to a fully saturated ring system. Alternatively, the alkynes are converted to cis-alkenes using the Lindlar catalyst (Pd—CaCO$_3$—PbO) or other suitable catalyst. Alkylation and deprotection as described in SCHEMES 1 and 2 affords the corresponding compounds of Formula I.

SCHEME 18

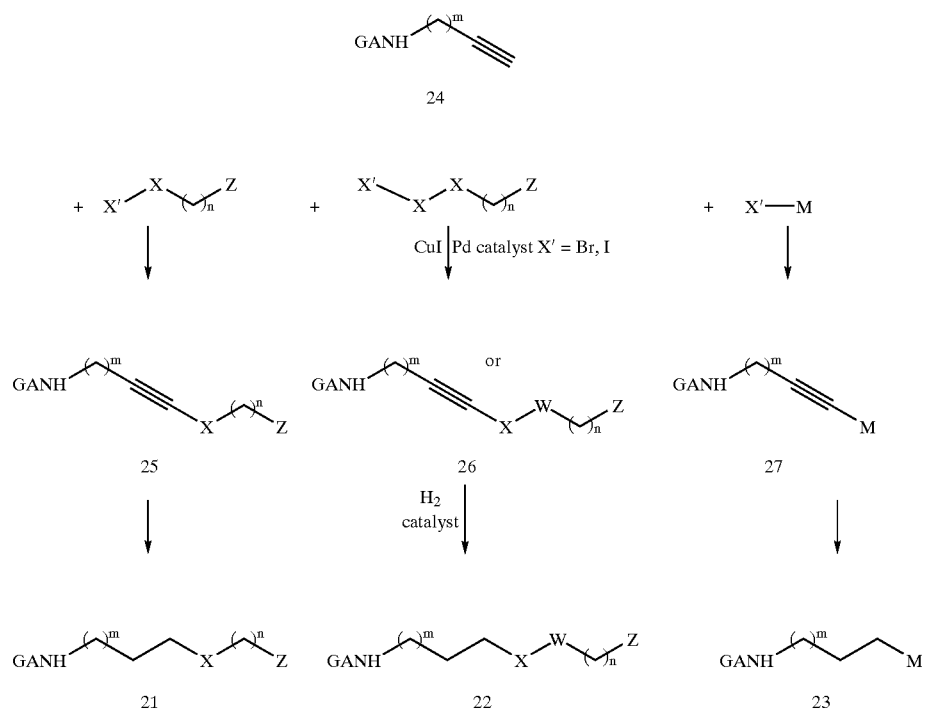

SCHEME 19

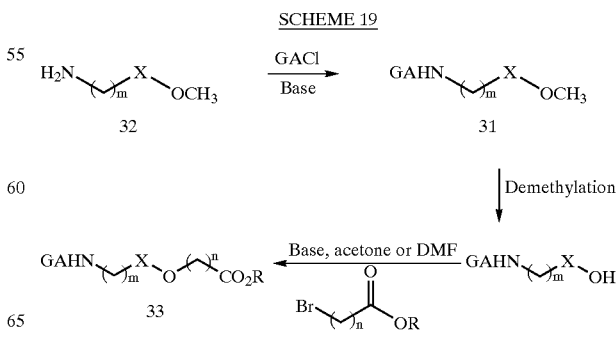

Compounds of Formula 33 are prepared from a suitable amine of Formula 32 (e.g., methoxyarylalkylamine). Amines of Formula 32 are commercially available or are prepared by methods well known to those skilled in the art (for example, see SCHEME 4). Amines of Formula 32 are converted to sulfonamides or amides of Formula 31 using methods, for example, described in SCHEME 3 and 4. The resulting aromatic methyl ether of Formula 31 is deprotected with reagents such as boron tribromide, pyridinium hydrochloride, hydrogen bromide/acetic acid, or other reagents as described in Protecting Groups in Organic Synthesis, Second Edition, T. W. Greene and P. G. M. Wuts, John Wiley and Sons, Inc., 1991. Alkylation with a bromoalkylester using a mild base such as potassium carbonate in an aprotic solvent such as dimethylformamide or acetone at a temperature of about 0° C. to about 100° C. generates an amide or sulfonamide of Formula 33.

SCHEME 20

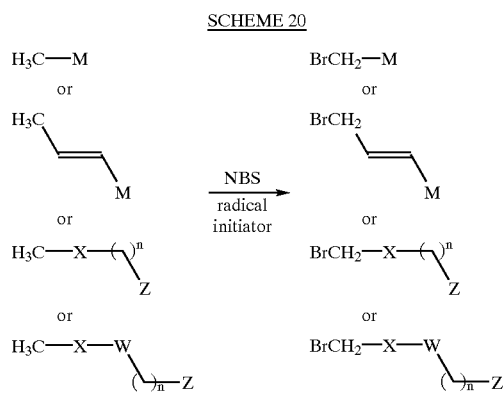

ALKYLATING AGENTS

Numerous methods exist for the synthesis of the desired alkylating agents used in the above procedures and are known to those skilled in the art (see "The Chemistry of the Carbon-Halogen Bond," Ed. S. Patai, J. Wiley, New York, 1973 and "The Chemistry of Halides, Pseudo-Halides, and Azides," Eds. S. Patai and Z. Rappaport, J. Wiley, New York, 1983). Some examples are shown in SCHEMES 20–24. As shown in Formula 20, tolyl or allylic substrates can be converted via halogenation to benzylic or allylic bromides wherein M, X, W and Z are as described above in the Summary of the Invention. This reaction is typically performed with N-bromosuccinimide (NBS) in the presence of a radical initiator such as 2,2'-azobisisobutyronitrile (AIBN) or a peroxide, preferably benzoyl peroxide. Alternatively, the reaction can be initiated with light. The reaction is performed in an inert solvent such as carbon tetrachloride or chloroform at a temperature of about 50° C. to about 100° C.

SCHEME 21

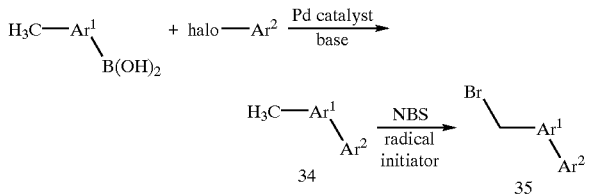

SCHEME 21 sets forth the synthesis of alkylating agents useful for preparing compounds of Formula I where M represents a biaryl or aryl cyclic group. Suzuki-type coupling of an aryl iodide or bromide or a ring system containing a vinyl bromide or iodide ($Ar^2$) with a methylaryl boronic acid ($Ar^1$) using the conditions described in SCHEME 9 provides compounds of Formula 34. Where a vinyl bromide or iodide is used, compounds of Formula 34 can be reduced to generate a fully saturated ring. The reduction is accomplished by hydrogenation in the presence of palladium or platinum catalysts typically in protic solvents such as methanol or ethanol; or in tetrahydrofuran or ethyl acetate. Halogenation of the methyl group using reagents and conditions as described in SCHEME 20 provides alkylating agents of Formula 35.

SCHEME 22

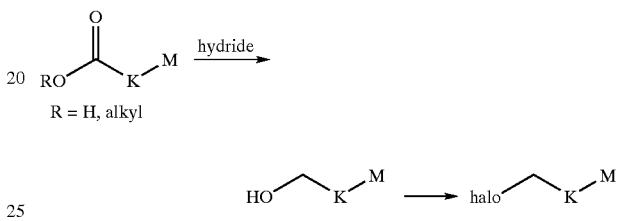

Another common method for accessing alkyl halides is by halogenation of an alcohol or an alcohol derivative. Alcohols are obtained from commercial sources or can be prepared using methods well known to those skilled in the art. For example, SCHEME 22 sets forth the reduction of a carboxylic acid or ester to the corresponding alcohol using reagents such as, but not limited to, sodium borohydride, lithium aluminum hydride, borane-tetrahydrofuran complex, borane-methyl sulfide complex, etc. The corresponding alkyl chlorides are typically prepared from the alcohols with reagents such as hydrogen chloride, thionyl chloride, phosphorous pentachloride, phosphorous oxychloride, or triphenylphosphine/carbon tetrachloride. For the preparation of alkyl bromides, the alcohol is commonly treated with reagents such as hydrogen bromide, phosphorous tribromide, triphenylphosphine/bromine, or carbonyldiimidazole/allyl bromide (Kamijo, T., Harada, H., Iizuka, K. Chem. Pharm. Bull. 1983, 38, 4189). To access alkyl iodides, an appropriate alcohol is typically reacted with reagents such as triphenylphosphine/iodine/imidazole or hydrogen iodide. Alternatively, alkyl chlorides can be converted to the more reactive alkyl bromides or alkyl iodides by reaction with an inorganic salt such as sodium bromide, lithium bromide, sodium iodide, or potassium iodide in solvents such as acetone or methyl ethyl ketone. Alkyl sulfonates can also be used as electrophiles or can be converted to alkyl halides. Alkyl sulfonates are prepared from the corresponding alcohol using a mild base such as triethylamine or pyridine and a sulfonyl chloride in an inert solvent such as methylene chloride or diethyl ether. If desired, conversion to the halide is accomplished by treating the alkyl sulfonate with an inorganic halide (sodium iodide, sodium bromide, potassium iodide, potassium bromide, lithium chloride, lithium bromide, etc) or a tetrabutylammonium halide.

SCHEME 23

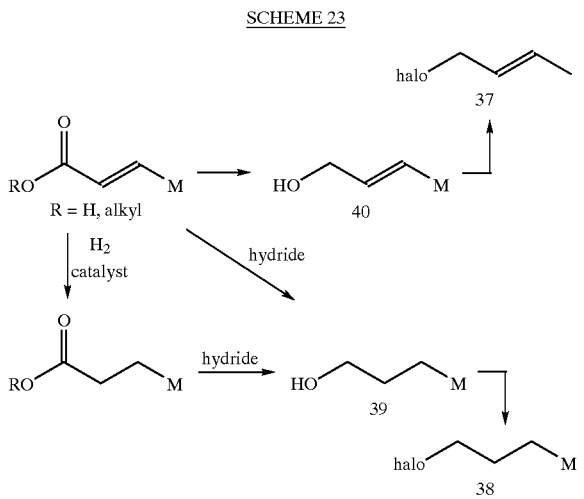

Cinnamic acids or esters are commonly available from commercial sources and can be converted to alkylating agents of Formulas 37 or 38 as follows (see SCHEME 23). The cinnamic acid or ester derivatives are reduced by hydrogenation in the presence of palladium or platinum catalysts typically in protic solvents (e.g., methanol or ethanol), tetrahydrofuran, or ethyl acetate. Reduction and conversion to the alkyl halide or sulfonate as described in SCHEME 22 provides the compounds of Formula 38. Where appropriate, the cinnamic acids or esters are converted directly to the alcohols of Formula 39 by treat those cinnamic acids or esters with reagents such as lithium aluminum hydride in an inert solvent such as tetrahydrofuran and diethyl ether. Alternatively, the cinnamic acid or ester can be reduced to an allylic alcohol of Formula 40 using reagents such as lithium aluminum hydride/aluminum chloride, diisobutylaluminum hydride or lithium borohydride. Conversion to the allylic halide or sulfonate as described in SCHEME 22 provides the compounds of Formula 37.

SCHEME 24

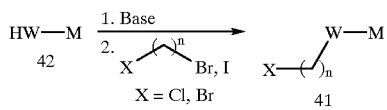

The preparation of alkylating agents of Formula 41 wherein W and M are as described above in the Summary of the Invention is set forth in SCHEME 24. Compounds of Formula 42 can be alkylated with a variety of bases. The choice of base is dependent on the nature of W and M. Some preferred bases include, but are not limited to, sodium hydroxide, sodium hydride, lithium diisopropylamide, lithium bis(trimethylsilyl)amide, potassium bis (trimethylsilyl)amide and potassium tert-butoxide. Treatment of the resulting anion with one of a variety of dialkylhalides generates the desired alkylating agents of Formula 41. For the preparation of compounds where W is an oxygen and M is an aromatic ring, it is preferred to form the alkoxide anion with sodium hydroxide followed by addition of a dihaloalkane, e.g. dibromoalkane. The reaction is normally performed in water at about 75° C. to about 125° C.

SCHEME 25

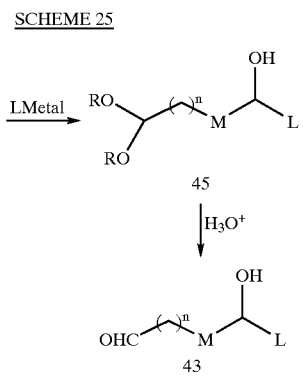

Aldehydes useful for the method described in SCHEME 5 are available from commercial sources or can be prepared from available intermediates using methods well known to those skilled in the art (for a general reference see "The Chemistry of the Carbonyl Group," Ed. S. Patai, Interscience, New York (1966–70)). SCHEME 25 demonstrates an exemplary method used to prepare Formula 43 hydroxy aldehydes where M in SCHEME 5 contains a hydroxy substituted alkyl group. Treatment of a dialdehyde, where one of the aldehydes is protected as an acetal of Formula 44 wherein the OR groups are conventional substituents used in an acetal protecting group, with an organometallic reagent (LMetal), preferably an organolithium or Grignard reagent, in an inert solvent such as tetrahydrofuran or diethyl ether, provides compounds of Formula 45. Subsequent acetal hydrolysis under mildly acidic conditions, e.g., dilute hydrogen chloride, Amberlyst-15® resin, silica gel, or other reagents as described in "Protecting Groups in Organic Synthesis," Second Edition, T. W. Greene and P. G. M. Wuts, John Wiley and Sons, Inc., 1991 provides the desired hydroxy aldehydes of Formula 43.

Aldehydes useful for the method described in SCHEME 5 may be prepared using the methods described in SCHEMES 26–28. For example, as shown in SCHEME 26, an aryl boronic acid which contains an aldehyde can be coupled to an aryl bromide, aryl iodide, or a ring system which contains a vinyl bromide or iodide using the Suzuki protocol described for SCHEME 9 to provide aldehydes of Formula 60.

SCHEME 27 describes the preparation of aldehydes of Formula 62 which contain a suitably protected acid moiety and can be used for the preparation of compounds of Formula 42A described in SCHEME 5. Selective reduction of nitriles (see SCHEMES 3–4 for preparations) of Formula 61 provides aldehydes of Formula 62. A preferred method for this reduction involves heating the nitrile with aluminum-nickel (Raney) alloy in the presence of an acid such as formic acid. Aldehydes of Formula 64 useful for the preparation of compounds of Formula 42 (SCHEME 5) may be prepared from starting nitriles of Formula 63 by treatment with a variety of reducing agents such as diisobutylaluminum hydride, tin (II) chloride/hydrogen chloride, or lithium triethoxyalanate.

A method for the preparation of proprionaldehydes of Formula 65 is described in SCHEME 28 and follows the procedures described by Kang (J. Org. Chem. 1996, 61, 2604) and by Jeffery (J. Chem. Soc. Chem. Commun. 1984, 19, 1287). An aryl iodide or bromide is coupled to allyl alcohol in the presence of a suitable palladium catalyst, preferably palladium acetate. The reaction is performed in a suitable polar, aprotic solvent, preferably dimethylformamide, with addition of a base, such as sodium bicarbonate, and an ammonium salt, such as tetrabutylammonium chloride and provides proprionaldehydes of Formula 65.

SCHEME 26

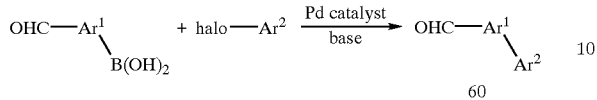

60

SCHEME 27

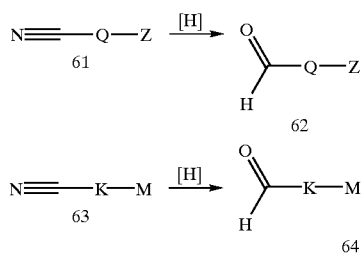

SCHEME 28

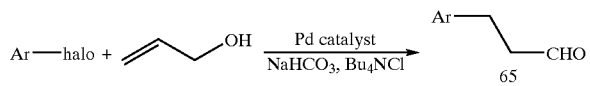

CHLOROMETHYL INTERMEDIATES

Intermediate chloromethyl compounds can be prepared as described in SCHEMES 29 and 30. In general, the appropriate Formula 66 or 68 sulfonamide or carboxamide is treated with a formaldehyde equivalent such as paraformaldehyde in an inert organic solvent such as methylene chloride or chloroform with a suitable catalyst such as HCl, zinc chloride or trimethylsilyl chloride at temperatures ranging from about 0° C. to about 60° C. to give the Formula 67 and 69 chloromethyl derivatives, respectively.

SCHEME 29

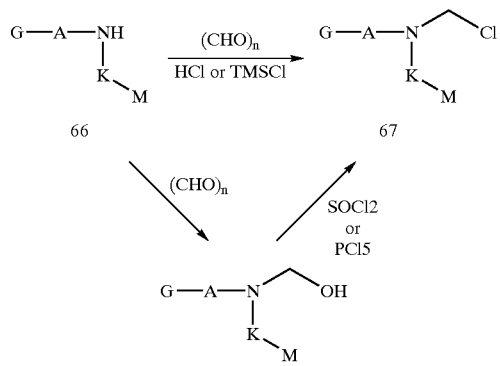

SCHEME 30

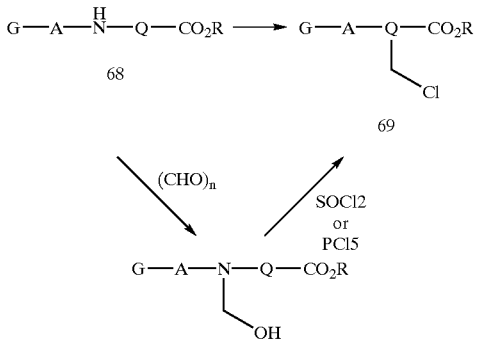

SCHEME 31 sets forth the synthesis of biaryl aldehydes of Formula 60. Fluorobenzonitriles of Formula 70 are heated with a nucleophilic group such as a pyrrazole or imidazole in a suitable solvent, preferably DMF to effect displacement of the fluoro group yielding intermediates of Formula 71. The desired biaryl aldehydes of Formula 60 are obtained by reduction of the nitrile via hydrogenation with Raney alloy in formic acid, or by reduction with a hydride source such as diisobutylaluminum hydride.

It will be recognized that the compounds of Formula I of this invention can exist in radiolabelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^{3}H$, $^{14}C$, $^{32}P$, $^{35}S$, $^{18}F$ and $^{36}Cl$, respectively. Compounds of Formula I of this invention which contain those radioisotopes and/or other radioisotopes of other atoms are within the scope of this invention. Tritiated, i.e., $^{3}H$, and carbon-14, i.e., $^{14}C$, radioisotopes are particularly preferred for their ease of preparation and detectability. Radiolabelled compounds of Formula I of this invention can generally be prepared of methods well known to those skilled in the art. Conveniently, such radiolabelled compounds can be prepared by carrying out the procedures disclosed in the above Schemes and/or in the Examples and Preparations below by substituting a readily available radiolabelled reagent for a non-radiolabelled reagent.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- 17β-ethynyl estradiol) may be used in conjunction with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, flurogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein be reference. Preferred polyphosphonates are geminal dipolyphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431, the disclosure of which is incorporated herein by reference.

Another preferred estrogen agonist/antagonist is 3-(4-(1, 2-diphenyl-but-1-enyl)-phenyl)-acrylic acid, which is disclosed in Wilson et al., Endocrinology, 1997, 138, 3901–3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl) hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795, the disclosure of which is incorporated herein by reference.

Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc.

Other preferred estrogen agonist/antagonists include compounds as described in commonly assigned U.S. Pat. No.

5,552,412, the disclosure of which is incorporated herein by reference. Especially preferred compounds described therein are:

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydro-naphthalene-2-ol;

cis-6-phenyl-5-(4-(2-pyrrolidin-1-yl-ethoxy)-phenyl)-5,6,7,8-tetrahydro-naphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843."

Any prostaglandin, or prostaglandin agonist/antagonist may be used as the second compound in certain aspects of this invention. This includes utilizing two different compounds of Formula I of this invention. Those skilled in the art will recognize that IGF-1, sodium fluoride, parathyroid hormone (PTH), active fragments of parathyroid hormone, growth hormone or growth hormone secretagogues may also be used. The following paragraphs described exemplary second compounds of this invention in greater detail.

Any prostaglandin may be used as the second compound in certain aspects of this invention. The term prostaglandin refers to compounds which are analogs of the natural prostaglandins $PGD_1$, $PGD_2$, $PGE_2$, $PGE_1$ and $PGF_2$ which are useful in the treatment of osteoporosis. These compounds bind to the prostaglandins receptors. Such binding is readily determined by those skilled in the art of standard assays (e.g., An S. et al., Cloning and Expression of the $EP_2$ Subtype of Human Receptors for Prostaglandin $E_2$. Biochemical and Biophysical Research Communications, 1993, 197(1):263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197, the disclosures of each of which are incorporated herein by reference.

Norrdin et al., *The Role of Prostaglandins in Bone in Vivo*, Prostaglandins Leukotriene Essential Fatty Acids 41, 139–150, 1990 is a review of bone anabolic prostaglandins.

Any prostaglandin agonist/antagonist may be used as the second compound in certain aspects of this invention. The term prostaglandin agonist/antagonist refers to compounds which bind to prostaglandin receptors (eg., An S. et al., Cloning and Expression of the $EP_2$ Subtype of Human Receptors for Prostaglandin $E_2$, Biochemical and Biophysical Research Communications, 1993, 197(1):263–270) and mimic the action of prostaglandin in vivo (e.g., stimulate bone formation and increase bone mass). Such actions are readily determined by those skilled in the art of standard assays. Eriksen E. F. et al., *Bone Histomorphometry*, Raven Press, New York, 1994, pages 1–74; Grier S. J. et al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd. London 1994, pages 1–296. A variety of these compounds are described and reference below. However, other prostaglandin agonists/antagonists will be known to those skilled in the art. Exemplary prostaglandin agonists/antagonists are disclosed as follows.

Commonly assigned U.S. Pat. No. 3,932,389, the disclosure of which is incorporated herein by reference, discloses 2-descarboxy-2-(tetrazol-5-yl)-11-desoxy-15-substituted-omega-pentanorprostaglandins useful for bone formation activity.

Commonly assigned U.S. Pat. No. 4,018,892, the disclosure of which is incorporated herein by reference, discloses 16-aryl-13,14-dihydro-$PGE_2$ p-biphenyl esters useful for bone formation activity.

Commonly assigned U.S. Pat. No. 4,219,483, the disclosure of which is incorporated herein by reference, discloses 2,3,6-substituted-4-pyrones useful for bone formation activity.

Commonly assigned U.S. Pat. No. 4,132,847, the disclosure of which is incorporated herein by reference, discloses 2,3,6-substituted-4-pyrones useful for bone formation activity.

U.S. Pat. No. 4,000,309, the disclosure of which is incorporated herein by reference, discloses 16-aryl-13,14-dihydro-$PGE_2$ p-biphenyl esters useful for bone formation activity.

U.S. Pat. No. 3,982,016, the disclosure of which is incorporated herein by reference, discloses 16-aryl-13,14-dihydro-$PGE_2$ p-biphenyl esters useful for bone formation activity.

U.S. Pat. No. 4,621,100, the disclosure of which is incorporated herein by reference, discloses substituted cyclopentanes useful for bone formation activity.

U.S. Pat. No. 5,216,183, the disclosure of which is incorporated herein by reference, discloses cyclopentanones useful for bone formation activity.

Sodium fluoride may be used as the second compound in certain aspects of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478, the disclosure of which is incorporated herein by reference. The activity of sodium fluoride is readily determined by those skilled in the art of biological protocols (e.g., see Eriksen E. F. et al., *Bone Histomorphometry*, Raven Press, New York, 1994, pages 1–74; Grier S. J. et al., The Use of Dual-Energy X-Ray Absorptiometry in Animals, Inv. Radiol., 1996, 31(1):50–62; Wahner H. W. and Fogelman I., The Evaluation of Osteoporosis: Duel Energy X-Ray Absorptiometry in Clinical Practice., Martin Dunitz Ltd., London 1994, pages 1–296).

Bone morphogenetic protein may be used as the second compound of this invention (e.g., see Ono, et al., Promotion of the Osteogenetic Activity of Recombinant Human Bone Morphogenetic Protein by Prostaglandin E1, Bone, 1996, 19(6), 581–588).

Any parathyroid hormone (PTH) may be used as the second compound in certain aspects of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays (e.g., see Eriksen E. F. et al., Bone Histomorphometry, Raven Press, New York, 1994, pages 1–74; Grier S. J. et al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below. However, other parathyroid hormone will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int. 1:162–170.

Any growth hormone or growth hormone secretagogue may be used as the second compound in certain aspects of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art.

In particular a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-667.

Other preferred growth hormone secretagogues include
2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt;
2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl) isobutyramide;
2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and
2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

Some of the preparation methods useful for the preparation of the compounds described herein may require protection of remote functionality (e.g., primary amino, secondary amine, carbonyl in Formula I precursors). The need for such protection will vary depending on the nature of the remote functionality and the conditions of the preparation methods. The need for such protection is readily determined by one skilled in the art. The use of such protection/deprotection method is also within the skill in the art. For a general description of protecting groups and their use, see T. W. Greene, Protective Groups in Organic Synthesis, John Wiley & Sons, New York, 1991.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

It will be recognized by persons of ordinary skill in the art that some of the compounds of this invention have at least one asymmetric carbon atom and therefore are enantiomers or diastereomers. Diasteromeric mixtures can be separated into their individual diastereomers on the basis of their physicochemical differences by methods known per se as, for example, by chromatography and/or fractional crystallization. Enantiomers can be separated by converting the enantiomeric mixture into a diastereometric mixture by reaction with an appropriate optically active compound (e.g., alcohol), separating the diastereomers and converting (e.g., hydrolyzing, including both chemical hydrolysis methods and microbial lipase hydrolysis methods, e.g., enzyme catalyzed hydrolysis) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Many of the compounds of this invention, including the compounds of Formula I, the anti-resorptive agents, bone anabolic agents, prostaglandin agonists/antagonists, parathyroid hormones, growth hormones and growth hormone secretagogues, are acidic and they form a salt with a pharmaceutically acceptable cation. Some of the compounds of this invention, including the compounds of Formula I, the anti-resorptive agents, bone anabolic agents, prostaglandin agonists/antagonists, parathyroid hormones, growth hormones and growth hormone secretagogues, are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention, including the compounds of Formula I, the anti-resorptive agents, bone anabolic agents, prostaglandin agonists/antagonists, parathyroid hormones, growth hormones and growth hormone secretagogues, form hydrates or solvates they are also within the scope of the invention.

In addition, all prodrugs of the compounds of this invention, including the compounds of Formula I, the anti-resorptive agents, bone anabolic agents, prostaglandin agonists/antagonists; parathyroid hormones, growth hormones and growth hormone secretagogues, are within the scope of this invention.

The compounds of this invention, prodrugs thereof and pharmaceutically acceptable salts of said compounds and prodrugs are all adapted to therapeutic use as agents that stimulate bone formation and increase bone mass in a vertebrates, e.g., mammals, and particularly humans. Since bone formation is closely related to the development of osteoporosis and bone related disorders, these compounds, prodrugs thereof and pharmaceutically acceptable salts of said compounds and said prodrugs, by virtue of their action on bone, prevent, arrest and/or regress osteoporosis.

The utility of the compounds of the present invention as medical agents in the treatment of conditions which present with low bone mass (e.g. osteoporosis) in a vertebrates, e.g., mammals (e.g. humans, particularly the female) is demonstrated by the activity of the compounds of this invention in conventional assays, including an in vivo assay, a receptor binding assay, a cyclic AMP assay and a fracture healing assay (all of which are described below). The in vivo assay (with appropriate modifications within the skill in the art) may be used to determine the activity of other anabolic agents as well as the prostaglandin agonists of this invention. The estrogen agonist/antagonist protocol may be used to determine the activity of estrogen agonist/antagonists in particular and also other anti-resorptive agents (with appropriate modifications within the skill in the art). The combination and sequential treatment protocol described below is useful for demonstrating the utility of the combinations of the anabolic agents (e.g., the compounds of this invention) and anti-resorptive agents (e.g., estrogen agonists/antagonists) described herein. Such assays also provide a means whereby the activities of the compounds of this invention (or the other anabolic agents and anti-resorptive agents described herein) can be compared to each other and with the activities of other known compounds. The results of these comparisons are useful for determining dosage levels in a vertebrates, e.g., mammals, including humans, for the treatment of such diseases.

Anabolic Agent In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with prostaglandin agonists at different doses (such a 1, 3, or 10 mg/kg/day) for 30 days. In the castrated rats, treatment is started at the next day after surgery (for the purpose of preventing bone loss) or at the time bone loss has already occured (for the purpose of restoring bone mass). during the study, all rats are allowed free access to water and a pelleted commercial diet (Teklad Rodent Diet #8064, Harlan Tekland, Madison, Wis.) containing 1.46% calcium, 0.99% phosphorus and 4.96 IU/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy X-ray absorptionmetry (CXA, QDR 1000/W, Hologic Inc., Waltham, Mass.) equipped with "Regional High Resolution Scan" software (Hologic Inc., Waltham, Mass.). The scan field size is 5.80×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analysis

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using a Reichert-Jung Polycut S microtome. The 4 $\mu$m sections are stained with modified Masson's Trichrome stain while the 10 $\mu$sections remained unstained. One 4 $\mu$m and one 10 $\mu$m sections from each rat are used for cancellous bone histomorphometry.

Cross sections of tibial shaft at 10 $\mu$m thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn. T.N.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I) Measurements and calculation related to trabecular bone volume and structure: (1) Total metaphyseal area (TV, $mm^2$): metaphyseal area between 1.2 and 3.6 mm distal to the growth plate-epiphyseal junction. (2) Trabecular bone area (BV, $mm^2$): total area of trabeculae within TV. (3) Trabecular bone perimeter (BS, mm): the length of total perimeter of trabeculae. (4) Trabecular bone volume (BV/TV, %): BT/TV×100. (5) Trabecular bone number (TBN, #/mm): 1.199/2×BT/TV. (6) Trabecular bone thickness (TBT, $\mu$m): (2000/1.199)×(BV/BS). (7) Trabecular bone separation (TBS, $\mu$m); (2000'1.199)×(TV-BV).

II) Measurement and calculations related to bone resorption: (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and calculations related to bone formation and turnover. (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, $\mu$m): average distance between two calcein labels. (4) Percent mineralizing perimeter (PMS, %): (SS/2+DS)/BS×100. (5) Mineral apposition rate (MAR, $\mu$m/day): ILW/label interval. (6) Bone formation rate/surface ref. (BFR/BS, $\mu m^2/d/\mu m$): (SLS/2+DLS)×MAR/BS (7) Bone turnover rate (BTR, %/y): (SLS/2+DLS)×MAR/BV×MAR/BV×100.

Cortical bone Histomorphometry

A Bioquant OS/2 histomorphometry system (R&M Biometrics, Inc. Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area—marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter×100], mineral apposition rate (interlabeled width/intervals); and bone formation rate [mineral apposition rate×[(single labeled perimeter/2+double labeled perimeter)/total perimeter] are calculated.

Statics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave., Berkeley, Calif. 94704-1014) are used to compare the differences between groups.

Determination of cAMP Elevation in 293-S cell Lines Stably Overexpressing Recombinant Human $EP_2$ and $EP_4$ Receptors cDNAs representing the complete open reading frames of the human $EP_2$ and $EP_4$ receptors are generated by reverse transcriptase polymerase chain reaction using oligonucleotide primers based on published sequences (1,2) and RNA from primary human kidney cells ($EP_2$) or primary human lung cells ($EP_4$) as templates. cDNAs are cloned into the multiple cloning site of pcDNA2 (Invitrogen Corporation, 3985B Serrento Valley Blvd. Sand Diego, Calif. 92121) and used to transfect 293-S human embryonic kidney cells via calcium phosphate co-precipitation. G418-resistant colonies are expanded and tested for specific [$^3$H]PGE$_2$ binding. Transfectants demonstrating high levels of specific [$^3$H] PGE$_2$ binding are further characterized by Scatchard analysis to determine Bmax and Kds for PGE$_2$. The lines selected for compound screening have approximately 338,400 receptors per cell and a Kd=12 nM for PGE$_2$ (EP$_2$), and approximately 256,400 receptors per cell and a Kd=2.9 nM for PGE$_2$ (EP$_4$). Constituitive expression of both receptors in parental 293-S cells is negligible. Cells are maintained in RPMI supplemented with fetal bovine serum (10% final) and G418 (700 ug/ml final).

cAMP responses in the 293-S/EP$_2$ and 293-S/EP$_4$ lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37° C., 5% CO$_2$, 95% relative humdity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000 X g for 5 minutes, and cleared lysates are transferred to fresh tubes. cAMP concentrations are determined using a commercially available cAMP radioimmunoassay kit RIA (NEK-033, DuPont/NEN Research Products, 549 Albany St., Boston, Mass. 02118) after diluted cleared lysates 1:10 in cAMP RIA assay buffer (included in kit). Typically, one treats cells with 6–8 concentrations of the compound to be tested in 1 log increments. EC50 calculations are performed on a calculator using linear regression analysis on the linear portion of the dose response curves.

REFERENCES

1. Regan, J. W. Bailey, T. J. Pepperi, D. J. Pierce, K. L. Bogardus, A. M. Donelo, J. E. Fairbairn, C. E. Kedzie, K. M. Woodward, D. F. and Gil, D. W. 1994 Cloning of a Novel Human Prostaglandin Receptor with Characteristics of the Pharmaclogically Defined EP$_2$ Subtype, Mol. Pharmacology 46:213–220.
2. Bastien, L., Sawyer, N., Grygorczyk, R., Metters, K., and Adam, M. 1994 Cloning, Functional Expression, and Characterization and of the Human Prostaglandin E2 Receptor EP2 Subtype, J. Biol. Chem. Vol 269, 16:11873–11877.

Assay for Binding to Prostaglandin E$_2$ Receptors

Membrane Preparation

All operations are performed at 4° C. Transfected cells expressing prostaglandin E$_2$ type 1 receptors (EP$_1$), type 2 (EP$_2$), type 3 (EP$_3$) or type 4 (EP$_4$) receptors are harvested and suspended to 2 million cells per ml in Buffer A [50 mM Tris-HCl (pH 7.4), 10 mM MgCl$_2$, 1 mM EDTA, 1 mM Pefabloc peptide, (Boehringer Mannheim Corp. Indianapolis, Ind.), 10 uM Phosporamidon peptide, (Sigma, St. Louis, Mo.), 1 uM pepstatin A peptide, (Sigma, St. Lous, Mo.), 10 uM elastatinal peptide, (Sigma, Mo.), 100 uM antipain peptide, (Sigma, St. Louis, Mo.)]. The cells are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000 ×g for 30 minutes. Pelleted membranes are resuspended to 3–10 mg protein per ml, protein concentration being determined of the method of Bradford [Bradford, M., Anal. Biochem., 72,248 (1976)]. Resuspended membranes are then stored frozen at −80° C. until use.

Binding Assay

Frozen membranes prepared as above are thawed and diluted to 1 mg protein per ml in Buffer A above. One volume of membrane preparation is combined with 0.05 volume test compound or buffer and one volume of 3 nM $^3$H-prostaglandin E$_2$ (#TRK 431, Amersham, Arlington Heights, Ill.) in Buffer A. The mixture (205 $\mu$L total volume) is incubated for 1 hour at 25° C. The membranes are then recovered by filtration through type GF/C glass fiber filters (#1205-401, Wallac, Gaithersburg, Md.) using a Tomtec harvester (Model Mach II/96, Tomtec, Orange, Conn.). The membranes with bound $^3$H-prostaglandin E$_2$ are trapped by the filter, while the buffer and unbound $^3$H-prostaglandin $E_2$ pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of $^3$H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound $^3$H-prostaglandin $E_2$.

The full length $EP_1$ receptor is made as disclosed in Funk et al., Journal of Biological Chemistry, 1993, 268, 26767–26772. The full length $EP_2$ receptor is made as disclosed in Regan et al., Molecular Pharmacology, 1994, 46, 213–220. The full length $EP_3$ receptor is made as disclosed in Regan et al., British Journal of Pharmacology, 1994, 112, 337–385. The full length $EP_4$ receptor is made as disclosed in Bastien, Journal of Biological Chemistry, 1994, 269, 11873–11877. These full length receptors are used to prepare 293S cells expressing the $EP_1$, $EP_2$, $EP_3$ and $EP_4$ receptors.

293S cells expressing either the human $EP_1$, $EP_2$, $EP_3$ or $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from human kidney (for $EP_1$), human lung (for $EP_2$), human lung (for $EP_3$) or human lymphocytes (for $EP_4$) as a source. PCR products are cloned by the TA overhang method into pCR2.1 (Invitrogen, Carlsbad, Calif.) and identity of the cloned receptor is confirmed by DNA sequencing.

293S cells (Mayo, Dept. of Biochemistry, Northwestern Univ.) are transfected with the cloned receptor in pcDNA3 by electroporation. Stable cell lines expressing the receptor are established following selection of transfected cells with G418.

Clonal cell lines expressing the maximal number of receptors are chosen following a whole cell $^3$H-$PGE_2$ binding assay using unlabeled $PGE_2$ as a competitor.

Fracture Healing Assays

Assay for Effects on Fracture Healing after Systemic Administration

Fracture Technique

Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethnanol= 95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft is stripped. Bones from 5–6 rats for each groups are stored in 70% ethanol for histological analysis, and bones from another 5–6 rats for each group are stored in a buffered Ringer's solution (+4° C., pH 7.4) for radiographs and biomechanical testing which is performed.

Histological Analysis

The methods for histologic analysis of fractured bone have been previously published by Mosekilde and Bak (The Effects of Growth Hormone on Fracture Healing in Rats: A Histological Description, Bone, 14:19–27, 1993). Briefly, the fracture side is sawed 8 mm to each side of the fracture line, embedded undecalcified in methymethacrylate, and cut frontals sections on a Reichert-Jung Polycut microtome in 8 μm thick. Masson-Trichrome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis

The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique

Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.; Effects of EHDP on Fracture Healing in Dogs. J Orthop Res 3:499–507; 1985). The wire is pulled through the fracture site to ensure complete anatomical disruption of the bone. Thereafter, local delivery of prostaglandin agonists to the fracture site is achieved by slow release of compound delivered by slow release pellets or by administration of the compounds in a suitable Formulation such as a paste gel solution or suspension for 10, 15, or 20 weeks.

Histological Analysis

The methods for histologic analysis of fractured bone have been previously published by Peter et al. (Peter. C. P.; Cook, W. O.; Nunamaker, D. M.; Provost, M. T.; Seedor, J. G.; Rodan, G. A. Effects of alendornate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, after sacrifice, the fracture side is sawed 3 cm to each side of the fraction line, embedded undecalcified in methymethacrylate, and cut on a Reichert-Jung Polycut microtome in 8 μm thick of frontal sections. Masson-Trichrome stained mid-frontal sections (including both tibia and fibula) are used for visualization of the cellular and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis

The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

ESTROGEN AGONIST/ANTAGONIST PROTOCOL

Estrogen agonist/antagonists are a class of compounds which inhibit bone turnover and prevent estrogen-deficiency induced bone loss. The ovariectomized rat bone loss model has been widely used as a model of postmenopausal bone loss. Using this model, one can test the efficacy of the estrogen agonist/antagonist compounds in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period: All rats are allowed free access to water and a pelleted commercial diet (Agway ProLab 000, Agway County Food, Inc., Syracuse, N.Y.) containing 0.97% calcium, 0.85% phosphorus, and 1.05 IU/g of Vitamin $D_3$.

A group of rats (8 to 10) are sham-operated and treated p.o. with vehicle (10% ethanol and 90% saline, 1 ml/day), while the remaining rats are bilaterally ovariectomized (OVX) and treated with either vehicle (p.o.), 17β-estradiol (Sigma, E-8876, $E_2$, 30 μg/kg, daily subcutaneous injection, or estrogen agonist/anatagonists (such as droloxifene at 5, 10, or 20 mg/kg, daily p.o.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are sacrificed and autopsied. The following endpoints are determined:

Body Weight Gain

Body weight at autopsy minus body weight at surgery.

Uterine Weight and Histology

The uterus is removed from each rat during autopsy, and weighed immediately. Thereafter, the uterus is processed for histologic measurements such as uterine cross-sectional tissue area, stromal thickness, and luminal epithelial thickness.

Total Serum Cholesterol

Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements

The right femur from each rat is removed at autopsy and scanned using dual energy X-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Proximal Tibial Metaphyseal Cancellous Bone Histomorphometric Analysis

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness are cut using a Reichert-Jung Polycut S microtome. One 4 μm and one 10 μm sections from each rat are used for cancellous bone histomorphometry. The 4 μm sections are stained with modified Masson's Trichrome stain while the 10 μm sections remained unstained.

A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region is omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and calculations related to trabecular bone volume and structure:

1. Total metaphyseal area (TV, $mm^2$): metaphyseal area between 1.2 and 3.6 mm distal to the growth plate-epiphyseal junction.

2. Trabecular bone area (BV, mm$^2$): total area of trabeculae within TV.
3. Trabecular bone perimeter (BS, mm): the length of total perimeter of trabeculae.
4. Trabecular bone volume (BV/TV, %): BV/TV×100.
5. Trabecular bone number (TBN, #/mm): 1.199/2×BS/TV.
6. Trabecular bone thickness (TBT, μm): (2000/1.199)× (BV/BS).
7. Trabecular bone separation (TBS, μm): (2000×1.199)× (TV—BV).

II. Measurements and calculations related to bone resorption:
1. Osteoclast number (OCN, #): total number of osteoclast within total metaphyseal area.
2. Osteoclast perimeter (OCP, mm): length of trabecular perimeter covered by osteoclast.
3. Osteoclast number/mm (OCN/mm, #/mm): OCN/BS.
4. Percent osteoclast perimeter (%OCP, %): OCP/BS+ 100.

III. Measurements and calculations related to bone formation and turnover:
1. Single-calcein labeled perimeter (SL, mm): total length of trabecular perimeter labeled with one calcein label.
2. Double-calcein labeled perimeter (DLS, mm): total length of trabecular perimeter labeled with two calcein labels.
3. Inter-labeled with (ILW, μm): average distance between two calcein labels.
4. Percent mineralizing perimeter (PMS, %): (SLS/2+ DLS)/BS×100.
5. Mineral apposition rate (MAR, μm/day): ILW/label interval.
6. Bone formation rate/surface ref. (BFR/BS, μm$^2$/d/μm) :(SLS/2+DLS)×MAR/BS.
7. Bone turnover rate (BTR, %/y): (SLS/2+DLS)×MAR/ BV×100.

Statistics

Statistics are calculated using StatView 4.0 packages (Abacus Concepts, Inc., Berkeley, Calif.). The analysis of variance (ANOVA) test followed by Fisher's PLSD (Stat View, Abacus Concepts Inc. 1918 Bontia Ave., Berkeley, Calif. 94704-1014) is used to compare the differences between groups.

COMBINATION AND SEQUENTIAL TREATMENT PROTOCOL

The following protocols can of course be varied by those skilled in the art. For example, intact male or female rats, sex hormone deficient male (orchidectomy) or female (ovarietomy) rats may be used. In addition, male or female rats at different ages (such as 12 months of age) can be used in the studies. The rats can be either intact or castrated (ovariectomized or orchidetomized), and administered to with anabolic agents such as the compounds of this invention at different doses (such as 1, 3 or 6 mg/kg/day) for a certain period (such as two weeks to two months), and followed by administration of an anti-resorptive agent such as droloxifene at different doses (such as 1, 5, 10 mg/kg/day) for a certain period (such as two weeks to two months), or a combination treatment with both anabolic agent and anti-resorptive agent at different doses for a certain period (such as two weeks to two months). In the castrated rats, treatment can be started on the next day after surgery (for the purpose of preventing bone loss) or at the time bone loss has already occurred (for the purpose of restoring bone mass).

The rats are sacrificed under ketamine anesthesia. The following endpoints are determined:

Femoral bone mineral measurements are performed as described above in the estrogen agonist/antagonist protocol.

Lumbar Vertebral Bone Mineral Measurements

Dual energy X-ray absorptiometry (QDR 1000/W, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1–6) in the anesthetized rats. The rats are anesthetized by injection (i.p.) of 1 ml/kg of a mixture of ketamine/rompun (ratio of 4 to 3), and then placed on a rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1–6).

Proximal tibial metaphyseal cancellous bone histomorphometric analyses are performed as described above for in the estrogen agonist/antagonist protocol.

Measurements and calculations related to trabecular bone volume and structure are performed as described above in the estrogen agonist/antagonist protocol. Further, measurements and calculations related to bone resorption are also performed as described above in the estrogen agonist/antagonist protocol. Still further, measurements and calculations related to bone formation and turnover are performed as described above in the estrogen agonist/antagonist protocol. Further still, the data obtained is analyzed using the statistical manipulations described above in the estrogen agonist/antagonist protocol.

Kidney Regeneration Assay

The role of an prostaglandin agonist in kidney regeneration is investigated by the ability of Prostaglandin E$_2$ (PGE$_2$) or a prostaglandin agonist to induce the expression of Bone Morphogenetic Protein 7 (BMP-7) in wild type 293S cells and in 293S cells transfected with EP$_2$.

Methods 293S and EP2 293S cells are grown in Dulbecco's Modified Egale medium (DMEM, Gibco, BRL; Gaithersburg, Md.). One day prior to treatment with PGE$_2$ or an prostaglandin agonist, cells are plated at a density of 1.5×10$^6$ cells/10 cm dish. Generally about 16 to 24 hours later the cell monolayer is washed once with OptiMEM (Gibco, BRL; Gaithersburg, Md.) followed by the addition of 10 ml OptiMEM/dish in the presence and absence of vehicle (DMSO), PGE$_2$ (10$^{-6}$M) or a prostaglandin agonist (10$^{-6}$M). Cells are harvested and RNA is extracted at 8, 16 and 24 hours. Northern blot analysis of total RNA (20 mg/lane) is carried out by probing the blots with $^{32}$P-labeled BMP-7 probe. The blots are normalized for RNA loading by hybridization with $^{32}$P-labeled 18s ribosomal RNA probe. PGE$_2$ and prostaglandin agonists induce the expression of BMP-7 in the EP$_2$ 293S cells in a time dependent manner. Such induction of expression is generally not observed in the parental cell line. Given the known role of BMP-7 in kidney regeneration and the ability of an prostaglandin agonist to induce BMP-7 expression in 293S kidney cells in a time and receptor specific manner indicates a role for prostaglandin agonist in kidney regeneration.

Administration of the compounds of this invention can be via any method which delivers a compound of this invention systemically and/or locally (e.g., at the site of the bone fracture, osteotomy, or orthopedic surgery). These methods include oral routes, parenteral, intraduodenal routes, etc. Generally, the compounds of this invention are administered orally, but parenteral administration (e.g., intravenous, intramuscular, transdermal, subcutaneous, rectal or intramedulary) may be utilized, for example, where oral administration is inappropriate for the target or where the patient is unable to ingest the drug.

The compounds are used for the treatment and promotion of healing of bone fractures and osteotomies by the local application (e.g., to the sites of bone fractures of osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier or diluent such as bone-wax, demineralized bone powder, polymeric bone cements, bone sealants, etc. Alternatively, local application can be achieved by applying a solution or dispersion of the compound in a suitable carrier or diluent onto the surface of, or incorporating it into solid or semi-solid implants conventionally used in orthopedic surgery, such as dacron-mesh, gel-foam and kiel bone, or prostheses.

The compounds of this invention may also be applied locally to the site of the fracture of osteotomy in a suitable carrier or diluent in combination with one or more of the anabolic agents or bone anti-resorptive agents described above.

Such combinations within the scope of this invention can be co-administered simultaneously or sequentially in any order, or a single pharmaceutical composition comprising a Formula I compound, a prodrug thereof or a pharmaceutical salt of said compound or said prodrug as described above and a second compound as described above in a pharmaceutically acceptable carrier or diluent can be administered.

For example, a bone an anti-resorptive agent can be used in this invention alone or in combination with an anti-resorptive for three months to three years, followed by an anti-resorptive agent alone for three months to three years, with optional repeat of the full treatment cycle. Alternatively, for example, the bone anabolic agent can be used alone or in combination with an anti-resorptive agent for three months to three years, followed by an anti-resorptive agent alone for the remainder of the patient's life. For example, in one preferred mode of administration, a Formula I compound, or a prodrug thereof or a pharmaceutically acceptable salt of said compound or said prodrug as described above may be administered once daily and a second compound as described above (e.g., estrogen agonist/antagonist) may be administered daily in single or multiple doses. Alternatively, for example, in another preferred mode of administration the two compounds may be administered sequentially wherein the Formula I compound, prodrug thereof or pharmaceutically acceptable salt of said compound or said prodrug as described above may be administered once daily for a period of time sufficient to augment bone mass to a level which is above the bone fracture threshold (World Health Organization Study "Assessment of Fracture Risk and its Application to Screening for Postmenopausal Osteoporosis (1994). Report of a World Health Organization Study Group, World Health Organization Technical Series 843") followed by administration of a second compound, as described above (e.g., estrogen agonist/antagonist), daily in single or multiple doses. It is preferred that the first compound as described above is administered once daily in a rapid delivery form such as oral delivery.

In any event, the amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the treatment (e.g., bone mass augmentation) that the physician considers appropriate for the patient. In considering the degree of treatment desired, the physician must balance a variety of factors such as bone mass starting level, age of the patient presence of preexisting disease, as well as presence of other diseases (e.g., cardiovascular disease).

In general an amount of a compound of this invention is used that is sufficient to augment bone mass to a level which is above the bone fracture threshold (as detailed in the World Health Organization Study previously cited herein).

In general an effective dosage for the anabolic agents used in this invention described above is in the range of 0.001 to 100 mg/kg/day, preferably 0.01 to 50 mg/kg/day.

The following paragraphs provide preferred dosage ranges for various anti-resorptive agents.

The amount of the anti-resorptive agent to be used is determined by its activity as a bone loss inhibiting agent. This activity is determined by means of the pharmacokinetics of an individual compound and its minimal versus maximal effective dose in inhibition of bone loss using a protocol such as described above (e.g., Estrogen Agonist/Antagonist Protocol).

In general, an effective dosage for an anti-resorptive agent is about 0.001 mg/kg/day to about 20 mg/kg/day.

In general, an effective dosage for progestins is about 0.1 to 10 mg per day; the preferred dose is about 0.25 to 5 mg per day.

In general, an effective dosage for polyphosphonates is determined by its potency as a bone resorption inhibiting agent of standard assays.

Ranges for the daily administration of some polyphosphonates are about 0.001 mg/kg/day to about 20 mg/kg/day.

In general an effective dosage for the treatment of this invention, for example the bone resorption treatment of this invention, for the estrogen agonists/antagonists of this invention is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for 2-(4-methoxy-phenyl)-3-[4-(2-piperidin-1-yl-ethoxy)-phenoxy]-benzo[b]thiophen-6-ol is 0.001 to 1 mg/kg/day.

In particular, an effective dosage for
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydronaphthalene-2-ol;
cis-6-phenyl-5-(4-(2-pyrrolidin-1-yl-ethoxy)-phenyl)-5,6,7,8-tetrahydronaphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol; or
1-(4'-pyrrolidinolethoxyphenyl)-2-phenyl-6-hydroxy-1,2,3,4-tetrahydroisoquinoline
is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15th Edition (1975).

Pharmaceutical compositions of the invention may contain 0.1%–95% of the compound(s) of this invention, preferably 1%–70%. In any event, the composition or Formulation to be administered will contain a quantity of a compound(s) of this invention in an amount effective to treat the disease/condition of the subject being treated, e.g., a bone disorder.

Since the present invention has an aspect that relates to the augmentation and maintenance of bone mass by treatment with a combination of active ingredients which may be administered separately, the invention also relates to combining separate pharmaceutical compositions in kit form. The kit comprises two separate pharmaceutical compositions: a compound of Formula I a prodrug thereof or a pharmaceutically acceptable salt of said compound or said prodrug and a second compound as described above. The kit comprises container means for containing the separate compositions such as a divided bottle or a divided foil packet, however, the separate compositions may also be contained within a single, undivided container. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day. Also, a daily dose of a Formula I compound, a prodrug thereof or a pharmaceutically acceptable salt of said compound or said prodrug can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient Formulation. The following Formulation examples only are illustrative and are not intended to limit the scope of the present invention.

In the Formulations which follow, "active ingredient" means a compound or compounds of this invention.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet Formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellufose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous Formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

The active ingredient above may also be a combination of agents.

The abbreviations "Me", "Et", "iPr", "Tf", "Bu", "Ph", "EDC" and "Ac", where used herein, define the terms "methyl", "ethyl", "isopropyl", "triflyl", "butyl", "phenyl", "1-(3-dimethylaminopropyl)-3-ethyl-carbodiimide hydrochloride" and "acetyl", respectively.

GENERAL EXPERIMENTAL PROCEDURES

Unless otherwise specified, all reactions were performed under an inert atmosphere such as nitrogen ($N_2$).

NMR spectra were recorded on a Varian XL-300 (Varian Co., Palo Alto, Calif.), a Bruker AM-300 spectrometer (Bruker Co., Billerica, Mass.) or a Varian Unity 400 at about 23° C. at 300 or 400 MHz for proton and 75.4 MHz for carbon nuclei. Chemical shifts are expressed in parts per million downfield from trimethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization (APCI) mass spectra were obtained on a Fisons Platform II Spectrometer. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Column chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatotron® (model 7924T, Harrison Research). Medium pressure chromatography was performed on a Flash 40 Biotage System (Biotage Inc, Dyax Corp., Charlottesville, Va.). Unless otherwise specified, reagents were used as obtained from commercial sources. Dimethylformamide, 2-propanol, acetonitrile, methanol, tetrahydrofuran, and dichloromethane, when used as reaction solvents, were the anhydrous grade supplied by Aldrich Chemical Company (Milwaukee, Wis.). The terms "concentrated" and "coevaporated" refer to removal of solvent at water aspirator pressure on a rotary evaporator with a bath temperature of less than 45° C. Reactions conducted at "0–20° C." or "0–25° C." were conducted with initial cooling of the vessel in an insulated ice bath which was allowed to warm to room temperature over several hours. The abbreviation "min" and "h" stand for "minutes" and "hours" respectively.

EXAMPLE 1

7-((4-Butyl-benzyl)-(pyridine-3-sulfonyl)-amino)-heptanoic acid

Step A: Reductive Amination 7-(4-Butyl-benzylamino)-heptanoic acid methyl ester. A solution of 7-amino-heptanoic acid methyl ester hydrochloride, prepared of Preparation 1, (1.12 g, 5.9 mmol), 4-butyl-benzaldehyde (0.915 g, 5.65 mmol) and triethylamine (0.83 mL, 5.98 mmol) in 20 mL MeOH was stirred at room temperature for 3 hours. After cooling to 0° C., $NaBH_4$ (0.342 g, 9.04 mmol) was added and the reaction was stirred for 15 minutes at room temperature. The mixture was quenched with 1:1 $NaHCO_3:H_2O$ and the MeOH was removed in vacuo. The resulting residue was diluted with $CH_2Cl_2$ and the organic solution was washed with water and brine, dried over $MgSO_4$, filtered and concentrated in vacuo to afford the title compound of Step A (1.4 g). $^1H$ NMR (400 MHz, $CDCl_3$) δ 7.08–7.38 (m, 4H), 3.62 (s, 2H), 3.29 (s, 3H), 2.52–2.66 (m, 4H), 2.25 (t, 2H), 1.53–1.63 (m, 6H), 1.25–1.40 (m, 6H), 0.85 (t, 3H); MS 306 (M+1).

Step B: Amide Formation 7-((4-Butyl-benzyl)-(pyridine-3-sulfonyl)-amino)-heptanoic acid methyl ester. A solution of 7-(4-butyl-benzylamino)-heptanoic acid methyl ester prepared of Example 1, Step A (0.10 g, 0.33 mmol), N,N-diisopropylethylamine (0.85 g 0.66 mmol) and pyridine-3-sulfonyl chloride hydrochloride, prepared of Preparation 2, (0.070 g, 0.33 mmol) in 3 mL $CH_2Cl_2$ was stirred at room temperature overnight. The mixture was diluted with $CH_2Cl_2$ and the organic solution was washed with water and brine, dried over $MgSO_4$, filtered and concentrated in vacuo. The product was purified by flash chromatography on silica gel (10% EtOAc/hexanes to 30% EtOAc/hexanes) to afford the title compound of Step B. $^1H$ NMR (400 MHz, $CDCl_3$) δ 9.01 (s, 1H), 8.75 (d, 1H), 8.04 (d, 1H), 7.41 (dd, 1H), 7.23 (m, 4H), 4.30 (s, 2H), 3.62 (s, 3H), 3.08 (t, 2H), 2.55 (t, 2H), 2.19 (t, 2H), 1.10–1.58 (m, 12H), 0.87 (t, 3H); MS 447 (M+1).

Step C: Ester Hydrolysis 7-((4-Butyl-benzyl)-(pyridine-3-sulfonyl)-amino)-heptanoic acid. A solution of 7-((4-butyl-benzyl)-(pyridine-3-sulfonyl)-amino)-heptanoic acid methyl ester prepared of Example 1, Step B (0.040 g, 0.158 mmol), in 2 mL MeOH and 0.5 mL 2N NaOH was stirred at room temperature overnight. The mixture was quenched with 2N HCl and was diluted with $CH_2Cl_2$. The organic layer was washed with 1N HCl and water, dried over $MgSO_4$, filtered and concentrated in vacuo. The product was purified by flash chromatography on silica gel (2% $MeOH/CH_2Cl_2$ to 5% $MeOH/CH_2Cl_2$) to afford the title compound (42 mg). $^1H$ NMR (400 MHz, $CDCl_3$) δ 9.09 (s, 1H), 8.77 (d, 1H), 8.08 (d, 1H), 7.48 (dd, 1H), 7.09 (m, 4H), 4.32 (s, 2H), 3.12 (s, 2H), 2.55 (t, 2H), 2.25 (t, 2H), 1.12–1.58 (m, 12H), 0.88 (t, 3H); MS 431 (M−1).

EXAMPLES 1a–1an

Examples 1a–1an were prepared from the appropriate starting materials in a manner analogous to the method of Example 1, with variations in reaction time, temperature, and reagents as noted.

EXAMPLE 1a 7-(Benzenesulfonyl-(4-butyl-benzyl)-amino)-heptanoic acid $^1H$ NMR (400 MHz, $CDCl_3$) δ 7.83 (d, 2H), 7.51–7.59 (m, 3H), 7.11 (m, 4H), 4.28 (s, 2H), 3.07 (t, 2H), 2.57 (t, 2H), 2.24 (t, 2H), 1.51–1.59 (m, 2H), 1.44–1.49 (m, 2H), 1.27–1.35 (m, 4H), 1.08–1.15 (m, 4H), 0.91 (t, 3H); MS 430 (M−1).

EXAMPLE 1b (3-(((1-Methyl-1H-indol-3-ylmethyl)-(pyridine-3-sulfonyl)-amino)-methyl)-phenyl)-acetic acid $^1H$ NMR (400 MHz, ($CDCl_3$) δ 8.93 (s, 1H), 8.66 (s, 1H), 7.96 (d, 1H), 7.39 (d, 1H), 7.01–7.37 (m, 9H), 6.77 (s, 1H), 4.56 (s, 2H), 4.41 (s, 2H), 3.66 (s, 3H), 3.52 (s, 2H); MS 448 (M−1).

EXAMPLE 1c (3-(((5-Phenyl-furan-2-ylmethyl)-(pyridine-3-sulfonyl)-amino)-methyl)-phenyl)-acetic acid $^1H$ NMR (400 MHz, ($CDCl_3$) δ 8.02 (d, 1H), 7.22–7.34 (m, 12H), 6.42 (d, 1H), 6.17 (d, 1H), 4.45 (s, 2H), 4.40 (s, 2H), 3.60 (s, 2H); MS 461 (M−1).

EXAMPLE 1d (3-(((5-Benzyl-pyridin-2-ylmethyl)-(pyridine-3-sulfonyl)-amino)-methyl)-phenyl)-acetic acid Step A: Reaction time of 3.5 h at room temperature. $^1$H NMR (400 MHz, CDCl$_3$) δ 8.97 (s, 1H), 8.71 (d, 1H), 8.15 (s, 1H), 7.98 (d, 1H), 7.44 (d, 1H), 7.04–7.34 (m, 10H), 4.54 (s, 2H), 4.43 (s, 2H), 3.87 (s, 2H), 3.50 (s, 2H); MS 486 (M–1).

EXAMPLE 1e 3-(((4-Phenethylsulfanyl-benzyl)-(pyridine-3-sulfonyl)-amino)-methyl)-phenyl)-acetic acid Step A: Reaction time of 4 h at room temperature. $^1$H NMR (400 MHz, CDCl$_3$) δ 8.00 (d, 1H), 7.50 (bs, 1H), 6.90–7.38 (m, 15H), 4.31 (s, 4H), 3.49 (s, 2H), 3.11 (t, 2H), 2.87 (t, 2H); MS 531 (M–1).

EXAMPLE 1f (3-(((3-Hydroxy-4-propoxy-benzyl)-(pyridine-3-sulfonyl)-amino)-methyl)-phenyl)-acetic acid Step A: Reaction time of 3.5 h at room temperature. $^1$H NMR (400 MHz, CDCl$_3$) δ 8.95 (s, 1H), 8.72 (s, 1H), 7.98 (d, 1H), 7.37 (m, 1H), 7.13–7.23 (m, 2H), 6.94–7.00 (m, 2H), 6.55–6.68 (m, 3H), 4.55 (s, 2H), 4.31 (s, 2H), 3.95 (t, 2H), 3.52 (s, 2H), 1.78 (m, 2H), 0.99 (t, 3H).

EXAMPLE 1g (3-(((4-Pentyl-benzyl)-(pyridine-3-sulfonyl)-amino)-methyl)-phenyl)-acetic acid Step A: Reaction time of 3.5 h at room temperature. $^1$H NMR (400 MHz, CDCl$_3$) δ 8.98 (s, 1H), 8.74 (s, 1H), 8.00 (d, 1H), 7.39 (m, 1H), 7.14–7.26 (m, 2H), 6.95–7.05 (m, 6H), 4.35 (s, 4H), 3.54 (s, 2H), 2.54 (t, 2H), 1.56 (m, 2H), 1.29 (m, 4H), 0.88 (t, 3H); MS 465 (M–1).

EXAMPLE 1h (3-(((4-Methylsulfamoyl-benzyl)-(pyridine-3-sulfonyl)-amino)-methyl)-phenyl)-acetic acid Step A: Reaction time of 3.5 h at room temperature. $^1$H NMR (400 MHz, CDCl$_3$) δ 9.06 (s, 1H), 8.85 (s, 1H), 8.16 (d, 1H), 7.53–7.64 (m, 3H), 6.91–7.26 (m, 6H), 4.39 (s, 2H), 4.35 (s, 2H), 3.50 (s, 2H), 2.63 (s, 3H); MS 488 (M–1).

EXAMPLE 1i (3-(((4-Isopropoxy-benzyl)-(pyridine-3-sulfonyl)-amino)-methyl)-phenyl)-acetic acid Step A: Reaction time of 3.5 h at room temperature. $^1$H NMR (400 MHz, CDCl$_3$) δ 8.97 (s, 1H), 8.74 (s, 1H), 8.03 (m, 1H), 7.42 (m, 1H), 6.94–7.25 (m, 6H), 6.72 (m, 2H), 4.48 (m, 1H), 4.32 (m, 4H), 3.52 (s, 2H), 1.29 (t, 6H); MS 453 (M–1).

EXAMPLE 1j (3-(((4-Chloro-thiophen-2-ylmethyl)-(pyridine-3-sulfonyl)-amino)-methyl)-phenyl)-acetic acid Step A: Reaction time of 3.5 h at room temperature. $^1$H NMR (400 MHz, CDCl$_3$) δ 9.01 (s, 1H), 8.79 (s, 1H), 8.07 (d, 1H), 7.45 (m, 1H), 7.20–7.29 (m, 2H), 7.12 (d, 1H), 7.10 (s, 1H), 7.07 (s, 1H), 4.46 (s, 2H), 4.42 (s, 2H), 3.60 (s, 2H); MS 435 (M–1).

EXAMPLE 1k (3-(((4-Butyl-benzyl)-(4-nitro-benzenesulfonyl)-amino)-methyl)-phenyl)-acetic acid $^1$H NMR (400 MHz, CDCl$_3$) δ 8.23 (m, 2H), 7.85 (m, 2H), 7.15–7.25 (m, 2H), 695–7.02 (m, 6H), 4.32 (m, 4H), 3.53 (s, 2H), 2.52 (m, 2H), 1.51 (m, 2H), 1.30 (m, 2H), 0.89 (t, 3H); MS 495 (M–1).

EXAMPLE 1l (3-(((4-Butyl-benzyl)-(4-cyano-benzenesulfonyl)-amino)-methyl)-phenyl)-acetic acid $^1$H NMR (400 MHz, CDCl$_3$) δ 8.21 (d, 1H), 7.67–7.84 (m, 3H), 6.89–7.24 (m, 8H), 4.46 (s, 1H), 4.38 (s, 1H), 4.32 (m, 2H), 3.54 (s, 1H), 3.38 (s, 1H), 2.55 (m, 2H), 1.58 (m, 2H), 1.33 (m, 2H), 1.29 (s, 1H), 0.89 (t, 3H); MS 475 (M–1).

EXAMPLE 1m (3-(((4-Butyl-benzyl)-(3-fluoro-benzenesulfonyl)-amino)-methyl)-phenyl)-acetic acid $^1$H NMR (400 MHz, CDCl$_3$) δ 7.58 (m, 1H), 7.45 (m, 1H), 6.92–7.24 (m, 10H), 4.29 (m, 4H), 3.52 (d, 2H), 2.52 (d, 2H), 1.52 (m, 2H), 1.29 (m, 2H), 0.90 (m, 3H); MS 468 (M–1).

EXAMPLE 1n (3-(((4-Butyl-benzyl)-(5-pyridin-2-yl-thiophene-3-sulfonyl)-amino)-methyl)-phenyl)-acetic acid Step B: N,N-diisopropylethylamine was replaced by triethylamine. Reaction time of 4 h at room temperature. $^1$H NMR (400 MHz, CDCl$_3$) δ 7.81 (m, 2H), 7.17–7.27 (m, 6H), 6.94–7.16 (m, 6H), 4.29 (d, 4H), 3.55 (s, 2H), 2.54 (m, 2H), 1.54 (m, 2H), 1.31 (m, 2H), 0.91 (t, 3H); MS 533 (M–1).

EXAMPLE 1o (3-(((4-Butyl-benzyl)-(toluene-4-sulfonyl)-amino)-methyl)-phenyl)-acetic acid Step B: N,N-diisopropylethylamine was replaced by triethylamine. Reaction time of 4 h at room temperature. $^1$H NMR (400 MHz, CDCl$_3$) δ 7.71 (d, 2H), 7.24–7.29 (m, 2H), 7.11–7.19 (m, 2H), 6.87–7.01 (m, 2H), 4.26(d, 4H), 3.52 (s, 2H), 2.55 (m, 2H), 2.43 (s, 3H), 1.54 (m, 2H), 1.32 (m, 2H), 0.91 (t, 3H); MS 464 (M–1).

EXAMPLE 1p (3-(((2,3-Dihydro-benzo[1,4]dioxin-6-ylmethyl)-(pyridine-3-sulfonyl)-amino)-methyl)-phenyl)-acetic acid $^1$H NMR (400 MHz, CDCl$_3$) δ 8.98 (s, 1H), 8.76 (s, 1H), 8.02 (d, 1H), 7.40 (m, 1H), 7.14–7.26 (m, 2H), 7.02 (d, 1H), 6.96 (s, 1H), 6.72 (d, 1H), 6.59 (m, 2H), 4.35 (s, 2H), 4.25 (s, 2H), 4.20 (s, 4H), 3.55 (s, 2H); MS 453 (M–1).

EXAMPLE 1q (3-((Benzofuran-2-ylmethyl-(pyridine-3-sulfonyl)-amino)-methyl)-phenyl)-acetic acid $^1$H NMR (400 MHz, CDCl$_3$) δ 9.05 (s, 1H), 8.66 (s, 1H), 8.04 (d, 1H), 7.11–7.42 (m, 9H), 6.44 (s, 1H), 4.45 (s, 1H), 4.39 (s, 1H), 3.59 (s, 1H); MS 435 (M–1).

EXAMPLE 1r (3-(((4-Butyl-benzyl)-(1-methyl-1H-imidazole-4-sulfonyl)-amino)-methyl)-phenyl)-acetic acid $^1$H NMR (400 MHz, CDCl$_3$) δ 7.58 (s, 1H), 7.28 (s, 1H), 6.99–7.26 (m, 8H), 4.33 (d, 4H), 3.65 (s, 3H), 3.52 (s, 2H), 2.54 (t, 2H), 1.54 (m, 2H), 1.32 (m, 2H), 0.91 (t, 3H); MS 454 (M−1).

EXAMPLE 1s (3-(((4-Imidazol-1-yl-benzyl)-(pyridine-3-sulfonyl)-amino)-methyl)-phenyl)-acetic acid $^1$H NMR (400 MHz, CDCl$_3$) δ 9.45 (m, 1H), 9.44 (s, 1H), 9.03 (m, 1H), 8.91 (d, 1H), 8.19 (t, 1H), 8.04 (m, 1H), 7.77 (s, 1H), 7.61 (d, 2H), 7.53 (d, 2H), 7.11 (m, 4H), 4.70 (s, 2H), 4.51 (s, 2H), 3.33 (s, 2H); MS 461 (M−1).

EXAMPLE 1t (3-(((Pyridine-3-sulfonyl)-(4-pyrimidin-2-yl-benzyl)-amino)-methyl)-phenyl)-acetic acid $^1$H NMR (400 MHz, CDCl$_3$) δ 9.10 (s, 1H), 8.80 (m, 3H), 8.14 (d, 1H), 8.02 (d, 2H), 7.47 (m, 1H), 7.06–7.25 (m, 6H), 6.83 (s, 1H), 4.40 (s, 2H), 4.33 (s, 2H), 3.41 (s, 2H); MS 473 (M−1).

EXAMPLE 1u (3-(((Pyridine-3-sulfonyl)-(4-thiazol-2-yl-benzyl)-amino)-methyl)-phenyl)-acetic acid $^1$H NMR (400 MHz, CDCl$_3$) δ 9.11 (s, 1H), 8.85 (s, 1H), 8.15 (d, 1H), 7.87 (s, 2H), 7.63 (d, 2H), 7.51 (m, 1H), 7.37 (s, 1H), 7.07–7.27 (m, 6H), 6.83 (s, 1H), 4.37 (s, 2H), 4.33 (s, 2H), 3.41 (s, 2H).

EXAMPLE 1v (3-(((1-Methyl-1H-imidazole-4-sulfonyl)-(4-thiazol-2-yl-benzyl)-amino)-methyl)-phenyl)-acetic acid Step B: N,N-diisopropylethylamine was replaced by triethylamine. $^1$H NMR (400 MHz, CDCl$_3$) δ 7.85 (s, 1H), 7.59 (m, 2H), 7.47 (s, 1H), 7.34 (s, 1H), 7.07–7.25 (m, 6H), 6.88 (s, 1H), 4.46 (s, 2H), 4.38 (s, 2H), 3.77 (s, 3H), 3.40 (s, 2H); MS 483 (M−1).

EXAMPLE 1w (3-(((4-Dimethylamino-benzyl)-(pyridine-3-sulfonyl)-amino]-methyl)-phenyl)-acetic acid Step A: Reaction time of 4 h at room temperature. Step B: N,N-diisopropylethylamine was replaced by triethylamine. $^1$H NMR (400 MHz, CD$_3$OD) δ 8.09 (d, 1H), 7.09–7.16 (m, 2H), 6.93–6.99 (m, 7H), 6.65 (d, 2H), 5.36 (s, 2H), 4.32 (s, 2H), 4.27 (s, 2H), 2.89 (s, 6H); MS 438 (M−1).

EXAMPLE 1x (3-(((4-Cyclohexyl-benzyl)-(pyridine-3-sulfonyl)-amino)-methyl)-phenoxy)-acetic acid Step B: N,N-diisopropylethylamine was replaced by triethylamine. $^1$H NMR (400 MHz, CDCl$_3$) δ 8.95 (s, 1H), 8.73 (d, 1H), 8.00 (d, 1H), 7.39 (m, 1H), 7.17 (t, 1H), 7.13 (d, 2H), 7.08 (d, 2H), 6.81 (d, 1H), 6.73 (d, 1H), 6.61 (s, 1H), 4.54 (s, 2H), 4.34 (s, 4H), 2.43 (m, 1H), 1.81 (d, 4H), 1.37 (t, 4H), 1.23 (m, 1H); MS 495 (M+1), 493 (M−1).

EXAMPLE 1y (3-(((2-(3,5-Dichloro-phenoxy)-ethyl)-(pyridine-3-sulfonyl)-amino)-methyl)-phenoxy)-acetic acid Step B: N,N-diisopropylethylamine was replaced by triethylamine. $^1$H NMR (400 MHz, CDCl$_3$) δ 9.07 (s, 1H), 8.78 (d, 1H), 8.12 (d, 1H), 7.47 (m, 1H), 7.25 (m, 1H), 6.82–6.91 (m, 4H), 6.53 (s, 2H), 4.61 (s, 2H), 4.47 (s, 2H), 3.91 (t, 2H), 3.54 (t, 2H); MS 511 (M+1), 509 (M−1).

EXAMPLE 1z (3-(((4-Dimethylamino-benzyl)-(pyridine-3-sulfonyl)-amino)-methyl)-phenoxy)-acetic acid Step B: N,N-diisopropylethylamine was replaced by triethylamine. $^1$H NMR (400 MHz, CDCl$_3$) δ 8.91 (s, 1H), 8.79 (m, 1H), 8.04 (d, 1H), 7.43 (m, 1H), 7.16 (t, 1H), 6.94 (d, 2H), 6.81 (d, 2H), 6.64 (d, 2H), 6.49 (s, 1H), 4.51 (s, 2H), 4.28 (s, 4H), 2.91 (s, 6H); MS 456 (M+1), 454 (M−1).

EXAMPLE 1aa (3-(((4-tert-Butyl-benzyl)-(pyridine-3-sulfonyl)-amino)-methyl)-phenoxy)-acetic acid Step B: N,N-diisopropylethylamine was replaced by triethylamine. $^1$H NMR (400 MHz, CDCl$_3$) δ 8.95 (s, 1H), 8.74 (s, 1H), 7.99 (d, 1H), 7.39 (m, 1H), 7.25 (m, 2H), 7.15 (t, 1H), 7.04 (d, 2H), 6.81 (d, 1H), 6.72 (d, 1H), 6.62 (s, 1H), 4.55 (s, 2H), 4.35 (s, 4H), 1.27 (s, 9H); MS 469 (M+1), 467 (M−1).

EXAMPLE 1ab (3-(((3-(3-Chloro-phenyl)-propyl)-(pyridine-3-sulfonyl)-amino)-methyl)-phenoxy)-acetic acid Step B: N,N-diisopropylethylamine was replaced by triethylamine. $^1$H NMR (400 MHz, CDCl$_3$) δ 8.98 (s, 1H), 8.77 (d, 1H), 8.07 (d, 1H), 7.48 (m, 1H), 7.21 (m, 2H), 6.91 (s, 1H), 6.86 (m, 3H), 6.78 (s, 1H), 4.61 (s, 2H), 4.31 (s, 2H), 3.15 (t, 2H), 2.43 (t, 2H), 1.68 (m, 2H); MS 475 (M+1), 473 (M−1).

EXAMPLE 1ac (3-(((4-tert-Butyl-benzyl)-(1-methyl-1H-imidazole-4-sulfonyl)-amino)-methyl)-phenoxy)-acetic acid Step B: N,N-diisopropylethylamine was replaced by triethylamine. $^1$H NMR (400 MHz, CDCl$_3$) δ 7.66 (s, 1H), 7.08–7.31 (m, 6H), 6.70–6.78 (m, 3H), 4.54 (s, 2H), 4.35 (s, 4H), 3.68 (s, 3H), 1.27 (s, 9H); MS 469.9 (M−1).

EXAMPLE 1ad (3-(((4-Cyclohexyl-benzyl)-(pyridine-3-sulfonyl)-amino)-methyl)-phenyl)-acetic acid Step B: N,N-diisopropylethylamine was replaced by triethylamine. $^1$H NMR (400 MHz, CDCl$_3$) δ 8.98 (bs, 1H), 8.75 (bs, 1H), 7.98 (d, 1H), 7.39 (bs, 1H), 6.97–7.25 (m, 8H), 4.36 (d, 4H), 3.54 (s, 2H), 2.44 (s, 1H), 1.72–1.82 (m, 4H), 1.24–1.36 (m, 5H); MS 476.9 (M−1).

EXAMPLE 1ae (3-(((1-Methyl-1H-imidazole-4-sulfonyl)-(4-phenoxy-benzyl)-amino)-methyl)-phenyl)-acetic acid Step B: N,N-diisopropylethylamine was replaced by triethylamine. $^1$H NMR (400 MHz, CDCl$_3$) δ 7.52 (s, 1H), 7.06–7.37 (m, 10H), 6.94 (d, 2H), 6.83 (d, 2H), 4.38 (s, 4H), 3.71 (s, 3H), 1.72–1.82 (m, 4H), 3.56 (s, 2H); MS 490 (M–1).

EXAMPLE 1af (3-(((4-Phenoxy-benzyl)-(pyridine-3-sulfonyl)-amino)-methyl)-phenyl)-acetic acid $^1$H NMR (400 MHz, CDCl$_3$) δ 9.00 (bs, 1H), 8.76 (bs, 1H), 8.04 (d, 1H), 7.41 (t, 1H), 7.35 (m, 1H), 6.86–7.32 (m, 10H), 6.84 (d, 2H), 4.37 (d, 4H), 3.54 (s, 2H); MS 487 (M–1).

EXAMPLE 1ag (3-(((4-(2-Oxo-pyrrolidin-1-yl)-benzyl)-(pyridine-3-sulfonyl)-amino)-methyl)-phenyl)-acetic acid Step B: N,N-diisopropylethylamine was replaced by triethylamine. $^1$H NMR (400 MHz, CDCl$_3$) δ 9.06 (bs, 1H), 8.80 (bs, 1H), 8.14 (m, 1H), 7.47 (m, 1H), 6.96–7.26 (m, 7H), 4.28 (m, 4H), 3.78 (m, 2H), 3.35 (m, 2H), 2.59 (m, 2H), 2.11 (m, 2H); MS 478 (M–1).

EXAMPLE 1ah (3-((Benzo[1,3]dioxol-5-ylmethyl-(pyridine-3-sulfonyl)-amino)-methyl)-phenyl)-acetic acid $^1$H NMR (400 MHz, CDCl$_3$) δ 8.98 (s, 1H), 8.76 (s, 1H), 8.04 (d, 1H), 7.41 (m, 1H), 7.14–7.20 (m, 2H), 7.00 (d, 1H), 6.94 (s, 1H), 6.64 (t, 2H), 6.55 (d, 1H), 4.34 (s, 2H), 4.26 (s, 2H), 3.54 (s, 2H); MS 439 (M–1).

EXAMPLE 1ai (3-(((1-Methyl-1H-imidazole-4-sulfonyl)-(4-pyrimidin-5-yl-benzyl)-amino)-methyl)-phenyl)-acetic acid Step B: N,N-diisopropylethylamine was replaced by triethylamine. $^1$H NMR (400 MHz, CDCl$_3$) δ 9.18 (s, 1H), 8.91 (s, 2H), 7.05–7.54 (m, 11H), 4.49 (s, 2H), 4.40 (s, 2H), 3.75 (s, 3H), 3.55 (s, 2H); MS 476 (M–1).

EXAMPLE 1aj (3-(((Pyridine-3-sulfonyl)-(4-pyrimidin-5-yl-benzyl)-amino)-methyl)-phenyl)-acetic acid $^1$H NMR (400 MHz, CD$_3$OD) δ 9.17 (s, 1H), 9.01 (s, 1H), 8.77 (s, 1H), 7.57 (m, 4H), 7.45 (d, 2H), 7.05–7.16 (m, 5H), 4.48 (s, 2H), 4.43 (s, 2H), 3.45 (s, 2H).

EXAMPLE 1ak (3-(((4-Pyrazin-2-yl-benzyl)-(pyridine-3-sulfonyl)-amino)-methyl)-phenyl)-acetic acid $^1$H NMR (400 MHz, DMSO-d$_6$) δ 9.18 (s, 1H), 9.02 (s, 1H), 8.83 (d, 1H), 8.68 (s, 1H), 8.57 (s, 1H), 8.25 (d, 1H), 7.96 (d, 2H), 7.60 (m, 1H), 7.26 (d, 2H), 7.15 (m, 2H), 7.05 (m, 2H), 4.42 (s, 2H), 4.41 (s, 2H).

EXAMPLE 1al (3-(((1-Methyl-1H-imidazole-4-sulfonyl)-(4-pyrimidin-2-yl-benzyl)-amino)-methyl)-phenyl)-acetic acid $^1$H NMR (400 MHz, CDCl$_3$) δ 8.78 (d, 2H), 7.94 (d, 2H), 7.54 (s, 1H), 7.44 (s, 1H), 7.22–7.03 (m, 6H), 6.87 (s, 1H), 4.45 (s, 2H), 4.39 (s, 2H), 3.73 (s, 3H), 3.38 (s, 2H); MS 476 (M–1).

EXAMPLE 1am (3-(((4-Butyl-benzyl)-phenylmethanesulfonyl-amino)-methyl)-phenyl)-acetic acid $^1$H NMR (400 MHz, CDCl$_3$) δ 7.31–6.96 (m, 13H), 4.13 (s, 2H), 4.05 (s, 2H), 4.03 (s, 2H), 3.62 (s, 2H), 2.60 (t, 2H), 1.58 (m, 2H), 1.33 (m, 2H), 0.91 (t, 3H); MS 464 (M–1).

EXAMPLE 1an 5-(3-((Pyridine-3-sulfonyl)-(4-thiazol-2-yl-benzyl)-amino)-propyl)-thiophene-2-carboxylic acid Step A: Triethylamine was replaced with N,N-diisopropylethylamine. $^1$H NMR (400 MHz, CDCl$_3$) δ 9.18 (d, 1H), 8.82 (d, 1H), 8.05 (d, 1H), 7.73–7.20 (m, 8H), 6.60 (d, 1H), 4.35 (s, 2H), 3.22 (t, 2H), 2.70 (t, 2H), 1.85–1.70 (m, 2H).

EXAMPLE 2

(3-(((2-(3-Chloro-phenoxy)-ethyl)-(pyridine-3-sulfonyl)-amino)-methyl)-phenyl)-acetic acid Step A: Alkylation (3-(((2-(3-Chloro-phenoxy)-ethyl)-(pyridine-3-sulfonyl)-amino)-methyl)-phenyl)-acetic acid methyl ester To a solution of sodium hydride (60% in mineral oil, 0.016 g, 0.3996 mmol) in 2 mL DMF was added (3-((pyridine-3-sulfonylamino)-methyl)-phenyl)-acetic acid methyl ester (from Preparation 14, 0.096 g, 0.333 mmol) at 0° C. and the reaction was stirred at room temperature for 30 minutes. After cooling to 0° C., 1-(2-bromo-ethoxy)-3-chloro-benzene (from Preparation 29, 0.094 g, 0.399 mmol) was added and the reaction was stirred at room temperature overnight. The DMF was removed in vacuo. The residue was diluted with EtOAc and the organic solution was washed with water and brine, dried over MgSO$_4$, filtered and concentrated in vacuo. The product was purified by flash chromatography on silica gel (0.5% MeOH/CH$_2$Cl$_2$ to 2% MeOH/CH$_2$Cl$_2$) to afford the title compound of Step A (0.025 g). MS 475 (M+1).

Step B: Ester Hydrolysis (3-(((2-(3-Chloro-phenoxy)-ethyl)-(pyridine-3-sulfonyl)-amino)-methyl)-phenyl)-acetic acid A solution of the compound of Example 2, Step A (0.025 g, 0.053 mmol), in 2 mL MeOH and 0.5 mL 2N NaOH was stirred at room temperature overnight. The mixture was quenched with 2N HCl and was diluted with CH$_2$Cl$_2$. The organic layer was washed with 1N HCl and water, dried over MgSO$_4$, filtered, and concentrated in vacuo. The product was purified by flash chromatography on silica gel (2% MeOH/CH$_2$Cl$_2$ to 5% MeOH/CH$_2$Cl$_2$) to afford the title compound (20 mg). $^1$H NMR (400 MHz, CDCl$_3$) δ 9.05 (s, 1H), 8.77 (d, 1H), 8.11 (d, 1H), 7.43 (m, 1H), 7.08–7.27 (m, 5H), 6.89 (d, 1H), 6.62 (s, 1H), 6.55 (d, 1H), 4.51 (s, 2H), 3.95 (t, 2H), 3.59 (s, 4H); MS 495 (M–2).

EXAMPLES 2a–2c

Examples 2a–2c were prepared from the appropriate starting materials in a manner analogous to the method of Example 2.

EXAMPLE 2a

Trans-(3-(((3-(3,5-Dichloro-phenyl)-allyl)-(pyridine-3-sulfonyl)-amino)-methyl)-phenyl)-acetic acid $^1$H NMR (400 MHz, CDCl$_3$) δ 9.08 (bs, 1H), 8.81 (bs, 1H), 8.11 (d, 1H), 7.48 (bs, 1H), 7.12–7.28 (m, 4H), 6.98 (s, 2H), 6.19 (d, 1H), 5.86 (m, 1H), 4.38 (s, 2H), 3.93 (d, 2H), 3.58 (s, 2H).

EXAMPLE 2b (3-(((2-(3,5-Dichloro-phenoxy)-ethyl)-(pyridine-3-sulfonyl)-amino)-methyl)-phenyl)-acetic acid $^1$H NMR (400 MHz, CDCl$_3$) δ 8.96 (bs, 1H), 8.70 (bs, 1H), 8.04 (d, 1H), 7.41 (m, 1H), 7.24–7.09 (m, 4H), 6.86 (s, 1H), 6.47 (s, 2H), 4.44 (s, 2H), 3.86 (m, 2H), 3.49 (s, 2H), 3.31 (m, 2H).

EXAMPLE 2c (3-(((4-(1-Hydroxy-hexyl)-benzyl)-(pyridine-3-sulfonyl)-amino)-methyl)-phenyl)-acetic acid $^1$H NMR (400 MHz, CDCl$_3$) δ 8.91 (bs, 1H), 8.72 (bs, 1H), 8.03 (d, 1H), 7.40 (bs, 1H), 7.16–6.99 (m, 7H), 6.81 (s, 1H), 4.57 (t, 1H), 4.29 (s, 4H), 3.43 (m, 2H), 1.70 (m, 1H), 1.61 (m, 1H), 1.32–1.16 (m, 8H), 0.82 (t, 3H).

EXAMPLE 3

5-(3-((2-Benzylsulfanyl-ethyl)-(pyridine-3-sulfonyl)-amino)-propyl)-thiophene-2-carboxylic acid Step A: Reductive Amination 5-(3-(2-Benzylsulfanyl-ethylamino)-propyl)-thiophene-2-carboxylic acid tert-butyl ester.

Step A was performed in a manner analogous to the method of Step A of Example 1.

Step B: Amide Formation 5-(3-((2-Benzylsulfanyl-ethyl)-(pyridine-3-sulfonyl)-amino)-propyl)-thiophene-2-carboxylic acid tert-butyl ester Step B was performed in a manner analogous to the method of Step B of Example 1, except triethylamine was used in place of N,N-diisopropylethylamine.

Step C: Ester Hydrolysis 5-(3-((2-Benzylsulfanyl-ethyl)-(pyridine-3-sulfonyl)-amino)-propyl)-thiophene-2-carboxylic acid.TFA A solution of 5-(3-((2-benzylsulfanyl-ethyl)-(pyridine-3-sulfonyl)-amino)-propyl)-thiophene-2-carboxylic acid tert-butyl ester prepared of Example 3, Step B (0.038 g) in 1 mL CH$_2$Cl$_2$ was cooled to 0° Cl and 1 mL TFA was added. The mixture was warmed to room temperature and was stirred for 1 h. The CH$_2$Cl$_2$ and TFA were removed by evaporation, azeotroping with added CH$_2$Cl$_2$ to yield the title compound (46.3 mg). MS 475 (M−1).

Examples 3a–3i were prepared from the appropriate starting materials in a manner analogous to the method of Example 3 with variations thereto noted.

EXAMPLE 3a 5-(3-((2-(3-Chloro-phenylsulfanyl)-ethyl)-(pyridine-3-sulfonyl)-amino)-propyl)-thiophene-2-carboxylic acid $^1$H NMR (400 MHz, CD$_3$OD) δ 8.93 (s, 1H), 8.78 (d, 1H), 8.21 (d, 1H), 7.64 (m, 1H), 7.57 (s, 1H), 7.35 (s, 1H), 7.19–7.28 (m, 3H), 6.87 (s, 1H), 3.16–3.35 (m, 6H), 2.87 (t, 2H), 1.89 (t, 2H); MS 497,499 (M+).

EXAMPLE 3b (3-(((Pyridine-3-sulfonyl)-(4-thiazol-2-yl-benzyl)-amino)-methyl)-phenoxy)-acetic acid.2TFA $^1$H NMR (400 MHz, CDCl$_3$) δ 9.40 (bs, 1H), 8.98 (s, 1H), 8.84 (s, 1H), 8.28 (m, 1H), 8.10 (s, 1H), 7.78 (m, 2H), 7.68 (m, 1H), 7.51 (s, 1H), 7.24 (m, 3H), 7.12 (t, 1H), 6.77 (m, 1H), 6.48 (s, 1H), 4.53 (s, 2H), 4.45 (s, 2H), 4.34 (s, 2H); MS 494 (M−1).

EXAMPLE 3c (3-(((Pyridine-3-sulfonyl)-(4-pyrimidin-2-yl-benzyl)-amino)-methyl)-phenoxy)-acetic acid.2HCl The TFA salt was converted to the HCl salt by stirring in 2 equivalents 1N HCl followed by removal of water and drying in vacuo. $^1$H NMR (400 MHz, CD$_3$OH) δ 9.00 (d, 2H), 8.78 (d, 1H), 8.25 (d, 2H), 8.08 (t, 1H), 7.60 (t, 1H), 7.42 (m, 3H), 7.11 (m, 1H), 6.81 (d, 1H), 6.72 (m, 3H), 4.65 (s, 2H), 4.60 (s, 2H), 4.49 (s, 2H).

EXAMPLE 3d (3-(((1-Methyl-1H-imidazole-4-sulfonyl)-(4-thiazol-2-yl-benzyl)-amino)-methyl)-phenoxy)-acetic acid.2TFA $^1$H NMR (400 MHz, CD$_3$OD) δ 7.93 (s, 1H), 7.85 (d, 1H), 7.76 (d, 2H), 7.70 (s, 1H), 7.60 (d, 1H), 7.26 (d, 2H), 7.09 (t, 1H), 6.75 (d, 2H), 6.68 (s, 1H), 4.51 (s, 2H), 4.41 (s, 2H), 4.35 (s, 2H), 3.76 (s, 3H); MS 498 (M+).

EXAMPLE 3e (3-(((Pyridine-3-sulfonyl)-(4-pyridin-2-yl-benzyl)-amino)-methyl)-phenoxy)-acetic acid.HCl No triethylamine was used in Step A. The TFA salt was converted to the HCl salt by stirring in 2 equivalents 1N HCl followed by removal of water and drying in vacuo. MS 490 (M+1), 488 (M−1).

EXAMPLE 3f (3-(((1-Methyl-1H-imidazole-4-sulfonyl)-(4-pyridin-2-yl-benzyl)-amino)-methyl)-phenoxy)-acetic acid.HCl No triethylamine was used in Step A. The TFA salt was converted to the HCl salt by stirring in 2 equivalents 1N HCl followed by removal of water and drying in vacuo. MS 493 (M+1), 491 (M−1).

EXAMPLE 3g (3-(((Pyridine-3-sulfonyl)-(4-pyridin-3-yl-benzyl)-amino)-methyl)-phenoxy)-acetic acid.HCl No triethylamine was used in Step A. The TFA salt was converted to the HCl salt by stirring in 2 equivalents 1N HCl followed by removal of water and drying in vacuo. MS 490 (M+1), 488 (M−1).

EXAMPLE 3h (3-(((1-Methyl-1H-imidazole-4-sulfonyl)-(4-pyridin-3-yl-benzyl)-amino)-methyl)-phenoxy)-acetic acid.HCl No triethylamine was used in Step A. The TFA salt was converted to the HCl salt by stirring in 2 equivalents 1N HCl followed by removal of water and drying in vacuo. MS 493 (M+1), 491 (M−1).

EXAMPLE 3i (3-(((Pyridine-3-sulfonyl)-(4-pyridin-4-yl-benzyl)-amino)-methyl)-phenoxy)-acetic acid.HCl No triethylamine was used in Step A. The TFA salt was converted to the HCl salt by stirring in 2 equivalents 1N HCl followed by removal of water and drying in vacuo. MS 490 (M+1), 488 (M−1).

EXAMPLE 4

5-(3-((3-(3-Chloro-phenyl)-propyl)-(pyridine-3-sulfonyl)-amino)-propyl)-thiophene-2-carboxylic acid Step A: Sulfonamide Formation 5-(3-((3-(3-Chloro-phenyl)-propyl)-(pyridine-3-sulfonyl)-amino)-propyl)-thiophene-2-carboxylic acid methyl ester A solution of 5-(3-(3-(3-chloro-phenyl)-propylamino)-propyl)-thiophene-2-carboxylic acid methyl ester (from Preparation 8, 0.0855 g, 0.243 mmol), triethylamine (0.0541 g 0.534 mmol), and pyridine-3-sulfonyl chloride hydrochloride (from Preparation 2, 0.0572 g, 0.267 mmol) in 10 mL $CH_2Cl_2$ combined at 0° C. was stirred at room temperature overnight. The organic solution was washed with water, saturated $NaHCO_3$ and brine, dried over $MgSO_4$, filtered and concentrated in vacuo to afford the title compound of Step A as an oil. MS 494 (M+1).

Step B: Ester Hydrolysis 5-(3-((3-(3-Chloro-phenyl)-propyl)-(pyridine-3-sulfonyl)-amino)-propyl)-thiophene-2-carboxylic acid A solution of 5-(3-((3-(3-chloro-phenyl)-propyl)-(pyridine-3-sulfonyl)-amino)-propyl)-thiophene-2-carboxylic acid methyl ester prepared of Example 4, Step B (0.119 g, 0.241 mmol), in 5 mL EtOH and 0.72 mL 1N NaOH was stirred at room temperature overnight. The reaction mixture was adjusted to pH 6.2 and the layers were separated. The organic solution was washed with water, dried over $MgSO_4$, filtered and concentrated in vacuo to afford the title compound (16 mg). $^1$H NMR (400 MHz, $CDCl_3$) δ 8.00 (d, 1H, J=8), 7.70 (d, 1H, J=4), 7.30–7.60 (m, 6H), 6.75 (d, 1H, J=4), 3.20 (m, 4H), 2.95 (t, 2H, J=7), 2.60 (t, 2H, J=7), 1.70–2.00 (m, 4H); MS 478 (M+1), 476 (M−1).

EXAMPLES 4a–4h

Examples 4a–4h were prepared from the appropriate starting in a manner analogous to the method of Example 4.

EXAMPLE 4a 5-(3-((3-(3-Chloro-phenyl)-propyl)-(4-methoxy-benzenesulfonyl)-amino)-propyl)-thiophene-2-carboxylic acid $^1$H NMR (400 MHz, $CDCl_3$) δ 7.70 (d, 1H, J=7), 7.00–7.40 (m, 8H), 6.80 (d, 1H, J=4), 3.89 (s, 3H), 3.10 (m, 4H), 2.95 (t, 2H, J=7), 2.50 (t, 2H, J=7), 1.70–2.00 (m, 2H); MS 508 (M+1), 506 (M−1).

EXAMPLE 4b 5-(3-((Benzo[1,2,5]thiadiazole-4-sulfonyl)-(3-(3-chloro-phenyl)-propyl)-amino)-propyl)-thiophene-2-carboxylic acid $^1$H NMR (400 MHz, $CDCl_3$) δ 7.00–7.70 (m, 8H), 6.70 (d, 1H, J=4), 3.05 (m, 4H), 2.90 (t, 2H, J=7), 2.54 (t, 2H, J=7), 1.72–1.92 (m, 2H); MS 536 (M+), 535 (M−1).

EXAMPLE 4c 5-(3-(Benzenesulfonyl-(3-(3-chloro-phenyl)-propyl)-amino)-propyl)-thiophene-2-carboxylic acid $^1$H NMR (400 MHz, $CDCl_3$) δ 6.70–7.92 (m, 11H), 3.26 (m, 4H), 3.05 (m, 4H), 2.73 (m, 2H), 2.50 (m, 2H), 1.70 (m, 2H); MS 578 (M+1), 576 (M−1).

EXAMPLE 4d 5-(3-((3-(3-Chloro-phenyl)-propyl)-phenylmethanesulfonyl-amino)-propyl)-thiophene-2-carboxylic acid $^1$H NMR (400 MHz, $CDCl_3$) δ 7.50 (d, 1H, J=4), 7.00–7.40 (m, 9H), 6.85 (d, 1H, J=4), 3.00 (m, 4H), 2.60 (m, 2H), 2.40 (m, 2H), 1.60–1.80 (m, 2H); MS 490 (M−1).

EXAMPLE 4e 5-(3-((3-(3-Chloro-phenyl)-propyl)-(pyridine-3-sulfonyl)-amino)-propyl)-furan-2-carboxylic acid $^1$H NMR (400 MHz, $CDCl_3$) δ 9.00 (m, 1H), 8.70 (m, 1H), 8.00 (d, 1H, J=6), 7.50 (m, 1H), 6.80–7.04 (m, 6H), 3.20 (m, 4H), 2.78 (m, 2H), 2.50 (m, 2H), 1.62–2.00 (m, 4H); MS 463 (M+1), 461 (M−1).

EXAMPLE 4f 5-(3-((3-(3-Chloro-phenyl)-propyl)-(naphthalene-2-sulfonyl)-amino)-propyl)-thiophene-2-carboxylic acid $^1$H NMR (400 MHz, $CDCl_3$) δ 8.40 (d, 1H, J=2), 7.00–8.00 (m, 11H), 6.80 (d, 1H, J=4), 3.20 (m, 4H), 2.82 (t, 2H, J=7), 2.60 (t, 2H, J=7), 1.80–2.00 (m, 2H); MS 528.9 (M+1).

EXAMPLE 4g 5-(3-((3-(3-Chloro-phenyl)-propyl)-(naphthalene-1-sulfonyl)-amino)-propyl)-thiophene-2-carboxylic acid $^1$H NMR (400 MHz, $CDCl_3$) δ 8.60 (d, 1H, J=5), 6.95–8.22 (m, 11H), 6.70 (d, 1H, J=4), 3.20 (m, 4H), 2.40 (t, 2H, J=7), 1.72–1.95 (m, 4H); MS 528.9 (M+1).

EXAMPLE 4h 5-(3-((2-Acetylamino-4-methyl-thiazole-5-sulfonyl)-(3-(3-chloro-phenyl)-propyl)-amino)-propyl)-thiophene-2-carboxylic acid $^1$H NMR (400 MHz, $CDCl_3$) δ 7.61 (d, 1H, J=4), 7.00–7.30 (m, 4H), 3.60 (d, 1H, J=3.8), 2.80 (t, 2H, J=7.0), 2.60 (t, 2H, J=6.8), 2.40 (s, 3H), 2.30 (s, 3H), 1.70–2.00 (m, 4H); MS 556 (M+1), 554 (M−1).

EXAMPLE 5

5-(3-((3-(3-Chloro-phenyl)-propyl)-(pyridine-3-carbonyl)-amino)-propyl)-thiophene-2-carboxylic acid Step A: Amide Formation 5-(3-((3-(3-Chloro-phenyl)-propyl)-(pyridine-3-carbonyl)-amino)-propyl)-thiophene-2-carboxylic acid methyl ester. A solution of 5-(3-(3-(3-chloro-phenyl)- propylamino)-propyl)-thiophene-2-carboxylic acid methyl ester (from Preparation 8, 0.075 g, 0.213 mmol), DCC (0.0483 g 0.234 mmol) and nicotinic acid (0.0289 g, 0.234 mmol) in 10 mL $CH_2Cl_2$ was stirred at room temperature overnight. The mixture was filtered and the filtrate was concentrated in vacuo. The residue was dissolved in 15 mL EtOAc and the insolubles were removed via filtration. The organic solution was washed with water followed by brine, dried over $MgSO_4$, filtered, and concentrated in vacuo to afford the title compound of Step A as an oil (113 mg). MS 457 (M+).

Step B: Ester Hydrolysis

Step B was performed in a manner analogous to the method of Step B of Example 4. $^1$H NMR (400 MHz, $CDCl_3$) δ 8.60 (d, 1H, J=8), 6.80–7.70 (m, 8H), 6.60 (d, 1H, J=4), 3.25 (m, 4H), 2.80 (m, 2H), 2.45 (m, 2H), 1.60–2.05 (m, 4H); MS 443 (M+1), 441 (M−1).

EXAMPLES 5a–5b

Examples 5a–5b were prepared from the appropriate starting in a manner analogous to the method of Example 5.

EXAMPLE 5a 5-(3-((3-(3-Chloro-phenyl)-propyl)-(pyridin-2-yl-acetyl)-amino)-propyl)-thiophene-2-carboxylic acid $^1$H NMR (400 MHz, $CDCl_3$) δ 8.60 (m, 1H), 7.00–7.80 (m, 8H), 6.60 (m, 1H), 4.00 (s, 2H), 3.32 (m, 4H), 2.72 (m, 2H), 2.50 (m, 2H), 1.70–2.00 (m, 4H); MS 457 (M+1), 455 (M−1).

EXAMPLE 5b 5-(3-((3-(3-Chloro-phenyl)-propyl)-(pyridin-3-yl-acetyl)-amino)-propyl)-thiophene-2-carboxylic acid $^1$H NMR (400 MHz, $CDCl_3$) δ 7.60–7.80 (m, 2H), 7.00–7.50 (m, 7H), 6.70 (d, 1H, J=4), 3.60 (s, 2H), 3.10–3.40 (m, 4H), 2.80 (m, 2H), 2.60 (m, 2H), 1.70–2.00 (m, 4H); MS 457 (M+1), 455 (M−1).

EXAMPLE 6

5-(3-((2-Chloro-benzenesulfonyl)-(3-(3-chloro-phenyl)-propyl)-amino)-propyl)-thiophene-2-carboxylic acid Step A: Amide Formation 5-(3-((2-Chloro-benzenesulfonyl)-(3-(3-chloro-phenyl)-propyl)-amino)-propyl)-thiophene-2-carboxylic acid tert-butyl ester. A stock solution of 5-(3-(3-(3-chloro-phenyl)-propylamino)-propyl)-thiophene-2-carboxylic acid tert-butyl ester (from Preparation 9, 0.10 g 0.254 mmol) in 10 mL $CH_2Cl_2$ was prepared and 1 mL of the solution (0.010 g, 0.0254 mmol) was added to a 1 dram vial. To this was added triethylamine (0.78 mL, 0.056 mmol) and 2-chloro-benzenesulfonyl chloride (0.0059 g, 0.028 mmol). The reaction was stirred overnight at room temperature and was diluted with 2 mL $CH_2Cl_2$. The organic solution was washed with 3 mL of 5.5% aqueous HCl solution (2×) and 3 mL saturated bicarbonate solution (2×). The organic layer was dried with $MgSO_4$ and was concentrated to yield the title compound of Step A (10 mg).

Step B: Ester Hydrolysis 5-(3-((2-Chloro-benzenesulfonyl)-(3-(3-chloro-phenyl)-propyl)-amino)-propyl)-thiophene-2-carboxylic acid. A solution of 5-(3-((2-chloro-benzenesulfonyl)-(3-(3-chloro-phenyl)-propyl)-amino)-propyl)-thiophene-2-carboxylic acid tert-butyl ester prepared of Example 6, Step A (0.010 g, 0.010 mmol) in 4N HCl in 1,4 dioxane (3 mL) and the reaction was stirred overnight at room temperature. HCl (g) was bubbled in until reaction was determined to be complete by thin layer chromatography. The reaction mixture was concentrated in vacuo. The resulting organic residue was azeotroped with $CCl_4$ to produce a powder (5 mg). $^1$H NMR (400 MHz, $CDCl_3$) δ 8.00 (d, 1H, J=4), 7.00–7.72 (m, 8H), 6.75 (d, 1H, J=4), 3.20–3.40 (m, 4H), 2.81 (m, 2H), 2.52 (m, 2H), 1.90 (m, 2H), 1.80 (m, 2H), 1.20 (m, 2H); MS 509.9 (M−1).

EXAMPLES 6a–6j

Examples 6a–6j were prepared from the appropriate starting material in a manner analogous to the method of Example 6.

EXAMPLE 6a 5-(3-((3-(3-Chloro-phenyl)-propyl)-(2,5-dimethyl-benzenesulfonyl)-amino)-propyl)-thiophene-2 carboxylic acid $^1$H NMR (400 MHz, $CDCl_3$) δ 7.70 (d, 1H, J=7), 7.00–7.40 (m, 7H), 6.80 (d, 1H, J=4), 3.32 (m, 4H), 2.50 (s, 3H), 2.36 (s, 3H), 1.84 (m, 2H), 1.75 (m, 2H), 1.22 (m, 2H); MS 506.1 (M+1), 504.1 (M−1).

EXAMPLE 6b 5-(3-((3-(3-Chloro-phenyl)-propyl)-(2,4-dioxo-1,2,3,4-tetrahydro-quinazoline-6-sulfonyl)-amino)-propyl)-thiophene-2-carboxylic acid $^1$H NMR (400 MHz, $CDCl_3$) δ 6.80–7.92 (m, 9H), 3.20 (m, 4H), 2.80 (m, 2H), 1.75–2.00 (m, 4H), 1.20 (m, 2H); MS 594.0 (M−1+Cl).

EXAMPLE 6c 5-(3-((4-(2-Carboxy-benzoylamino)-butane-1-sulfonyl)-(3-(3-chloro-phenyl)-propyl)-amino)-propyl)-thiophene-2-carboxylic acid $^1$H NMR (400 MHz, $CDCl_3$) δ 7.70 (d, 1H, J=6), 7.62 (d, 1H, J=4), 7.55 (d, 1H, J=8), 7.45–7.20 (m, 6H), 6.80–6.90 (m, 10H), 3.22 (m, 4H), 2.70 (m, 2H), 2.60 (m, 2H), 1.80–2.00 (m, 4H), 1.22 (m, 2H); MS 620.1 (M−1).

EXAMPLE 6d 5-(3-((3-(3-Chloro-phenyl)-propyl)-(4-(3,5-dioxo-4,5-dihydro-3H-[1,2,4]triazin-2-yl)-benzenesulfonyl)-amino)-propyl)-thiophene-2-carboxylic acid $^1$H NMR (400 MHz, $CDCl_3$) δ 7.60–7.92 (m, 4H), 6.80 (m, 7H), 3.22 (m, 4H), 2.80 (m, 2H), 2.60 (m, 2H), 1.82 (m, 2H), 1.22 (m, 2H); MS 587.1 (M−1).

EXAMPLE 6e 5-(3-((3-(3-Chloro-phenyl)-propyl)-(2-methoxycarbonyl-benzenesulfonyl)-amino)-propyl)-thiophene-2-carboxylic acid $^1$H NMR (400 MHz, $CDCl_3$) δ 7.75 (d, 1H, J=4), 7.00–7.70 (m, 8H), 6.85 (d, 1H, J=4), 3.90 (s, 3H), 3.31 (m, 4H), 2.70 (m, 2H), 2.50 (m, 2H), 1.82–2.00 (m, 4H), 1.20 (m, 2H); MS 534.1 (M−1).

EXAMPLE 6f 5-(3-((4-Bromo-benzenesulfonyl)-(3-(3-chloro-phenyl)-propyl)-amino)-propyl)-thiophene-2-carboxylic acid $^1$H NMR (400 MHz, CDCl$_3$) δ 7.75 (d, 1H, J=4), 7.00–7.70 (m, 8H), 6.80 (d, 1H, J=4), 3.10 (m, 4H), 2.86 (m, 2H), 2.55 (m, 2H), 1.90 (m, 2H), 1.80 (m, 2H); MS 557.9 (M+1), 555.9 (M−1).

EXAMPLE 6g 5-(3-((3-(3-Chloro-phenyl)-propyl)-(4-(1,1-dimethyl-propyl)-benzenesulfonyl)-amino)-propyl)-thiophene-2-carboxylic acid $^1$H NMR (400 MHz, CDCl$_3$) δ 7.95 (d, 1H, J=4), 7.00–7.80 (m, 8H), 6.80 (d, 1H, J=4), 3.20 (m, 4H), 2.80 (m, 2H), 2.50 (m, 2H), 1.30 (s, 3H), 1.70–1.90 (m, 4H), 1.55 (m, 2H), 0.60 (t, 3H, J=7); MS 548 (M+1).

EXAMPLE 6h 5-(3-((3-(3-Chloro-phenyl)-propyl)-(3,5-dimethyl-isoxazole-4-sulfonyl)-amino)-propyl)-thiophene-2-carboxylic acid $^1$H NMR (400 MHz, CDCl$_3$) δ 6.95–7.40 (m, 4H), 6.80 (d, 1H, J=8), 6.75 (d, 1H, J=8), 2.91 (m, 2H), 2.60 (s, 3H), 2.40 (m, 2H), 2.20 (s, 3H), 1.72–1.92 (m, 4H), 1.20 (m, 2H); MS 495 (M−1).

EXAMPLE 6i 5-(3-((3-(3-Chloro-phenyl)-propyl)-(2,5-dimethoxy-benzenesulfonyl)-amino)-propyl)-thiophene-2-carboxylic acid $^1$H NMR (400 MHz, CDCl$_3$) δ 7.70 (d, 1H, J=4), 7.00–7.50 (m, 7H), 6.80 (d, 1H, J=4), 4.00 (s, 3H), 3.80 (s, 3H), 3.25 (m, 4H), 2.85 (m, 2H), 2.52 (m, 2H), 1.70–2.00 (m, 2H); MS 538.1 (M+1), 536.1 (M−1).

EXAMPLE 6j 5-(3-((3-(3-Chloro-phenyl)-propyl)-(2-fluoro-benzenesulfonyl)-amino)-propyl)-thiophene-2-carboxylic acid $^1$H NMR (400 MHz, CDCl$_3$) δ 7.00–8.00 (m, 9H), 6.80 (d, 1H, J=7.2), 3.30 (m, 4H), 2.85 (m, 2H), 2.55 (m, 2H), 1.70–2.00 (m, 4H), 1.20 (m, 2H); MS 494.1 (M−1).

EXAMPLE 7

5-(3-(1-(3-(3-Chloro-phenyl)-propyl)-3-ethyl-ureido)-propyl)-thiophene-2-carboxylic acid

Step A: Isocyanate Addition 5-(3-(1-(3-(3-Chloro-phenyl)-propyl)-3-ethyl-ureido)-propyl)-thiophene-2-carboxylic acid tert-butyl ester. A stock solution of 5-(3-(3-(3-chloro-phenyl)-propylamino)-propyl)-thiophene-2-carboxylic acid tert-butyl ester (from Preparation 9, 0.10 g, 0.254 mmol) in 10 mL CH$_2$Cl$_2$ was prepared and 1 mL (0.010 g, 0.0254 mmol) was added to a 1 dram vial. Triethylamine (0.7 mL, 0.051 mmol) and ethyl isocyanate (0.004 g, 0.051 mmol) were added and the mixture was stirred overnight at room temperature. The solution was diluted with 2 mL CH$_2$Cl$_2$. The organic solution was washed with 3 mL of 5.5% aqueous HCl solution (2×) followed by 3 mL saturated bicarbonate solution (2×). The organic layer was dried with MgSO$_4$ and was concentrated to yield the title compound of Step A (10 mg).

Step B: Ester Hydrolysis

Step B was performed in a manner analogous to the method of Step B of Example 6. $^1$H NMR (400 MHz, CDCl$_3$) δ 7.70 (d, 1H, J=4), 7.00–7.40 (m, 4H), 6.80 (d, 1H, J=4), 3.20 (m, 6H), 2.80 (m, 2H), 2.60 (m, 2H), 1.80–2.00 (m, 4H), 1.05 (t, 3H, J=7); MS 409.1 (M+1), 407.1 (M−1).

EXAMPLES 7a–7j

Examples 7a–7j were prepared from the appropriate starting materials in a manner analogous to the method of Example 7.

EXAMPLE 7a 5-(3-(1-(3-(3-Chloro-phenyl)-propyl)-3-isopropyl-ureido)-propyl)-thiophene-2-carboxylic acid $^1$H NMR (400 MHz, CDCl$_3$) δ 7.70 (d, 1H, J=4), 7.00–7.40 (m, 4H), 6.80 (d, 1H, J=4), 3.20 (m, 4H), 2.85 (m, 2H), 2.60 (m, 2H), 1.75–2.00 (m, 4H), 1.05 (d, 6H, J=7); MS 423.1 (M+1), 421.1 (M−1).

EXAMPLE 7b 5-(3-(1-(3-(3-Chloro-phenyl)-propyl)-3-phenyl-ureido)-propyl)-thiophene-2-carboxylic acid $^1$H NMR (400 MHz, CDCl$_3$) δ 7.75 (d, 1H, J=7), 7.00–7.50 (m, 9H), 6.80 (d, 1H, J=4), 3.20 (m, 4H), 2.90 (m, 2H), 2.60 (m, 2H), 1.80–2.00 (m, 4H); MS 457.1 (M+1), 455.2 (M−1).

EXAMPLE 7c 5-(3-(1-(3-(3-Chloro-phenyl)-propyl)-3-(3,4-dichloro-phenyl)-ureido)-propyl)-thiophene-2-carboxylic acid $^1$H NMR (400 MHz, CDCl$_3$) δ 6.80–7.60 (m, 9H), 3.20 (m, 4H), 2.90 (m, 2H), 2.60 (m, 2H), 1.86–2.00 (m, 4H); MS 527.0 (M+1), 525.0 (M−1).

EXAMPLE 7d 5-(3-(1-(3-(3-Chloro-phenyl)-propyl)-3-propyl-ureido)-propyl)-thiophene-2-carboxylic acid $^1$H NMR (400 MHz, CDCl$_3$) δ 7.70 (d, 1H, J=4), 7.00–7.30 (m, 4H), 6.80 (d, 1H, J=4), 3.20–3.30 (m, 5H), 2.95 (t, 2H, J=7), 2.60 (t, 2H, J=7), 1.70–2.00 (m, 4H), 0.95 (t, 3H, J=7); MS 423 (M+1), 421 (M−1).

EXAMPLE 7e 5-(3-(3-(4-Chloro-phenyl)-1-(3-(3-chloro-phenyl)-propyl)-ureido)-propyl)-thiophene-2-carboxylic acid $^1$H NMR (400 MHz, CDCl$_3$) δ 7.70 (d, 1H, J=4), 7.00–7.30 (m, 8H), 6.80 (d, 1H, J=4), 3.22 (m, 4H), 2.90 (m, 2H), 2.65 (m, 2H), 1.69–2.02 (m, 4H); MS 491 (M+1), 489 (M−1).

EXAMPLE 7f 5-(3-(1-(3-(3-Chloro-phenyl)-propyl)-3-(2,3-dichloro-phenyl)-ureido)-propyl)-thiophene-2-carboxylic acid $^1$H NMR (400 MHz, CDCl$_3$) δ 7.70 (bs, 1H), 7.00–7.30 (m, 7H), 6.80 (bs, 1H), 3.20 (m, 4H), 2.80 (m, 2H), 2.60 (m, 2H), 1.75–2.00 (m, 4H); MS 527 (M+1), 525.1 (M−1).

EXAMPLE 7g 5-(3-(1-(3-(3-Chloro-phenyl)-propyl)-3-(3,5-dichloro-phenyl)-ureido)-propyl)-thiophene-2-carboxylic acid $^1$H NMR (400 MHz, CDCl$_3$) δ 7.70 (d, 1H, J=4), 7.00–7.30 (m, 7H), 6.80 (d, 1H, J=4), 3.20 (m, 4H), 2.80 (m, 2H), 2.60 (m, 2H), 1.70–2.00 (m, 4H); MS 527.1 (M+1), 525.1 (M−1).

EXAMPLE 7h 5-(3-(1-(3-(3-Chloro-phenyl)-propyl)-3-(2,6-difluoro-phenyl)-ureido)-propyl)-thiophene-2-carboxylic acid $^1$H NMR (400 MHz, CDCl$_3$) δ 7.70 (d, 1H, J=4), 7.00–7.30 (m, 7H), 6.80 (d, 1H, J=4), 3.20 (m, 4H), 2.86 (m, 2H), 2.65 (m, 2H), 1.73–1.95 (m, 4H); MS 493.1 (M+1), 491.1 (M−1).

EXAMPLE 7i 5-(3-(1-(3-(3-Chloro-phenyl)-propyl)-3-(4-fluoro-phenyl)-ureido)-propyl)-thiophene-2-carboxylic acid $^1$H NMR (400 MHz, CDCl$_3$) δ 7.70 (bs, 1H), 7.00–7.60 (m, 8H), 6.80 (bs, 1H), 3.30 (m, 4H), 2.90 (m, 2H), 2.60 (m, 2H), 1.80–2.00 (m, 4H); MS 475.1 (M+1), 473.1 (M−1).

EXAMPLE 7j 5-(3-(3-Butyl-1-(3-(3-chloro-phenyl)-propyl)-ureido)-propyl)-thiophene-2-carboxylic acid $^1$H NMR (400 MHz, CDCl$_3$) δ 7.70 (bs, 1H), 7.00–7.20 (m, 4H), 6.80 (bs, 1H), 3.20 (m, 6H), 2.90 (m, 2H), 2.60 (m, 2H), 1.70–2.00 (m, 4H), 0.95 (t, 3H, J=6.8); MS 437.2 (M+1), 435.2 (M−1).

EXAMPLE 8

5-(3-((3-(3-Chloro-phenyl)-propyl)-(pyrrolidine-1-carbonyl)-amino)-propyl)-thiophene-2-carboxylic acid

Step A: Amide Formation 5-(3-(1-(3-(3-Chloro-phenyl)-propyl)-3-ethyl-ureido)-propyl)-thiophene-2-carboxylic acid tert-butyl ester. A stock solution of 5-(3-(3-(3-chloro-phenyl)-propylamino)-propyl)-thiophene-2-carboxylic acid tert-butyl ester (from Preparation 9, 0.10 g, 0.254 mmol) in 10 mL CH$_2$Cl$_2$ was prepared and 1 mL (0.010 g, 0.0254 mmol) was added to a 1 dram vial. Triethylamine (0.7 mL, 0.051 mmol) and ethyl isocyanate (0.004 g, 0.051 mmol) were added and the reaction was stirred overnight at room temperature. The reaction was diluted with 2 mL CH$_2$Cl$_2$ and the organic solution was washed with 3 mL of 5.5% aqueous HCl solution (2×) followed by 3 mL saturated bicarbonate solution (2×). The organic layer was dried with MgSO$_4$ and concentrated to yield the titled compound of Step A (10 mg).

Step B: Ester Hydrolysis

Step B was performed in a manner analogous to the method of Step B of Example 6. $^1$H NMR (400 MHz, CDCl$_3$) δ 7.70 (d, 1H, J=4), 7.00–7.40 (m, 4H), 6.80 (d, 1H, J=4), 3.20 (m, 8H), 2.80 (m, 2H), 2.60 (m, 2H), 1.70–2.00 (m, 8H), 1.20 (m, 4H); MS 435.1 (M+1), 433.2 (M−1).

EXAMPLES 8a–8c

Examples 8a–8c were prepared from the appropriate starting material in a manner analogous to the method of Example 8.

EXAMPLE 8a 5-(3-((3-(3-Chloro-phenyl)-propyl)-(morpholine-4-carbonyl)-amino)-propyl)-thiophene-2-carboxylic acid $^1$H NMR (400 MHz, CDCl$_3$) δ 7.65 (d, 1H, J=4), 7.00–7.40 (m, 4H), 6.80 (d, 1H, J=4), 3.60 (m, 4H), 3.00–3.20 (m, 8H), 2.80 (m, 2H), 2.60 (m, 2H), 1.70–2.00 (m, 4H); MS 451.1 (M+1), 449.2 (M−1).

EXAMPLE 8b 5-(3-((3-(3-Chloro-phenyl)-propyl)-isopropoxycarbonyl-amino)-propyl)-thiophene-2-carboxylic acid $^1$H NMR (400 MHz, CDCl$_3$) δ 6.70 (d, 1H, J=4), 7.00–7.30 (m, 4H), 6.80 (d, 1H, J=4), 3.20 (m, 4H), 2.80 (t, 2H, J=6.7), 2.60 (t, 2H, J=6.7), 1.80–2.00 (m, 4H), 1.01 (d, 6H); MS 424 (M+1), 422 (M−1).

EXAMPLE 8c 5-(3-((3-(3-Chloro-phenyl)-propyl)-propoxycarbonyl-amino)-propyl)-thiophene-2-carboxylic acid $^1$H NMR (400 MHz, CDCl$_3$) δ 7.70 (bs, 1H), 7.00–7.30 (m, 4H), 6.80 (bs, 1H), 4.00 (t, 2H, J=6.8), 3.30 (m, 4H), 2.80 (m, 2H), 2.60 (m, 2H), 1.40–2.00 (m, 6H), 0.90 (t, 3H, J=7); MS 424 (M+1), 422.2 (M−1).

EXAMPLE 9

(3-(((4-Butyl-benzyl)-(pyridine-3-sulfonyl)-amino)-methyl)-phenyl)-acetic acid

Step A: Reductive Amination (3-((4-Butyl-benzylamino)-methyl)-phenyl)-acetic acid methyl ester. A solution of 4-butyl-benzylamine (from Preparation 15, 0.918 g, 6 mmol) in MeOH was added to 4N HCl in dioxane (0.75 mL, 3 mmol) followed by addition of (3-formyl-phenyl)-acetic acid methyl ester (from Preparation 13, 0.534 g, 3.0 mmol). NaCNBH$_3$ (0.194 mL, 3 mmol) was added and the reaction was stirred at room temperature overnight. The mixture was diluted with EtOAc and 2N NaOH was added. The organic solution was dried over MgSO$_4$, filtered, and concentrated in vacuo. The product was purified via flash chromatography (50% hexanes, 50% EtOAc, 0.1% Et$_3$N) to afford the title compound of Step A. $^1$H NMR (400 MHz, CDCl$_3$) δ 7.08–7.38 (m, 8H), 3.75 (s, 2H), 3.73 (s, 2H), 3.70 (s, 3H), 3.62 (s, 2H), 2.61 (t, 2H), 1.58 (m, 2H), 1.37 (m, 2H), 0.92 (t, 3H); MS 326 (M+1).

Step B: Amide Formation (3-(((4-Butyl-benzyl)-(pyridine-3-sulfonyl)-amino)-methyl)-phenyl)-acetic acid methyl ester. Step B was performed in a manner analogous to the method of Step B of Example 1 to provide the title compound.

Step C: Ester Hydrolysis (3-(((4-Butyl-benzyl)-(pyridine-3-sulfonyl)-amino)-methyl)-phenyl)-acetic acid. Step C was performed in a manner analogous to the method of Step C of Example 1 to provide the title compound. $^1$H NMR (400 MHz, CDCl$_3$) δ 8.99 (bs, 1H), 8.74 (bs, 1H), 7.99 (d, 1H), 7.36 (bs, 1H), 7.20–7.25 (m, 2H), 6.95–7.19 (m, 6H), 4.33 (s, 4H), 3.3.54 (s, 2H), 2.54 (m, 2H), 1.54 (m, 2H), 1.32 (m, 2H), 0.91 (t, 3H).

EXAMPLES 9a–9d

Examples 9a–9d were prepared from the appropriate starting materials in a manner analogous to the method of Example 9.

EXAMPLE 9a (3-((Benzenesulfonyl-(4-butyl-benzyl)-amino)-methyl)-phenyl)-acetic acid $^1$H NMR (400 MHz, CDCl$_3$) δ 7.83 (d, 2H), 7.46–7.58 (m, 3H), 7.24 (s, 1H), 7.14 (m, 2H), 6.86–6.98 (m, 5H), 4.29 (d, 4H), 3.51 (s, 2H), 2.52 (t, 2H), 1.53 (m, 2H), 1.30 (m, 2H), 0.90 (t, 2H); MS 450 (M−1).

EXAMPLE 9b (3-(((4-Butyl-benzyl)-(thiophene-2-sulfonyl)-amino)-methyl)-phenyl)-acetic acid $^1$H NMR (400 MHz, CDCl$_3$) δ 7.53 (m, 2H), 7.16 (m, 2H), 6.89–7.14 (m, 7H), 4.27 (d, 4H), 3.52 (s, 2H), 2.49 (t, 2H), 1.51 (m, 2H), 1.29 (m, 2H), 0.88 (t, 2H); MS 456 (M−1).

EXAMPLE 9c (3-(((4-Acetylamino-benzenesulfonyl)-(4-butyl-benzyl)-amino)-methyl)-phenyl)-acetic acid $^1$H NMR (400 MHz, CDCl$_3$) δ 7.69 (m, 2H), 7.49 (d, 2H), 7.06–7.23 (m, 6H), 6.91 (d, 1H), 6.68 (s, 1H), 4.30 (d, 4H), 3.44 (s, 2H), 2.54 (t, 2H), 2.17 (s, 3H), 1.54 (m, 2H), 1.29 (m, 2H), 0.89 (t, 2H); MS 507 (M−1).

EXAMPLE 9d (3-(((Benzo[1,2,5]oxadiazole-4-sulfonyl)-(4-butyl-benzyl)-amino)-methyl)-phenyl)-acetic acid $^1$H NMR (400 MHz, CDCl$_3$) δ 7.94 (d, 1H), 7.88 (d, 2H), 7.36 (t, 1H), 7.07 (s, 2H), 6.90–6.96 (m, 6H), 53 (d, 4H), 3.46 (s, 2H), 2.46 (t, 2H), 1.47 (m, 2H), 1.26 (m, 2H), 0.88 (t, 2H); MS 4.92 (M−1).

EXAMPLE 10

(3-(((1-Methyl-1H-imidazole-4-sulfonyl)-(4-pyrimidin-2-yl-benzyl)-amino)-methyl)-phenoxy)-acetic acid•HCl Step A: Reductive Amination (3-((4-Pyrimidin-2-yl-benzylamino)-methyl)-phenoxy)-acetic acid t-butyl ester. Step A was performed in a manner analogous to the method of Step A of Example 1.

Step B: Amide Formation (3-(((1-Methyl-1H-imidazole-4-sulfonyl)-(4-pyrimidin-2-yl-benzyl)-amino)-methyl)-phenoxy)-acetic acid tert-butyl ester. Step B was performed in a manner analogous to the method of Step B of Example 1 using triethylamine in place of N,N-diisopropylethylamine as base.

Step C: Ester Hydrolysis (3-(((1-Methyl-1H-imidazole-4-sulfonyl)-(4-pyrimidin-2-yl-benzyl)-amino)-methyl)-phenoxy)-acetic acid•HCl. A solution of (3-(((1-methyl-1H-imidazole-4-sulfonyl)-(4-pyrimidin-2-yl-benzyl)-amino)-methyl)-phenoxy)-acetic acid tert-butyl ester prepared of Example 10, Step B (0.094 g, 0.17 mmol) in 1N HCl in diethyl ether was stirred for 20 minutes as a precipitate formed. To the mixture was added 1 mL water and 1 mL dioxane and the reaction was stirred for 3 hours. The solvent was removed in vacuo, azeotroping with ethanol to yield the title compound as a solid (54 mg). $^1$H NMR (400 MHz, CD$_3$OD) δ 9.09 (m, 2H), 8.95 (bs, 1H), 8.24 (d, 2H), 8.04 (s, 1H), 7.71 (s, 1H), 7.44 (d, 2H), 7.13 (m, 1H), 6.82 (d, 1H), 6.76 (d, 1H), 6.69 (s, 1H), 4.61 (s, 2H), 4.54 (s, 2H), 4.46 (s, 2H), 3.92 (s, 3H); MS 494 (M+1).

EXAMPLES 11a–11z, 12a–12z

Examples 11a–11z, 12a–12z were prepared from the appropriate starting materials in a manner analogous to the method of Example 1, with variations in reaction time, temperature, and reagents as noted.

EXAMPLE 11a 3-(3-{[Benzenesulfonyl-(4-pyrazin-2-yl-benzyl)-amino]-methyl}-phenyl)-propionic acid Step A: Reductive Amination 3-{3-[(4-Pyrazin-2-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-pyrazin-2-yl-benzaldehyde, of Preparation 27, using the method described in Example 1, Step A except the imine was formed in MeOH at reflux over 2 h. $^1$H NMR (400 MHz, CDCl$_3$) δ 9.01 (s, 1H), 8.62 (dd, 1H), 8.49 (d, 1H), 7.98 (d, 2H), 7.66 (m, 1H), 7.54–7.43 (m, 3H), 7.24 (m, 1H), 7.09 (m, 1H), 3.88 (s, 2H), 3.80 (s, 2H), 3.66 (s, 3H), 2.94 (t, 2H), 2.63 (t, 2H); MS 362 (M+1).

Step B: Amide Formation 3-(3-{[Benzenesulfonyl-(4-pyrazin-2-yl-benzyl)-amino]-methyl}-phenyl)-propionic acid methyl ester. The title compound of Step B was prepared from 3-{3-[(4-pyrazin-2-yl-benzylamino)-methyl]-phenyl}-propionic acid methyl ester, of Step A, and benzenesulfonyl chloride following the method described in Example 1, Step B using triethylamine in place of N,N-diisopropylethylamine. $^1$H NMR (400 MHz, CDCl$_3$) δ 8.98 (s, 1H), 8.60 (m, 1H), 8.50 (d, 1H), 7.87 (m, 4H), 7.63 (m, 1H), 7.56 (m, 2H), 7.17 (d, 2H), 7.12 (m, 1H), 7.02 (d, 1H), 6.87 (d, 1H), 6.78 (s, 1H), 4.37 (s, 2H), 4.32 (s, 2H), 3.64 (s, 3H), 2.78 (t, 2H), 2.47 (t, 2H); MS 502 (M+1).

Step C: Ester Hydrolysis 3-(3-{[Benzenesulfonyl-(4-pyrazin-2-yl-benzyl)-amino]-methyl}-phenyl)-propionic acid. The title compound was prepared following the method described in Example 1, Step C from 3-(3-{[benzenesulfonyl-(4-pyrazin-2-yl-benzyl)-amino]-methyl}-phenyl)-propionic acid methyl ester of Step B. MS 486 (M−1).

EXAMPLE 11b 3-(3-{[Benzenesulfonyl-(4-pyridin-3-yl-benzyl)-amino]-methyl}-phenyl)-propionic acid Step A: Reductive Amination 3-{3-[(4-Pyridin-3-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-pyridin-3-yl-benzaldehyde, of Preparation 23, using the method described in Example 1, Step A. $^1$H NMR (400 MHz, CDCl$_3$) δ 8.81 (d, 1H), 8.55 (dd, 1H), 7.84 (m, 1H), 7.53 (d, 2H), 7.44 (d, 2H), 7.33 (m, 1H), 7.26–7.18 (m, 3H), 7.07 (d, 1H), 3.84 (s, 2H), 3.79 (s, 2H), 3.64 (s, 3H), 2.92 (t, 2H), 2.61 (t, 2H); MS 361 (M+1).

Step B: Amide Formation 3-(3-{[Benzenesulfonyl-(4-pyridin-3-yl-benzyl)-amino]-methyl}-phenyl)-propionic acid methyl ester. The title compound of Step B was prepared from 3-{3-[4-pyridin-3-yl-benzylamino)-methyl]-phenyl}-propionic acid methyl ester, of Step A, and benzenesulfonyl chloride following the method described in Example 1, Step B using triethylamine in place of N,N-diisopropylethylamine. $^1$H NMR (400 MHz, CDCl$_3$) δ 8.79 (s, 1H), 8.58 (d, 1H), 7.87 (m, 3H), 7.61 (m, 1H), 7.54 (m, 2H), 7.40 (m, 3H), 7.18 (m, 3H), 7.03 (d, 1H), 6.88 (d, 1H), 6.79 (s, 1H), 4.36 (s, 2H), 4.33 (s, 2H), 3.65 (s, 3H), 2.79 (t, 2H), 2.48 (t, 2H); MS 501 (M+1).

Step C: Ester Hydrolysis 3-(3-{[Benzenesulfonyl-(4-pyridin-3-yl-benzyl)-amino]-methyl}-phenyl)-propionic acid. The title compound was prepared following the method described in Example 1, Step C from 3-(3-{[benzenesulfonyl-(4-pyridin-3-yl-benzyl)-amino]-methyl}-phenyl)-propionic acid methyl ester of Step B. $^1$H NMR (400 MHz, CDCl$_3$) δ 9.14 (s, 1H), 8.63 (d, 1H), 8.46 (d, 1H), 7.90 (m, 3H), 7.63 (m, 3H), 7.40 (d, 2H), 7.22 (m, 2H), 6.91 (m, 3H), 6.75 (d, 1H), 4.36 (s, 2H), 4.27 (s, 2H), 2.81 (t, 2H), 2.56 (t, 2H); MS 485 (M−1).

EXAMPLE 11c

7-[(Pyridine-2-sulfonyl)-(4-thiazol-2-yl-benzyl)-amino]-heptanoic acid

Step A: Reductive Amination 7-(4-Thiazol-2-yl-benzylamino)-heptanoic acid methyl ester. The title compound was prepared following the procedure described in Step A of Example 1 from 7-amino-heptanoic acid methyl ester hydrochloride, of Preparation 1, and 4-thiazol-2-yl-benzaldehyde, of Preparation 25. $^1$H NMR (400 MHz, CDCl$_3$) δ 7.91 (d, 2H), 7.84 (d, 1H), 7.38 (d, 2H), 7.30 (d, 1H), 3.82 (s, 2H), 3.65 (s, 3H), 2.62 (t, 2H), 2.29 (t, 2H), 1.61 (m, 2H), 1.51 (m, 2H), 1.33 (m, 4H); MS 333 (M+1).

Step B: Sulfonamide Formation

7-[(Pyridine-2-sulfonyl)-(4-thiazol-2-yl-benzyl)-amino]-heptanoic acid methyl ester. The title compound of Step B was prepared following the procedure described in Step B of Example 1 from 7-(4-thiazol-2-yl-benzylamino)-heptanoic acid methyl ester, of Step A and pyridine-2-sulfonyl chloride hydrochloride, of Preparation 47. $^1$H NMR (400 MHz, CDCl$_3$) δ 9.06 (d, 1H), 8.81 (m, 1H), 8.10 (m, 1H), 7.91 (d, 2H), 7.86 (m, 1H), 7.46 (m, 1H), 7.34 (m, 3H), 4.39 (s, 2H), 3.62 (s, 3H), 3.15 (t, 2H), 2.21 (t, 2H), 1.48 (m, 2H), 1.37 (m, 2H), 1.15 (m, 4H); MS 474 (M+1).

Step C: Ester Hydrolysis

7-[(Pyridine-2-sulfonyl)-(4-thiazol-2-yl-benzyl)-amino]-heptanoic acid. The title compound was prepared following the procedure described in Step C of Example 1 from 7-[(pyridine-2-sulfonyl)-(4-thiazol-2-yl-benzyl)-amino]-heptanoic acid methyl ester, of Step B. $^1$H NMR (400 MHz, CDCl$_3$) δ 9.07 (s, 1H), 8.81 (m, 1H), 8.11 (m, 1H), 7.87 (m, 3H), 7.48 (m, 1H), 7.37 (m, 3H), 4.37 (s, 2H), 3.14 (t, 2H), 2.23 (t, 2H), 1.51 (m, 2H), 1.48 (m, 2H), 1.13 (m, 4H).

EXAMPLE 11d (3-{[(4-Butyl-benzyl)-(1-methyl-1H-imidazole-4-sulfonyl)-amino]-methyl}-phenyl)-acetic acid Step A: Amide Formation (3-{[(4-Butyl-benzyl)-(1-methyl-1H-imidazole-4-sulfonyl)-amino]-methyl}-phenyl)-acetic acid methyl ester. The title compound of Step B was prepared following the procedure described in Step B of Example 1 from {3-[(4-butyl-benzylamino)-methyl]-phenyl}-acetic acid methyl ester, prepared in Step A of Example 9, and 1-methyl-1H-imidazole-4-sulfonyl chloride. $^1$H NMR (400 MHz, CDCl$_3$) δ 7.47 (s, 1H), 7.34 (s, 1H), 7.18–7.02 (m, 8H), 4.38 (s, 4H), 3.71 (s, 3H), 3.68 (s, 3H), 3.52 (s, 2H), 2.55 (t, 2H), 1.55 (m, 2H), 1.32 (m, 2H), 0.91 (t, 3H); MS 470 (M+1).

Step B: Ester Hydrolysis (3-{[(4-Butyl-benzyl)-(1-methyl-1H-imidazole-4-sulfonyl)-amino]-methyl}-phenyl)-acetic acid. The title compound was prepared following the procedure described in Step C of Example 1 from (3-{[(4-butyl-benzyl)-(1-methyl-1H-imidazole-4-sulfonyl)-amino]-methyl}-phenyl)-acetic acid methyl ester of Step A. $^1$H NMR (400 MHz, CDCl$_3$) δ 7.58 (s, 1H), 7.28 (s, 1H), 7.15–6.99 (m, 8H), 4.36 (s, 2H), 4.33 (s, 2H), 3.65 (s, 3H), 3.52 (s, 2H), 2.54 (t, 2H), 1.54 (m, 2H), 1.32 (m, 2H), 0.91 (t, 3H); MS 454 (M−1).

EXAMPLE 11e 3-(3-{[(1-Methyl-1H-imidazole-4-sulfonyl)-(4-thiazol-2-yl-benzyl)-amino]-methyl}-phenyl)-propionic acid Step A: Reductive Amination 3-{3-[(4-Thiazol-2-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-thiazol-2-yl-benzaldehyde, of Preparation 25, using the method described in Example 1, Step A, except the imine was formed in MeOH at reflux over 2 h. $^1$H NMR (400 MHz, CDCl$_3$) δ 7.93 (d, 2H), 7.85 (d, 1H), 7.43 (d, 2H), 7.31 (d, 1H), 7.28–7.09 (m, 4H), 3.84 (s, 2H), 3.79 (s, 2H), 3.66 (s, 3H), 2.94 (t, 2H), 2.63 (t, 2H); MS 367 (M+1).

Step B: Amide Formation 3-(3-{[(1-Methyl-1H-imidazole-4-sulfonyl)-(4-thiazol-2-yl-benzyl)-amino]-methyl}-phenyl)-propionic acid methyl ester. The title compound of Step B was prepared from 3-{3-[(4-thiazol-2-yl-benzylamino)-methyl]-phenyl}-propionic acid methyl ester, of Step A, and 1-methyl-1H-imidazole-4-sulfonyl chloride following the method described in Example 1, Step B. MS 511 (M+1).

Step C: Ester Hydrolysis 3-(3-{[(1-Methyl-1H-imidazole-4-sulfonyl)-(4-thiazol-2-yl-benzyl)-amino]-methyl}-phenyl)-propionic acid. The title compound was prepared following the method described in Example 1, Step C from 3-(3-{[(1-methyl-1H-imidazole-4-sulfonyl)-(4-thiazol-2-yl-benzyl)-amino]-methyl}-phenyl)-propionic acid methyl ester of Step B. $^1$H NMR (400 MHz, CDCl$_3$) δ 7.86 (d, 2H), 7.69 (d, 2H), 7.59 (s, 1H), 7.46 (s, 1H), 7.36 (m, 1H), 7.19 (d, 2H), 7.15–6.99 (m, 3H), 6.88 (s, 1H), 4.46 (s, 2H), 4.37 (s, 2H), 3.76 (s, 3H), 2.80 (t, 2H), 2.50 (t, 2H); MS 495 (M−1).

EXAMPLE 11f

7-[(4-Pyrazol-1-yl-benzyl)-(pyridine-2-sulfonyl)-amino]-heptanoic acid

Step A: Reductive Amination 7-(4-Pyrazol-1-yl-benzylamino)-heptanoic acid methyl ester. The title compound of Step A was prepared from 7-amino-heptanoic acid methyl ester hydrochloride, of Preparation 1, and 4-pyrazol-1-yl-benzaldehyde, of Preparation 42, using the method described in Example 1, Step A. $^1$H NMR (400 MHz, CDCl$_3$) δ 7.90 (m, 1H), 7.70 (d, 1H), 7.63 (d, 2H), 7.39 (d, 2H), 6.45 (m, 1H), 3.80 (s, 2H), 3.65 (s, 3H), 2.61 (t, 2H), 2.29 (t, 2H), 1.63–1.32 (m, 4H), 1.25 (m, 4H); MS 316 (M+1).

Step B: Amide Formation

7-[(4-Pyrazol-1-yl-benzyl)-(pyridine-2-sulfonyl)-amino]-heptanoic acid methyl ester. The title compound of Step B was prepared from 7-(4-pyrazol-1-yl-benzylamino)-heptanoic acid methyl ester, of Step A, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 9.06 (m, 1H), 8.80 (dd, 1H), 8.10 (m, 1H), 7.92 (d, 1H), 7.71 (d, 1H), 7.65 (d, 2H), 7.48 (m, 1H), 7.36 (d, 2H), 6.46 (d, 1H), 4.38 (s, 2H), 3.62 (s, 3H), 3.14 (t, 2H), 2.21 (t, 2H), 1.48 (m, 2H), 1.36 (m, 2H), 1.25 (m, 4H); MS 457 (M+1).

Step C: Ester Hydrolysis

7-[(4-Pyrazol-1-yl-benzyl)-(pyridine-2-sulfonyl)-amino]-heptanoic acid. The title compound was prepared following the method described in Example 1, Step C, from 7-[(4-pyrazol-1-yl-benzyl)-(pyridine-2-sulfonyl)-amino]-heptanoic acid methyl ester of Step B. $^1$H NMR (400 MHz, CDCl$_3$) δ 9.07 (d, 1H), 8.82 (dd, 1H), 8.12 (m, 1H), 7.88 (d, 1H), 7.74 (d, 1H), 7.62 (d, 2H), 7.48 (m, 1H), 7.41 (d, 2H), 6.48 (m, 1H), 4.35 (s, 2H), 3.13 (t, 2H), 2.22 (t, 2H), 1.47 (m, 2H), 1.32 (m, 2H), 1.17 (m, 4H); MS 441 (M−1).

EXAMPLE 11g

7-[(4-Pyrazol-1-yl-benzyl)-(pyridine-3-sulfonyl)-amino]-heptanoic acid

Step A: Amide Formation

7-[(4-Pyrazol-1-yl-benzyl)-(pyridine-3-sulfonyl)-amino]-heptanoic acid methyl ester. The title compound of Step A was prepared from 7-(4-pyrazol-1-yl-benzylamino)-heptanoic acid methyl ester, of Example 11f, Step A, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 8.70 (m, 1H), 7.99–7.87 (m, 3H), 7.71 (d, 1H), 7.63 (d, 2H), 7.46 (m, 1H), 7.42 (d, 2H), 6.46 (dd, 1H), 4.56 (s, 2H), 3.62 (s, 3H), 3.25 (t, 2H), 2.20 (t, 2H), 1.46 (m, 2H), 1.34 (m, 2H), 1.25 (m, 4H); MS 457 (M+1).

Step B: Ester Hydrolysis

7-[(4-Pyrazol-1-yl-benzyl)-(pyridine-3-sulfonyl)-amino]-heptanoic acid. The title compound was prepared following the method described in Example 1, Step C, from 7-[(4-pyrazol-1-yl-benzyl)-(pyridine-3-sulfonyl)-amino]-heptanoic acid methyl ester of Step B. $^1$H NMR (400 MHz, CDCl$_3$) δ 8.71 (m, 1H), 7.99 (d, 1H), 7.90 (m, 2H), 7.74 (d, 1H), 7.60 (d, 2H), 7.48 (m, 3H), 6.47 (m, 1H), 4.56 (s, 2H), 3.24 (t, 2H), 2.20 (t, 2H), 1.46 (m, 2H), 1.29 (m, 2H), 1.12 (m, 2H), 1.05 (m, 2H); MS 441 (M−1).

EXAMPLE 11h 3-(3-{[Benzenesulfonyl-(4-pyrazol-1-yl-benzyl)-amino]-methyl}-phenyl)-propionic acid Step A: Reductive Amination 3-{3-[(4-Pyrazol-1-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-pyrazol-1-yl-benzaldehyde, of Preparation 42, using the method described in Example 1, Step A except the imine was formed in MeOH at reflux over 2 h. $^1$H NMR (400 MHz, CDCl$_3$) δ 7.81 (s, 1H), 7.44 (d, 2H), 7.32 (d, 2H), 7.24 (m, 2H), 7.17 (m, 3H), 7.07 (d, 1H), 3.82 (s, 2H), 3.77 (s, 2H), 3.64 (s, 3H), 2.92 (t, 2H), 2.61 (t, 2H); MS 350 (M+1).

Step B: Amide Formation 3-(3-{[Benzenesulfonyl-(4-pyrazol-1-yl-benzyl)-amino]-methyl}-phenyl)-propionic acid methyl ester. The title compound of Step B was prepared from 3-{3-[(4-pyrazol-1-yl-benzylamino)-methyl]-phenyl}-propionic acid methyl ester of Step A and benzenesulfonyl chloride following the method described in Example 1, Step B using triethylamine in place of N,N-diisopropylethylamine. $^1$H NMR (400 MHz, CDCl$_3$) δ 7.87 (d, 2H), 7.84 (s, 1H), 7.64–7.53 (m, 3H), 7.20 (m, 5H), 7.11 (m, 1H), 7.02 (d, 1H), 6.84 (d, 1H), 6.78 (d, 1H), 4.33 (s, 2H), 4.31 (s, 2H), 3.65 (s, 3H), 2.78 (t, 2H), 2.47 (t, 2H); MS 490 (M+1).

Step C: Ester Hydrolysis 3-(3-{[Benzenesulfonyl-(4-pyrazol-1-yl-benzyl)-amino]-methyl}-phenyl)-propionic acid. The title compound was prepared following the method described in Example 1, Step C, from 3-(3-{[benzenesulfonyl-(4-pyrazol-1-yl-benzyl)-amino]-methyl}-phenyl)-propionic acid methyl ester of Step B. $^1$H NMR (400 MHz, CDCl$_3$) (selected peaks) δ 4.44 (s, 2H), 4.36 (s, 2H), 2.88 (t, 2H), 2.65 (t, 2H); MS 474 (M−1).

EXAMPLE 11i

7-[(Pyridine-3-sulfonyl)-(4-pyrimidin-2-yl-benzyl)-amino]-heptanoic acid

Step A: Reductive Amination 7-(4-Pyrimidin-2-yl-benzylamino)-heptanoic acid methyl ester. The title compound of Step A was prepared from 7-amino-heptanoic acid methyl ester hydrochloride, of Preparation 1, and 4-pyrimidin-2-yl-benzaldehyde, of Preparation 21, using the method described in Example 1, Step A. $^1$H NMR (400 MHz, CDCl$_3$) δ 8.78 (d, 2H), 8.37 (d, 2H), 7.42 (d, 2H), 7.16 (t, 1H), 3.85 (s, 2H), 3.64 (s, 3H), 2.62 (t, 2H), 2.28 (t, 2H), 1.55 (m, 4H), 1.32 (m, 4H); MS 328 (M+1).

Step B: Amide Formation

7-[(Pyridine-3-sulfonyl)-(4-pyrimidin-2-yl-benzyl)-amino]-heptanoic acid methyl ester. The title compound of Step B was prepared from 7-(4-pyrimidin-2-yl-benzylamino)-heptanoic acid methyl ester of Step A and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 9.07 (d, 1H), 8.80 (m, 3H), 8.37 (d, 2H), 8.10 (m, 1H), 7.46 (m, 1H), 7.37 (d, 2H), 7.19 (m, 1H), 4.43 (s, 2H), 3.62 (s, 3H), 3.15 (t, 2H), 2.20 (t, 2H), 1.48 (m, 2H), 1.38 (m, 2H), 1.14 (m, 4H); MS 469 (M+1).

Step C: Ester Hydrolysis

7-[(Pyridine-3-sulfonyl)-(4-pyrimidin-2-yl-benzyl)-amino]-heptanoic acid. The title compound was prepared following the method described in Example 1, Step C, from 7-[(pyridine-3-sulfonyl)-(4-pyrimidin-2-yl-benzyl)-amino]-heptanoic acid methyl ester of Step B. $^1$H NMR (400 MHz, CDCl$_3$) δ 9.08 (s, 1H), 8.82 (m, 3H), 8.29 (d, 2H), 8.13 (m, 1H), 7.48 (m, 1H), 7.42 (d, 2H), 7.24 (m, 1H), 4.40 (s, 2H), 3.14 (t, 2H), 2.22 (t, 2H), 1.48 (m, 2H), 1.32 (m, 2H), 1.14 (m, 2H), 1.06 (m, 2H); MS 453 (M−1).

EXAMPLE 11j

7-[(1-Methyl-1H-imidazole-4-sulfonyl)-(4-thiazol-2-yl-benzyl)-amino]-heptanoic acid

Step A: Reductive Amination 7-(4-Thiazol-2-yl-benzylamino)-heptanoic acid methyl ester. The title compound of Step A was prepared from 7-amino-heptanoic acid methyl ester hydrochloride, of Preparation 1, and 4-thiazol-2-yl-benzaldehyde, of Preparation 25, using the method described in Example 1, Step A. $^1$H NMR (400 MHz, CDCl$_3$) δ 7.91 (d, 2H), 7.84 (d, 1H), 7.38 (d, 2H), 7.30 (d, 1H), 3.82 (s, 2H), 3.65 (s, 3H), 2.62 (t, 2H), 2.29 (t, 2H), 1.61 (m, 2H), 1.51 (m, 2H), 1.33 (m, 4H); MS 333 (M+1).

Step B: Amide Formation

7-[(1-Methyl-1H-imidazole-4-sulfonyl)-(4-thiazol-2-yl-benzyl)-amino]-heptanoic acid methyl ester. The title compound of Step B was prepared from 7-(4-thiazol-2-yl-benzylamino)-heptanoic acid methyl ester of Step A and 1-methyl-1H-imidazole-4-sulfonyl chloride following the method described in Example 1, Step B using triethylamine in place of N,N-diisopropylethylamine. $^1$H NMR (400 MHz, CDCl$_3$) δ 7.90 (d, 2H), 7.85 (d, 1H), 7.49 (s, 1H), 7.43 (m, 3H), 7.32 (d, 1H), 4.47 (s, 2H), 3.74 (s, 3H), 3.62 (s, 3H), 3.20 (t, 2H), 2.20 (t, 2H), 1.48 (m, 2H), 1.40 (m, 2H), 1.15 (m, 4H); MS 477 (M+1).

Step C: Ester Hydrolysis

7-[(1-Methyl-1H-imidazole-4-sulfonyl)-(4-thiazol-2-yl-benzyl)-amino]-heptanoic acid. The title compound was prepared following the method described in Example 1, Step C, from 7-[(1-methyl-1H-imidazole-4-sulfonyl)-(4-thiazol-2-yl-benzyl)-amino]-heptanoic acid methyl ester of Step B. $^1$H NMR (400 MHz, CDCl$_3$) δ 7.87 (m, 3H), 7.48–7.34 (m, 4H), 7.32 (d, 1H), 4.46 (s, 2H), 3.75 (s, 3H), 3.19 (t, 2H), 2.21 (t, 2H), 1.48 (m, 2H), 1.31 (m, 2H), 1.24 (m, 2H), 1.16 (m, 2H).

EXAMPLE 11k

5-{3-[(Pyridine-3-sulfonyl)-(4-thiazol-2-yl-benzyl)-amino]-propyl}-thiophene-2-carboxylic acid

Step A: Reductive Amination

5-[3-(4-Thiazol-2-yl-benzylamino)-propyl]-thiophene-2-carboxylic acid methyl ester. The title compound of Step A was prepared from 5-(3-amino-propyl)-thiophene-2-carboxylic acid methyl ester, of Preparation 5, and 4-thiazol-2-yl-benzaldehyde, of Preparation 25, using the method described in Example 1, Step A, except N,N-diisopropylethylamine was used in place of triethylamine. $^1$H NMR (400 MHz, CDCl$_3$) δ 8.97–7.32 (m, 7H), 6.72 (d, 1H, J=4 Hz), 3.82 (s, 3H), 3.70 (s, 2H), 2.91 (t, 2H, J=7 Hz), 2.62 (t, 2H, J=7 Hz), 1.90 (m, 2H); MS 373 (M+1).

Step B: Amide Formation

5-{3-[(Pyridine-3-sulfonyl)-(4-thiazol-2-yl-benzyl)-amino]-propyl}-thiophene-2-carboxylic acid methyl ester. The title compound of Step B was prepared from 5-[3-(4-thiazol-2-yl-benzylamino)-propyl]-thiophene-2-carboxylic acid methyl ester of Step A and pyridine-3-sulfonyl chloride hydrochloride, of Preparation 2, following the method described in Example 1, Step B using triethylamine in place of N,N-diisopropylethylamine. MS 514 (M+1).

Step C: Ester Hydrolysis

5-{3-[(Pyridine-3-sulfonyl)-(4-thiazol-2-yl-benzyl)-amino]-propyl}-thiophene-2-carboxylic acid. The title compound was prepared following the method described in Example 1, Step C, from 5-{3-[(pyridine-3-sulfonyl)-(4-thiazol-2-yl-benzyl)-amino]-propyl}-thiophene-2-carboxylic acid methyl ester of Step B using EtOH in place of MeOH as solvent. $^1$H NMR (400 MHz, CDCl$_3$) δ 9.12 (d, 1H, J=4 Hz), 8.81 (d, 1H, J=5 Hz), 8.17–7.21 (m, 9H), 6.61 (d, 1H, J=4 Hz), 4.41 (s, 2H), 3.25 (t, 2H, J=6.5 Hz), 2.72 (t, 2H, J=6.5 Hz), 1.73 (m, 2H); MS 498 (M−1).

EXAMPLE 11l

5-(3-{[3-(3-Chloro-phenyl)-propyl]-cyclopropanesulfonyl-amino}-propyl)-thiophene-2-carboxylic acid

Step A: Amide Formation 5-(3-{[3-(3-Chloro-phenyl)-propyl]-cyclopropane-sulfonyl-amino}-propyl)-thiophene-2-carboxylic acid methyl ester. To a solution of 5-{3-[3-(3-chloro-phenyl)-propylamino]-propyl}-thiophene-2-carboxylic acid methyl ester (51.5 mg, 0.1463 mmol), of Preparation 8, in CH$_2$Cl$_2$ (10 mL) at 0° C. was added cyclopropanesulfonyl chloride (22.6 mg, 0.161 mmol) and triethylamine (0.45 mL, 0.32 mmol). The reaction was warmed to room temperature and was stirred for 48 h. The reaction was heated at reflux for 48 h and additional triethylamine (0.45 mL) and cyclopropane-sulfonyl chloride (22.6 mg) were added. The reaction was heated at reflux for 7.5 h, was cooled to room temperature and was stirred for 72 h. The reaction was heated at reflux for 24 h. The organic solution was washed sequentially with 5.5% aqueous HCl, water, saturated sodium bicarbonate solution, and brine. The organic solution was dried (MgSO$_4$), filtered, and concentrated to provide the title compound of Step A (78.1 mg). MS 456 (M+).

Step B: Ester Hydrolysis 5-(3-{[3-(3-Chloro-phenyl)-propyl]-cyclopropane-sulfonyl-amino}-propyl)-thiophene-2-carboxylic acid. The title compound was prepared following the method described in Example 1, Step C from 5-(3-{[3-(3-chloro-phenyl)-propyl]-cyclopropanesulfonyl-amino}-propyl)-thiophene-2-carboxylic acid methyl ester of Step A except the reaction was performed in EtOH. $^1$H NMR (400

MHz, CDCl$_3$) δ 7.62 (d, 1H, J=3.4 Hz), 7.42–7.00 (m, 4H), 6.62 (d, 1H, J=3.4 Hz), 3.25 (m, 2H), 2.92 (m, 2H), 2.31 (m, 1H), 2.20 (m, 2H), 1.32–0.90 (m, 4H); MS 440 (M−1).

EXAMPLE 11m 3-(3-{[(Pyridine-3-sulfonyl)-(4-pyridin-3-yl-benzyl)-amino]-methyl}-phenyl)-propionic acid Step A: Reductive Amination 3-{3-[(4-Pyridin-3-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-pyridin-3-yl-benzaldehyde, of Preparation 23, using the method described in Example 1, Step A. $^1$H NMR (400 MHz, CDCl$_3$) δ 8.79 (s, 1H), 8.55 (m, 1H), 7.81 (d, 1H), 7.53 (d, 2H), 7.46 (d, 2H), 7.32 (m, 1H), 7.22 (m, 3H), 7.09 (d, 1H), 3.84 (s, 2H), 3.80 (s, 2H), 3.63 (s, 3H), 2.92 (t, 2H), 2.61 (t, 2H).

Step B: Amide Formation 3-(3-{[(Pyridine-3-sulfonyl)-(4-pyridin-3-yl-benzyl)-amino]-methyl}-phenyl)-propionic acid methyl ester. The title compound of Step B was prepared from 3-{3-[(4-pyridin-3-yl-benzylamino)-methyl]-phenyl}-propionic acid methyl ester, of Step A, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 9.05 (d, 1H), 8.80 (m, 2H), 8.60 (d, 1H), 8.06 (m, 1H), 7.91 (m, 1H), 7.44 (m, 4H), 7.21 (d, 2H), 7.15 (m, 1H), 7.06 (d, 1H), 6.92 (d, 1H), 6.87 (s, 1H), 4.41 (s, 2H), 4.38 (s, 2H), 3.65 (s, 3H), 2.82 (t, 2H), 2.51 (t, 2H); MS 502 (M+1).

Step C: Ester Hydrolysis 3-(3-{[(Pyridine-3-sulfonyl)-(4-pyridin-3-yl-benzyl)-amino]-methyl}-phenyl)-propionic acid. The title compound was prepared following the method described in Example 1, Step C, from 3-(3-{[(pyridine-3-sulfonyl)-(4-pyridin-3-yl-benzyl)-amino]-methyl}-phenyl)-propionic acid methyl ester of Step B. $^1$H NMR (400 MHz, CDCl$_3$) δ 9.02 (s, 1H), 8.89 (m, 1H), 8.78 (s, 1H), 8.58 (m, 1H), 8.08 (m, 1H), 7.99 (d, 1H), 7.44 (m, 4H), 7.21 (m, 2H), 7.07 (m, 2H), 6.87 (m, 2H), 4.37 (s, 2H), 4.34 (s, 2H), 2.83 (t, 2H), 2.54 (t, 2H); MS 486 (M−1).

EXAMPLE 11n 3-(3-{[(Pyridine-2-sulfonyl)-(4-pyridin-3-yl-benzyl)-amino]-methyl}-phenyl)-propionic acid Step A: Amide Formation 3-(3-{[(Pyridine-2-sulfonyl)-(4-pyridin-3-yl-benzyl)-amino]-methyl}-phenyl)-propionic acid methyl ester. The title compound of Step A was prepared from 3-{3-[(4-pyridin-3-yl-benzylamino)-methyl]-phenyl}-propionic acid methyl ester, prepared in Step A of Example 11m, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 8.79 (s, 1H), 8.69 (d, 1H), 8.59 (d, 1H), 7.98 (m, 1H), 7.88 (m, 2H), 7.49–7.38 (m, 4H), 7.24 (m, 2H), 7.11 (m, 1H), 7.02 (d, 1H), 6.95 (d, 1H), 6.90 (s, 1H), 4.54 (s, 2H), 4.49 (s, 2H), 3.65 (s, 3H), 2.80 (t, 2H), 2.49 (t, 2H); MS 502 (M+1).

Step B: Ester Hydrolysis 3-(3-{[(Pyridine-2-sulfonyl)-(4-pyridin-3-yl-benzyl)-amino]-methyl}-phenyl)-propionic acid. The title compound was prepared following the method described in Example 1, Step C, from 3-(3-{[(pyridine-2-sulfonyl)-(4-pyridin-3-yl-benzyl)-amino]-methyl}-phenyl)-propionic acid methyl ester of Step A. $^1$H NMR (400 MHz, CDCl$_3$) δ 8.84 (s, 1H), 8.69 (m, 1H), 8.55 (d, 1H), 7.97 (m, 2H), 7.87 (m, 1H), 7.47 (m, 2H), 7.37 (m, 2H), 7.22 (m, 2H), 7.02 (m, 2H), 6.89 (m, 2H), 4.52 (s, 2H), 4.45 (s, 2H), 2.80 (t, 2H), 2.52 (t, 2H); MS 486 (M−1).

EXAMPLE 11o 3-(3-{[(4-Pyrazol-1-yl-benzyl)-(pyridine-3-sulfonyl)-amino]-methyl}-phenyl)-propionic acid Step A: Reductive Amination 3-{3-[(4-Pyrazol-1-yl-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-pyrazol-1-yl-benzaldehyde, of Preparation 42, using the method described in Example 1, Step A except the imine was formed in MeOH at reflux over 2 h. $^1$H NMR (400 MHz, CDCl$_3$) δ 7.89 (dd, 1H), 7.70 (d, 1H), 7.65 (d, 2H), 7.45 (d, 2H), 7.28–7.19 (m, 3H), 7.10 (d, 1H), 6.45 (dd, 1H), 3.83 (s, 2H), 3.79 (s, 2H), 3.66 (s, 3H), 2.94 (t, 2H), 2.63 (t, 2H); MS 350 (M+1).

Step B: Amide Formation 3-(3-{[(4-Pyrazol-1-yl-benzyl)-(pyridine-3-sulfonyl)-amino]-methyl}-phenyl)-propionic acid methyl ester. The title compound of Step B was prepared from 3-{3-[(4-pyrazol-1-yl-benzylamino)-methyl]-phenyl}-propionic acid methyl ester, of Step A, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 9.03 (s, 1H), 8.77 (d, 1H), 8.04 (m, 1H), 7.87 (d, 1H), 7.68 (d, 1H), 7.54 (m, 2H), 7.42 (m, 1H), 7.14 (m, 3H), 7.07 (m, 1H), 6.88 (d, 1H), 6.83 (s, 1H), 6.44 (dd, 1H), 4.36 (s, 2H), 4.32 (s, 2H), 3.62 (s, 3H), 2.79 (t, 2H), 2.49 (t, 2H); MS 491 (M+1).

Step C: Ester Hydrolysis 3-(3-{[(4-Pyrazol-1-yl-benzyl)-(pyridine-3-sulfonyl)-amino]-methyl}-phenyl)-propionic acid. The title compound was prepared following the method described in Example 1, Step C, from 3-(3-{[(4-pyrazol-1-yl-benzyl)-(pyridine-3-sulfonyl)-amino]-methyl}-phenyl)-propionic acid methyl ester of Step B. $^1$H NMR (400 MHz, CDCl$_3$) δ 9.08 (bs, 1H), 8.85 (m, 1H), 8.18 (d, 1H), 7.82 (s, 1H), 7.72 (d, 1H), 7.52 (m, 1H), 7.47 (d, 2H), 7.14 (m, 3H), 7.07 (d, 1H), 6.96 (d, 1H), 6.83 (s, 1H), 6.46 (s, 1H), 4.38 (s, 2H), 4.34 (s, 2H), 2.82 (t, 2H), 2.52 (t, 2H); MS 475 (M−1).

EXAMPLE 11p 3-(3-{[(4-Pyrazol-1-yl-benzyl)-(pyridine-2-sulfonyl)-amino]-methyl}-phenyl)-propionic acid Step A: Amide Formation 3-(3-{[(4-Pyrazol-1-yl-benzyl)-(pyridine-2-sulfonyl)-amino]-methyl}-phenyl)-propionic acid methyl ester. The title compound of Step A was prepared from 3-{3-[(4-pyrazol-1-yl-benzylamino)-methyl]-phenyl}-propionic acid methyl ester, prepared in Step A of Example 11o, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 8.66 (m, 1H), 7.96 (m, 1H), 7.85 (m, 2H), 7.68 (d, 1H), 7.50 (d, 2H), 7.46 (m, 1H), 7.16 (d, 2H), 7.09 (m, 1H), 6.99 (d, 1H), 6.92 (d, 1H), 6.88 (s, 1H), 6.43 (m, 1H), 4.48 (s, 2H), 4.44 (s, 2H), 3.63 (s, 3H), 2.78 (t, 2H), 2.48 (t, 2H); MS 491 (M+1).

Step B: Ester Hydrolysis 3-(3-{[(4-Pyrazol-1-yl-benzyl)-(pyridine-2-sulfonyl)-amino]-methyl}-phenyl)-propionic acid. The title compound was prepared following the method described in Example 1, Step C, from 3-(3-{[(4-pyrazol-1-yl-benzyl)-(pyridine-2-sulfonyl)-amino]-methyl}-phenyl)-propionic acid methyl ester of Step A. $^1$H NMR (400 MHz, CDCl$_3$) δ 8.75 (m, 1H), 8.04 (m, 1H), 7.93 (m, 1H), 7.79 (d, 1H), 7.74 (s, 1H), 7.52 (m, 1H), 7.39 (d, 2H), 7.16–6.99 (m, 5H), 6.80 (s, 1H), 6.46 (d, 1H), 4.55 (s, 2H), 4.44 (s, 2H), 2.78 (t, 2H), 2.47 (t, 2H); MS 475 (M−1).

EXAMPLE 11q 3-(3-{[(1-Methyl-1H-imidazole-4-sulfonyl)-(4-pyrazol-1-yl-benzyl)-amino]-methyl}-phenyl)-propionic acid Step A: Amide Formation 3-(3-{[(1-Methyl-1H-imidazole-4-sulfonyl)-(4-pyrazol-1-yl-benzyl)-amino]-methyl}-phenyl)-propionic acid methyl ester. The title compound of Step A was prepared from 3-{3-[(4-pyrazol-1-yl-benzylamino)-methyl]-phenyl}-propionic acid methyl ester, of Step A of Example 11o, and 1-methyl-1H-imidazole-4-sulfonyl chloride following the method described in Example 1, Step B using triethylamine in place of N,N-diisopropylethylamine. $^1$H NMR (400 MHz, CDCl$_3$) δ 7.89 (d, 1H), 7.70 (s, 1H), 7.54 (m, 3H), 7.39 (d, 1H), 7.24 (m, 2H), 7.14 (m, 1H), 7.04–6.97 (m, 3H), 6.45 (m, 1H), 4.43 (s, 2H), 4.40 (s, 2H), 3.74 (s, 3H), 3.65 ), 2.83 (t, 2H), 2.53 (t, 2H); MS 494 (M+1).

Step B: Ester Hydrolysis 3-(3-{[(1-Methyl-1 H-imidazole-4-sulfonyl)-(4-pyrazol-1-yl-benzyl)-amino]-methyl}-phenyl)-propionic acid The title compound was prepared following the method described in Example 1, Step C, from 3-(3-{[(1-methyl-1 H-imidazole-4-sulfonyl)-(4-pyrazol-1-yl-benzyl)-amino]-methyl}-phenyl)-propionic acid methyl ester of Step A. $^1$H NMR (400 MHz, CDCl$_3$) δ 7.79 (d, 1H), 7.70 (d, 1H), 7.57 (s, 1H), 7.46 (s, 1H), 7.40 (d, 2H), 7.18 (d, 2H), 7.11 (m, 1H), 7.02 (m, 2H), 6.86 (s, 1H), 6.44 (m, 1H), 4.45 (s, 2H), 4.36 (s, 2H), 3.75 (s, 3H), 2.79 (t, 2H), 2.47 (t, 2H); MS 478 (M−1).

EXAMPLE 11r 3-(3-{[(Pyridine-3-sulfonyl)-(4-thiazol-2-yl-benzyl)-amino]-methyl}-phenyl)-propionic acid Step A: Amide Formation 3-(3-{[(Pyridine-3-sulfonyl)-(4-thiazol-2-yl-benzyl)-amino]-methyl}-phenyl)-propionic acid methyl ester The title compound of Step A was prepared from 3-{3-[(4-thiazol-2-yl-benzylamino)-methyl]-phenyl}-propionic acid methyl ester, of 11e, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 8.68 (d, 1H), 7.97 (d, 1H), 7.87 (m, 2H), 7.79 (d, 2H), 7.47 (m, 1H), 7.33 (d, 1H), 7.18 (d, 2H), 7.12 (m, 1H), 7.02 (d, 1H), 6.94 (d, 1H), 6.90 (s, 1H), 4.52 (s, 2H), 4.47 (s, 2H), 3.65 (s, 3H), 2.80 (t, 2H), 2.50 (t, 2H); MS 508 (M+1).

Step B: Ester Hydrolysis 3-(3-{[(Pyridine-3-sulfonyl)-(4-thiazol-2-yl-benzyl)-amino]-methyl}-phenyl)-propionic acid The title compound was prepared following the method described in Example 1, Step C, from 3-(3-{[(pyridine-3-sulfonyl)-(4-thiazol-2-yl-benzyl)-amino]-methyl}-phenyl)-propionic acid methyl ester of Step A. $^1$H NMR (400 MHz, CDCl$_3$) δ 8.72 (d, 1H), 8.00 (d, 1H), 7.89 (m, 1H), 7.83 (d, 1H), 7.64 (d, 2H), 7.49 (m, 1H), 7.33 (d, 1H), 7.13 (d, 2H), 7.07 (m, 1H), 6.98 (m, 2H), 6.80 (s, 1H), 4.53 (s, 2H), 4.42 (s, 2H), 2.76 (t, 2H), 2.46 (t, 2H); MS 492 (M−1).

EXAMPLE 11s 3-(3-{[(Pyridine-2-sulfonyl)-(4-thiazol-2-yl-benzyl)-amino]-methyl}-phenyl)-propionic acid Step A: Amide Formation 3-(3-{[(Pyridine-2-sulfonyl)-(4-thiazol-2-yl-benzyl)-amino]-methyl}-phenyl)-propionic acid methyl ester The title compound of Step A was prepared from 3-{3-[(4-thiazol-2-yl-benzylamino)-methyl]-phenyl}-propionic acid methyl ester, prepared in Step A of Example 11e, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 9.05 (s, 1H), 8.80 (d, 1H), 8.05 (m, 1H), 7.84 (m, 3H), 7.43 (m, 1H), 7.34 (d, 1H), 7.15 (m, 3H), 7.06 (d, 1H), 6.91 (d, 1H), 6.86 (s, 1H), 4.39 (s, 2H), 4.36 (s, 2H), 3.65 (s, 3H), 2.82 (t, 2H), 2.51 (t, 2H); MS 508 (M+1).

Step B: Ester Hydrolysis 3-(3-{[(Pyridine-2-sulfonyl)-(4-thiazol-2yl-benzyl)-amino]-methyl}-phenyl)-propionic acid The title compound was prepared following the method described in Example 1, Step C, from 3-(3{[(pyridine-2-sulfonyl)-(4-thiazol-2-yl-benzyl)-amino]-methyl}-phenyl)-propionic acid methyl ester of Step A. $^1$H NMR (400 MHz, CDCl$_3$) δ 9.03 (s, 1H), 8.80 (m, 1H), 8.13 (m, 1H), 7.84 (m, 1H), 7.71 (d, 2H), 7.47 (m, 1H), 7.34 (d, 1H), 7.12 (m, 3H), 7.06 (m, 1H), 6.92 (d, 1H), 6.82 (s, 1H), 4.36 (s, 2H), 4.32 (s, 2H), 2.80 (t, 2H), 2.51 (t, 2H); MS 492 (M−1).

EXAMPLE 11t 3-(3-{[Benzenesulfonyl-(4-pyrimidin-5-yl-benzyl)-amino]-methyl}-phenyl)-propionic acid Step A: Reductive Amination 3-{3-[(4-Pyrimidin-5-yl-benzylamino)-methyl]-phenyl}-propionic acid methyl ester The title compound of Step A was prepared from 3-(3-aminomethyl--phenyl)-propionic acid methyl ester hydrochloride salt, of Preparation 44, and 4-pyrimidin-5-yl-benzaldehyde, of Preparation 26, using the method described in Example 1, Step A except the imine was formed in MeOH at reflux over 2 h. $^1$H NMR (400 MHz, CDCl$_3$)δ 9.19 (s, 1H), 8.92 (s, 2H), 7.55 (m, 4H), 7.25 (m, 3H), 7.11 (d, 1H), 3.87 (s, 2H), 3.81 (s, 2H), 3.66 (s, 3H), 2.95 (t, 2H), 2.63 (t, 2H); MS 362 (M+1).

Step B: Amide Formation 3-(3-{[Benzenesulfonyl-(4-pyrimidin-5-yl-benzyl)-amino]-methyl}-phenyl)-propionic acid methyl ester The title compound of Step B was prepared from 3-{3-[(4-pyrimidin-5-yl-benzylamino)-methyl]-phenyl}-propionic acid methyl ester, of Step A, and benzenesulfonyl chloride following the method described in Example 1, Step B using triethylamine in place of N,N-diisopropylethylamine. $^1$H NMR (400 MHz, CDCl$_3$) δ 9.20 (s, 1H), 8.90 (s, 2H), 7.88 (m, 2H), 7.62 (m, 1H), 7.55 (m, 2H), 7.42 (d, 2H), 7.21 (d, 2H), 7.12 (m, 1H), 7.03 (d, 1H), 6.87 (d, 1H), 6.78 (s, 1H), 4.36 (s, 2H), 4.33 (s, 2H), 3.65 (s, 3H), 2.78 (t, 2H), 2.47 (t, 2H).

Step C: Ester Hydrolysis 3-(3-{[Benzenesulfonyl-(4-pyrimidin-5-yl-benzyl)-amino]-methyl}-phenyl)-prpionic acid The title compound was prepared following the method described in Example 1, Step C, from 3-(3-{[benzenesulfonyl-(4pyrimidin-5-yl-benzyl)-amino]-methyl}-phenyl)-propionic acid methyl ester of Step B. $^1$H NMR (400 MHz, CDCl$_3$), δ 9.19 (s, 1H), 8.93 (s, 2H), 7.89 (m, 2H), 7.63 (m, 1H), 7.55 (m 2H), 7.43 (d, 2H), 7.21 (d, 2H), 7.11 (m, 1H), 7.03 (d, 1H), 6.87 (d, 1H), 6.81 (s, 1H), 4.36 (s, 2H), 4.33 (s, 2H), 2.80 (t, 2H), 2.52 (t, 2H); MS 486 (M−1).

EXAMPLE 11u 3-(3-{[(Pyridine-3-sulfonyl)-4-pyrimdin-5-yl-benzyl)-amino]-methyl}-phenyl)-propionic acid Step A: Amide Formation 3-(3-{[(Pyridine-3-sulfonyl)-(4-pyrimidin-5-yl-benzyl)-amino]-methyl}-phenyl)-propionic acid The title compound of Step A was prepared from 3-{3-[(4-pyrimidin-5-yl-benzylamino)-methyl]-phenyl}-propionic acid methyl ester, of Step A of Example 11t, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 9.20 (s, 1H), 9.06 (s, 1H), 8.92 (s, 2H), 8.81 (s, 1H), 8.80 (m, 1H), 7.46 (m, 3H), 7.26 (m, 2H), 7.15 (m, 1H), 7.06 (d, 1H), 6.91 (d, 1H), 6.86 (s, 1H), 4.42 (s, 2H), 4.37 (s, 2H), 3.65 (s, 3H), 2.82 (t, 2H), 2.50 (t, 2H).

Step B: Ester Hydrolysis 3-(3-{[(Pyridine-3-sulfonyl)-(4-pyrimidin-5-yl-benzyl)-amino]-methyl}-phenyl)-propionic acid The title compound was prepared following the method described in Example 1, Step C, from 3-(3-{[(pyridine-3-sulfonyl)-(4-pyrimidin-5-yl-benzyl)-amino]-methyl}-phenyl)-propionic acid methyl ester of Step A. $^1$H NMR (400 MHz, CDCl$_3$) δ 9.20 (s, 1H), 8.98 (d, 1H), 8.93 (s, 2H), 8.79 (d, 1H), 8.15 (m, 1H), 7.48 (m, 3H), 7.31 (d, 2H), 7.20–7.09 (m, 2H), 6.95 (s, 1H), 6.91 (d, 1H), 4.42 (s, 2H), 4.40 (s, 2H), 2.87 (t, 2H), 2.58 (t, 2H); MS 487 (M−1).

EXAMPLE 11v 3-(3-{[(Pyridine-2-sulfonyl)-(4-pyrimidin-5-yl-benzyl)-amino]-methyl}-phenyl)-propionic acid Step A: Amide Formation 3-(3-{[(Pyridine-2-sulfonyl)-(4-pyrimidin-5-yl-benzyl)-amino]-methyl}-phenyl)-propionic acid methyl ester The title compound of Step A was prepared from 3-{3-[(4-pyrimidin-5-yl-benzylamino)-methyl]-phenyl}-propionic acid methyl ester, of Step A of Example 11t, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 9.20 (s, 1H), 8.90 (s, 2H), 8.70 (d, $_1$H), 7.99 (m, 1H), 7.89 (m, 1H), 7.49 (m, 1H), 7.42 (d, 2H), 7.29 (d, 2H), 7.10 (m, 1H), 7.01 (d, 1H), 6.93 (d, 1H), 6.89 (s, 1H), 4.56 (s, 2H), 4.48 (s, 2H), 3.66 (s, 3H), 2.79 (t, 2H), 2.48 (t, 2H); MS 503 (M+1).

Step B: Ester Hydrolysis 3-(3-{[(Pyridine-2-sulfonyl)-(4-pyrimidin-5-yl-benzyl)-amino]-methyl}-phenyl)-propionic acd The title compound was prepared following the method described in Example 1, Step C, from 3-(3-{[(pyridine-2-sulfonyl)-(4-pyrimidin-5-yl-benzyl)-amino]-methyl}-phenyl)-propionic acid methyl ester of Step A. $^1$H NMR (400 MHz, CDCl$_3$) δ 9.19 (s, 1H), 8.94 (s, 2H), 8.71 (m, 1H), 8.01 (d, 1H), 7.90 (m, 1H), 7.50 (m, 1H), 7.42 (d, 2H), 7.29 (d, 2H), 7.09 (m, 1H), 7.02 (d, 1H), 6.92 (m, 2H), 4.56 (s, 2H), 4.48 (s, 2H), 2.81 (t, 2H), 2.54 (t, 2H); MS 487 (M−1).

EXAMPLE 11w 3-(3-{[(4-Chloro-benzenesulfonyl)-(4-pyrimidin-5-yl-benzyl)-amino]-methyl}-phenyl)-propionic acid Step A: Amide Formation 3-(3-{[(4-Chloro-benzenesulfonyl)-(4-pyrimidin-5-yl-benzyl)-amino]-methyl}-phenyl)-propionic acd methyl ester The title compound of Step A was prepared from 3-{3-[(4-pyrimidin-5-yl-benzylamino)-methyl]-phenyl}-propionic acid methyl ester, of Step A of Example 11t, and 4-chlorobenzenesulfonyl chloride, following the method described in Example 1, Step B using triethylamine in place of N,N-diisopropylethylamine. $^1$H NMR (400 MHz, CDCl$_3$) δ 9.20 (s, 1H), 8.91 (s, 2H), 7.78 (d, 2H), 7.49 (d, 2H), 7.44 (d, 2H), 7.23 (m, 2H), 7.14 (m, 1H), 7.05 (d, 1H), 6.89 (d, 1H), 6.81 (s, 1H), 4.36 (s, 2H), 4.32 (s, 2H), 3.65 (s, 3H), 2.80 (t, 2H), 2.49 (t, 2H); MS 536 (M+).

Step B: Ester Hydrolysis 3-(3-{[(4-Chloro-benzenesulfonyl)-(4-pyrimidin-5-yl-benzyl)-amino]-methyl}-phenyl)-propionic acid The title compound was prepared following the method described in Example 1, Step C, from 3-(3-{[(4-chlorobenzenesulfonyl)-(4-pyrimidin-5-yl-benzyl)-amino]-methyl}-phenyl)-propionic acid methyl ester of Step A. $^1$H NMR (400 MHz, CDCl$_3$) δ 9.20 (s, 1H), 8.92 (s, 2H), 7.79 (d, 2H), 7.50 (d, 2H), 7.44 (d, 2H), 7.23 (m, 2H), 7.14 (m, 1H), 7.06 (m, 1H), 6.89 (d, 1H), 6.85 (s, 1H), 4.36 (s, 2H), 4.32 (s, 2H), 2.82 (t, 2H), 2.55 (t, 2H); MS 522 (M+).

EXAMPLE 11x 3-(3-{[(4-Pyrazin-2-yl-benzyl)-(pyridine-3-sulfonyl)-amino]-methyl}-phenyl)-propionic acid Step A: Reductive Amination 3-{3-[(4-Pyrazin-2-yl-benzylamino)-methyl]-phenyl}-propionic acid methyl ester The title compound of Step A was prepared from 3-(3-aminomethyl-phenyl)-propionic acid methyl ester hydrochloride salt, of Preparation 44, and 4-pyrazin-2-yl-benzaldehyde, of Preparation 27, using the method described in Example 1, Step A except the imine was formed in MeOH at reflux over 2 h. $^1$H NMR (400 MHz, CDCl$_3$) δ 9.02 (d, 1H), 8.61 (m, 1H), 8.48 (d, 1H), 7.98 (d, 2H), 7.49 (d, 2H), 7.25 (m, 1H), 7.19 (m, 2H), 7.09 (d,1H), 3.87 (s, 2H), 3.79 (s, 2H), 3.66 (s, 3H), 2.94 (t, 2H), 2.63 (t, 2H); MS 362 (M+1).

Step B: Amide Fomration 3-(3-{[(4-Pyrazin-2-yl-benzyl)-(pyridine-3-sulfonyl)-amino]-methyl}-phenyl)-propionic acid methyl ester The title compound of Step B was prepared from 3-{3-[(4-pyrazin-2-yl-benzylamino)-methyl]-phenyl}-propionic acid methyl ester, of Step A, and pyridine-3-sulfonyl chloride hydrochloride, of Preparation 2, following the method described in Example 1, Step B using triethylamine in place of N,N-diisopropylethylamine. $^1$H NMR (400 MHz, CDCl$_3$) δ 9.06 (s, 1H), 8.99 (s, 1H), 8.80 (d, 1H), 8.62 (s, 1H), 8.51 (d, 1H), 8.06 (m, 1H), 7.89 (d, 2H), 7.43 (m, 1H), 7.23 (m, 2H), 7.15 (m, 1H), 7.06 (d, 1H), 6.92 (d, 1H), 6.86 (s, 1H), 4.42 (s, 2H), 4.37 (s, 2H), 3.65 (s, 3H), 2.82 (t, 2H), 2.50 (t, 2H); MS 502 (M+1).

Step C: Ester Hydrolysis 3-(3-{[(4-Pyrazin-2-yl-benzyl)-(pyridine-3-sulfonyl)-amino]-methyl}-phenyl)-propionic acid The title compound was prepared following the method decribed in Example 1, Step C, from 3-(3-{[(4-pyrazin-2-yl-benzyl)-(pyridine-3-sulfonyl)-amino]-methyl}-phenyl)-propionic acid methyl ester of Step B. $^1$H NMR (400 MHz, CDCl$_3$) δ 9.02 (s, 1H), 8.96 (s, 1H), 8.78 (m, 1H), 8.58 (s, 1H), 8.53 (d, 1H), 8.13 (m, 1H), 7.78 (d, 2H), 7.46 (m, 1H), 7.22 (m, 2H), 7.13 (m, 1H), 7.06 (d, 1H), 6.93 (d, 1H), 6.85 (s, 1H), 4.40 (s, 2H), 4.34 (s, 2H), 2.82 (t, 2H), 2.53 (t, 2H); MS 487 (M−1).

EXAMPLE 11y 3-(3-{[(4-Pyrazin-2-yl-benzyl)-(pyridine-2-sulfonyl)-amino]-methyl}-phenyl)-propionic acid Step A: Amide Formation 3-(3-{[(4-Pyrazin-2-yl-benzyl)-(pyridine-2-sulfonyl)-amino]-methyl}-phenyl)-propionic acid methyl ester The title compound of Step A was prepared from 3-{3-[(4-pyrazin-2-yl-benzylamino)-methyl]-phenyl}-propionic acid methyl ester, prepared in Step A of Example 11x, and pyridine-2-sulfonyl chloride hydrochloride, of Preparation 47, following the method described in Example 1, Step B using triethylamine in place of N,N-diisopropylethylamine. $^1$H NMR (400 MHz, CDCl$_3$) δ 8.98 (d, 1H), 8.69 (m, 1H), 8.62 (m, 1H), 8.50 (d, 1H), 7.99 (m, 1H), 7.86 (m, 3H), 7.48 (m, 1H), 7.26 (m, 2H), 7.11 (m, 1H), 7.01 (d, 1H), 6.94 (d, 1H), 6.89 (s, 1H), 4.56 (s, 2H), 4.48 (s, 2H), 3.65 (s, 3H), 2.80 (t, 2H), 2.49 (t, 2H); MS 503 (M+1).

Step B: Ester Hydrolysis 3-(3-{[(4-Pyrazin-2-yl-benzyl)-(pyridine-2-sulfonyl)-amino]-methyl}-phenyl)-propionic acid The title compound was prepared following the method described in Example 1, Step C, from 3-(3-{[(4-pyrazin-2-yl-benzyl)-(pyridine-2-sulfonyl)-amino]-methyl}-phenyl)-propionic acid methyl ester of Step A. $^1$H NMR (400 MHz, CDCl$_3$) δ 8.96 (s, 1H), 8.73 (d, 1H), 8.60 (s, 1H), 8.54 (s, 1H), 8.02 (d, 1H), 7.91 (m, 1H), 7.74 (d, 2H), 7.51 (m, 1H), 7.23 (m, 2H), 7.12 (m, 1H), 7.04 (m, 2H), 6.85 (s, 1H), 4.57 (s, 2H), 4.46 (s, 2H), 2.80 (t, 2H), 2.52 (t, 2H); MS 487 (M−1).

EXAMPLE 11z 3-(3-{[(1-Methyl-1 H-imidazole-4-sulfonyl)-(4-sulfonyl)-(4-pyrimidin-2-yl-benzyl)-amino]-methyl}-phenyl)-propionic acid Step A: Reductive Amination 3-{3-[(4-Pyrimidin-2-yl-benzylamino)-methyl]-phenyl}-propionic acid methyl ester The title compound of Step A was prepared from 3-(3-aminomethyl-phenyl)-propionic acid methyl ester hydrochlorde salt, of Preparation 44, and 4-pyrimidin-2-yl-benzaldehyde, of Preparation 21, using the method described in Example 1, Step A except that the imine was formed in MeOH at reflux with a reaction time of 2 h. $^1$H NMR (400 MHz, CDCl$_3$) δ 8.79 (d, 2H), 8.40 (d, 2H), 7.49 (d, 2H), 3.88 (s, 2H), 3.80 (s, 2H), 3.65 (s, 3H), 2.94 (t, 2H), 2.63 (t, 2H).

Step B: Amide Formation 3-(3-{[(1-Methyl-1 H-imidazole-4-sulfonyl)-(4-pyrimidin-2-yl-benzyl)-amino]-methyl}-phenyl)-propionic acid methyl ester The title compound of Step B was prepared following the method described in Step B of Example 1 from 3-{3-[(4-pyrimidin-2-yl-benzylamino)-methyl]-phenyl}-propionic acid methyl ester, prepared in Step A, and 1-methyl-1 H-imidazole-4-sulfonyl chloride. $^1$H NMR (400 MHz, CDCl$_3$) δ 8.81 (m, 2H), 8.30 (d, 2H), 7.52 (s, 1H), 7.39 (s, 1H), 7.28–7.20 (m, 3H), 7.14 (m, 1H), 7.04–6.63 (m, 3H), 4.46 (s, 2H), 4.43 (s, 2H), 3.72 (s, 3H), 3.65 (s, 3H), 2.83 (t, 2H), 2.52 (t, 2H); MS 506 (M+1).

Step C: Ester Hydrolysis 3-(3-{[(1-Methyl-1 H-imidazole-4-sulfonyl)-(4-pyrimidin-2-yl-benzyl)-amino]-methyl}-phenyl)-propionic acid The title compound was prepared following the method described in Example 1, Step C from 3-(3-{[(1-methyl-1

H-imidazole-4-sulfonyl)-(4-pyrimidin-2-yl-benzyl)-amino]-methyl}-phenyl)-propionic acid methyl ester of Step B. $^1$H NMR (400 MHz, CDCl$_3$) δ 8.80 (d, 2H), 8.04 (d, 2H), 7.57 (s, 1H), 7.47 (s, 1H), 7.25–6.99 (m, 6H), 6.88 (s, 1H), 4.49 (s, 2H), 4.39 (s, 2H), 3.76 (s, 3H), 2.81 (t, 2H), 2.52 (t, 2H); MS 490 (M−1).

EXAMPLE 12a 3-(3-{[(4-Chloro-benzenesulfonyl)-(4-pyrazin-2-yl-benzyl)-amino]-methyl}-phenyl)-propionic acid Step A: Amide Formation 3-(3-{[(4-Chloro-benzenesulfonyl)-(4-pyrazin-2-yl-benzyl)-amino]-methyl}-phenyl)-propionic acid methyl ester The title compound of Step A was prepared from 3-{3-[(4-pyrazin-2-yl-benzylamino)-methyl]-phenyl}-propionic acid methyl ester, prepared in Step A of Example 11x, and 4-chlorobenzenesulfonyl chloride, following the method described in Example 1, Step B using triethylamine in place of N,N-diisopropylethylamine. $^1$H NMR (400 MHz, CDCl$_3$) δ 8.99 (s, 1H), 8.62 (m, 1H), 8.51 (d, 1H), 7.89 (d, 2H), 7.79 (d, 2H), 7.49 (d, 2H), 7.22 (m, 2H), 7.14 (m, 1H), 7.05 (d, 1H), 6.89 (d, 1H), 6.81 (s, 1H), 4.37 (s, 2H), 4.32 (s, 2H), 3.64 (s, 3H), 2.80 (t, 2H), 2.49 (t, 2H); MS 536 (M+1).

Step B: Ester Hydrolysis 3-(3-{[(4-Chloro-benzenesulfonyl)-(4-pyrazin-2-yl-benzyl)-amino]-methyl}-phenyl)-propionic acid The title compound was prepared following the method described in Example 1, Step C, from 3-(3-{[(4-chloro-benzenesulfonyl)-(4-pyrazin-2-yl-benzyl)-amino]-methyl}-phenyl)-propionic acid methyl ester of Step A. $^1$H NMR (400 MHz, CDCl$_3$) δ 9.05 (s, 1H), 8.64 (s, 1H), 8.50 (d, 1H), 7.91 (d, 2H), 7.86 (d, 2H), 7.59 (d, 2H), 7.27 (d, 2H), 7.09 (m, 1H), 7.02 (d, 1H), 6.94 (d, 1H), 6.83 (s, 1H), 4.41 (s, 2H), 4.35 (s, 2H), 2.72 (t, 2H), 2.42 (s, 2H); MS 520 (M−1).

EXAMPLE 12b 3-(3-{[Benzenesulfonyl-(4-thiazol-2-yl-benzyl)-amino]-methyl}-phenyl)-propionic acid Step A: Amide Formation 3-(3-{[Benzenesulfonyl-(4-thiazol-2-yl-benzyl)-amino]-methyl}-phenyl)-propionic acid methyl ester The title compound of Step A was prepared from 3-{3-[(4-thiazol-2-yl-benzylamino)-methyl]-phenyl}-propionic acid methyl ester, prepared in Step A of Example 11e, and benzenesulfonyl chloride, following the method described in Example 1, Step B using triethylamine in place of N,N-diisopropylethylamine. $^1$H NMR (400 MHz, CDCl$_3$) δ 7.87 (m, 3H), 7.80 (d, 2H), 7.62 (m, 1H), 7.56 (m, 2H), 7.33 (d, 1H), 7.11 (m, 3H), 7.03 (d, 1H), 6.87 (d, 1H), 6.78 (s, 1H), 4.34 (s, 2H), 4.32 (s, 2H), 3.65 (s, 3H), 2.79 (t, 2H), 2.48 (t, 2H); MS 507 (M+1).

Step B: Ester Hydrolysis 3-(3-{[Benzenesulfonyl-(4-thiazol-2-yl-benzyl)-amino]-methyl}-phenyl)-propionic acid The title compound was prepared following the method described in Example 1, Step C, from 3-(3-{[benzenesulfonyl-(4-thiazol-2-yl-benzyl)-amino]-methyl}-phenyl)-propionic acid methyl ester of Step A. $^1$H NMR (400 MHz, CDCl$_3$) δ 7.86 (m, 3H), 7.67–7.53 (m, 5H), 7.34 (s, 1H), 7.06 (m, 3H), 6.98 (d, 1H), 6.90 (d, 1H), 6.71 (s, 1H), 4.32 (s, 2H), 4.26 (s, 2H), 2.75 (t, 2H), 2.46 (t, 2H); MS 491 (M−1).

EXAMPLE 12c

7-[(Pyridine-3-sulfonyl)-(4-thiazol-2-yl-benzyl)-amino]-heptanoic acid

Step A: Amide Formation

7-[(Pyridine-3-sulfonyl)-(4-thiazol-2-yl-benzyl)-amino]-heptanoic acid methyl ester The title compound of Step A was prepared from 7-(4-thiazol-2-yl-benzylamino)-heptanoic acid methyl ester, prepared in Step A of Example 11c, and pyridine-3-sulfonyl chloride hydrochloride, of Preparation 2, following the method of Example 1, Step B. $^1$H NMR (400 MHz, CDCl$_3$) δ 9.06 (d, 1H), 8.80 (m, 1H), 8.09 (m, 1H), 7.91 (d, 2H), 7.86 (m, 1H), 7.46 (m, 1H), 7.34 (m, 3H), 4.39 (s, 2H), 3.62 (s, 3H), 3.15 (t, 2H), 2.21 (t, 2H), 1,48 (m, 2H), 1.37 (m, 2H), 1.14 (m, 4H); MS 474 (M+1)

Step B: Ester Hydrolysis

7-[(Pyridine-3-sulfonyl)-(4-thiazol-2-yl-benzyl)-amino]-heptanoic acid

The title compound was prepared following the method described in Example 1, Step C, from 7-[(pyridine-3-sulfonyl)-(4-thiazol-2-yl-benzyl)-amino]-heptanoic acid methyl ester of Step A. $^1$H NMR (400 MHz, CDCl$_3$) δ 9.07 (s, 1H), 8.81 (m, 1H), 8.11 (m, 1H), 7.87 (m, 3H), 7.48 (m, 1H), 7.39 (d, 2H), 7.36 (d, 1H), 4.37 (s, 2H), 3.14 (t, 2H), 2.23 (t, 2H), 1.48 (m, 2H), 1.30 (m, 2H), 1.14 (m, 2H), 1.07 (m, 2H)); MS 458 (M−1).

EXAMPLE 12d

7-[(4Pyrazin-2-yl-benzyl)-(pyridine-3-sulfonyl)-amino]-heptanoic acid

Step A: Reductive Amination 7-(4-Pyrazin-2-yl-benzylamino)-heptanoic acid methyl ester The title compound of Step A was prepared from 7-amino-heptanoic acid methyl ester hydrochloride, of Preparation 1, and 4-pyrazin-2-yl-benzaldehyde, of Preparation 27, using the method described in Example 1, Step A. $^1$H NMR (400 MHz, CDCl$_3$) δ 9.01 (d, 1H), 8.61 (m, 1H), 8.48 (d, 1H), 7.97 (d, 2H), 7.46 (d, 2H), 3.85 (s, 2H), 3.65 (s, 3H), 2.63 (t, 2H), 2.29 (t, 2H), 1.62 (m, 2H), 1.54 (m, 2H), 1.33 (m, 4H); MS 328 (M+1).

Step B: Amide Formation

7-[(4-Pyrazin-2-yl-benzyl)-(pyridine-3-sulfonyl)-amino]-heptanoic acid methyl ester The title compound of Step A was prepared from 7-(4-pyrazin-2-yl-benzylamino)-heptanoic acid methyl ester, of Step A, and pyridine-3-sulfonyl chloride hydrochloride, of Preparation 2, following the method of Exmaple 1, Step B. $^1$H NMR (400 MHz, CDCl$_3$) δ 9.04 (d, 1H), 8.99 (d, 1H), 8.78 (m, 1H), 8.60 (dd, 1H), 8.49 (d, 1H), 8.08 (m, 1H), 7.95 (m, 2H), 7.46–7.39 (m, 3H), 4.40 (s, 2H), 3.60 (s, 3H), 3.14 (t, 2H), 2.18 (t, 2H), 1.45 (m, 2H), 1.36 (m, 2H), 1.12 (m, 4H).

Step C: Ester Hydrolysis

7-[(4-Pyrazin-2-yl-benzyl)-(pyridine-3-sulfonyl)-amino]-heptanoic acid

The title compound was prepared following the method described in Example 1, Step C, from 7-[(4-pyrazin-2-yl-benzyl)-(pyridine-3-sulfonyl)-amino]-heptanoic acid methyl ester of Step B. $^1$H NMR (400 MHz, CDCl$_3$) δ 9.07 (m, 1H), 9.01 (d, 1H), 8.82 (dd, 1H), 8.63 (m, 1H), 8.55 (m, 1H), 8.13 (m, 1H), 7.92 (d, 2H), 7.47 (m, 3H), 4.41 (s, 2H), 3.15 (t, 2H), 2.23 (t, 2H), 1.48 (m, 2H), 1.33 (m, 2H), 1.13 (m, 4H); MS 453 (M−1).

EXAMPLE 12e

7-[(4-Imidazol-1-yl-benzyl)-(pyridine-2-sulfonyl)-amino]-heptanoic acid

Step A: Reductive Amination 7-(4-Imidazol-1-yl-benzylamino)-heptanoic acid methyl ester The title compound of Step A was prepared from 7-amino-heptanoic acid methyl ester hydrochloride, of Preparation 1, and 4-imidazoly-1-yl-benzaldehyde, of Preparation 43, using the method described in Example 1, Step A except that the imine was formed in MeOH with a reaction tim of 1 h. $^1$H NMR (400 MHz, CDCl$_3$) δ 7.82 (m, 1H), 7.43 (d, 2H), 7.33 (d, 2H), 7.25 (m, 1H), 7.18 (m, 1H), 3.82 (s, 2H), 3.65 (s, 3H), 2.62 (t, 2H), 2.29 (t, 2H), 1.61 (m, 2H), 1.52 (m, 2H), 1.33 (m, 4H).

Step B: Amide Formation

7-[(4-Imidazol-1-yl-benzyl)-(pyridine-2-sulfonyl)-amino]-heptanoic acid methyl ester The title compound of Step A was prepared from 7-(4-imidazol-1-yl-benzylamino)-heptanoic acid methyl ester, of Step A, and pyridine-2-sulfonyl chloride hydrochloride, of Preparation 47, following the method of Example 1, Step B with a reaction time of 20 h and using triethylamine in place of N,N-diisopropylethylamine. $^1$H NMR (400 MHz, CDCl$_3$) δ 8.70 (m, 1H), 7.98 (m, 1H), 7.89 (m, 1H), 7.84 (s, 1H), 7.48 (m, 3H), 7.34 (d, 2H), 7.27 (s, 1H), 7.20 (s, 1H), 4.59 (s, 2H), 3.62 (t, 3H), 3.25 (t, 2H), 2.19 (t, 2H), 1.45 (m, 2H), 1.34 (m, 2H), 1.13 (m, 4H).

Step C: Ester Hydrolysis

7-[(4-Imidazol-1-yl-benzyl)-(pyridine-2-sulfonyl)-amino]-heptanoic acid

A mixutre of 7-[(4-imidazol-1-yl-benzyl)-(pyridine-2-sulfonyl)-amino]-heptanoic acid methyl ester (52 mg), porcine pancreas lipase (81 mg), acetone (1 mL), and phosphate buffer (pH=7, 5 mL) was stirred at room temperature for 20 h. The produce was extracted into CH$_2$Cl$_2$ (3×). The organic solution was dried (MgSO$_4$), filtered, and concentrated to provide the title compound (44 mg). $^1$H NMR (400 MHz, CD$_3$OD) δ 8.71 (m, 1H), 8.24 (s, 1H), 8.07–7.98 (m, 2H), 7.64–7.54 (m, 6H), 7.19 (s, 1H), 4.57 (s, 2H), 3.29 (t, 2H), 2.15 (t, 2H), 1.41 (m, 2H), 1.33 (m, 2H), 1.13 (m, 4H).

EXAMPLE 12f 3-(3-{[Benzenesulfonyl-(4-pyrimidin-2-yl-benzyl)-amino]-methyl}-phenyl)-propionic acid Step A: Amide Formation 3-(3-{[Benzenesulfonyl-(4-pyrimidin-2-yl-benzyl)-amino]-methyl}-phenyl)-propionic acid methyl ester The title compound of Step B was prepared following the method described in Step B of Example 1 from 3-{3-[(4-pyrimidin-2-yl-benzylamino)-methyl]-phenyl}-propionic acid methyl ester, prepared in Step A of Example 11z, and benzenesulfonyl chloride using triethylamine in place of N,N-diisopropylethylamine. $^1$H NMR (400 MHz, CDCl$_3$) δ 8.79 (m, 2H), 8.27 (dd, 2H), 7.88 (m, 2H), 7.61 (m, 1H), 7.55 (m, 2H), 7.18 (m, 1H), 7.12 (m, 3H), 7.03 (d, 1H), 6.88 (d, 1H), 6.79 (s, 1H), 4.38 (s, 2H), 4.32 (s, 2H), 3.65 (s, 3H), 2.79 (t, 2H), 2.48 (t, 2H); MS 502 (M+1).

Step B: Ester Hydrolysis 3-(3-{[Benzenesulfonyl-(4-pyrimidin-2-yl-benzyl)-amino]-methyl}-phenyl)-propionic acid The title compound was prepared following the method described in Example 1, Step C, from 3-(3{[benzenesulfonyl-(4-pyrimidin-2-yl-benzyl)-amino]-methyl}-phenyl)-propionic acid methyl ester of Step B. $^1$H NMR (400 MHz, CDCl$_3$) δ 8.80 (d, 2H), 8.07 (m, 2H), 7.92 (m, 2H), 7.63 (m, 1H), 7.55 (m, 2H), 7.24 (m, 1H), 7.10 (m, 3H), 7.01 (d, 1H), 6.94 (d, 1H), 6.74 (s, 1H), 4.38 (s, 2H), 4.29 (s, 2H), 2.79 (t, 2H), 2.51 (t, 2H); MS 486 (M−1).

EXAMPLE 12g 3-(3{[(Pyridine-2-sulfonyl)-(4-pyrimidin-2-yl-benzyl)-amino]-methyl}-phenyl)-propionic acid Step A: Amide Formation 3-(3-{[(Pyridine-2-sulfonyl)-(4-pyrimidin-2-yl-benzyl)-amino]- methyl}-phenyl)-propionic acid methyl ester The title compound of Step A was prepared following the method described in Step B of Example 1 from 3-{3-[(4-pyrimidin-2-yl-benzylamino)-methyl]-phenyl}-propionic acid methyl ester, prepared in Step A of Example 11z, and pyridine-2-sulfonyl chloride hydrochloride salt, of Preparation 47, using triethylamine in place of N,N-diisopropylethylamine. $^1$H NMR (400 MHz, CDCl$_3$) δ 8.80 (d, 2H), 8.68 (m, 1H), 8.27 (d, 2H), 7.98 (m, 1H), 7.86 (m, 1H), 7.46 (m, 1H), 7.20 (m, 3H), 7.12 (m, 1H), 7.02 (d, 1H), 6.96 (d, 1H), 6.91 (s, 1H), 4.55 (s, 2H), 4.48 (s, 2H), 3.65 (s, 3H), 2.80 (t, 2H), 2.50 (t, 2H); MS 503 (M+1).

Step B: Ester Hydrolysis 3-(3-{[(Pyridine-2-sulfonyl)-(4-pyrimidin-2-yl-benzyl)-amino]-methyl}-phenyl)-propionic acid The title compound was prepared following the method described in Example 1, Step C, from 3-(3{[(pyridine-2-sulfonyl)-(4-pyrimidin-2-yl-benzyl)-amino]-methyl}-phenyl)-propionic acid methyl ester of Step A. $^1$H NMR (400 MHz, CDCl$_3$) δ 8.82 (d, 2H), 8.75 (m, 1H), 8.06 (m, 3H), 7.92 (m, 1H), 7.52 (m, 1H), 7.26 (m, 1H), 7.17 (m, 2H), 7.10 (m, 1H), 7.01 (m, 2H), 6.84 (s, 1H), 4.57 (s, 2H), 4.46 (s, 2H), 2.80 (t, 2H), 2.53 (t, 2H); MS 487 (M−1).

EXAMPLE 12h 3-(3-{[(Pyridine-3-sulfonyl)-(4-pyrimidin-2-yl-benzyl)-amino]-methyl}-phenyl)-propionic acid

Step A: Amide Formation 3-(3-{[(Pyridine-3-sulfonyl)-(4-pyrimidin-2-yl-benzyl)-amino]-methyl}-phenyl)-propionic acid methyl ester The title compound of Step A was prepared following the method described in Step B of Example 1 from 3-{3-[(4-pyrimidin-2-yl-benzylamino)-methyl]-phenyl}-propionic acid methyl ester, prepared in Step A of Example 11z, and pyridine-3-sulfonyl chloride hydrochloride salt, of Preparation 2, using triethylamine in place of N,N-diisopropylethylamine. $^1$H NMR (400 MHz, CDCl$_3$) δ 9.03 (d, 1H), 8.77 (m, 3H), 8.29 (d, 2H), 8.03 (m, 1H), 7.40 (m, 1H), 7.15 (m, 4H), 7.04 (d, 1H), 6.90 (d, 1H), 6.84 (s, 1H), 4.41 (s, 2H), 4.34 (s, 2H), 3.62 (s, 3H), 2.80 (t, 2H), 2.49 (t, 2H); MS 487 (M−1).

Step B: Ester Hydrolysis 3-(3-{[(Pyridine-3-sulfonyl)-(4-pyrimidin-2-yl-benzyl)-amino]-methyl}-phenyl)-propionic acid The title compound was prepared following the method described in Example 1, Step C, from 3(3-{[(pyridine-3-sulfonyl)-(4-pyrimidin-2-yl-benzyl)-amino]-methyl}-phenyl)-propionic acid methyl ester of Step A. $^1$H NMR (400 MHz, CDCl$_3$) δ 9.05 (s, 1H), 8.81 (m, 3H), 8.16 (m, 3H), 7.49 (m, 1H), 7.24 (m, 1H), 7.16 (m, 3H), 7.06 (d, 1H), 6.95 (d, 1H), 6.86 (s, 1H), 4.42 (s, 2H), 4.35 (s, 2H), 2.84 (t, 2H), 2.56 (t, 2H); MS 487 (M−1).

EXAMPLE 12i 3-(3{[(4-Chloro-benzenesulfonyl)-(4-pyrimidin-2-yl-benzyl)-amino]-methyl}-phenyl)-propionic acid

Step A: Amide Formation 3-(3-{[(4-Chloro-benzenesulfonyl)-(4-pyrimidin-2-yl-benzyl)-amino]-methyl}-phenyl)-propionic acid methyl ester The title compound of Step A was prepared following the method described in Step B of Example 1 from 3-{3-[(4-pyrimidin-2-yl-benzylamino)-methyl]-phenyl}-propionic acid methyl ester, prepared in Step A of Example 11z, and 4-chlorobenzensulfonyl chloride using triethylamine in place of N,N-iisopropylethylamine. $^1$H NMR (400 MHz, CDCl$_3$) δ 8.78 (m, 2H), 8.28 (d, 2H), 7.76 (d, 2H), 7.46 (d, 2H), 7.15 (m, 4H), 7.03 (d, 1H), 6.88 (d, 1H), 6.80 (s, 1H), 4.36 (s, 2H), 4.29 (s, 2H), 3.63 (s, 3H), 2.79 (t, 2H), 2.48 (t, 2H); MS 536 (M+1).

Step B: Ester Hydrolysis 3-(3-{[(4-Chloro-benzenesulfonyl)-(4-pyrimidin-2-yl-benzyl)-amino]-methyl}-phenyl)-propionic acid The title compound was prepared following the method described in Example 1, Step C, from 3-(3{[(4-Chloro-benzenesulfonyl)-(4-pyrimidin-2-yl-benzyl)-amino]-methyl}-phenyl)-propionic acid methyl ester of Step A. $^1$H NMR (400 MHz, CDCl$_3$) δ 8.80 (d, 2H), 8.09 (d, 2H), 7.83 (d, 2H), 7.53 (d, 2H), 7.11 (m, 4H), 7.02 (d, 1H), 6.95 (d, 1H), 6.76 (s, 1H), 4.37 (s, 2H), 4.28 (s, 2H), 2.80 (t, 2H), 2.53 (t, 2H); MS 520 (M−1)

EXAMPLE 12j 3-(3-{[Benzenesulfonyl-(4-pyrazol-1-yl-benzyl)-amino]-methyl}-phenyl)-2-methyl-propionic acid

Step A: Reduction 3-(3-Cyano-phenyl)-propionic acid methyl ester

A mixture of 3-(3-cyano-phenyl)-acrylic acid methyl ester (3.24 g, 17.31 mmol), prepared in Step B of Preparation 44, and palladium on carbon (10%, 0.600 g) in EtOAc (30 mL) was hydrogenated at 25 psi in a Parr shaker for 1 h. The catalyst was removed via filtration through Celite and the solution was concentrated in vacuo. Medium pressure chromatography (6:1 hexanes:EtOAc) provided the title compound of Step A as a clear oil (2.98 g). $^1$H NMR (400 MHz, CDCl$_3$) δ 7.50–7.36 (m, 4H), 3.65 (s, 3H), 2.97 (t, 2H), 2.63 (t, 2H); MS 190 (M+1).

Step B: Alkylation 3-(3-Cyano-phenyl)-2-methyl-propionic acid methyl ester

To a solution of 3-(3-cyano-phenyl)-propionic acid methyl ester of Step A (220 mg, 1.16 mmol) in THF (5 mL) at −78° C. was added sodium bis(trimethylsilyl)amide (1 M in THF, 1.2 mL, 1.2 mmol). The reaction was stirred for 0.5 h and MeI (0.08 mL, 1.28 mmol) was added. After 1 h, a solution of saturated NaHCO$_3$:water (1:1) was added and the reaction was warmed to room temperature. The aqueous solution was washed with CH$_2$Cl$_2$ (3×) and the combined organic solutions were dried (MgSO$_4$), filtered, and concentrated. Medium pressure chromatography (6:1 hexanes:EtOAc) provided the title compound of Step B as a colorless oil (62 mg). $^1$H NMR (400 MHz, CDCl$_3$) δ 7.50–7.34 (m, 4H), 3.62 (s, 3H), 3.01 (m, 1H), 2.71 (m, 2H), 1.16 (d, 3H).

Step C: Reduction 3-(3-Aminomethyl-phenyl)-2-methyl-propionic acid methyl ester A mixture of 3-(3-cyano-phenyl)-2-methyl-propionic acid methyl ester of Step B (62 mg, 0.30 mmol) and palladium on carbon (10%, 50 mg) in MeOH (10 mL), EtOAc (10 mL), and ammonium hydroxide (5 mL) was hydrogenated at 40 psi for 24 h. The catalyst was removed via filtration through Celite with the aid of MeOH. The solvent was removed in vacuo. Chromatography (1:1 hexanes:EtOAc to CH$_2$Cl$_2$:MeOH:NH$_4$OH, 95:5:0.1) provided the title compound of Step C (45 mg). $^1$H NMR (400 MHz, CD$_3$OD) δ 7.31–7.14 (m, 4H), 3.94 (s, 2H), 3.59 (s, 3H), 2.96 (m, 1H), 2.72 (m, 2H), 1.12 (d, 3H); MS 208 (M+1).

Step D: Reductive Amination

2-Methyl-3-{3-[(4-pyrazol-1-yl-benzylamino)-methyl]-phenyl}-propionic acid methyl ester The title compound of Step δ was prepared from 3-(3-aminomethyl-phenyl)-2-methyl-propionic acid methyl ester of Step C and 4-pyrazol-1-yl-benzaldehyde, of Preparation 42, using the method described in Example 1, Step A, except no base was used. $^1$H NMR (400 MHz, CDCl$_3$) δ 7.90 (m, 1H), 7.66 (m, 3H), 7.41 (m, 2H), 7.24–7.02 (m, 4H), 6.45 (m, 1H), 3.81 (s, 2H), 3.77 (s, 2H), 3.61 (s, 3H), 3.01 (dd, 1H), 2.76–2.60 (m, 2H), 1.14 (d, 3H); MS 364 (M+1).

Step E: Amide Formation 3-(3-{[Benzenesulfonyl-(4-pyrazol-1-yl-benzyl)-amino]-methyl}-phenyl)-2-methyl-propionic acid methyl ester The title compound of Step E was prepared from 2-methyl-3-{3-[(4-pyrazol-1-yl-benzylamino)-methyl]-phenyl-}-propionic acid methyl ester of Step δ and benzenesulfonyl chloride, following the method descirbed in Example 1, Step B using triethylamine in place of N,N-diisopropylethylamine and with a reaction time of 4 h. $^1$H NMR (400 MHz, CDCl$_3$) δ 7.87 (m, 3H), 7.69 (m, 1H), 7.61 (m, 1H), 7.54 (m, 4H), 7.10 (m, 3H), 6.98 (d, 1H), 6.85 (d, 1H), 6.75 (s, 1H), 6.44 (m, 1H), 4.31 (s, 2H), 4.29 (s, 2H), 3.61 (s, 3H), 2.87 (dd, 1H), 2.61–2.47 (m, 2H), 1.06 (d, 3H); MS 504 (M+1).

Step F: Ester Hydrolysis 3-(3-{[Benzenesulfonyl-(4-pyrazol-1-yl-benzyl)-amino]-methyl}-phenyl)-2-methyl-propionic acid The title compound was prepared following the method described in Example 1, Step C, from 3-(3-{[benzenesulfonyl-(4-pyrazol-1-yl-benzyl)-amino]-methyl}-phenyl)-2-methyl-propionic acid methyl ester of Step E, except that the hydrolysis was performed in MeOH at reflux over 24 h. $^1$H NMR (400 MHz, CD$_3$OD) δ 8.14 (m, 1H), 7.90 (m, 2H), 7.69–7.53 (m, 6H), 7.17 (m, 2H), 7.07 (m, 1H), 6.99 (m, 1H), 6.90 (m, 1H), 6.79 (m, 1H), 6.49 (m 1H), 4.34 (s, 2H), 4.31 (s, 2H), 2.79 (m, 1H), 2.50 (m, 2H), 1.02 (d, 3H); MS 488 (M−1).

EXAMPLE 12k 3-(3-{[(1-Methyl-1 H-imidazole-4-sulfonyl)-(4-sulfonyl)-(4-pyrazin-2-yl-benzyl)-amino]-methyl}-phenyl)-propionic acid Step A: Amide Formation 3-(3-{[(1-Methyl-1 H-imidazole-4-sulfonyl)-(4-pyrazin-2-yl-benzyl)-amino]-methyl}-phenyl)-propionic acid methyl ester The title compound of Step A was prepared following the method described in Step B of Example 1 from 3-{3-[(4-pyrazin-2-yl-benzylamino)-methyl]-phenyl}-propionic acid methyl ester, of Step A of Example 11a, and 1-methyl-1 H-imidazole-4-sulfonyl chloride using triethylamine in place of N,N-diisopropylethylamine. $^1$H NMR (400 MHz, CDCl$_3$) δ 8.99 (d, 1H), 8.63 (m, 1H), 8.50 (d, 1H), 7.88 (d, 2H), 7.55 (s, 1H), 7.42 (s, 1H), 7.32 (d, 2H), 7.13 (m, 1H), 7.04–6.97 (m, 3H), 4.47 (s, 2H), 4.41 (s, 2H), 3.75 (s, 3H), 3.65 (s, 3H), 2.82 (t, 2H), 2.51 (t, 2H); MS 506 (M+1)

Step B: Ester Hydrolysis 3-(3-{[(1-Methyl-1 H-imidazole-4-sulfonyl)-(4-pyrazin-2-yl-benzyl)-amino]-methyl}-phenyl)-propionic acid The title compound was prepared following the method described in Example 1, Step C from 3-(3-{[(1-methyl-1 H-imidazole-4-sulfonyl)-(4-pyrazon-2-yl-benzyl)-amino]-methyl}-phenyl)-propionic acid methyl ester of Step A. $^1$H NMR (400 MHz, CDCl$_3$) δ 8.96 (s, 1H), 8.59 (s, 1H), 8.52 (s, 1H), 7.78 (d, 2H), 7.59 (s, 1H), 7.44 (s, 1H), 7.28 (d, 2H), 7.11 (m, 1H), 7.01 (m, 2H), 6.93 (s, 1H), 4.47 (s, 2H), 4.38 (s, 2H), 3.74 (s, 3H), 2.81 (t, 2H), 2.52 (t, 2H), EXAMPLE 12m 3-{3-[(Benzenesulfonyl-biphenyl-4-ylmethyl-amino)-methyl]-phenyl}-propionic acid Step A: Reductive Amination 3-(3-{[(Biphenyl-4-methyl)-amino]-methyl}-phenyl)-propionic acid methyl ester The title compound of Step A was prepared from 3-(3-aminomethyl-phenyl)-propionic acid methyl ester hydrochloride salt, of Preparation 44, and biphenyl-4-carbaldehyde using the method described in Example 1, Step A except the imine was formed in MeOH at reflux over 3 h. $^1$H NMR (400 MHz, CDCl$_3$) δ 7.55 (m, 4H), 7.40 (m, 4H), 7.32 (m, 1H), 7.29–7.22 (m, 2H), 7.17 (m, 1H), 7.07 (d, 1H), 3.82 (s, 2H), 3.79 (s, 2H), 3.64 (s, 3H), 2.93 (t, 2H), 2.61 (t, 2H); MS 360 (M+1).

Step B: Amide Formation

3-{3-[(Benzenesulfonyl-biphenyl-4-ylmethyl-amino)-methyl]-phenyl}-propionic acid methyl ester The title compound of Step B was prepared following the method described in Step B of Example 1 from 3-(3-{[(biphenyl-4-ylmethyl)-amino]-methyl}-phenyl)-propionic acid methyl ester of Step A and benzenesulfonyl chloride using triethylamine in place of N,N-diisopropylethylamine. $^1$H NMR (400 MHz, CDCl$_3$) δ 7.85 (d, 2H), 7.60–7.29 (m, 10H), 7.08 (m, 3H), 7.01 (d, 1H), 6.88 (d, 1H), 6.78 (s, 1H), 4.33 (s, 2H), 4.32 (s, 2H), 3.63 (s, 3H), 2.78 (t, 2H), 2.47 (t, 2H); MS 500 (M+1).

Step C: Ester Hydrolysis

3-{3-[(Benzenesulfonyl-biphenyl-4-ylmethyl-amino)-methyl]-phenyl}-propionic acid The title compound was prepared following the method described in Example 1, Step C from 3-{3-[(benzenesulfonyl-biphenyl-4-ylmethyl-amino)-methyl]-phenyl}-propionic acid methyl ester of Step B. $^1$H NMR (400 MHz, CDCl$_3$) δ 7.85 (m, 2H), 7.60–7.29 (m, 10H), 7.13–7.01 (m, 4H), 6.88 (d, 1H), 6.79 (s, 1H), 4.33 (s, 2H), 4.32 (s, 2H), 2.78 (t, 2H), 2.52 (t, 2H); MS 484 (M−1).

EXAMPLE 12n 3-(3-{[Benzenesulfonyl-(2,3-dihydro-benzo[1,4] dioxin-6-ylmethyl)-amino]-methyl}-phenyl)-propionic acid Step A: Reductive Amination 3-(3-{[(2,3-Dihydro-benzo[1,4]dioxin-6-ylmethyl)-amino]-methyl}-phenyl)-propionic acid methyl ester The title compound of Step A was prepared from 3-(3-aminomethyl-phenyl)-propionic acid methy ester hydrochloride salt, of Preparation 44, and 2,3- dihydro-benzo[1, 4]-dioxine-6-carbaldehyde using the method described in Example 1, Step A except the imine was formed in MeOH at reflux over 3 h. ¹H NMR (400 MHz, CDCl₃) δ 7.26–7.16 (m, 3H), 7.07 (d, 1H), 6.85–6.78 (m, 3H), 4.24 (s, 4H), 3.75 (s, 2H), 3.68 (s, 2H), 3.66 (s, 3H), 2.94 (t, 2H), 2.62 (t, 2H); MS 342 (M+1).

Step B: Amide Formation 3-(3-{[Benzenesulfonyl-(2,3-dihydro-benzo[1,4]-dioxin-6-ylmethyl)-amino]-methyl}-phenyl)-propionic acid methyl ester The title compound of Step B was prepared following the method described in Step B of Example 1 from 3-(3-{[(2,3-dihydro-benzo[1,4]dioxin-6-ylmethyl)-amino]-methyl}-phenyl)-propionic acid methyl ester of Step A and benzenesulfonyl chloride using triethylamine in place of N,N-diisopropylethylamine. ¹H NMR (400 MHz, CDCl₃) δ 7.84 (m, 2H), 7.60–7.49 (m, 3H), 7.14 (m, 1H), 7.04 (d, 1H), 6.89 (d, 1H), 6.78 (s, 1H), 6.69 (d, 1H), 6.51 (m, 2H), 4.29 (s, 2H), 4.20 (m, 6H), 3.67 (s, 3H), 2.81 (t, 2H), 2.51 (t, 2H).

Step C: Ester Hydrolysis 3-(3-{[benzenesulfonyl-(2,3-dihydro-benzo[1,4]dioxin-6-ylmethyl)-amino]-methyl}-phenyl)-propionic acid The title compound was prepared following the method described in Example 1, Step C from 3(3-{[benzenesulfonyl-(2,3-dihydro-benzo[1,4]dioxin-6-ylmethyl)-amino]-methyl}-phenyl)-propionic acid methyl ester of Step B. ¹H NMR (400 MHz, CDCl₃) δ 7.82 (dd, 2H), 7.59–7.47 (m, 3H), 7.12 (m, 1H), 7.03 (d, 1H), 6.88 (d, 1H), 6.78 (s, 1H), 6.67 (d, 1H), 6.49 (m, 2H), 4.26 (s, 2H), 4.18 (s, 4H), 4.16 (s, 2H), 2.81 (t, 2H), 2.55 (t, 2H); MS 466 (M–1).

EXAMPLE 12o 3-(3-{[(2,3-Dihydro-benzo[1,4]dioxin-6-ylmethyl)-(pyridine-2-sulfonyl)-amino]-methyl}-phenyl)-propionic acid Step A: Amide Formation 3-(3-{[(2,3-Dihydro-benzo[1,4]dioxin-6-ylmethyl)-(pyridine-2-sulfonyl)-amino]-methyl}-pheny)-propionic acid methyl ester The title compound of Step A was prepared following the method described in Step B of Example 1 from 3-(3-{[(2,3-dihydro-benzo[1,4]dioxin-6-ylmethyl)-amino]-methyl}-phenyl)-propionic acid methyl ester, prepared in Step A of Example 12n, and pyridine-2-sulfonyl chloride hydrochloride, of Preparation 47, using triethylamine in place of N,N-diisopropylethylamine. ¹H NMR (400 MHz, CDCl₃) δ 8.66 (m, 1H), 7.95 (d, 1H), 7.85 (m, 1H), 7.45 (m, 1H), 7.15–6.91 (m, 4H), 6.68–6.54 (m, 3H), 4.45 (s, 2H), 4.36 (s, 2H), 4.19 (s, 4H), 3.68 (s, 3H), 2.82 (t, 2H), 2.53 (t, 2H); MS 483 (M+1).

Step B: Ester Hyrolysis 3-(3-{[(2,3-Dihydro-benzo[1,4]dioxin-6-ylmethyl)-(pyridine-2-sulfonyl)-amino]-methyl}-phenyl)-propionic acid The title compound was prepared following the method described in Example 1, Step C from 3-(3{[(2,3-dihydro-benzo[1,4]dioxin-6-ylmethyl)-(pyridine-2-sulfonyl)-amino]-methyl}-phenyl)propionic acid methyl ester of Step A. ¹H NMR (400 MHz, CDCl₃) δ 8.65 (m, 1H), 7.93 (d, 1H), 7.84 (m, 1H), 7.43 (m, 1H), 7.12 (m, 1H), 7.02 (d, 1H), 6.95 (d, 1H), 6.88 (s, 1H), 6.65 (d, 1H), 6.55 (m, 2H), 4.43 (s, 2H), 4.33 (s, 2H), 4.17 (s, 4H), 2.81 (t, 2H), 2.56 (t, 2H); MS 467 (M–1).

EXAMPLE 12p 3-(3-{[(4-Chloro-benzenesulfonyl)-(4-thiazol-2-yl-benzyl)-amino]-methyl}-phenyl)-propionic acid Step A: Amide Formation 3-(3-{[(4-Chloro-benzenesulfonyl)-(4-thiazol-2-yl-benzyl)-amino]-methyl}-phenyl)-propionic acid methyl ester The title compound of Step A was prepared following the method described in Step B of Example 1 from 3-{3-[(4-thiazol-2-yl-benzylamino)-methyl]-phenyl}-propionic acid methyl ester, prepared in Step A of Example 11e, and 4-chlorobenzenesulfonyl chloride using triethylamine in place of N,N-diisopropylethylamine. ¹H NMR (400 MHz, CDCl₃) δ 7.85 (d, 1H), 7.81 (d, 2H), 7.77 (d, 2H), 7.48 (d, 2H), 7.32 (d, 1H), 7.12 (m, 3H), 7.04 (d, 1H), 6.88 (d, 1H), 6.80 (s, 1H), 4.33 (s, 2H), 4.30 (s, 2H), 3.64 (s, 3H), 2.80 (t, 2H), 2.49 (t, 2H), Step B: Ester Hydrolysis 3-(3-{[(4-Chloro-benzenesulfonyl)-(4-thiazol-2-yl-benzyl)-amino]-methyl}-phenyl)-propionic acid The title compound was prepared following the method described in Example 1, Step C from 3-(3-{[(4-chloro-benzenesulfonyl)-(4-thiazol-2-yl-benzyl)-amino]-methyl}-phenyl)-propionic acid methyl ester of Step A. ¹H NMR (400 MHz, CDCl₃) δ 7.84 (d, 1H), 7.82 (dd, 2H), 7.68 (d, 2H), 7.51 (d, 2H), 7.34 (m, 1H), 7.13–7.01 (m, 4H), 6.92 (d, 1H), 6.74 (s, 1H), 4.33 (s, 2H), 4.27 (s, 2H), 2.78 (t, 2H), 2.49 (t, 2H).

EXAMPLE 12q 3-(3-{[Biphenyl-4-ylmethyl-(pyridine-2-sulfonyl)-amino]-methyl}-phenyl)-propionic acid Step A: Amide Formation 3-(3-{[Biphenyl-4-ylmethyl-(pyridine-2-sulfonyl)-amino]-methyl}-phenyl)-propionic acid methyl ester The title compound of Step B was prepared following the method described in Step B of Example 1 from 3-(3-{[(biphenyl-4-ylmethyl)-amino]-methyl}-phenyl)-propionic acid methyl ester, prepared in Step A of Example 12m and pyridine-2-sulfonyl chloride hydrochloride, of Preparation 47, using triethylamine in place of N,N-diisopropylethylamine. ¹H NMR (400 MHz, CDCl₃) δ 8.65 (d, 1H), 7.95 (d, 1H), 7.83 (m, 1H), 7.51 (dd, 2H), 7.45–7.29 (m, 6H), 7.16–7.10 (m, 3H), 7.08–6.90 (m, 3H), 4.50 (s, 2H), 4.48 (s, 2H), 3.64 (s, 3H), 2.79 (t, 2H), 2.49 (t, 2H); MS 501 (M+1).

Step B: Ester Hydrolysis 3-(3-{[Biphenyl-4-ylmethyl-(pyridine-2-sulfonyl)-amino]-methyl}-phenyl)-propionic acid The title compound was prepared following the method described in Example 1, Step C from 3-(3-{[biphenyl-4- ylmethyl-(pyridine-2-sulfonyl)-amino]-methyl}-phenyl)-propionic acid methyl ester of Step B. $^1$H NMR (400 MHz, CDCl$_3$) δ 8.68 (m, 1H), 7.97 (m, 1H), 7.85 (m, 1H), 7.53 (dd, 2H), 7.47–7.31 (m, 6H), 7.18–7.11 (m, 3H), 7.04–6.93 (m, 3H), 4.52 (s, 2H), 4.51 (s, 2H), 2.82 (t, 2H), 2.56 (t, 2H); MS 485 (M−1).

EXAMPLE 12r

3-{3[(Biphenyl-4-ylmethyl-methanesulfonyl-amino)-methyl]-phenyl}-propionic acid

Step A: Amide Formation

3-{3-[(Biphenyl-4-ylmethyl-methanesulfonyl-amino)-methyl]-phenyl}-propionic acid methyl ester The title compound of Step A was prepared following the method described in Step B of Example 1 from 3-(3-{[(biphenyl-4-ylmethyl)-amino]-methyl}-phenyl)-propionic acid methyl ester, prepared in Step A of Example 12m, and methanesulfonyl chloride using triethylamine in place of N,N-diisopropylethylamine. $^1$H NMR (400 MHz, CDCl$_3$) δ 7.56 (m, 4H), 7.44–7.23 (m, 6H), 7.14 (m, 3H), 4.35 (s, 2H), 4.33 (s, 2H), 3.64 (s, 3H), 2.92 (t, 2H), 2.78 (s, 3H), 2.59 (t, 2H).

Step B: Ester Hydrolysis

3-{3-[(Biphenyl-4-ylmethyl-methanesulfonyl-amino)-methyl]-phenyl}-propionic acid The title compound was prepared following the method described in Example 1, Step C from 3-{3-[(biphenyl-4-ylmethyl-methanesulfonyl-amino)-methyl]-phenyl}-propionic acid methyl ester of Step A. $^1$H NMR (400 MHz, CDCl$_3$) δ 7.57 (m, 4H), 7.45–7.24 (m, 6H), 7.15 (m, 3H), 4.36 (s, 2H), 4.34 (s, 2H), 2.94 (t, 2H), 2.79 (s, 3H), 2.66 (t, 2H); MS 422 (M−1).

EXAMPLE 12s 3-(3-{[(4-tert-Butyl-benzyl)-(pyridine-2-sulfonyl)-amino]-methyl}-phenyl)-propionic acid Step A: Reductive Amination 3-{3-[(4-tert-Butyl-benzylamino)-methyl]-phenyl}-propionic acid methyl ester The title compound of Step A was prepared from 3-(3-aminomethyl-phenyl)-propionic acid methyl ester hydrochloride salt, of Preparation 44, and 4-tert-butyl-benzaldehyde using the method described in Example 1, Step A except the imine was formed in MeOH at reflux over 3 h. $^1$H NMR (400 MHz, CDCl$_3$) δ 7.35 (m, 2H), 7.25 (m, 2H), 7.18 (m, 2H), 7.08 (d, 1H), 3.79 (s, 2H), 3.77 (s, 2H), 3.66 (s, 3H), 2.94 (t, 2H), 2.63 (t, 2H), 1.31 (s, 9H); MS 340 (M+1).

Step B: Amide Formation 3-(3-{[(4-tert-Butyl-benzyl)-(pyridine-2-sulfonyl)-amino]-methyl}-phenyl)-propionic acid methyl ester The title compound of Step B was prepared following the method described in Step B of Example 1 from 3-{3-[(4-tert-butyl-benzylamino)-methyl]-phenyl}-propionic acid methyl ester of Step A and pyridine-2sulfonyl chloride hydrochloride, of Preparation 47 using triethylamine in place of N,N-diisopropylethylamine. $^1$H NMR (400 MHz, CDCl$_3$) δ 8.62 (m, 1H), 7.90 (m, 1H), 7.81 (m, 1H), 7.41 (m, 1H), 7.17 (d, 2H), 7.09 (m, 1H), 6.99 (m, 3H), 6.92 (m, 2H), 4.48 (s, 2H), 4.43 (s, 2H), 3.65 (s, 3H), 2.80 (t, 2H), 2.51 (t, 2H), 1.24 (t, 9H); MS 481 (M+1).

Step C: Ester Hydrolysis 3-(3-{[(4-tert-Butyl-benzyl)-(pyridine-2-sulfonyl)-amino]-methyl}-phenyl)-propionic acid The title compound was prepared following the method described in Example 1, Step C from 3-(3-{[(4-tert-butyl-benzyl)-(pyridine-2-sulfonyl)-amino]-methyl}-phenyl)-propionic acid methyl ester of Step B. $^1$H NMR (400 MHz, CDCl$_3$) δ 8.64 (m, 1H), 7.92 (m, 1H), 7.83 (m, 1H), 7.43 (m, 1H), 7.19 (d, 2H), 7.12 (m, 1H), 7.02 (m, 3H), 6.94 (m, 2H), 4.48 (s, 2H), 4.43 (s, 2H), 2.82 (t, 2H), 2.57 (t, 2H), 1.26 (t, 9H); MS 465 (M−1).

EXAMPLE 12t

3(3{[(Benzenesulfonyl-(4-tert-butyl-benzyl)-amino]-methyl}-phenyl)-propionic acid Step A: Amide Formation 3-(3{[Benzenesulfonyl-(4-tert-buytl-benzyl)-amino]-methyl}-phenyl)-propionic acid methyl ester The title compound of Step A was prepared following the method described in Step B of Example 1 from 3-{3-[(4-tert-butyl-benzylamino)-methyl]-phenyl}-propionic acid methyl ester, prepared in Step A of Examples 12s, and benzenesulfonyl chloride using triethylamine in place of N,N-diisopropylethylamine. $^1$H NMR (400 MHz, CDCl$_3$) δ 7.81 (dd, 2H), 7.56 (m, 1H), 7.48 (m, 2H), 7.19 (d, 2H), 7.10 (m, 1H), 7.01 (d, 1H), 6.94 (d, 2H), 6.86 (d, 1H), 6.79 (s, 1H), 4.28 (s, 2H), 4.26 (s, 2H), 3.65 (s, 3H), 2.79 (t, 2H), 2.49 (t, 2H), 1.25 (s, 9H); MS 480 (M+1).

Step B: Ester Hydrolysis 3-(3-{[(Benzenesulfonyl-(4-tert-butyl-benzyl)-amino]-methyl}-phenyl)-propionic acid The title compound was prepared following the method described in Example 1, Step C from 3-(3-{[benzene-sulfonyl-(4-tert-butyl-benzyl)-amino]-methyl}-phenyl-propionic acid methyl ester of Step A. $^1$H NMR (400 MHz, CDCl$_3$) δ 7.82 (dd, 2H), 7.59–7.47 (m, 3H), 7.21 (d, 2H), 7.12 (m, 1H), 7.03 (d, 1H), 6.95 (d, 2H), 6.88 (d, 1H), 6.81 (s, 1H), 4.30 (s, 2H), 4.27 (s, 2H), 2.81 (t, 2H), 2.55 (t, 2H), 1.26 (s, 9H); MS 464 (M−1).

EXAMPLE 12u

3-{3-[(Benzenesulfonyl-benzofuran-2-ylmethyl-amino)-methyl]-phenyl}-propionic acid Step A: Reductive Amination 3-(3-{[(Benzofuran-2-ylmethyl)-amino]-methyl}-phenyl)-propionic acid methyl ester The title compound of Step A was prepared from 3-(3-aminomethyl-phenyl)-propionic acid methyl ester hydrochloride salt, of Preparation 44, and benzofuran-2-carbaldehyde using the method described in Example 1, Step A except the imine was formed in MeOH at reflux over 3 h. $^1$H NMR (400 MHz, CDCl$_3$) δ 7.50 (dd, 1H), 7.42 (d, 1H), 7.25–7.14 (m, 5H), 7.07 (d, 1H), 6.55 (d, 1H), 3.91 (s, 2H), 3.79 (s, 2H), 3.64 (s, 3H), 2.92 (t, 2H), 2.60 (t, 2H).

Step B: Amide Formation

3-{3-[(Benzenesulfonyl-benzofuran-2-ylmethyl-amino)-methyl]-phenyl}-propionic acid methyl ester The title compound of Step B was prepared following the method describe in Step B of Example 1 from 3-(3-{[(benzofuran-2-ylmethyl)-amino]-methyl}-phenyl)-propionic acid methyl ester of Step A and benzenesulfonyl chloride using triethylamine in place of N,N-diisopropylethylamine. $^1$H NMR (400 MHz, CDCl$_3$) δ 7.83 (m, 2H), 7.52–7.42 (m, 3H), 7.26–7.09 (m, 8H), 6.39 (d, 1H), 4.46 (s, 2H), 4.39 (s, 2H), 3.68 (s, 3H), 2.88 (t, 2H), 2.57 (t, 2H).

Step C: Ester Hydrolysis

3-{3-[(Benzenesulfonyl-benzofuran-2-ylmethyl-amino)-methyl]-phenyl}-propionic acid The title compound was prepared following the method described in Example 1, Step C from 3-{3-[(benzenesulfonyl-benzofuran-2-ylmethyl-amino)-methyl]-phenyl}-propionic acid methyl ester of Step B. $^1$H NMR (400 MHz, CDCl$_3$) δ 7.81 (m, 2H), 7.51–7.37 (m, 3H), 7.25–7.06 (m, 8H), 6.36 (d, 1H), 4.43 (s, 2H), 4.37 (s, 2H), 2.86 (t, 2H), 2.58 (t, 2H); MS 448 (M−1).

EXAMPLE 12v 3-(3-{[Benzofuran-2-ylmethyl-(4-fluror-benzenesulfonyl)-amino]-methyl}-phenyl)-propionic acid Step A: Amide Formation 3-(3-{[Benzofuran-2-ylmethyl-(4-fluro-benzenesulfonyl)-amino]-methyl}-phenyl)-propionic acid methyl ester The title compound of Step A was prepared following the method described in Step B of Example 1 from 3-(3-{[(benzofuran-2-ylmethyl)-amino]-methyl}-phenyl)-propionic acid methyl ester, prepared in Step A of Example 12u, and 4-fluorobenzenesulfonyl chloride using triethylamine in place of N,N-diisopropylethylamine. $^1$H NMR (400 MHz, CDCl$_3$) δ 7.82 (m, 2H), 7.46 (m, 1H), 7.28–7.03 (m, 9H), 6.42 (s, 1H), 4,45 (s, 2H), 4.38 (s, 2H), 3.67 (s, 3H), 2.90 (t, 2H), 2.58 (t, 2H).

Step B: Ester Hydrolysis

3(3-{[Benzofuran-2ylmethyl-(4-fluoro-benzenesulfonyl)-amino]-methyl}-phenyl)-propionic acid The title compound was prepared following the method described in Example 1, Step C from 3-(3-{[benzofuran-2-ylmethyl-(4-fluoro-benzenesulfonyl)-amino]-methyl}-phenyl)-propionic acid methyl ester of Step B. $^1$H NMR (400 MHz, CDCl$_3$) δ 7.81 (m, 2H), 7.45 (m, 1H), 7.24–7.03 (m, 9H), 6.41 (s, 1H), 4.44 (s, 2H), 4.38 (s, 2H), 2.90 (t, 2H), 2.62 (t, 2H); MS 466 (M−1).

EXAMPLE 12w 3-(3-{[(2,3-Dihydro-benzofuran-5-ylmethyl)-methanesulfonyl-amino]-methyl}-phenyl)-propionic acid Step A: Reductive Amination 3-(3-{[(2,3-Dihydro-benzofuran-5-ylmethyl)-amino]-methyl}-phenyl)-propionic acid methyl ester The title compound of Step A was prepared from 3-(3-aminomethyl-phenyl)-propionic acid methyl ester hydrochloride salt, of Preparation 44, and 2,3-dihydro-benzofuran-5-carbaldehyde using the method described in Example 1, Step A except the imine was formed in MeOH at refulx over 3 h. $^1$H NMR (400 MHz, CDCl$_3$) δ 7.23 (m, 4H), 7.07 (m, 2H), 6.73 (d, 1H), 4.54 (t, 2H), 3.77 (s, 2H), 3.71 (s, 2H), 3.66 (s, 3H), 3.18 (t, 2H), 2.94 (t, 2H), 2.63 (t, 2H); MS 326 (M+1).

Step B: Amide Formation 3-(3-{[(2,3-Dihydro-benzofuran-5-ylmethyl)-methanesulfonyl-amino]-methyl}-phenyl)-propionic acid methyl ester The title compound of Step B was prepared following the method described in Step B of Example 1 from 3-(3{[(2,3-dihydro-benzofuran-5-ylmethyl)-amino]-methyl}-phenyl)-propionic acid methyl ester of Step A and methanesulfonyl chloride using triethylamine in place of N,N-diisopropylethylamine. $^1$H NMR (400 MHz, CDCl$_3$) δ 7.27 (m, 2H), 7.14 (m, 3H), 6.98 (d, 1H), 6.73 (d, 1H), 4.57 (t, 2H), 4.29 (s, 4H), 4.24 (s, 2H), 3.66 (s, 3H), 3.19 (t, 2H), 2.94 (t, 2H), 2.75 (s, 3H), 2.61 (t, 2H).

Step C: Ester Hydrolysis

3(3{[(2,3-Dihydro-benzofuran-5-ylmethyl)-methanesulfonyl-amino]-methyl}-phenyl)-propionic acid The title compound was prepared following the method described in Example 1, Step C from 3-(3{[[(2,3-dihydro-benzofuran-5-ylmethyl)-methanesulfonyl-amino]-methyl}-phenyl)-propionic acid methyl ester of Step B. $^1$H NMR (400 MHz, CDCl$_3$) δ 7.27 (m, 2H), 7.15 (m, 3H), 6.98 (d, 1H), 6.72 (d, 1H), 4.57 (t, 2H), 4.29 (s, 2H), 4.24 (s, 2H), 3.18 (t, 2H), 2.94 (t, 2H), 2.75 (s, 3H), 2.66 (t, 2H); MS 388 (M−1).

EXAMPLE 12x 3-(3-{[Benzenesulfonyl-(2,3-dihydro-benzofuran-5-ylmethyl)-amino]-methyl}-phenyl)-propionic acid Step A: Amide Formation 3-(3-{[Bensenesulfonyl-(2,3-dihydro-benzofuran-5-ylmethyl)-amino]-methyl}-phenyl)-propionic acid methyl ester The title compound of Step B was prepared following the method described in Step A of Example 1 from 3-(3-{[(2,3-dihydro-benzofuran-5-ylmethyl)-amino]-methyl}-phenyl)-propionic acid methyl ester, prepared in Step A of Example 12w, and benzenesulfonyl chloride using triethylamine in place of N,N-diisopropylethylamine. $^1$H NMR (400 MHz, CDCl$_3$) δ 7.82 (m, 2H), 7.58–7.47 (m, 3H), 7.10 (m, 1H), 7.00 (d, 1H), 6.89 (s, 1H), 6.85 (d, 1H), 6.74 (s, 1H), 6.68 (d, 1H), 6.56 (d, 1H), 4.50 (t, 2H), 4.26 (s, 2H), 4.21 (s, 2H), 3.65 (s, 3H), 3.06 (t, 2H), 2.78 (t, 2H), 2.47 (t, 2H).

Step B: Ester Hydrolysis 3-(3{[Benzenesulfonyl-(2,3-dihydro-benzofuran-5-ylmethyl)-amino]-methyl}-phenyl)-propionic acid The title compound was prepared following the method described in Example 1, Step C from 3-(3-{[benzenesulfonyl-(2,3-dihydro-benzofuran-5-ylmethyl)-amino]- methyl}-phenyl)-propionic acid methyl ester of Step A. $^1$H NMR (400 MHz, CDCl$_3$) δ 7.82 (dd, 2H), 7.59–7.47 (m, 3H), 7.11 (m, 1H), 7.02 (d, 1H), 6.88 (m, 2H), 6.73 (s, 1H), 6.68 (m, 1H), 6.56 (d, 1H), 4.50 (t, 2H), 4.26 (s, 2H), 4.21 (s, 2H), 3.06 (t, 2H), 2.78 (t, 2H), 2.52 (t, 2H); MS 450 (M−1).

EXAMPLE 12y 3-(3{[(2,3-Dihydro-benzofuran-5-ylmethyl)-(4-fluoro-benzenesulfonyl)-amino]-methyl}-phenyl)-propionic acid

Step A: Amide Formation 3-(3-{[(2,3-Dihydro-benzofuran-5-ylmethyl)-(4-fluoro-benzenesulfonyl)-amino]-methyl}-phenyl)-propionic acid methyl ester The title compound of Step A was prepared following the method described in Step A of Example 1 from 3-(3-{[(2,3-dihydro-benzofuran-5-ylmethyl)-amino]-methyl}-phenyl)-propionic acid methyl ester, prepared in Step A of Example 12w, and 4-fluorobenzenesulfonyl chloride using triethylamine in place of N,N-diisopropylethylamine. $^1$H NMR (400 MHz, CDCl$_3$) δ 7.79 (m, 2H), 7.14 (m, 3H), 7.03 (d, 1H), 6.88 (m, 2H), 6.79 (s, 1H), 6.71 (d, 1H), 6.58 (d, 1H), 4.51 (t, 2H), 4.25 (s, 2H), 4.21 (s, 2H), 3.64 (s, 3H), 3.08 (t, 2H), 2.80 (t, 2H), 2.50 (t, 2H).

Step B: Ester Hydrolysis 3-(3-{[(2,3-Dihydro-benzofuran-5-ylmethyl)-(4-fluoro-benzenesulfonyl)-amino]-methyl}-phenyl)-propionic acid.

The title compound was prepared following the method described in Example 1, Step C from 3-(3{[(2,3-dihydro-benzofuran-5-ylmethyl)-(4-fluoro-benzenesulfonyl)-amino]-methyl}-phenyl)-propionic acid methyl ester of Step A. $^1$H NMR (400 MHz, CDCl$_3$) δ 7.79 (m, 2H), 7.14 (m, 3H), 7.03 (d, 1H), 6.89 (m, 2H), 6.79 (s, 1H), 6.70 (d, 1H), 6.58 (d, 1H), 4.51 (t, 2H), 4.25 (s, 2H), 4.20 (s, 2H), 3.07 (t, 2H), 2.81 (t, 2H), 2.55 (t, 2H); MS 468 (M−1).

EXAMPLE 12z 3-(3-{[Benzenesulfonyl-(4-isobutyl-benzyl)-amino]-methyl}-phenyl)-propionic acid

Step A: Reductive Amination

3-{3-[(4-Isobutyl-benzylamino)-methyl]-phenyl}-propionic acid methyl ester

A solution of 3-(3-aminomethyl-phenyl)-propionic acid methyl ester hydrochloride salt (400 mg, 1.74 mmol), 4-iosbutylbenzaldehyde (311 mg, 1.91 mmol), and triethylamine (0.26 mL, 1.19 mmol) in CH$_2$Cl$_2$ (4 mL) was stirred at room temperature for 4 h. Sodium triacetoxyborohydride (590 mg, 2.78 mmol) was added and the reaction was stirred for 20 h. Aqueous NaHCO$_3$ was added and the aqueous solution was washed with CH$_2$Cl$_2$. The organic solution was dried (MgSO$_4$), filtered, and concentrated. Flash chromatography (65% EtOAc in hexanes) provided the title compound of Step A (178 mg). $^1$H NMR (400 MHz, CDCl$_3$) δ 7.26–7.04 (m, 8H), 3.77 (s, 2H), 3.75 (s, 2H), 3.63 (s, 3H), 2.91 (t, 2H), 2.60 (t, 2H), 2.41 (d, 2H), 1.80 (m, 1H), 0.85 (m, 6H); MS 340 (M+1).

Step B: Amide Formation 3-(3-{[Benzenesulfonyl-(4-isobutyl-benzyl)-amino]-methyl}-phenyl)-propionic acid methyl ester The title compound of Step B was prepared following the method described in Step A of Example 1 from 3-{3-[(4-isobutyl-benzylamino)-methyl]-phenyl}-propionic acid methyl ester of Step A and benzenesulfonyl chloride using triethylamine in place of N,N-diisopropylethylamine. $^1$H NMR (400 MHz, CDCl$_3$) δ 7.83 (dd, 2H), 7.57 (m, 1H), 7.52 (m, 2H), 7.11 (m, 1H), 7.03–6.86 (m, 6H), 6.79 (s, 1H), 4.29 (s, 2H), 4.28 (s, 2H), 3.67 (s, 3H), 2.80 (t, 2H), 2.50 (t, 2H), 2.40 (d, 2H), 1.80 (m, 1H), 0.86 (m, 6H); MS 480 (M+1).

Step C: Ester Hydrolysis 3-(3-{[Benzenesulfonyl-(4-iosbutyl-benzyl)-amino]-methyl}-phenyl)-propionic acid The title compound was prepared following the method described in Example 1, Step C from 3-(3-{[benzene-sulfonyl-(4-isobutyl-benzyl)-amino]-methyl}-phenyl)-propionic acid methyl ester of Step B. $^1$H NMR (400 MHz, CDCl$_3$) δ 7.82 (d, 2H), 7.58–7.46 (m, 3H), 7.10 (m, 1H), 7.02–6.84 (m, 6H), 6.78 (s, 1H), 4.27 (s, 2H), 4.26 (s, 2H), 2.79 (t, 2H), 2.53 (t, 2H), 2.38 (d, 2H), 1.77 (m, 1H), 0.84 (m, 6H); MS 464 (M−1).

Example 13a–z, 14a–14e

Examples 13a–13z, 14a–14e were prepared from the appropriate starting materials in a manner analogous to the method of Example 3, with variations in reactions time, temperature, and reagents as noted.

EXAMPLE 13a (3-{[Benzenesulfonyl-(4-pyrazol-1-yl-benzyl)-amino]-methyl}-phenoxy)-acetic acid hydrochloride salt

Step A: Reductive Amination

{3-[(4-Pyrazol-1-yl-benzylamino)-methyl]-phenoxy}-acetic acid tert-butyl ester

The title compound of Step A was prepared from (3-aminomethyl-phenoxy)-acetic acid tert-butyl ester, of Preparation 20, and 4-pyrazol-1-yl-benzaldehyde, of Preparation 42, using the method described in Example 3, Step A, except no triethylamine was used. $^1$H NMR (400 MHz, CDCl$_3$) δ 7.90 (m, 1H), 7.70 (m, 1H), 7.63 (d, 2H), 7.41 (d, 2H), 7.23 (m, 1H), 6.94 (m, 2H), 6.78 (dd, 1H), 6.44 (dd, 1H), 4.51 (s, 2H), 3.81 (s, 2H), 3.77 (s, 2H), 1.47 (s, 9H); MS 394 (M+1).

Step B: Amide Formation (3-{[Benzenesulfonyl-(4-pyrazol-1-yl-benzyl)-amino]-methyl}-phenoxy)-acetic acid tert-butyl ester The title compound of Step B was prepared from {3-[(4-pyrazol-1-yl-benzylamino)-methyl-phenoxy}-acetic acid tert-butyl ester of Step A and benzenesulfonyl chloride following the method described in Example 3, Step B with a reaction time of 2 h. $^1$H NMR (400 MHz, CDCl$_3$) δ 8.01 (d, 1H), 7.86–7.49 (m, 8H), 7.07 (m, 3H), 6.73 (m, 1H), 6.60 (d, 1H), 6.56 (s, 1H), 6.42 (m, 1H), 4.33 (s, 2H), 4.32 (s, 2H), 4.27 (s, 2H), 1.46 (s, 9H); MS 534 (M+1).

Step C: Ester Hydrolysis (3-{[Benzenesulfonyl-(4-pyrazol-1-yl-benzyl)-amino]-methyl}-phenoxy)-acetic acid hydrochloride salt The TFA salt was prepared following the method described in Example 3, Step C from (3-{[benzenesulfonyl- (4-pyrazol-1-yl-benzyl)-amino]-methyl}-phenoxy)-acetic acid tert-butyl ester of Step B. The HCl salt was prepared by dissolving the TFA salt in THF (2 mL) followed by addition of 0.18 mL of 1N HCl. The solution was concentrated in vacuo, azeotroping with $CH_2Cl_2$ (3×) to provide the title compound. $^1$H NMR (400 MHz, $CD_3OD$) δ 8.16 (d, 1H), 7.89–7.51 (m, 8H), 7.17 (d, 2H), 7.06 (t, 1H), 6.73 (dd, 1H), 6.67 (d, 1H), 6.59 (s, 1H), 6.52 (m, 1H), 4.46 (s, 2H), 4.34 (s, 2H), 4.29 (s, 2H), 1.46 (s, 9H); MS 476 (M−1).

EXAMPLE 13b (3-{[(4-Pyrazin-2-yl-benzyl)-(pyridine-3-sulfonyl)-amino]-methyl)-phenoxy)-acetic acid hydrochloride salt

Step A: Reductive Amination

{3-[(4-Pyrazin-2-yl-benzylamino)-methyl]-phenoxy}-acetic acid tert-butyl-ester

The title compound of Step A was prepared from (3-aminomethyl-phenoxy)-acetic acid tert-butyl ester, of Preparation 20, and 4-pyrazin-2-yl-benzaldehyde, of Preparation 27, using the method described in Example 3, Step A, except no triethylamine was used. $^1$H NMR (400 MHz, $CDCl_3$) δ 9.00 (s, 1H), 8.60 (m, 1H), 8.47 (d, 1H), 7.96 (d, 2H), 7.62 (m, 1H), 7.47 (d, 2H), 7.22 (m, 1H), 6.94 (m, 1H), 6.76 (dd, 1H), 4.50 (s, 2H), 3.85 (s 2H), 3.78 (s, 2H), 1.46 (s, 9H); MS 406 (M+1).

Step B: Amide Formation (3-{[(4-Pyrazin-2-yl-benzyl)-(pyridine-3-sulfonyl)-amino]-methyl}-phenoxy)-acetic acid tert-butyl ester The title compound of Step B was prepared from {3-[(4-pyrazin-2-yl-benzylamino)-methyl]-phenoxy}-acetic acid tert-butyl ester of Step A and pyridine-3-sulfonyl hydrochloride, of Preparation 2, following the method described in Example 3, Step B $^1$H NMR (400 MHz, $CDCl_3$) δ 9.05 (s, 1H), 8.97 (m, 1H), 8.78 (m, 1H), 8.60 (m, 1H), 8.50 (d, 1H), 8.03 (m, 1H), 7.88 (m, 2H), 7.42 (m, 1H), 7.23 (m, 2H), 7.13 (m, 1H), 6.66 (m, 1H), 6.65 (m, 2H), 4.43 (s, 2H), 4.39 (s, 2H), 4.35 (s, 2H), 1.47 (s, 9H); MS 547 (M+1).

Step C: Ester Hydrolysis (3-{[(4-Pyrazin-2-yl-benzyl)-(pyridine-3-sulfonyl)-amino]-methyl}-phenoxy)-acetic acid hydrochloride salt The title compound was prepared following the method described in Example 3, Step C from (3-{[(4-pyrazin-2-yl-benzyl)-(pyridine-3-sulfonyl)-amino]-methyl}-phenoxy)-acetic acid tert-butyl ester of Step B. The HCl salt was prepared following the procedure described in Step C of Example 13a to provide the title compound. $^1$H NMR (400 MHz, $CD_3OD$) δ 9.25 (s, 1H), 9.16 (d, 1H), 9.00 (m, 2H), 8.87 (d, 1H), 8.66 (d, 1H), 8.17 (m, 1H), 8.04 (m, 2H), 7.45 (m, 2H), 7.10 (m, 1H), 6.81 (d, 1H), 6.73 (m, 2H), 4.60 (s, 2H), 4.55 (s, 2H), 4.50 (s, 2H); MS 489 (M−1).

EXAMPLE 13c (3-{[(4-Pyrazol-1-yl-benzyl)-pyridine-2-sulfonyl)-amino]-methyl}-phenoxy)-acetic acid TFA salt

Step A: Amide Formation (3-{[(4-Pyrazol-1-yl-benzyl)-pyridine-2-sulfonyl)-amino]-methyl}-phenoxy)-acetic acid tert-butyl ester The title compound of Step A was prepared from {3-[(4-pyrazol-1-yl-benzylamino)-methyl]-phenoxy}-acetic acid tert-butyl ester, of Step A of Example 13a, and pyridine-2-sulfonyl chloride hydrochloride, of Preparation 47, following the method described in Example 3, Step B with a reaction time of 2 h. $^1$H NMR (400 MHz, $CDCl_3$) δ 8.66 (m, 1H), 7.95 (d, 1H), 7.85 (m, 2H), 7.68 (d, 1H), 7.49 (d, 2H), 7.45 (m, 1H), 7.16 (d, 2H), 7.08 (t, 1H), 6.70 (m, 3H), 6.43 (m, 1H), 4.49 (s, 2H), 4.44 (s, 2H), 4.38 (s, 2H) 1.46 (s, 9H); MS 535 (M+1).

Step B: Ester Hydrolysis (3-{[(4-Pyrazol-1-yl-benzyl)-pyridine-2-sulfonyl)-amino]-methyl}-phenoxy)-acetic acid TFA salt The title compound was prepared following the method described in Example 3, Step C from (3-{[(4-pyrazol-1-yl-benzyl)-(pyridine-2-sulfonyl)-amino]-methyl}-phenoxy)-acetic acid tert-butyl ester of Step A. $^1$H NMR (400 MHz, $CD_3OD$) δ 8.68 (m, 1H), 8.15 (m, 1H), 7.96 (m, 2H), 7.68 (d, 1H), 7.60 (m, 1H), 7.55 (d, 2H), 7.24 (d, 2H), 7.09 (t, 1H), 6.73 (m, 3H), 6.49 (m, 1H), 4.52 (s, 2H), 4.49 (s, 2H), 4.46 (s, 2H); MS 477 (M−1).

EXAMPLE 13d (3-{[Benzenesulfonyl-(4-pyridin-2-yl-benzyl)-amino]-methyl}-phenoxy)-acetic acid sodium salt

Step A: Reductive Amination

{3-[(4-Pyridin-2-yl-benzylamino)-methyl]-phenoxy}-acetic acid tert-butyl ester

The title compound of Step A was prepared from (3-aminomethyl-phenoxy)-acetic acid tert-butyl ester, of Preparation 20, and 4-pyridin-2-yl-benzaldehyde, of Preparation 22, using the method described in Example 3, Step A, except no triethylamine was used. $^1$H NMR (400 MHz, $CDCl_3$) δ 8.67 (d, 1H), 7.94 (d, 2H), 7.72 (m, 2H), 7.44 (d, 2H), 7.22 (m, 2H), 6.95 (m, 2H), 6.78 (dd, 1H), 4.51 (s, 2H), 3.84 (s, 2H), 3.78 (s, 2H), 1.47 (s, 9H); MS 405 (M+1).

Step B: Amide Formation (3-{[Benzenesulfonyl-(4-pyridin-2-yl-benzyl)-amino]-methyl}-phenoxy)-acetic acid tert-butyl ester The title compound of Step B was prepared from {3-[(4-pyridin-2-yl-benzylamino)-methyl]-phenoxy}-acetic acid tert-butyl ester of Step A and benzenesulfonyl chloride following the method described in Example 3, Step B $^1$H NMR (400 MHz, $CDCl_3$) δ 8.67 (d, 1H), 7.86 (m, 4H), 7.77–7.51 (m, 5H), 7.24 (m, 1H), 7.11 (m, 3H), 6.76 (dd, 1H), 6.64 (d, 1H), 6.59 (d, 1H), 4.38 (s, 2H), 4.35 (s, 2H), 4.30 (s, 2H), 1.48 (s, 9H); MS 545 (M+1).

Step C: Ester Hydrolysis (3-{[Benzenesulfonyl-(4-pyridin-2-yl-benzyl)-amino]-methyl}-phenoxy)-acetic acid sodium salt The title compound was prepared following the method described in Example 3, Step C from (3-{[benzenesulfonyl-(4-pyridin-2-yl-benzyl)-amino]-methyl}-phenoxy)-acetic acid tert-butyl ester of Step B. The TFA salt was diluted with EtOAc and water and the aqueous solution was basified to about pH 11 with NaOH (1N). The aqueous solution was acidified with glacial acetic acid to about pH 5 and was washed with EtOAc (3×). The organic solution was dried ($MgSO_4$), filtered, and concentrated, azeotroping with toluene, to provide the free acid (128 mg). The acid was dissolved in a mixture of acetone (4 mL), MeOH (4 mL) and water (0.5 mL), and NaHCO$_3$ (22 mg, 0.258 mmol) was added. The reaction was stirred for 24 h and was concentrated in vacuo, azeotroping with EtOH (3×) and CHCl$_3$ (1×) to provide the title sodium salt (137 mg). $^1$H NMR (400 MHz, CD$_3$OD) δ 8.56 (dd, 1H), 7.89–7.76 (m, 6H), 7.65–7.56 (m, 3H), 7.33 (m, 1H), 7.21 (d, 2H), 7.05 (t, 1H), 6.74 (d, 1H), 6.63 (m, 2H), 4.40 (s, 2H), 4.31 (s, 2H), 4.21 (s, 2H); MS 487 (M−1).

EXAMPLE 13e (3-{[Benzenesulfonyl-(4-pyridin-3-yl-benzyl)-amino]-methyl}-phenoxy)-acetic acid sodium salt Step A: Reductive Amination {3-[(4-Pyridin-3-yl-benzylamino)-methyl]-phenoxy}-acetic acid tert butyl ester The title compound of Step A was prepared from (3-aminomethyl-phenoxy)-acetic acid tert-butyl ester, of Preparation 20, and 4-pyridin-3-yl-benzaldehyde, of Preparation 23, using the method described in Example 3, Step A, except no triethylamine was used. $^1$H NMR (400 MHz, CDCl$_3$) δ 8.82 (d, 1H), 8.56 (m, 1H), 7.85 (m, 1H), 7.53 (d, 2H), 7.45 (d, 2H), 7.34 (m, 1H), 7.24 (m, 1H), 6.96 (m, 2H), 6.78 (dd, 1H), 4.51 (s, 2H), 3.84 (s, 2H), 3.80 (s, 2H), 1.47 (s, 9H); MS 405 (M+1).

Step B: Amide Formation (3-{[Benzenesulfonyl-(4-pyridin-3-yl-benzyl)-amino]-methyl}-phenoxy)acetic-acid tert-butyl ester The title compound of Step B was prepared from {3-[(4-pyridin-3-yl-benzylamino)-methyl]-phenoxy}-acetic acid tert-butyl ester of Step A and benzenesulfonyl chloride following the method described in Example 3, Step B $^1$H NMR (400 MHz, CDCl$_3$) δ 8.80 (s, 1H), 8.59 (d, 1H), 7.89 (m, 3H), 7.60 (m, 1H), 7.50 (m, 2H), 7.41 (m, 3H), 7.17 (d, 2H), 7.10 (t, 1H), 6.74 (m, 1H), 6.64 (d, 1H), 6.58 (d, 1H), 4.37 (s, 2H), 4.34 (s, 2H), 4.32 (s, 2H), 1.48 (s, 9H); MS 545 (M+1).

Step C: Ester Hydrolysis (3-{[Benzenesulfonyl-(4-pyridin-3-yl-benzyl)-amino]-methyl}-phenoxy)-acetic acid sodium salt The title compound was prepared following the method described in Example 3, Step C from (3-{[benzenesulfonyl-(4-pyridin-3-yl-benzyl)-amino]-methyl}-phenoxy)-acetic acid tert-butyl ester of Step B. The sodium salt was prepared following the method described in Step C of Example 13d. $^1$H NMR (400 MHz, CD$_3$OD) δ 8.74 (s, 1H), 8.48 (d, 1H), 8.05 (dd, 1H), 7.88 (dd, 2H), 7.67–7.47 (m, 6H), 7.23 (d, 2H), 7.05 (t, 1H), 6.74 (d, 1H), 6.63 (d, 1H), 6.59 (s, 1H), 4.39 (s, 2H), 4.30 (s, 2H), 4.20 (s, 2H); MS 487 (M−1).

EXAMPLE 13f (3{[Benzenesulfonyl-(4-pyridin-4-yl-benzyl)-amino]-methyl}-phenoxy)-acetic acid sodium salt Step A: Reductive Amination {3-[(4-Pyridin-4-yl-benzylamino)-methyl]-phenoxy}-acetic tert-butyl ester.

The compound of Step A was prepared from (3-aminomethyl-phenoxy)-acetic acid tert-butyl ester, of Preparation 20, and 4-pyridin-4-yl-benzaldehyde, of Preparation 24, using the method described in Example 3, Step A, except no triethylamine was used. $^1$H NMR (400 MHz, CDCl$_3$) δ 8.63 (dd, 2H), 7.60 (dd, 2H), 7.47 (m, 4H), 7.24 (m, 1H), 6.96 (m, 2H), 6.78 (dd, 1H), 4.52 (s, 2H), 3.85 (s, 2H), 3.80 (s, 2H), 1.47 (s, 9H); MS 405 (M+1).

Step B: Amide Formation (3-{[Benzenesulfonyl-(4-pyridin-4-yl-benzyl)-amino]-methyl}-phenoxy)-acetic acid tert-butyl ester The title compound of Step B was prepared from {3-[(4-pyridin-4-yl-benzylamino)-methyl]-phenoxy}-acetic acid tert-butyl ester of Step A and benzenesulfonyl chloride following the method described in Example 3, Step B with a reaction time of 3 h. $^1$H NMR (400 MHz, CDCl$_3$) δ 8.63 (d, 2H), 7.86 (dd, 2H), 7.62–7.46 (m, 7H), 7.17 (d, 2H), 7.07 (t, 1H), 6.71 (dd, 1H), 6.60 (d, 1H), 6.54 (s, 1H), 4.35 (s, 2H), 4.32 (s, 2H), 4.29 (s, 2H), 1.46 (s, 9H); MS 545 (M+1).

Step C: Ester Hydrolysis (3-{[Benzenesulfonyl-(4-pyridin-4-yl-benzyl)-amino]-methyl}-phenoxy)-acetic acid sodium salt The title compound was prepared following the method described in Example 3, Step C from (3-{[benzenesulfonyl-(4-pyridin-4-yl-benzyl)-amino]-methyl}-phenoxy)-acetic acid tert-butyl ester of Step B. The sodium salt was prepared following the procedure described in Step C of Example 13d. $^1$H NMR (400 MHz, CD$_3$OD) δ 8.56 (bs, 2H), 7.89 (d, 2H), 7.68–7.59 (m, 7H), 7.25 (d, 2H), 7.04 (t, 1H), 6.74 (d, 1H), 6.63 (d, 1H), 6.59 (s, 1H), 4.39 (s, 2H), 4.30 (s, 2H), 4.20 (s, 2H); MS 487 (M−1).

EXAMPLE 13g (3-{[(Pyridine-3-sulfonyl)-(4-pyrimidin-5-yl-benzyl)-amino]-methyl}-phenoxy)-acetic hydrochloride salt Step A: Reductive Amination {3-[(4-Pyrimidin-5-yl-benzylamino)-methyl]-phenoxy}-acetic acid tert-butyl ester The title compound of Step A was prepared from (3-aminomethyl-phenoxy)-acetic acid tert-butyl ester, of Preparation 20, and 4-pyrimidin-5-yl-benzaldehyde, of Preparation 26, using the method described in Example 3, Step A, except that the reaction time for imine formation was 1.5 h and no triethylamine was used. $^1$H NMR (400 MHz, CDCl$_3$) δ 9.18 (s, 1H), 8.93 (s, 2H), 7.65 (m, 1H), 7.48 (m, 3H), 7.24 (m, 1H), 6.94 (m, 2H), 6.77 (d, 1H), 4.51 (s, 2H), 3.85 (s, 2H), 3.79 (s, 2H), 1.46 (s, 9H); MS 406 (M+1).

Step B: Amide Formation (3-{[(Pyridine-3-sulfonyl)-(4-pyrimidin-5-yl-benzyl)-amino]-methyl}-phenoxy)-acetic tert-butyl ester The title compound of Step B was prepared from {3-[(4-pyrimidin-5-yl-benzylamino)-methyl]-phenoxy}-acetic acid tert-butyl ester of Step A and pyridine-3-sulfonyl chloride hydrochloride, of Preparation 2, followed the method described in Example 3, Step B $^1$H NMR (400 MHz, CDCl$_3$) δ 9.19 (s, 1H), 9.05 (s, 1H), 8.89 (s, 2H), 8.79 (dd, 1H), 8.06

(m, 1H), 7.65 (m, 1H), 7.44 (m, 2H), 7.24 (m, 2H), 7.12 (t, 1H), 6.74 (dd, 1H), 6.66 (m, 2H), 4.42 (s, 2H), 4.39 (s, 2H), 4.34 (s, 2H), 1.47 (s, 9H); MS 547 (M+1).

Step C: Ester Hydrolysis (3-{[(Pyridine-3-sulfonyl)-(4-pyrimidin-5-yl-benzyl)-amino]-methyl}-phenoxy)-acetic acid hydrochloride salt The title compound was prepared following the method described in Example 3, Step C from (3-{[(pyridine-3-sulfonyl)-(4-pyrimidin-5-yl-benzyl)-amino]-methyl}-phenoxy)-acetic tert-butyl ester of Step B. The HCl salt was prepared following the method described in Step C of Example 13a. $^1$H NMR (400 MHz, CD$_3$OD) δ 9.40 (s, 2H), 9.17 (m, 1H), 9.00 (m, 1H), 8.80 (m, 1H), 8.11 (m, 1H), 7.72–7.29 (m, 5H), 7.10 (m, 1H), 6.80–6.65 (m, 3H), 4.65 (s, 2H), 4.55 (s, 2H), 4.47 (s, 2H); MS 489 (M−1).

EXAMPLE 13h (3-{[(4-Pyrazol-1-yl-benzyl)-pyridine-3-sulfonyl)-amino]-methyl}-phenoxy)-acetic acid hydrochloride salt Step A: Reductive Amination {3-[(4-Pyrazol-1-yl-benzylamino)-methyl]-phenoxy}-acetic acid tert-butyl ester The title compound of Step A was prepared from (3-aminomethyl-phenoxy)-acetic acid tert-butyl ester, of Preparation 20, and 4-pyrazol-1-yl-benzaldehyde, of Preparation 42, using the method described in Example 3, Step A, except no triethylamine was used. $^1$H NMR (400 MHz, CDCl$_3$) δ 7.89 (m, 1H), 7.68 (m, 1H), 7.63 (d, 2H), 7.41 (d, 2H), 7.23 (m, 1H), 6.93 (m, 2H), 6.77 (dd, 1H), 6.44 (m, 1H), 4.50 (s, 2H), 3.81 (s, 2H), 3.77 (s, 2H), 1.47 (s, 9H); MS 394 (M+1).

Step B: Amide Formation (3{[(4-Pyrazol-1-yl-benzyl)-(pyridine-3-sulfonyl)-amino]-methyl}-phenoxy)-acetic acid tert-butyl ester The title compound of Step B was prepared from {3-[(4-pyrazol-1-yl-benzylamino)-methyl]-phenoxy}-acetic acid tert-butyl ester of Step A and pyridine-3-sulfonyl chloride hydrochloride, of Preparation 2, following the method described in Example 3, Step B with a reaction time of 2 h. $^1$H NMR (400 MHz, CDCl$_3$) δ 9.05 (s, 1H), 8.78 (d, 1H), 8.03 (dd, 1H), 7.88 (m, 1H), 7.69 (m, 1H), 7.55 (d, 2H), 7.42 (m, 1H), 7.13 (m, 3H), 6.76 (d, 1H), 6.66 (m, 2H), 6.45 (m, 1H), 4.39 (s, 2H), 4.38 (s, 2H), 4.33 (s, 2H), 1.47 (s, 9H); MS 535(M+1).

Step C: Ester Hydrolysis (3-{[(4-Pyrazol-1-yl-benzyl)-(pyridine-3-sulfonyl)-amino]-methyl}-phenoxy)-acetic acid hydrochloride salt The title compound was prepared following the method described in Example 3, Step C from (3-{[(4-pyrazol-1-yl-benzyl)-(pyridine-3-sulfonyl)-amino]-methyl}-phenoxy)-acetic acid tert-butyl ester of Step B. The HCl salt was prepared following the method described in Step C of Example 13a. $^1$H NMR (400 MHz, CD$_3$OD) δ 9.15 (m, 1H), 9.02 (m, 1H), 8.88 (m, 1H), 8.26 (m, 1H), 8.18 (m, 1H), 7.82 (m, 1H), 7.63 (m, 2H), 7.39 (m, 2H), 7.12 (t, 1H), 6.82–6.72 (m, 3H), 6.58 (m, 1H), 4.63 (s, 2H), 4.62 (s, 2H), 4.49 (s, 2H); MS 477 (M−1).

EXAMPLE 13i (3-{[(4-Chloro-benzenesulfonyl)-(4-thiazol-2-yl-benzyl)-amino]-methyl}-phenoxy)-acetic acid Step A: Reductive Amination {3-[(4-Thiazol-2-yl-benzylamino)-methyl]-phenoxy}-acetic acid tert-butyl ester The title compound of Step A was prepared from (3-aminomethyl-phenoxy)-acetic acid tert-butyl ester, of Preparation 20, and 4-thiazol-2-yl-benzaldehyde, of Preparation 25, following the procedure described in Example 3, Step A except no triethylamine was used. $^1$H NMR (400 MHz, CDCl$_3$) δ 7.90 (d, 2H), 7.82 (d, 1H), 7.39 (d, 2H), 7.28 (d, 1H), 7.22 (m, 1H), 6.92 (m, 2H), 6.77 (m, 1H), 4.50 (s, 2H), 3.80 (s, 2H), 3.76 (s, 2H), 1.46 (s, 9H); MS 411 (M+1).

Step B: Amide Formation (3-{[(4-Chloro-benzenesulfonyl)-(4-thiazol-2-yl-benzyl)-amino]-methyl}-phenoxy)-acetic acid tert-butyl ester The title compound of Step B was prepared from {3-[(4-thiazol-2-yl-benzylamino-methyl]-phenoxy}-acetic acid tert-butyl ester of Step A and 4-chlorobenzenesulfonyl chloride following the method described in Example 3, Step B with a reaction time of 96 h. MS 584 (M+1).

Step C: Ester Hydrolysis (3-{[(4-Chloro-benzenesulfonyl)-(4-thiazol-2-yl-benzyl)-amino]-methyl}-phenoxy)-acetic acid To (3-{[(4-chloro-benzenesulfonyl)-(4-thiazol-2-yl-benzyl)-amino]-methyl}-phenoxy)-acetic acid tert-butyl ester (48 mg), of Step B, was added HCl in dioxane (4M, 3 mL) at room temperature for 24 h. The reaction was concentrated in vacuo, azeotroping with CH$_2$Cl$_2$ to provide the title compound (32 mg). $^1$H NMR (400 MHz, CDCl$_3$) δ 8.20–6.80 (m, 11H), 6.75 (s, 1H), 6.65 (s, 1H), 6.38 (s, 1H), 4.50 (s, 2H), 4.23 (s, 2H), 4.16 (s, 2H); MS 526 (M−1).

EXAMPLE 13j (3-{[Benzenesulfonyl-(4-pyrazin-2-yl-benzyl)-amino]-methyl}-phenoxy)-acetic acid hydrochloride salt Step A: Amide Formation (3-{[Benzenesulfonyl-(4-pyrazin-2-yl-benzyl)-amino]-methyl}-phenoxy)-acetic acid tert-butyl ester The title compound of Step A was prepared from {3-[(4-pyrazin-2-yl-benzylamino)-methyl]-phenoxy}-acetic acid tert-butyl ester, prepared in Step A of Example 13b, and benzenesulfonyl chloride following the method described in Example 3, Step B $^1$H NMR (400 MHz, CDCl$_3$) δ 8.97 (s, 1H), 8.60 (m, 1H), 8.49 (m, 1H), 7.87 (m, 4H), 7.61–7.51 (m, 3H), 7.26–7.08 (m, 3H), 6.75 (m, 1H), 6.63 (m, 1H), 6.58 (m, 1H), 4.38 (s, 2H), 4.34 (s, 2H), 4.31 (s, 2H), 1.47 (s, 9H); MS 546 (M+1).

Step B: Ester Hydrolysis (3-{[Benzenesulfonyl-(4-pyrazin-2-yl-benzyl)-amino]-methyl}-phenoxy)-acetic acid hydrochloride salt The title compound was prepared following the method described in Example 3, Step C from (3-{[benzenesulfonyl-(4-pyrazin-2-yl-benzyl)-amino]-methyl}-phenoxy)-acetic acid tert butyl ester of Step A. The HCl salt was prepared following the procedure described in Step C of Example 13a. $^1$H NMR (400 MHz, CD$_3$OD) δ 9.18 (s, 1H), 8.91 (s, 1H), 8.62 (s, 1H), 7.91 (m, 4H), 7.69–7.58 (m, 3H), 7.26 (m, 2H), 7.05 (m, 1H), 6.69 (m, 2H), 6.57 (m, 1H), 4.48 (s, 2H), 4.38 (s, 2H), 4.30 (s, 2H); MS 4.88 (M−1).

EXAMPLE 13k (3-{[(1-Methyl-1H-imidazole-4-sulfonyl)-(4-pyrazol-1-yl-benzyl)-amino]-methyl}-phenoxy)-acetic acid hydrochloride salt

Step A: Amide Formation (3-{[(1-Methyl-1H-imidazole-4-sulfonyl)-(4-pyrazol-1-yl-benzyl)-amino]-methyl}-phenoxy)-acetic acid tert-butyl ester The title compound of Step A was prepared from {3-[(4-pyrazol-1-yl-benzylamino)-methyl]-phenoxy}-acetic acid tert-butyl ester, prepared in Step A of Example 13h, and 1methyl-1H-imidazole-4-sulfonyl chloride following the method described in Example 3, Step B with a reaction time of 2 h. $^1$H NMR (400 MHz, CDCl$_3$) δ 7.87 (d, 1H), 7.67 (d, 1H), 7.52 (d, 2H), 7.48 (d, 1H), 7.37 (d, 1H), 7.23 (d, 2H), 7.10 (t, 1H), 6.73 (m, 3H), 6.42 (m, 1H), 4.41 (s, 4H), 4.36 (s, 2H), 3.70 (s, 3H), 1.46 (s, 9H); MS 538 (M+1).

Step B: Ester Hydrolysis (3-{[(1-Methyl-1H-imidazole-4-sulfonyl)-(4-pyrazol-1-yl-benzyl)-amino]-methyl}-phenoxy)-acetic acid hydrochloride salt The title compound was prepared following the method described in Example 3, Step C from (3-{[(1-methyl-1H-imidazole-4-sulfonyl)-(4-pyrazol-1-yl-benzyl)-amino]-methyl}-phenoxy)-acetic acid tert-butyl ester of Step B. The HCl salt was prepared following the method described in Step C of Example 13a. MS 480 (M−1).

EXAMPLE 13l (3-{[Benzenesulfonyl-(4-imidazol-1-yl-benzyl)-amino]-methyl}-phenoxy)-acetic acid hydrochloride salt

Step A: Reductive Amination

{3-[(4-imidazol-1-yl-benzylamino)-methyl]-phenoxy}-acetic acid tert-butyl ester

The title compound of Step A was prepared from (3-aminoethyl-phenoxy)-acetic acid tert-butyl ester, of Preparation 20, and 4-imidazol-1-yl-benzaldehyde, of Preparation 43, using the method described in Example 3, Step A, except no triethylamine was used. $^1$H NMR (400 MHz, CDCl$_3$) δ 7.78 (s, 1H), 7.40 (d, 2H), 7.28 (d, 2H), 7.22 (m, 2H), 7.13 (m, 1H), 6.89 (m, 2H), 6.73 (m, 1H); 4.47 (s, 2H), 3.78 (s, 2H), 3.74 (s, 2H), 1.43 (s, 9H); MS 394 (M+1).

Step B: Amide Formation (3-{[Benzenesulfonyl-(4-imidazol-1-yl-benzyl)-amino]-methyl}-phenoxy)-acetic acid tert-butyl ester The title compound of Step B was prepared from {3-[(4-imidazol-1-yl-benzylamino)-methyl]phenoxy}-acetic acid tert-butyl ester of Step A and benzenesulfonyl chloride following the method described in Example 3, Step B. $^1$H NMR (400 MHz, CDCl$_3$) δ 7.86 (m, 3H), 7.62–7.52 (m, 3H), 7.22 (m, 6H), 7.15 (t, 1H), 6.71 (d, 1H), 6.61 (d, 1H), 6.56 (s, 1); MS 534 (M+1).

Step C: Ester Hydrolysis (3-{[Benzenesulfonyl-(4-imidazol-1-yl-benzyl)-amino]-methyl}-phenoxy)-acetic acid hydrochloride salt The title compound was prepared following the method described in Example 3, Step C (3-{[benzenesulfonyl-(4-imidazol-1-yl-benzyl)-amino]-methyl}-phenoxy)-acetic acid tert-butyl ester of Step B. The HCl salt was prepared following the method described in Step C of Example 13a. $^1$H NMR (400 MHz, CDCl$_3$) δ 9.67 (s, 1H), 7.91 (d, 2H), 7.67–7.59 (m, 3H), 7.46 (s, 1H), 7.33 (s, 1H), 7.27–7.18 (m, 4H), 6.85 (t, 1H), 6.74 (s, 1H), 6.67 (d, 1H), 6.34 (dd, 1H), 4.58 (s, 2H), 4.36 (s, 2H), 4.26 (s, 2H; MS 476 M−1).

EXAMPLE 13m (3-{[(4-imidazol-1-yl-benzyl)-(pyridine-3-sulfonyl)-amino]-methyl}-phenoxy)-acetic acid hydrochloride salt

Step A: Amide Formation (3-{[4-Imidazol-1-yl-benzyl)-(pyridine-3-sulfonyl)-amino]-methyl}-phenoxy)-acetic acid tert-butyl ester The title compound of Step A was prepared from {3-[(4-imidazol-1-yl-benzylamino)-methyl]-phenoxy}-acetic acid tert-butyl ester, prepared in Step A of Example 13l, and pyridine-3-sulfonyl chloride hydrochloride, of Preparation 2, following the method described in Example 3, Step B. $^1$H NMR (400 MHz, CDCl$_3$) δ 9.04 (d, 1H), 8.80 dd, 1H), 8.06 (d, 1H), 7.83 (s, 1H), 7.44 (dd, 1H), 7.22 (m, 6H), 7.11 (t, 1H), 6.73 (dd, 1H), 6.64 (m, 2H), 4.39 (s, 2H), 4.38 (s, 2H), 4.32 (s, 2H), 1.47 (s, 9H).

Step B: Ester Hydrolysis (3-{[(4-Imidazol-1-yl benzyl)-(pyridine-3-sulfonyl)-amino]-methly}-phenoxy)-acetic acid hydrochloride salt The title compound was prepared following the method described in Example 3, Step C from (3-{[(4-imidazol-1-yl-benzyl)-(pyridine-3-sulfonyl)-amino]-methyl}-phenoxy)-acetic acid tert-butyl ester of Step B. The HCl salt was prepared following the procedure described in Step C of Example 13a. $^1$H NMR (400 MHz, CD$_3$OD, selected peaks) δ 4.67 (s, 2H), 4.58 (s, 2H), 4.48 (s, 2H); MS 477 (M−1).

EXAMPLE 13n (3-{[(4-Pyrazol-1-yl-benzyl)-(thiophene-2-sulfonyl)-amino]-methyl}-phenoxy)-acetic acid hydrochloride salt

Step A: Amide Formation (3-{[(4-Pyrazol-1-yl-benzyl)-(thiophene-2-sulfonyl)-amino]-methyl}-phenoxy)-acetic acid tert-butyl ester To a solution of {3-[(4-pyrazol-1-yl-benzylamino)-methyl]-phenoxy}-acetic acid tert-butyl ester (78.9 mg, 0.200 mmol), prepared in Step A of Example 13a, triethylamine (44.6 mg, 0.221 mmol) and dichloroethane (10 mL) was added thiophene-2-sulfonyl chloride (40.3 mg, 0.221 mmol). The reaction was stirred for 24 h and additional triethylamine (0.221 mmol) and thiophene-2-sulfonyl chloride (40.3 mg, 0.221 mmol) were added. After stirring for 24 h at room temperature the reaction was heated at reflux for 24 h and was cooled to room temperature. The organic solution was washed sequentially with 5.5% HCl, water, saturation sodium bicarbonate solution, and brine. The organic solution was dried (MgSO$_4$), filtered, and concentrated. Flash chromatography (CH$_3$:MeOH 99.1) provided the title compound of Step A (58 mg). MS 539 (M+1).

Step B: Ester Hydrolysis (3-{[(4-Pyrazol-1-yl-benzyl)-(thiophene-2-sulfonyl)-amino]-methyl}-phenoxy)-acetic acid hydrochloride salt The title compound was prepared following the method described in Example 13i, Step C from (3-{[(4-pyrazol-1-yl-benzyl)-(thiophene-2-sulfonyl)-amino]-methyl}-phenoxy)-acetic acid tert-butyl ester of Step A. $^1$H NMR (400 MHz, CDCl$_3$) δ 8.22–6.80 (m, 10H), 6.72 (m, 2H), 6.64 (s, 1H), 6.52 (s, 1H), 4.47 (s, 2H), 4.39 (s, 2H), 4.36 (s, 2H); MS 481 (M−1).

EXAMPLE 13o (3-{[Benzenesulfonyl-(4-pyrimidin-2-yl-benzyl)-amino]-methyl}-phenoxy)-acetic acid sodium salt Step A: Reductive Amination {3-[(4-Pyrimidin-2-yl-benzylamino)-methyl]-phenoxy}-acetic tert-butyl ester The title compound of Step A was prepared from (3-aminomethyl-phenoxy)-acetic acid tert-butyl ester, of Preparation 20, and 4-pyrimidin-2-yl-benzaldehyde, of Preparation 21, using the method described in Example 3, Step A, except no triethylamine was used. $^1$H NMR (400 MHz, CDCl$_3$) δ 8.89 (d, 2H), 8.38 (d, 2H), 7.46 (d, 2H), 7.23 (m, 1H), 7.17 (m, 1H), 6.95 (m, 2H), 6.78 (dd, 1H), 4.51 (s, 2H), 3.86 (s, 2H), 3.79 (s, 2H), 1.47 (s, 9H); MS 406 (M+1).

Step B: Amide Formation (3-{[Benzenesulfonyl-(4-pyrimidin-2-yl-benzyl)-amino]-methyl}-phenoxy)-acetic acid tert-butyl ester The title compound of Step B was prepared from {3-[(4-pyrimidin-2-yl-benzylamino)-methyl]-phenoxy}-acetic acid tert-butyl ester, of Step A, and benzenesulfonyl chloride following the method described in Example 3, Step B. $^1$H NMR (400 MHz, CDCl$_3$) δ 8.78 (dd, 2H), 8.27 (d, 2H), 7.87 (m, 2H), 7.59–7.50 (m, 3H), 7.18 (m, 1H), 7.11 (m, 3H), 6.75 (d, 1H), 6.64 (d, 1H), 6.59 (s, 1H), 4.39 (s, 2H), 4.35 (s, 2H), 4.31 (s, 2H), 1.48 (s, 9H); MS 546 (M+1).

Step C: Ester Hydrolysis (3-{[Benzenesulfonyl-(4-pyrimidin-2-yl-benzyl)-amino]-methyl}-phenoxy)-acetic acid sodium salt The TFA salt was prepared following the method described in Example 3, Step C from (3-{[benzenesulfonyl-(4-pyrimidin-2-yl-benzyl)-amino]-methyl}-phenoxy)-acetic acid tert-butyl ester of Step B. The sodium salt was prepared following the method described in Step C of Example 13d using MeOH (5 mL) and water (1 mL) as solvent. $^1$H NMR (400 MHz, CD$_3$OD) δ 8.80 (d, 2H), 8.23 (d, 2H), 7.89 (m, 2H), 7.67–7.56 (m, 3H), 7.32 (m, 1H), 7.21 (d, 2H), 7.06 (m, 1H), 6.75 (dd, 1H), 6.63 (m, 2H), 4.41 (s, 2H), 4.32 (s, 2H), 4.21 (s, 2H); MS 488 (M−1).

EXAMPLE 13p (3-{[(5-Pyridin-2-yl-thiophene-2-sulfonyl)-(4-thiazol-2-yl-benzyl)-amino]-methyl}-phenoxy)-acetic acid hydrochloride salt Step A: Amide Formation (3-{[(5-Pyridin-2-yl-thiophene-2-sulfonyl)-(4-thiazol-2-yl-benzyl)-amino]-methyl}-phenoxy)-acetic acid tert-butyl ester To a solution of {3-[(4-thiazol-2-yl-benzylamino)-methyl-]-phenoxy}-acetic acid tert butyl ester (111 mg, 0.270 mmol), prepared in Step A of Example 13i, triethylamine (120 mg, 1.19 mmol) and dichloroethane (10 mL) was added 5-pyridin-2-yl-thiophene-2-sulfonyl chloride (77.2 mg, 0.297 mmol). The reaction was stirred for 72 h and additional 5 pyridin-2-yl-thiophene-2-sulphonyl chloride (38.5 mg) was added. The reaction was stirred for an additional 48 h. The organic solution was washed sequentially with 5.5% HCl, water, saturated sodium bicarbonate solution, and brine. The organic solution was dried (MgSO$_4$), filtered, and concentrated. Flash chromatography (CHCl$_3$:MeOH 99:1) provided the title compound of Step A (58 mg). MS 633 (M+1).

Step B: Ester Hydrolysis (3-{[(5-Pyridin-2-yl-thiophene-2-sulfonyl)-(4-thiazol-2-yl-benzyl)-amino]-methyl}-phenoxy)-acetic acid hydrochloride salt The title compound was prepared following the method described in Example 13i, Step C from (3-{[(5-pyridin-2-yl-thiophene-2-sulfonyl)-(4-thiazol-2-yl-benzyl)-amino]-methyl}-phenoxy)-acetic acid tert-butyl ester of Step A. $^1$H NMR (400 MHz, CDCl$_3$) δ 8.75 (d, J=5.2 Hz, 1H), 8.39 (t, J=7.5 Hz, 1H), 8.20 (d, J=8.1 Hz, 1H), 8.15 (d, J=3.7 Hz, 1H), 8.00–7.40 (m, 8H), 7.10 (t, J=8.1 Hz, 1H), 6.80 (d, J=7.5 Hz, 1H), 6.75 (d, J=5.3 Hz, 1H), 6.70 (s, 1H), 4.50 (s, 2H), 4.49 (s, 2H), 4.42 (s, 2H); MS 575 (M−1).

EXAMPLE 13q (3-{[(3,5-Dimethyl-isoxazole-4-sulfonyl)-4-pyrimidin-2-yl-benzyl)-amino]-methyl}-phenoxy)-acetic acid hydrochloride salt Step A: Amide Formation (3-{[(3,5-Dimethyl-isoxazole-4-sulfonyl)-(4-pyrimidin-2-yl-benzyl)-amino]-methyl}-phenoxy)-acetic acid tert-butyl ester To a solution of {3-[(4-pyrimidin-2-yl-benzylamino)-methyl]-phenoxy}-acetic acid tert-butyl ester (83.3 mg, 0.2054 mmol), prepared in Step A of Example 13o, in CH$_2$Cl$_2$ was added triethylamine (0.94 mL, 0.68 mmol) and 3,5-dimethyl-isoxazole-4-sulfonyl chloride (44.2 mg, 0.226 mmol) and the reaction was heated at reflux overnight. After cooling to room temperature, additional triethylamine (0.94 mL) and 3,5-dimethyl-isoxazole-4-sulfonyl chloride (44 mg) was added. The reaction was heated at reflux for 72 h and was cooled to room temperature. The organic solution was washed sequentially with 5.5% aqueous HCl, water, saturated sodium bicarbonate solution, and brine. The organic solution was dried (MgSO$_4$), filtered, and concentrated. Flash chromatography (CHCl$_3$:MeOH 99:1) provide the title compound of Step A (61 mg). MS 565 (M+1).

Step B: Ester Hydrolysis (3-{[(3,5-Dimethyl-isoxazole-4-sulfonyl)-(4-pyrimidin-2-yl-benzyl)-amino]-methyl}-phenoxy)-acetic acid hydrochloride salt The title compound was prepared following the method described in Example 3, Step C from (3-{[(3,5-dimethyl-isoxazole-4-sulfonyl)-(4-pyrimidin-2-yl-benzyl)-amino]-methyl}-phenoxy)-acetic acid tert-butyl ester of Step A. The HCl salt was prepared by treating the TFA salt with HCl in dioxane (4M) as described in Step C of Example 13i. $^1$H NMR (400 MHz, CDCl$_3$) δ 8.92 (d, 1H, J=4.1 Hz), 8.25 (d, 1H, J=2.9 Hz), 7.55–6.71 (m, 8H), 6.62 (m, 1H), 4.55 (s, 2H), 4.52 (s, 2H), 4.45 (s, 2H), 2.62 (s, 3H), 2.43 (s, 3H); M 507 (M−1).

EXAMPLE 13r (3-{[(Pyridine-2-sulfonyl)-(4-pyrimidin-2-yl-benzyl)-amino]-methyl}-phenoxy)-acetic acid sodium salt Step A: Amide Formation (3-{[(Pyridine-2-sulfonyl)-(4-pyrimidin-2-yl-benzyl)-amino]-methyl}-phenoxy)-acetic acid tert-butyl ester The title compound of Step A was prepared from {3-[(4-pyrimidin-2-yl-benzylamino)-methyl]-phenoxy}-acetic acid tert-butyl ester, prepared in Step A of Example 13o, and pyridine-2-sulfonyl chloride hydrochloride, of Preparation 47, following the method described in Example 3, Step B. $^1$H NMR (400 MHz, CDCl$_3$) δ 8.78 (d, 2H), 8.67 (d, 1H), 8.26 (d, 2H), 7.96 (d, 1H), 7.85 (m, 1H), 7.44 (m, 1H), 7.19–7.09 (m, 4H), 6.73 (m, 3H), 4.54 (s, 2H), 4.48 (s, 2H), 4.40 (s, 2H), 1.48 (s, 9H); MS 547 (M+1).

Step B: Ester Hydrolysis (3-{[(Pyridine-2-sulfonyl)-(4-pyrimidin-2-yl-benzyl)-amino]-methyl}-phenoxy)-acetic acid sodium salt The TFA salt was prepared following the method described in Example 3, Step C from (3-{[(pyridine-2-sulfonyl)-(4-pyrimidin-2-yl-benzyl)-amino]-methyl}-phenoxy)-acetic acid tert-butyl ester of Step B. The sodium salt was prepared following the method described in Step C of Example 13d using MeOH (5 mL) and water (1 mL) as solvent. $^1$H NMR (400 MHz, CD$_3$OD) δ 8.79 (d, 2H), 8.65 (d, 1H), 8.23 (d, 2H), 7.96 (m, 2H), 7.56 (m, 1H), 7.31 (m, 1H), 7.27 (d, 2H), 7.04 (m, 1H), 6.72 (d, 1H), 4.56 (s, 2H), 4.44 (s, 2H), 4.22 (s, 2H); MS 489 (M−1)

EXAMPLE 13s (3-{[(4-Thiazol-2-yl-benzyl)-(thiophene-2-sulfonyl)-amino]-methyl}-phenoxy-acetic acid Step A: Amide Formation (3-{[(4-Thiazol-2-yl-benzyl)-(thiophene-2-sulfonyl)-amino]-methyl}-phenoxy)-acetic acid tert-butyl ester To a solution of {3-[(4-thiazol-2-yl-benzylamino)-methyl]-phenoxy}-acetic acid tert-butyl ester (87.3 mg, 0.213 mmol), prepared in Step A of Example 13i, triethylamine (47.3 mg, 0.234 mmol) and dichloroethane (10 mL) was added thiophene-2-sulfonyl chloride (42.7 mg, 0.234 mmol). The reaction was stirred for 24 h and additional triethylamine (0.234 mmol) and thiophene-2-sulfonyl chloride (42.7 mg, 0.234 mmol) were added. The reaction was stirred for an additional 24 h. The organic solution was washed sequentially with 5.5% HCl, water, saturated sodium bicarbonate solution, and brine. The organic solution was dried (MgSO$_4$), filtered, and concentrated. Flash chromatography (CHCl$_3$:MeOH 99:1) provided the title compound of Step A (63 mg). MS 556 (M+1)

Step B: Ester Hydrolysis (3-{[(4-Thiazol-2-yl-benzyl)-(thiophene-2-sulphonyl)-amino]-methyl}-phenoxy)-acetic acid The title compound was prepared following the method described in Example 13i, Step C from (3-{[(4-thiazol-2-yl-benzyl)-(thiophene-2-sulfonyl-amino]-methyl}-phenoxy)-acetic acid tert-butyl ester of Step A. $^1$H NMR (400 MHz, CDCl$_3$) δ 8.20–7.00 (m, 9H), 6.73 (m, 3H), 6.62 (s, 1H), 4.46 (s, 2H), 4.41 (s, 2H), 4.32 (s, 2H); MS 499 (M−1).

EXAMPLE 13t (3-{[(4-Pyrazol-1-yl-benzyl)-(pyrrolidine-1-carbonyl)-amino]-methyl}-phenoxy)-acetic acid hydrochloride salt Step A: Amide Formation (3-{[(4-Pyrazol-1-yl-benzyl)-(pyrrolidine-1-carbonyl)-amino]-methyl}-phenoxy)-acetic acid tert-butyl ester A solution of {3-[(4-pyrazol-1-yl-benzylamino)-methyl]-phenoxy}-acetic acid tert-butyl ester (15 mg, 0.038 mmol), prepared in Step A of Example 13a, pyrrolidine-1-carbonyl chloride (5 eq), and triethylamine (5 eq) in CH$_2$Cl$_2$ (1–2 mL) was stirred at room temperature for 72 h. Additional pyrrolidine-1-carbonyl chloride (5 eq) and triethylamine (5 eq) were added and the reaction was stirred for 24 h followed by addition of tris (2-aminoethyl)amine on polymer support. The reaction was stirred for 24 h and the resin was removed by filtration with the aid of CH$_2$Cl$_2$. The organic solution was washed sequentially with 5.5% aqueous HCl and saturated NaHCO$_3$ solution. The organic solution was concentrated and was used in Step B without further purification.

Step B: Ester Hydrolysis (3-{[(4-Pyrazol-1-yl-benzyl)-(pyrrolidine-1-carbonyl)-amino]-methyl}-phenoxy)-acetic acid hydrochloride salt The title compound was prepared following the method described in Example 13i, Step C from (3-{[(4-pyrazol-1-yl-benzyl)-(pyrrolidine-1-carbonyl)-amino]-methyl}-phenoxy)-acetic acid tert-butyl ester of Step A. $^1$H NMR (400 MHz, CDCl$_3$) δ 8.35 (s, 1H), 7.95–7.20 (m, 9H), 6.55 (s, 1H), 4.65 (s, 2H), 4.39 (s, 2H), 4.33 (s, 2H), 3.42 (m, 4H), 1.82 (m, 4H); MS 433 (M−1).

EXAMPLE 13u (3-{[(4-Chloro-benzenesulfonyl)-(4-pyrazol-1-yl-benzyl)-amino]-methyl}-phenoxy)-acetic acid hydrochloride salt Step A: Amide Formation (3-{[(4-Chloro-benzenesulfonyl)-(4-pyrazol-1-yl-benzyl)-amino]-methyl}-phenoxy)-acetic acid tert-butyl ester A solution of {3-[(4-pyrazol-1-yl-benzylamino)-methyl]-phenoxy}-acetic acid tert-butyl ester (15 mg, 0.038 mmol), prepared in Step A of Example 13a, 4-chlorobenzenesulfonyl chloride (5 eq), and triethylamine (5 eq) in CH$_2$Cl$_2$ (1–2 mL) was stirred at room temperature for 72 h. Additional 4-chlorobenzenesulfonyl chloride (5 eq) and triethylamine (5 eq) were added and the reaction was stirred for 24 h followed by addition of tris(2-aminoethyl)amine on polymer support. The reaction was stirred for 24 h and the resin was removed by filtration with the aid of CH$_2$Cl$_2$. The organic solution was washed sequentially with 5.5% aqueous HCl and saturated NaHCO$_3$ solution. The organic solution was concentrated and was used in Step B without further purification.

Step B: Ester Hydrolysis (3-{[(4-Chloro-benzenesulfonyl)-(4-pyrazol-1-yl-benzyl)-amino]-methyl}-phenoxy)-acetic acid hydrochloride salt The title compound was prepared following the method described in Example 13i, Step C from (3-{[(4-chloro-benzenesulfonyl)-(4-pyrazol-1-yl-benzyl)-amino]-methyl}-phenoxy)-acetic acid tert-butyl ester of Step A. $^1$H NMR (400 MHz, CDCl$_3$) δ 8.37 (s, 1H), 8.00–6.72 (m, 13H), 6.55 (s, 1H), 4.61 (s, 2H), 4.43 (s, 2H), 4.39 s, 2H); MS 510 (M–1).

EXAMPLE 13v (3-{[(4-Pyrazol-1-yl-benzyl)-(5-pyridin-2-yl-thiophene-2-sulfonyl)-amino]-methyl}-phenoxy) acetic acid hydrochloride salt Step A: Amide Formation (3-{[(4-Pyrazol-1-yl-benzyl)-(5-pyridin-2-yl-thiophene-2-sulfonyl)-amino]-methyl}-phenoxy)-acetic acid tert-butyl ester A solution of {3-[(4-pyrazol-1-yl-benzylamino)-methyl]-phenoxy}-acetic acid tert-butyl ester (15 mg, 0.038 mmol), prepared in Step A of Example 13a, 5-pyridin-2-yl-thiophene-2-sulfonyl chloride (5 eq), and triethylamine (5 eq), in CH$_2$Cl$_2$ (1–2 mL) was stirred at room temperature for 72 h. Additional 5-pyridin-2-yl-thiophene-2-sulfonyl chloride (5 eq) and triethylamine (5 eq) were added and the reaction was stirred for 24 h followed by addition of tris(2-aminoethyl)amine on polymer support. The reaction was stirred for 24 h and the resin was removed by filtration with the aid of CH$_2$Cl. The organic solution was washed sequentially with 5.5% aqueous HCl and saturated NaHCO$_3$ solution. The organic solution was concentrated and was used in Step B without further purification.

Step B: Ester Hydrolysis (3-{[(4-Pyrazol-1-yl-benzyl)-(5-pyridin-2-yl-thiophene-2-sulfonyl)-amino]-methyl}-phenoxy)-acetic acid hydrochloride salt The title compound was prepared following the method described in Example 13i, Step C from (3-{[(4-pyrazol-1-yl-benzyl)-(5-pyridin-2-yl-thiophene-2-sulfonyl)-amino]-methyl}-phenoxy)-acetic acid tert-butyl ester of Step A. $^1$H NMR (400 MHz, CDCl$_3$) δ 8.61 (s, 1H), 8.00–6.72 (m, 15H), 6.46 (s, 1H), 4.49 (s, 2H), 4.39 (s, 2H), 4.32 (s, 2H); MS 559 (M–1).

EXAMPLE 13w (3-{[(4-Methoxy-benzensulfonyl)-(4-thiazol-2-yl-benzyl)-amino]-methyl}-phenoxy)-acetic acid Step A: Amide Formation (3-{[(4-Methoxy-benzenesulfonyl)-(4-thiazol-2-yl-benzyl)-amino]-methyl}-phenoxy)-acetic acid tert-butyl ester A stock solution of Et$_3$N (0.515 mL) in CH$_2$Cl$_2$ (80 mL) was prepared, and 2 mL was added to {3-[(4-thiazol-2-yl-benzylamino)-methyl]-phenoxy}-acetic acid tert-butyl ester (29.80 mg, 0.0726 mmol), prepared in Step A of Example 13i. A solution of 4-methoxybenzenesulfonyl chloride (17 mg, 0.084 mmol) in CH$_2$Cl$_2$ (1 mL) and DMF (1 mL) was prepared, and 0.56 mL was added to the reaction mixture. The reaction was stirred at room temperature for 24 h and was diluted with aqueous HCl (0.5N, 1 mL). The aqueous solution was washed with CH$_2$Cl$_2$ (2×) and the combined organic solutions were dried (Na$_2$SO$_4$) and concentrated. Purification by reverse phase HPLC using a water:acetonitrile:0.1% TFA solvent gradient provided the title compound of Step A (20.4 mg). MS 581 (M+1).

Step B: Ester Hydrolysis (3-{[(4-Methoxy-benzenesulfonyl)-(4-thiazol-2-yl-benzyl)-amino]-methyl}-phenoxy)-acetic acid To a solution of (3-{[(4-methoxy-benzenesulfonyl)-(4-thiazol-2-yl-benzyl)-amino]-methyl}-phenoxy)-acetic acid tert-butyl ester of Step A in CH$_2$Cl$_2$ (2mL) at 0° C. was added cold TFA (1 mL) and the reaction was stirred at room temperature for 1 h. The reaction was concentrated using a stream of nitrogen. Additional CH$_2$Cl$_2$ (1 mL) was added and the solution was concentrated using a stream of nitrogen. This procedure was repeated and the residue was dried in vacuo to provide the title compound (24.6 mg). MS 524 (M–1).

EXAMPLE 13x (3-{[(5-Chloro-thiophene-2-sulfonyl)-(4-thiazol-2-yl-benzyl)-amino]-methyl}-phenoxy)-acetic acid Step A: Amide Formation (3-{[(5-Chloro-thiophene-2-sulfonyl)-(4-thiazol-2-yl-benzyl)-amino]-methyl}-phenoxy)-acetic acid tert-butyl ester The title compound of Step A was prepared following the method described in Step A of Example 13w from {3-[(4-thiazol-2-yl-benzylamino)-methyl]-phenoxy}-acetic acid tert-butyl ester, prepared in Step A of Example 13i, and 5-chlorothiophene-2-sulfonyl chloride with the following exception. The sulfonyl chloride was dissolved in CH$_2$Cl$_2$ (1 mL) and 0.28 mL was added to the reaction mixture. $^1$H NMR (400 MHz, CDCl$_3$) δ 8.03 (d, 1H), 7.79 (d, 2H), 7.43 (d, 1H), 7.34 (d, 1H), 7.24 (m, 3H), 7.13 (m, 1H), 6.94 (d, 1H), 6.76 (m, 1H), 6.68 (m, 2H), 4.41 (s, 2H), 4.35 (s, 2H), 4.30 (s, 2H), 1.48 (s, 9H); MS 591 (M+).

Step B: Ester Hydrolysis (3-{[(5-Chloro-thiophene-2-sulphonyl)-(4-thiazol-2-yl-benzyl)-amino]-methyl}-phenoxy-acetic acid The title compound was prepared following the method described in Step B of Example 13w from (3{[(5-chloro-thiophene-2-sulfonyl)-(4-thiazol-2-yl-benzyl)-amino]-methyl}-phenoxy)-acetic acid tert-butyl ester of Step A MS 524 (M–1).

EXAMPLE 13y (3-{[(3-Fluoro-benzenesulfonyl)-(4-thiazol-2-yl-benzyl)-amino]-methyl}-phenoxy)-acetic acid Step A: Amide Formation (3-{[(3-Fluoro-benzenesulfonyl)-(4-thiazol-2-yl-benzyl)-amino]-methyl}-phenoxy)-acetic acid tert-butyl ester The title compound of Step A was prepared following the method described in Step A of Example 13w from {3-[(4- thiazol-2-yl-benzylamino)-methyl]-phenoxy}-acetic acid tert-butyl ester, prepared in Step A of Example 13i, and 3-fluorobenzenesulfonyl chloride with the following exception. The sulfonyl chloride was dissolved in $CH_2Cl_2$ (1 mL) and 0.28 mL was added to the reaction mixture. MS 569 (M+1).

Step B: Ester Hydrolysis (3-{[(3-Fluoro-benzenesulfonyl)-(4-thiazol-2-yl-benzyl)-amino]-methyl}-phenoxy)-acetic acid The title compound was prepared following the method described in Step B of Example 13w (3-{[(3-fluoro-benzenesulfonyl)-(4-thiazol-2-yl-benzyl)-amino]-methyl}-phenoxy)-acetic acid tert-butyl ester of Step A. MS 534 (M−1).

EXAMPLE 13z (3-{[(4-Methoxy-benzenesulfonyl)-(4-pyrazol-1-yl-benzyl)-amino]-methyl}-phenoxy)-acetic acid Step A: Amide Formation (3-{[(4-Methoxy-benzenesulfonyl)-(4-pyrazol-1-yl-benzyl)-amino]-methyl}-phenoxy)-acetic acid tert-butyl ester The title compound of Step A was prepared following the method described in Step A of Example 13w from {3-[(4-pyrazol-1-yl-benzylamino)-methyl]-phenoxy}-acetic acid tert-butyl ester, prepared in Step A of Example 13a, and 4-methoxybenzenesulfonyl chloride. MS 564 (M+1).

Step B: Ester Hydrolysis (3-{[(4-Methoxy-benzenesulfonyl)-(4-pyrazol-1-yl-benzyl)-amino]-methyl}-phenoxy)-acetic acid The title compound was prepared following the method described in Step B of Example 13w from (3-{[(4-methoxy-benzenesulfonyl)-(4-pyrazol-1-yl-benzyl)-amino]-methyl}-phenoxy)-acetic acid tert-butyl ester of Step A. $^1$H NMR (400 MHz, $CD_3OD$) δ 8.14 (m, 1H), 7.81 (d, 2H), 7.68 (s, 1H), 7.54 (d, 2H), 7.19 (m, 2H), 7.09 (m, 3H), 6.72 (m, 2H), 6.60 (s, 1H), 6.49 (s, 1H), 4.47 (s, 2H), 4.32 (s, 2H), 4.28 (s, 2H), 3.87 (s, 3H); MS 507 (M−1).

EXAMPLE 14a (3-{[(5-Chloro-thiophene-2-sulfonyl)-(4-pyrazol-1-yl-benzyl)-amino]-methyl}-phenoxy)-acetic acid Step A: Amide Formation (3-{[(5-Chloro-thiophene-2-sulfonyl)-(4-pyrazol-1-yl-benzyl)-amino]-methyl}-phenoxy)-acetic acid tert-butyl ester The title compound of Step A was prepared following the method described in Step A of Example 13w from {3-[(4-pyrazol-1-yl-benzylamino)-methyl]-phenoxy}-acetic acid tert-butyl ester, prepared in Step A of Example 13a, and 5-chlorothiophene-2-sulfonyl chloride with the following exception. The sulfonyl chloride was dissolved in $CH_2Cl_2$ (1 mL) and 0.28 mL was added to the reaction mixture. MS 574 (M+).

Step B: Ester Hydrolysis (3-{[(5-Chloro-thiophene-2-sulfonyl)-(4-pyrazol-1-yl-benzyl)-amino]-methyl}-phenoxy)-acetic acid The title compound was prepared following the method described in Step B of Example 13w from (3-{[(5-chloro-thiophene-2-sulfonyl)-(4-pyrazol-1-yl-benzyl)-amino]-methyl}-phenoxy)-acetic acid tert-butyl ester of Step A. MS 517 (M−1).

EXAMPLE 14b (3-{[(3-Fluoro-benzenesulfonyl)-(4-pyrazol-1-yl-benzyl)-amino]-methyl}-phenoxy)-acetic acid Step A: Amide Formation (3-{[(3-Fluoro-benzenesulfonyl)-(4-pyrazol-1-yl-benzyl)-amino]-methyl}-phenoxy)-acetic acid tert-butyl ester The title compound of Step A was prepared following the method described in Step A of Example 13w from {3-[(4-pyrazol-1-yl-benzylamino)-methyl]-phenoxy}-acetic acid tert-butyl ester, prepared in Step A of Example 13a, and 3-fluorobenzenesulfonyl chloride with the following exception. The sulfonyl chloride was dissolved in $CH_2Cl_2$ (1 mL) and 0.28 mL was added to the reaction mixture. MS 522 (M+1).

Step B: Ester Hydrolysis (3-{[(3-Fluoro-benzenesulfonyl)-(4-pyrazol-1-yl-benzyl)-amino]-methyl}-phenoxy)-acetic acid The title compound was prepared following the method described in Step B of Example 13w from (3{[(3-fluoro-benzenesulfonyl)-(4-pyrazol-1-yl-benzyl)-amino]-methyl}-phenoxy)-acetic acid tert-butyl ester of Step A. MS 495 (M−1).

EXAMPLE 14c (3-{[(3-Chloro-benzenesufonyl)-(4-thiazol-2-yl-benzyl)-amino]-methyl}-phenoxy)-acetic acid Step A: Amide Formation (3-{[(3-Chloro-benzenesulfonyl)-(4-thiazol-2-yl-benzyl)-amino]-methyl}-phenoxy)-acetic acid tert-butyl ester The title compound of Step A was prepared following the method described in Step A of Example 13w from {3-[(4-thiazol-2-yl-benzylamino)-methyl]-phenoxy}-acetic acid tert-butyl ester, prepared in Step A for Example 13i, and 3-chlorobenzenesulfonyl chloride with the following exception. The sulfonyl chloride was dissolved in $CH_2Cl_2$ (1 mL) and 0.28 mL was added to the reaction mixture. MS 585 (M+).

Step B: Ester Hydrolysis (3-{[(3-Chloro-benzenesulfonyl)-(4-thiazol-2-yl-benzyl)-amino]-methyl}-phenoxy)-acetic acid The title compound was prepared following the method described in Step B of Example 13w from (3-{[(3-chloro-benzenesulfonyl)-(4-thiazol-2-yl-benzyl)-amino]-methyl}-phenoxy)-acetic acid tert-butyl ester of Step A. MS 529 (M+).

EXAMPLE 14d (3-{[(4-Pyrazol-1-yl-benzyl)-(thiazole-2-sulfonyl)-amino]-methyl}-phenoxy)-acetic acid hydrochloride salt Step A: Amide Formation (3-{[(4-Pyrazol-1-yl-benzyl)-(thiazole-2-sulfonyl)-amino]-methyl}-phenoxy)-acetic acid tert-butyl ester The title compound of Step A was prepared following the method described in Step B of Example 3 from {3-[(4- pyrazol-1-yl-benzylamino)-methyl]-phenoxy}-acetic acid tert-butyl ester, prepared in Step A of Example 13a, and thiazole-2-sulfonyl chloride, of Preparation 45 with a reaction time of 3 h. $^1$H NMR (400 MHz, CD$_3$OD) δ 7.95 (d, 1H), 7.87 (d, 1H), 7.69 (m, 1H), 7.59 (dd, 1H), 7.54 (d, 2H), 7.15 (m, 3H), 6.74 (m, 3H), 6.44 (m, 1H), 4.49 (s, 2H), 4.46 (s, 2H), 4.42 (s, 2H), 1.49 (s, 9H); MS 541 (M+1).

Step B: Ester Hydrolysis (3-{[(4-Pyrazol-1-yl-benzyl)-(thiazole-2-sulfonyl)-amino]-methyl}-phenoxy)-acetic acid hydrochloride salt The title compound was prepared following the method described in Step C of Example 3 from (3-{[(4-pyrazol-1-yl-benzyl)-(thiazole-2-sulfonyl)-amino]-methyl}-phenoxy)-acetic acid tert-butyl ester of Step A with a reaction time of 2 h. The TFA salt was converted to hydrochloride salt as described in Step C of Example 13a. $^1$H NMR (400 MHz, CD$_3$OD) δ 8.02 (d, 1H), 7.83 (s, 1H), 7.79 (d, 1H), 7.66 (d, 1H), 7.39 (d, 2H), 7.18 (d, 2H), 7.13 (m, 1H), 6.81 (d, 1H), 6.75 (d, 1H), 6.50 (s, 2H), 4.53 (s, 4H), 4.43 (s, 2H); MS 483 (M−1).

EXAMPLE 14e

{3-[(4-tert-Butyl-benzyl)-(pyridine-3-sulfonyl)-amino]-methyl}-phenoxy acetic acid sodium salt Step A: Reductive Amination {3-[(4-tert-Butyl-benzylamino)-methyl]-phenoxy}acetic acid tert-butyl ester To a solution of (3-aminomethyl-phenoxy)-acetic acid tert-butyl ester prepared in Step C of Preparation 20, (0.497 g, 2.09 mmol) in MeOH (8 mL) was added 4-tert-butylbenzaldehyde (0.33 mL, 1.97 mmol), and the mixture was stirred at room temperature for 2 h. The solution was cooled to 0° C. and sodium borohydride (0.119 g, 3.15 mmol) was added in one portion. The mixture was stirred for 10 min, and a 1:1 solution of water:aqueous saturated sodium bicarbonate was added to the solution. The product was extracted into CH$_2$Cl$_2$ (3×) and the combined organic solutions were dried (MgSO$_4$) and concentrated in vacuo. The product was purified via silica gel chromatography (EtOAc followed by 5% MeOH in CH$_2$Cl$_2$) to give the title compound of Step A (0.691 g) as a clear oil. $^1$H NMR (400 MHz, CDCl$_3$) δ 7.30–7.38 (m, 2H), 7.19–7.28 (m, 3H), 6.87–6.96 (m, 2H), 6.77 (d, 1H), 4.50 (s, 2H), 3.77 (s, 2H), 3.75 (s, 2H), 1.46 (s, 9H), 1.30 (s, 9H); MS 384 (M+1).

Step B: Amide Formation

{3-[(4-tert-Butyl-benzyl)-(pyridine-3-sulfonyl)-amino]-methyl}-phenoxy acetic acid tert-butyl ester To a solution of {3-[(4-tert-butyl-benzylamino)-methyl]-phenoxy}acetic acid tert-butyl ester (10.0 g, 26.1 mmol), prepared in Step A, in CH$_2$Cl$_2$ (75 mL) at 0° C. was added triethylamine (8.0 mL, 57.4 mmol), and pyridine-3-sulfonyl chloride hydrochloride (6.10 g, 28.7 mmol), of Preparation 2. The mixture was stirred for 0.5 h, the ice bath was removed, and the mixture was stirred for an additional 1.5 h. A 1:1 solution of water:aqueous saturated sodium bicarbonate was added to the solution, and the product was extracted into CH$_2$Cl$_2$ (3×). The combined organic solutions were dried over MgSO$_4$ and concentrated in vacuo and the product was purified via silica gel chromatography (2:1 Hex:EtOAc) to give the title compound of Step B (11.0 g) as a clear oil. $^1$H NMR (400 MHz, CDCl$_3$) δ 9.01 (s, 1H), 8.75 (d, 1H), 7.97 (d, 1H), 7.38 (m, 1H), 7.11–7.23 (m, 3H), 6.97 (d, 2H), 6.71 (d, 1H), 6.65 (d, 1H), 6.60 (s, 1H), 4.40 (s, 2H), 4.32 (s, 4H), 1.48 (s, 9H), 1.26 (s, 9H); MS 525 (M+1).

Step C: Ester Hydrolysis

{3-[(4-tert-Butyl-benzyl)-pyridine-3-sulfonyl)-amino]-methyl}-phenoxy acetic acid To a solution of {3-[(4-tert-butyl-benzyl)-(pyridine-3-sulfonyl)-amino]methyl}-phenoxy acetic acid tert-butyl ester (11.0 g, 21.0 mmol), prepared in Step B, in CH$_2$Cl$_2$ (50 mL) at 0° C. was added trifluoroacetic acid (25 mL). After 10 min the ice bath was removed and the mixture was stirred for an additional 1.5 h. An additional 5 mL of trifluoroacetic acid was added, the mixture was stirred for 30 min, and the reaction was concentrated in vacuo. The residue was azeotroped with CH$_2$Cl$_2$ (3×), and the resulting oil was partitioned between water and EtOAc.

The aqueous phase was adjusted to pH 5.0 with 1N NaOH and the resulting precipitated solid (4.86 g) was collected by filtration. The filtrate layers were separated and the aqueous layer was extracted with EtOAc (2×). The combined organic solutions were dried over MgSO$_4$ and concentrated in vacuo to give a white foam (2.64 g). The precipitated solid and the white foam were combined and recrystallized from ethanol to give the title compound (5.68 g) as a while solid. $^1$H NMR (400 MHz, CD$_3$OD) δ 8.91 (s, 1H), 8.15 (d, 1H), 7.54 (m, 1H), 7.22 (d, 2H), 7.11 (t, 1H), 7.04 (d, 2H), 6.71–6.92 (m, 2H), 6.65 (s, 1H), 4.50 (s, 2H), 4.36 (s, 4H), 1.25 (s, 9H); MS 469 (M+1).

Step D: Salt Formation

{3-[(4-tert-Butyl-benzyl)-(pyridine-3-sulfonyl)-amino]-methyl}-phenoxy Acetic Acid Sodium Salt To a solution of {3-[(4-tert-butyl-benzyl)-(pyridine-3-sulfonyl)-amino]-methyl}-phenoxy acetic acid (5.68 g, 12.13 mmol), prepared in Step C, in 10:1 MeOH:water (66 mL) was added sodium bicarbonate (1.02 g, 12.14 mmol) and the mixture was stirred for 18 h at room temperature. The mixture was azeotroped with ethanol and concentrated in vacuo to give the title compound (5.95 g) as a white solid. $^1$H NMR (400 MHz, CD$_3$OD) δ 8.88 (s, 1H), 8.71 (d, 1H), 8.13 (d, 1H), 7.52 (m, 1H), 7.24 (d, 2H), 7.04–7.11 (m, 3H), 6.78 (d, 1H), 6.68 (m, 2H), 4.37 (s, 2H), 4.35 (s, 2H), 4.25 (s, 2H), 1.25 (s, 9H); MS 469 (M+1).

EXAMPLES 15a–15g

Examples 15a–15g were prepared from the appropriate starting materials in a manner analogous to the method of Example 1, with variations in reaction time, temperature, and reagents as noted.

EXAMPLE 15a

3-{3-[(Benzenesulfonyl-benzoyl[1,3]dioxol-5-ylmethyl-amino)-methyl]-phenyl}-propionic acid Step A: Reductive Amination 3-(3-{[(Benzo[1,3]dioxol-5-ylmethyl)-amino]-methyl}-phenyl)-propionic acid methyl ester. The title compound of Step A was prepared from 3-(3-aminomethyl-phenyl)- propionic acid methyl ester hydrochloride salt, of Preparation 44, and benzo[1,3]dioxole-5-carbaldehyde using the method described in Example 1, Step A except the imine was formed in MeOH at reflux over 4 h. $^1$H NMR (400 MHz, CDCl$_3$) δ 7.27–6.74 (m, 7H), 5.90 (s, 2H), 3.77 (s, 2H), 3.71 (s, 2H), 3.64 (s, 3H), 2.92 (t, 2H), 2.62 (t, 2H); MS 328 (M+1).

Step B: Amide Formation

3-{3-[(Benzenesulfonyl-benzo[1,3]dioxol-5-ylmethyl-amino)-methyl]-phenyl}-propionic acid methyl ester. The title compound of Step B was prepared following the method described in Step A of Example 1 from 3-(3-{[(benzo[1,3]dioxol-5-ylmethyl)-amino]-methyl}-phenyl)-propionic acid methyl ester of Step A and benzenesulfonyl chloride using triethylamine in place of N,N-diisopropylethylamine. $^1$H NMR (400 MHz, CDCl$_3$) δ 7.85 (d, 2H), 7.62–7.50 (m, 3H), 7.13 (m, 1H), 7.03 (m, 1H), 6.88 (m, 1H), 6.78 (s, 1H), 6.62 (d, 1H), 6.54 (s, 1H), 6.46 (d, 1H), 5.90 (s, 2H), 4.28 (s, 2H), 4.21 (s, 2H), 3.67 (s, 3H), 2.81 (t, 2H), 2.50 (t, 2H).

Step C: Ester Hydrolysis

3-{3-[(Benzenesulfonyl-benzo[1,3]dioxol-5-ylmethyl-amino)-methyl]-phenyl}-propionic acid. The title compound was prepared following the method described in Example 1, Step C from 3-{3-[(benzenesulfonyl-benzo[1,3]dioxol-5-ylmethyl-amino)-methyl]-phenyl}-propionic acid methyl ester of Step B. $^1$H NMR (400 MHz, CDCl$_3$) δ 7.84 (d, 2H), 7.61–7.50 (m, 3H), 7.13 (m, 1H), 7.04 (m, 1H), 6.88 (m, 1H), 6.79 (s, 1H), 6.61 (d, 1H), 6.51 (s, 1H), 6.46 (m, 1H), 5.90 (s, 2H), 4.28 (s, 2H), 4.19 (s, 2H), 2.82 (t, 2H), 2.55 (t, 2H); MS 452 (M−1).

EXAMPLE 15b 3-(3-{[Benzo[1,3]dioxol-5-ylmethyl-(4-fluoro-benzenesulfonyl)-amino]-methyl}-phenyl)-propionic acid Step A: Amide Formation 3-(3-{[Benzo[1,3]dioxol-5-ylmethyl-(4-fluoro-benzenesulfonyl)-amino]-methyl}-phenyl)-propionic acid methyl ester. The title compound of Step A was prepared following the method described in Step A of Examples 1 from 3-(3-{[(benzo[1,3]dioxol-5-ylmethyl)-amino]-methyl}-phenyl)-propionic acid methyl ester, prepared in Step A of Example 15a, and 4-fluorobenzenesulfonyl chloride using triethylamine in place of N,N-diisopropylethylamine. $^1$H NMR (400 MHz, CDCl$_3$) δ 7.82 (m, 2H), 7.17 (m, 3H), 7.05 (d, 1H), 6.89 (d, 1H), 6.83 (s, 1H), 6.64 (d, 1H), 6.56 (s, 1H), 6.48 (m, 1H), 5.91 (s, 2H), 4.27 (s, 2H), 4.19 (s, 2H), 3.67 (s, 3H), 2.83 (t, 2H), 2.52 (t, 2H).

Step B: Ester Hydrolysis 3-(3-{[Benzo[1,3]dioxol-5-ylmethyl-(4-fluoro-benzenesulfonyl)-amino]-methyl}-phenyl)-propionic acid. The title compound was prepared following the method described in Example 1, Step C from 3-(3-{[benzo[1,3]dioxol-5-ylmethyl-(4-fluoro-benzenesulfonyl)-amino]-methyl}-phenyl)-propionic acid methyl ester of Step B. $^1$H NMR (400 MHz, CDCl$_3$) δ 7.81 (m, 2H), 7.19–7.04 (m, 4H), 6.90 (d, 1H), 6.84 (s, 1H), 6.63 (d, 1H), 6.53 (s, 1H), 6.48 (d, 1H), 5.90 (s, 2H), 4.27 (s, 2H), 4.19 (s, 2H), 2.84 (t, 2H), 2.58 (t, 2H); MS 470 (M−1).

EXAMPLE 15c 3-(3-{[Methanesulfonyl-(4-phenoxy-benzyl)-amino]-methyl}-phenyl)-propionic acid Step A: Reductive Amination 3-{3-[(4-Phenoxy-benzylamino)-methyl]-phenyl}-propionic acid methyl ester. The title compound of Step A was prepared from 3-(3-aminomethyl-phenyl)-propionic acid methyl ester hydrochloride salt, of Preparation 44, and 4-phenoxybenzaldehyde using the method described in Example 12z, Step A. $^1$H NMR (400 MHz, CDCl$_3$) δ 7.37–6.95 (m, 13H), 3.82 (s, 2H), 3.79 (s, 2H), 3.64 (s, 3H), 2.93 (t, 2H), 2.63 (t, 2H); MS 376 (M+1).

Step B: Amide Formation 3-(3-{[Methanesulfonyl-(4-phenoxy-benzyl)-amino]-methyl}-phenyl)-propionic acid methyl ester. The title compound of Step B was prepared following the method described in Step A of Example 1 from 3-{3-[(4-phenoxy-benzylamino)-methyl]-phenyl}-propionic acid methyl ester of Step A and methanesulfonyl chloride using triethylamine in place of N,N-diisopropylethylamin. $^1$H NMR (400 MHz, CDCl$_3$) δ 7.36–7.24 (m, 5H), 7.14 (m, 4H), 6.97 (m, 4H), 4.31 (s, 2H), 4.30 (s, 2H), 3.66 (s, 3H), 2.94 (t, 2H), 2.78 (s, 3H), 2.61 (t, 2H).

Step C: Ester Hydrolysis 3-(3-{[Methanesulfonyl-(4-phenoxy-benzyl)-amino]-methyl}-phenyl)-propionic acid. The title compound was prepared following the method described in Example 1, Step C from 3-(3-{[methanesulfonyl-(4-phenoxy-benzyl)-amino]-methyl}-phenyl)-propionic acid methyl ester of Step B. $^1$H NMR (400 MHz, CDCl$_3$) δ 7.35–7.22 (m, 5H), 7.11 (m, 4H), 6.96 (m, 4H), 4.31 (s, 2H), 4.29 (s, 2H), 2.93 (t, 2H), 2.77 (s, 3H), 2.65 (t, 2H).

EXAMPLE 15d 3-(3-{[(4-Pyrazol-1-yl-benzyl)-(thiazole-2-sulfonyl)-amino]-methyl}-phenyl)-propionic acid Step A: Amide Formation 3-(3-{[(4(Pyrazol-1-yl-benzyl)-(thiazole-2-sulfonyl)-amino]-methyl}-phenyl)-propionic acid methyl ester. The title compound of Step A was prepared following the method described in Step A of Example 1 from 3-{3-[(4-pyrazol-1-yl-benzylamino)-methyl]-phenyl}-propionic acid methyl ester, prepared in Step A of Example 11h, and thiazole-2-sulfonyl chloride using triethylamine in place of N,N-diisopropylethylamine. $^1$H NMR (400 MHz, CDCl$_3$) δ 7.95 (d, 1H), 7.88 (d, 1H), 7.69 (d, 1H), 7.60 (d, 1H), 7.54 (d, 2H), 7.19–7.12 (m, 3H), 7.04 (m, 1H), 6.93 (m, 2H), 6.44 (m, 1H), 4.49 (s, 2H), 4.46 (s, 2H), 3.64 (s, 3H), 2.82 (t, 2H), 2.51 (t, 2H); MS 497 (M+1).

Step B: Ester Hydrolysis 3-(3-{[(4-Pyrazol-1-yl-benzyl)-(thiazole-2-sulfonyl)-amino]-methyl}-phenyl)-propionic acid. The title compound was prepared following the method described in Example 1, Step C from 3-(3-{[(4-pyrazol-1-yl-benzyl)-(thioazole-2-sulfonyl)-amino]-methyl}-phenyl)-propionic acid methyl ester of Step A. $^1$H NMR (400 MHz, CDCl$_3$) δ 7.99 (m, 1H), 7.81 (d, 1H), 7.71 (d, 1H), 7.63 (m, 1H), 7.45 (m, 2H), 7.13 (m, 3H), 7.02 (m, 2H), 6.83 (s, 1H), 6.44 (m, 1H), 4.52 (s, 2H), 4.45 (s, 2H), 2.80 (t, 2H), 2.50 (t, 2H); MS 481 (M−1).

EXAMPLE 15e

3-(3-{[(4-tert-Butyl-benzyl)-(thiazole-2-sulfonyl)-amino]-methyl}-phenyl)-propionic acid

Step A: Amide Formation 3-(3-{[(4-tert-Butyl-benzyl)-(thiazole-2-sulfonyl)-amino]-methyl}-phenyl)-propionic acid methyl ester. The title compound of Step A was prepared following the method described in Step A of Example 1 from 3-{3-[(4-tert-butyl-benzylamino)-methyl]-phenyl}-propionic acid methyl ester, prepared in Step A of Example 12s, and thiazole-2-sulfonyl chloride using triethylamine in place of N,N-diisopropylethylamine. $^1$H NMR (400 MHz, CDCl$_3$) δ 7.93 (d, 1H), 7.56 (d, 1H), 7.23 (d, 2H), 7.14 (m, 1H), 7.04 (m, 3H), 6.98 (m, 2H), 4.47 (s, 2H), 4.41 (s, 2H), 3.67 (s, 3H), 2.84 (t, 2H), 2.54 (t, 2H), 1.27 (s, 9H); MS 487 (M+1).

Step B: Ester Hydrolysis 3-(3-{[(4-tert-Butyl-benzyl)-(thiazole-2-sulfonyl)-amino]-methyl}-phenyl)-propionic acid. The title compound was prepared following the method described in Example 1, Step C from 3-(3-{[(4-tert-butyl-benzyl)-(thiazole-2-sulfonyl)-amino]-methyl}-phenyl)-propionic acid methyl ester of Step A with the following exception. The reaction was heated at reflux for 1.5 h and was cooled to room temperature. The reaction was acidified to pH=5 and the aqueous solution was washed with CH$_2$Cl$_2$ (3×) The combined organic layers were dried (MgSO$_4$), filtered, and concentrated. Flash chromatography (98:2 CH$_2$Cl$_2$:MeOH) provided the title compound. $^1$H NMR (400 MHz, CDCl$_3$) δ 7.92 (d, 1H), 7.56 (d, 1H), 7.24–6.93 (m, 8H), 4.47 (s, 2H), 4.44 (s, 2H), 2.84 (t, 2H), 2.58 (t, 2H), 1.26 (s, 9H); MS 471 (M−1).

EXAMPLE 15f

3-(3-{[(4-Pyrimidin-2-yl-benzyl)-(thiazole-2-sulfonyl)-amino]-methyl}-phenyl)-propionic acid

Step A: Amide Formation 3-(3-{[(4-Pyrimidin-2-yl-benzyl)-(thiazole-2-sulfonyl)-amino]-methyl}-phenyl)-propionic acid methyl ester. The title compound of Step A was prepared following the method described in Step A of Example 1 from 3-{3-[(4-pyrimidin-2-yl-benzylamino)-methyl]-phenyl}-propionic acid methyl ester, prepared in Step A of Example 11z, and thiazole-2-sulfonyl chloride using triethylamine in place of N,N-diisopropylethylamine. $^1$H NMR (400 MHz, CDCl$_3$) δ 8.80 (d, 2H), 8.30 (d, 2H), 7.96 (d, 1H), 7.59 (m, 1H), 7.24–7.13 (m, 4H), 7.05 (d, 1H), 6.96 (d, 1H), 6.92 (s, 1H), 4.54 (s, 2H), 4.49 (s, 2H), 3.64 (s, 3H), 2.82 (t, 2H), 2.51 (t, 2H); MS 509 (M+1).

Step B: Ester Hydrolysis 3-(3-{[(4-Pyrimidin-2-yl-benzyl)-(thiazole-2-sulfonyl)-amino]-methyl}-phenyl)-propionic acid. The title compound was prepared following the method described in Example 15e, Step B from 3-(3-{[(4-pyrimidin-2-yl-benzyl)-(thiazole-2-sulfonyl)-amino]-methyl}-phenyl)-propionic acid methyl ester of Step A. $^1$H NMR (400 MHz, CDCl$_3$) δ 8.79 (d, 2H), 8.18 (d, 2H), 7.98 (m, 1H), 7.61 (m, 1H), 7.25–7.11 (m, 4H), 7.05–6.98 (m, 2H), 6.87 (s, 1H), 4.55 (s, 2H), 4.48 (s, 2H), 2.81 (t, 2H), 2.54 (t, 2H); MS 493 (M−1).

EXAMPLE 15g

3-(3-{[(4-Pyrazin-2-yl-benzyl)-(thiazole-2-sulfonyl)-amino]-methyl}-phenyl)-propionic acid

Step A: Amide Formation 3-(3-{[(4-Pyrazin-2-yl-benzyl)-(thiazole-2-sulfonyl)-amino]-methyl}-phenyl)-propionic acid methyl ester. The title compound of Step A was prepared following the method dissolved in Step A of Example 1 from 3-{3-[(4-pyrazin-2-yl-benzylamino)-methyl]-phenyl}-propionic acid methyl ester, prepared in Step A of Example 11a, and thiazole-2-sulfonyl chloride using triethylamine in place of N,N-diisopropylethylamine. $^1$H NMR (400 MHz, CDCl$_3$) δ 8.98 (s, 1H), 8.61 (s, 1H), 8.50 (s, 1H), 7.96 (d, 1H), 7.88 (d, 2H), 7.60 (d, 1H), 7.26 (d, 2H), 7.13 (m, 1H), 7.04 (m, 1H), 6.95 (m, 1H), 6.91 (s, 1H), 4.54 (s, 2H), 4.48 (s, 2H), 3.64 (s, 3H), 2.81 (t, 2H), 2.52 (t, 2H); MS 509 (M+1).

Step B: Ester Hydrolysis 3-(3-{[(4-Pyrazin-2-yl-benzyl)-(thiazole-2-sulfonyl)-amino]-methyl}-phenyl)-propionic acid. The title compound was prepared following the method described in Example 15e, Step B from 3-(3-{[(4-pyrazin-2-yl-benzyl)-(thiazole-2-sulfonyl)-amino]-methyl}-phenyl)-propionic acid methyl ester of Step A. $^1$H NMR (400 MHz, CDCl$_3$) δ 8.79 (s, 1H), 8.46 (s, 1H), 8.31 (s, 1H), 7.81 (d, 1H), 7.69 (d, 2H), 7.56 (d, 1H), 7.09 (d, 2H), 6.95 (m, 1H), 6.88 (m, 1H), 6.76 (m, 1H), 6.72 (s, 1H), 4.36 (s, 2H), 4.40 (s, 2H), 2.62 (t, 2H), 2.30 (t, 2H); MS 493 (M−1).

EXAMPLE 16a

3-[3-({Benzenesulfonyl-[3-(3,5-dichloro-phenyl)-propyl]-amino}-methyl-phenyl]-propionic acid

Step A: Alkylation

3-[3-({Benzenesulfonyl-[3-(3,5-dichloro-phenyl)-allyl]-amino}-methyl)-phenyl]-propionic acid methyl ester. Following the procedure described in Step A of Example 2, 3-[3-(benzenesulfonylamino-methyl)-phenyl]-propionic acid methyl ester was alkylated with 1-(3-bromo-propenyl)-3,5-dichloro-benzene to provide the title compound of Step A. $^1$H NMR (400 MHz, CDCl$_3$) δ 7.87 (dd, 2H), 7.63 (m, 1H), 7.55 (m, 2H), 7.22 (m, 2H), 7.07 (m, 3H), 6.93 (s, 2H), 6.11 (d, 1H), 5.77 (m, 1H), 4.34 (s, 2H), 3.87 (d, 2H), 3.66 (s, 3H), 2.87 (t, 2H), 2.54 (t, 2H).

Step B: Hydrogenation

3-[3-({Benzenesulfonyl-[3-(3,5-dichloro-phenyl)-propyl]-amino}-methyl)-phenyl]-propionic acid methyl ester. A mixture of 3-[3-{benzenesulfonyl-[3-(3,5-dichlorophenyl)-allyl]-amino}-methyl)-phenyl]-propionic acid methyl ester of Step A (237 mg), PtO$_2$ (30 mg), and MeOH was hydrogenated on a Parr shaker at 50 psi for 2 h. The catalyst was removed by filtration through Celite and the volatiles were removed in vacuo to provide the title compound (240 mg). $^1$H NMR (400 MHz, CDCl$_3$) δ 7.82 (d, 2H), 7.76–7.50 (m, 3H), 7.23 (m, 1H), 7.07 (m, 4H), 6.74 (s, 2H), 4.26 (s, 2H), 3.64 (s, 3H), 3.09 (t, 2H), 2.90 (t, 2H), 2.56 (t, 2H), 2.37 (t, 2H), 1.56 (m, 2H).

Step C: Ester Hydrolysis

3-[3-({Benzenesulfonyl-[3-(3,5-dichloro-phenyl)-propyl]-amino}-methyl)-phenyl]-propionic acid. Following the general procedure described in Step C of Example 1, 3-[3-({benzenesulfonyl-[3-(3,5-dichloro-phenyl)-propyl]-amino}-methyl)-phenyl]-propionic acid methyl ester of Step B was hydrolyzed to provide the title compound. $^1$H NMR (400 MHz, CDCl$_3$) δ 7.82 (dd, 2H), 7.62–7.48 (m, 3H), 7.26–7.09 (m, 5H), 6.74 (s, 2H), 4.27 (s, 2H), 3.10 (t, 2H), 2.91 (t, 2H), 2.62 (t, 2H), 2.38 (t, 2H), 1.56 (m, 2H); MS 506 (M+).

EXAMPLE 16b

3-[3-({Benzenesulfonyl-[2-(3-chloro-phenoxy)-ethyl]-amino}-methyl)-phenyl]-propionic acid

Step A: Alkylation

3-[3-({Benzenesulfonyl-[2-(3-chloro-phenoxy)-ethyl]-amino}-methyl)-phenyl]-propionic acid methyl ester. Following the procedure described in Step A of Example 2, 3-[3-(benzenesulfonylamino-methyl)-phenyl]-propionic acid methyl ester was alkylated with 1-(2-bromo-ethoxy)-3-chloro-benzene to provide the title compound of Step A. $^{1}$H NMR (400 MHz, CDCl$_{3}$) δ 7.86 (dd, 2H), 7.60–7.49 (m, 3H), 7.22 (d, 1H), 7.13–7.06 (m, 4H), 6.88 (m, 1H), 6.60 (d, 1H), 6.52 (m, 1H), 4.42 (s, 2H), 3.88 (s, 2H), 3.65 (s, 3H), 3.47 (t, 2H), 2.87 (t, 2H), 2.54 (t, 2H).

Step C: Ester Hydrolysis

3-[3-{(Benzenesulfonyl-[2-(3-chloro-phenoxy)-ethyl]-amino}-methyl)-phenyl]-propionic acid. The title compound was prepared following the method described in Step C of Example 1 from 3-[3-{(benzenesulfonyl-[2-(3-chloro-phenoxy)-ethyl]-amino}-methyl-phenyl]-propionic acid methyl ester of Step B. $^{1}$H NMR (400 MHz, CDCl$_{3}$) δ 7.84 (dd, 2H), 7.60–7.49 (m, 3H), 7.23 (m, 1H), 7.10 (m, 4H), 6.88 (m, 1H), 6.60 (m, 1H), 6.52 (m, 1H), 4.43 (s, 2H), 3.88 (t, 2H), 3.47 (t, 2H), 2.87 (t, 2H), 2.59 (t, 2H).

Preparation 1

7-Amino-heptanoic Acid Methyl Ester Hydrochloride

A solution of 7-amino-heptanoic acid (3.0 g, 21.0 mmol), in 25 mL MeOH and 2.4 mL concentrated HCl was heated at reflux for 4 hours and was stirred at room temperature for 60 h. The mixture was concentrated in vacuo to afford the title compound (3.3 g). $^{1}$H NMR (400 MHz, CD$_{3}$OD) δ 3.62 (s, 3H), 2.89 (m, 2H), 2.31 (t, 2H), 1.62 (m, 4H), 1.37 (m, 4H).

Preparation 2

Pyridine-3-sulfonyl Chloride Hydrochloride

The title compound was prepared using the method described in Karaman, R. and coworkers. J. Am. Chem. Soc. 114, 12, 1992, 4889–4898.

Preparation 3

3-(3-Chloro-phenyl)-propionaldehyde

A solution of 1-chloro-3-iodobenzene (9.63 g, 40.38 mmol), allyl alcohol (5.86 g, 100.96 mmol), sodium bicarbonate (8.48 g, 100.96 mmol), tetrabutylammonium chloride (11.22 g, 40.38 mmol), and Pd(OAc)$_{2}$ (317 mg, 1.413 mmol) in 25 mL DMF was stirred at 50° C. for 16 h. The mixture was cooled to room temperature, diluted with water, and the aqueous solution was washed with EtOAc. The organic solution was washed with water followed by brine, dried over MgSO$_{4}$, filtered and concentrated in vacuo. The product was purified via flash chromatography on silica gel (9:1 hexanes:EtOAc) to afford the title compound as an oil (5.04 g).

Preparation 4

5-(3-Oxo-propyl)-thiophene-2-carboxylic Acid tert-butyl Ester

Step A: Ester Formation

5-Bromo-thiophene-2-carboxylic acid tert-butyl ester. To a solution of anhydrous MgSO$_{4}$ (11.60 g, 96.4 mmol) in 100 mL CH$_{2}$Cl$_{2}$ was added concentrated H$_{2}$SO$_{4}$ (1.45 mL, 24.1 mmol) and the mixture was stirred for 15 minutes followed by addition of 5-bromo-thiophene-2-carboxylic acid (5.0 g, 24.1 mmol). After stirring for 1 minute, tert-butanol (11.6 g, 20 mmol) was added and the reaction was stirred at room temperature for 16 h. The reaction was quenched with saturated NaHCO$_{3}$. The layers were separated, the aqueous layer was extracted with CH$_{2}$Cl$_{2}$, and the combined organic layers were dried over MgSO$_{4}$. The organic solution was concentrated to give a clear oil which was purified via medium pressure chromatography (3% EtOAc in hexanes) to afford the title compound of Step A (4.97 g). $^{1}$H NMR (400 MHz, CDCl$_{3}$) δ 7.45 (d, 1H), 7.02 (d, 1H), 1.54 (s, 9H).

Step B: Aldehyde Formation 5-(3-Oxo-propyl)-thiophene-2-carboxylic Acid tert-butyl Ester To a solution of 5-bromo-thiophene-2-carboxylic acid tert-butyl ester prepared of the method of Preparation 4, Step A (0.50 g, 1.89 mmol) in 5 mL DMF was added allyl alcohol (0.51 mL, 7.57 mmol) followed by NaHCO$_{3}$ (0.397 g, 4.72 mmol), tetrabutylammonium chloride (0.525 g, 1.89 mmol), and palladium acetate (0.021 g, 0.094 mmol). The reaction was placed in an oil bath heated to 65° C. and was heated to 90° C. for 2 h. The mixture was diluted with EtOAc and 25 mL water and the solids were removed by filtration through Celite®. The layers were separated, and the organic solution was washed with water (4x), dried over MgSO$_{4}$ and concentrated to a dark yellow oil which was purified via medium pressure chromatography (7:1 hexanes:EtOAc) to afford the title compound (0.190 g). $^{1}$H NMR (400 MHz, CDCl$_{3}$) δ 9.80 (s, 1H), 7.51 (d, 1H), 6.78 (d, 1H), 3.14 (t, 2H), 2.86 (t, 2H), 1.54 (s, 9H).

Preparation 5

5-(3-Amino-propyl)-thiophene-2-carboxylic acid methyl ester

Step A 5-(3-tert-Butoxycarbonylamino-prop-1-ynyl)-thiophene-2-carboxylic acid methyl ester. A mixture of prop-2-ynyl-carbamic acid tert-butyl ester (from Preparation 41, 1.67 mmol, 0.011 mmol), 5-bromo-thiophene-2-carboxylic acid methyl ester (2.50 g, 0.011 mmol), tetrakistriphenyl-pyosphine(O) palladium (0.622 g, 0.0538 mmol), CuI (0.102 g, 0.538 mmol) and triethylamine (1.57 mL, 0.011 mmol) in 50 mL acetronitrile was heated at reflux for 16 h. The reaction was cooled to room temperature, diluted with 75 mL EtOAc, washed with 5.5% HCl, water and brine, dried over MgSO$_{4}$, filtered and concentrated in vacuo to an oil. The product was purified via flash chromatography (9:1 to 4:1 hexanes:EtOAc) to afford the title compound of Step A as an oil (2.06 g). MS 313 (M+18).

Step B 5-(3-tert-Butoxycarbonylamino-propyl)-thiophene-2-carboxylic acid methyl ester. A solution of 5-(3-tert-butoxycarbonylamino-1-prop-1-ynyl)-thiophene-2-carboxylic acid methyl ester prepared of Preparation 5, Step A (2.06 g) and 10% Pd/C (1.03 g) in 50 mL MeOH was hydrogenated on a Parr shaker at 50 psi H$_{2}$ for 16 h. The reaction was filtered through Celite® with the aid of MeOH and the filtrate was concentrated in vacuo to afford the title compound of Step B as a solid (1.93 g). MS 317 (M+18).

Step C 5-(3-Amino-propyl)-thiophene-2-carboxylic acid methyl ester. A solution of 5-(3-tert-butoxycarbonylamino-propyl)- thiophene-2-carboxylic acid methyl ester prepared of Preparation 5, Step B (0.118 g, 0.5 mmol) in 50 mL MeOH was cooled to 0° C. and was saturated with HCl (g). The reaction was stirred at room temperature for 90 minutes. The solution was concentrated to a solid which was partitioned between EtOAc and saturated NaHCO$_3$. The layers were separated, and the combined organic layers were washed with brine, dried over MgSO$_4$, filtered and concentrated in vacuo to afford the title compound as an oil (399 mg). MS 200 (M+1).

Preparation 6

5-(3-Amino-propyl)-furan-2-carboxylic acid methyl ester hydrochloride salt. The compound of Preparation 6 was prepared from the appropriate starting materials in a manner analogous to the method of Preparation 5 with the following exceptions: (1) the hydrogenation performed in Step B was carried out for 5.5 h; and (2) in Step C, the reaction was stirred for 16 h at room temperature and was concentrated in vacuo to provide the title compound as the hydrochloride salt.

Preparation 7

5-(3-Amino-propyl)-thiophene-2-carboxylic acid tert-butyl ester

Step A

Prop-2-ynyl-carbamic acid benzyl ester. To a solution of propargylamine (6.4 g, 71.2 mmol) in pyridine (100 mL) was added benzylchloroformate (13.37 g, 78.2 mmol) in 10 mL CH$_2$Cl$_2$ over 0.5 h. The reaction was stirred for 16 h and the volatiles were removed in vacuo. The residue was dissolved in EtOAc and the organic solution was washed with water (2×). The organic solution was washed with dilute aqueous HCl followed by saturated NaHCO$_3$. The organic solution was dried over MgSO$_4$, filtered, and concentrated in vacuo to provide the title compound of Step A (4.43 g).

Step B 5-(3-Benzyloxycarbonylamino-prop-1-ynyl)-thiophene-2-carboxylic acid tert-butyl ester. The title compound of Step B was prepared from the appropriate starting material in a manner analogous to the method used in Step A of Preparation 5.

Step C 5-(3-Amino-propyl)-thiophene-2-carboxylic acid tert-butyl ester. To a solution of 5-(3-benzyloxycarbonylamino-prop-1-ynyl)-thiophene-2-carboxylic acid tert-butyl ester prepared of Preparation 7, Step B (1.0 g, 2.69 mmol) in 15 mL MeOH and 2.69 mL 1N HCl (aq) was added Pd(OH)$_2$. The mixture was hydrogenated on a Parr shaker at 45 psi H$_2$ for 16 h. The mixture was filtered through Celite®, the catalyst was replaced, and the reaction was shaken for another 6 h. The mixture was filtered through Celite® and concentrated in vacuo. The residue was chased with CCl$_4$ and was triturated with Et$_2$O. The product was isolated as a solid (360 mg).

Preparation 8

5-(3-(3-(3-Chloro-phenyl)-propylamino)-propyl)-thiophene-2-carboxylic acid methyl ester. A solution of 5-(3-amino-propyl)-thiophene-2-carboxylic acid methyl ester (from Preparation 5, Step C, 0.118 g, 0.5 mmol) and N,N-diisopropylethylamine (0.071 g, 0.55 mmol) in 10 mL MeOH was stirred at room temperature for 30 minutes and 3-(3-chloro-phenyl)-propionaldehyde (from Preparations 3, 0.093 g, 0.55 mmol) was added. The mixture was stirred for 90 minutes. The reaction was cooled to 0° C., NaBH$_4$ (30.3 mg, 0.801 mmol) was added and the mixture was stirred for 30 minutes. The reaction was quenched with 1:1 NaHCO$_3$:H$_2$O and was washed with CH$_2$Cl$_2$. The CH$_2$Cl$_2$ extracts were washed with brine, dried over MgSO$_4$, filtered, and concentrated in vacuo to afford the title compound as an oil (171 mg). MS 352 (M+1).

Preparations 9–10

The compounds of Preparations 9 and 10 were prepared from the appropriate starting materials in a manner analogous to the method of Preparation 8.

Preparation 9

5-(3-(3-(3-Chloro-phenyl)-propylamino)-propyl)-thiophene-2-carboxylic acid tert-butyl ester Preparation 10

5-(3-(3-(3-Chloro-phenyl)-propylamino)-propyl)-furan-2-carboxylic acid methyl ester MS 336 (M+1).

Preparation 11

(3-Formyl-phenoxy)-acetic acid methyl ester. A mixture of (3-formyl-phenoxy)-acetic acid (3.6 g, 20.0 mmol), potassium carbonate (3.30 g, 23.9 mmol) and methyl iodide (1.86 g, 30.0 mmol) in 25 mL DMF was heated to 110° C. for 2 hours and was stirred at room temperature for 16 h. The mixture was diluted with water and the aqueous solution was extracted with EtOAc. The organic solution was washed with water, dried over MgSO$_4$, filtered and concentrated in vacuo. The product was purified via silica gel chromatography (4:1 hexanes:EtOAc) to afford the title compound as a pale yellow oil (3.4 g). $^1$H NMR (400 MHz, CDCl$_3$) δ 9.94 (s, 1H), 7.48 (m, 2H), 7.33 (s, 1H), 7.23 (m, 1H), 4.68 (s, 2H), 3.79 (s, 3).

Preparation 12

3-(3-Chloro-phenyl)-propylamine

Step A 3-(3-Chloro-phenyl)-acrylamide. A solution of 3-(3-chloro-phenyl)-acrylic acid (Aldrich, 15.0 g, 82.15 mmol) in 50 mL thionyl chloride was heated at reflux for 30 minutes. The excess thionyl chloride was removed via distillation at atmospheric pressure. The residue was azeotroped with benzene in vacuo to give 17.288 g of an orange oil. The oil was dissolved in 25 mL CH$_2$Cl$_2$ and the solution was added slowly to liquid NH$_3$ (20 mL, 80.07 mmol) in CHCl$_3$ (50 mL) at −78° C. The resulting suspension was warmed to room temperature and was concentrated in vacuo to afford the title compound of Step A as a gray solid (19.38 g). $^1$H (NMR (400 MHz, CD$_3$OD) δ 7.457 (s, 1H), 7.45 (m, 2H), 7.36 (m, 1H), 6.64 (d, 1H); MS 182 (M+1), 180 (M−1).

Step B 3-(3-Chloro-phenyl)-propylamine. A 1.0 M solution of LiAlH$_4$ in THF (6.0 mL) was added dropwise to a suspension of 3-(3-chloro-phenyl)-acrylamide prepared of Preparation 12, Step A (1.0 g, 5.51 mmol) in 30 mL THF at 0° C.

The reaction was warmed to room temperature and was stirred for 5 h. An additional 4 mL of 1 M LiAlH$_4$ was added and the reaction was stirred for 18 h. An additional 2 mL of 1 M LiAlH$_4$ was added and the reaction was stirred for 24 h. The reaction mixture was quenched by dropwise addition of water. The mixture was concentrated in vacuo to remove THF and was diluted with water. The aqueous solution was extracted with EtOAc. The organic solution was washed with water, dried over MgSO$_4$, filtered and concentrated in vacuo. The residue was dissolved in CHCl$_3$ and the organic solution was washed with 1M HCl. The aqueous solution was basified to pH 11 with 1M NaOH and the product was extracted into CHCl$_3$. The organic solution was dried over MgSO$_4$, filtered and concentrated in vacuo to afford the title compound as a yellow oil (0.134 g). $^1$H NMR (400 MHz, CDCl$_3$) δ 7.20–7.22 (m, 3H), 7.16 (m, 1H), 2.74 (t, 2H), 2.61 (t, 2H), 1.74 (m, 2H); MS 170 (M+1).

Preparation 13

(3-Formyl-phenyl)-acetic acid methyl ester

Step A (3-Cyano-phenyl)-acetic acid methyl ester. Nitrogen was bubbled through a mixture of (3-bromo-phenyl)-acetic acid methyl ester (22.85 g, 99.78 mmol), Zn(CN)$_2$ 7.25 g, 61.75 mmol), and DMF (100 mL) for about 5 minutes followed by addition of tetrakistriphenylphosphine(O) palladium (4.60 g, 3.98 mmol). The mixture was heated for 3 h at 80° C. and was cooled to room temperature. Aqueous 2N NH$_4$OH was added and the product was extracted into EtOAc (3×). The organic solution was washed with 2N NH$_4$OH (2×) followed by brine (2×). The organic solution was dried (MgSO$_4$), filtered, and concentrated in vacuo. Purification by flash chromatography (6:1 hexanes:EtOAc) provided the title compound of Step A as an oil (15.19 g). $^1$H NMR (400 MHz, CDCl$_3$) δ 7.57–7.41 (m, 4H), 3.706 (s, 3H), 3.703 (s, 2H).

Step B (3-Formyl-phenyl)-acetic acid methyl ester. A mixture of (3-cyano-phenyl)-acetic acid methyl ester prepared of Preparation 13, Step A (1.56 g, 8.91 mmol), aluminum-nickel alloy (1.63 g) and 75% formic acid (25 mL) was heated at reflux for 1.75 h. The mixture was cooled to room temperature and the solids were removed by filtration through Celite® with the aid of boiling EtOH. Water was added, and the aqueous solution was washed with CH$_2$Cl$_2$ (3×). Aqueous saturated NaHCO$_3$ was carefully added to the organic solution until the pH was about 8–9. The organic solution was washed with brine, dried over MgSO$_4$, and concentrated. Purification by flash chromatography (5:1 hexanes:EtOAc) provided the title compound as a clear and colorless oil (870 mg). $^1$H NMR (400 MHz, CDCl$_3$) δ 9.98 (s, 1H), 7.77 (m, 2H), 7.55–7.46 (m, 2H), 3.68 (s, 5H).

Preparation 14

(3-((Pyridine-3-sulfonylamino)-methyl)-phenyl)-acetic acid methyl ester. To a solution of (3-aminomethyl-phenyl)-acetic acid methyl ester hydrochloride (from Preparation 18, 0.56 g) and diisopropylamine (2.2 mL) in 10 mL dichloromethane was added pyridine-3-sulfonyl chloride (from Preparation 2, 0.601 g, 2.83 mmol) and the reaction was stirred at room temperature for 16 h. Aqueous 1N HCl was added and the solution was washed with CH$_2$Cl$_2$. The organic solution was washed with saturated NaHCO$_3$, dried over MgSO$_4$, filtered and concentrated in vacuo to afford the title compound. Purification via flash chromatography on silica gel (2:1 hexanes:EtOAc) afforded the title compound as a white solid. $^1$H NMR (400 MHz, CDCl$_3$) δ 8.91 (s, 1H), 8.71 (d, 1H), 8.04 (d, 1H), 7.37 (m, 1H), 7.05–7.24 (m, 4H), 5.87 (bs, 1H), 4.14 (s, 2H), 3.62 (s, 3H), 3.52 (s, 2H).

Preparation 15

Method A

4-Butylbenzylamine. A solution of 4-butylbenzonitrile (3.63 g, 22.8 mmol) in THF (10 mL) was placed in a three-neck round bottom flask equipped with a Vigreux column and short-path distillation head. The solution was heated to reflux and BH$_3$-methyl sulfide complex (2.0 M in THF, 15 mL, 30 mmol) was added dropwise over 15 minutes. Methyl sulfide was distilled off from the reaction mixture over 1 h and the solution was cooled to room temperature. Aqueous HCl (6N, 25 mL) was added slowly via an addition funnel and the mixture was heated at reflux for 30 minutes. The reaction was cooled to 0° C. and NaOH (7.0 g) was added protionwise. The aqueous solution was washed with EtOAc (3×) and the organic solution was dried (MgSO$_4$), filtered, and concentrated to provide the title compound of Method A (4.01 g). $^1$H NMR (400 MHz, CDCl$_3$) δ 7.34 (m, 2H), 7.24 (m, 2H), 4.04 (s, 2H), 2.62 (t, 2H), 1.58 (m, 2H), 1.34 (m, 2H), 0.92 (t, 3H).

Method B

4-Butylbenzylamine hydrochloride. A solution of 4-butylbenzonitrile (30.09 g) in EtOH (380 mL) and HCl (4N in dioxane, 50 mL, 200 mmol) was hydrogenated at 50 psi on a Parr shaker in the presence of 10% palladium on carbon (6.09 g). The catalyst was removed via filtration through Celite® and the solution was concentrated in vacuo. The residue was suspended in Et$_2$O and filtered to provide 4-butylbenzylamine hydrochloride as an off-white solid (32.47 g). $^1$H NMR (400 MHz, CD$_3$OD) δ 7.33 (d, 2H), 4.04 (s, 2H), 2.60 (t, 2H), 1.56 (m, 2H), 1.31 (m, 2H), 0.89 (t, 3H).

Using the appropriate starting materials, the compounds of Preparations 16–18 were prepared in a manner analogous to the method of Preparation 15.

Preparation 16

2-(3,5-Dichloro-phenoxy)-ethylamine. The title compound was prepared following Method A of Preparation 15.

Preparation 17

2-(3-Chloro-phenoxy)-ethylamine. The title compound was prepared following Method A of Preparation 15.

Preparation 18

(3-Aminomethyl-phenyl)-acetic acid methyl ester hydrochloride. The title compound was prepared from (3-cyano-phenyl)-acetic acid methyl ester (from Preparation 13, Step A) using the procedure described for Preparation 15, Method B except the hydrogenation was performed in MeOH. The catalyst was removed via filtration and the organic solution was concentrated in vacuo. The resulting solid was stirred in EtOAc and filtered to provide the title compound as a white solid. $^1$H NMR (400 MHz, CD$_3$OD) δ 7.42–7.32 (m, 4H), 4.09 (s, 2H), 3.69 (s, 2H), 3.67 (s, 3H); MS 180 (M+1).

Preparation 19 trans-1-(3-Bromo-propenyl)-3,5-dichloro-benzene

Step A 1-(3,5-Dichloro-phenyl)-prop-2-en-1-ol. A solution of 3,5-dichlorobenzaldehyde (7.5 g, 43 mmol) in THF (75 mL)

was cooled to 0° C. and vinylmagnesium bromide (1M in THF, 48 mL, 48 mmol) was added dropwise. The reaction was warmed to room temperature and was stirred for 16 h. Aqueous HCl (1N) and EtOAc were added. The aqueous solution was washed with EtOAc and the organic solution was dried (MgSO$_4$), filtered, and concentrated. The residue was used in the next step without further purification.

Step B

The residue prepared in Step A was dissolved in Et$_2$O and HBr gas was slowly bubbled into the solution for about 15 minutes. The reaction was stirred at room temperature for 24 h and water and EtOAc were added. The aqueous solution was extracted with EtOAc and the organic solution was dried (MgSO$_4$), filtered, and concentrated. Purification by flash chromatography (hexanes) provided the title compound of Preparation 19 (6.91 g). $^1$H NMR (400 MHz, CDCl$_3$) δ 7.24 (s, 3H), 6.53 (d, 1H), 6.40 (m, 1H), 4.10 (m, 2H).

Preparation 20

(3-Aminomethyl-phenoxy)-acetic acid tert-butyl ester

Step A (3-Formyl-phenoxy)-acetic acid tert-butyl ester. To a solution of 3-hydroxybenzaldehyde (5.00 g, 40.9 mmol) in DMF (40 mL) was added 1M potassium tert-butoxide in tert-butanol (40.9 mL, 40.9 mmol). The reaction was stirred for 2 minutes and tert-butyl bromoacetate (6.61 mL, 40.9 mmol) was added. The reaction was stirred for 1 hour and was quenched with 200 mL water. The product was extracted into EtOAc and the organic solution was washed with water, dried over MgSO$_4$, filtered, and concentrated in vacuo. Purification via flash chromatography on silica gel (9:1 hexanes:EtOAc) afforded the title compound of Step A as a clear oil (3.53 g). $^1$H NMR (400 MHz, CDCl$_3$) δ 9.94 (s, 1H), 7.48 (m, 2H), 7.32 (s, 1H), 7.21 (m, 1H), 4.56 (s, 2H), 1.45 (s, 9H).

Step B (3-Hydroxyimino-methyl)-phenoxy)-acetic acid tert-butyl ester. To a solution of (3-formyl-phenoxy)-acetic acid tert-butyl ester prepared of Preparation 20, Step A (2.05 g, 8.68 mmol) in MeOH (30 mL) was added NH$_2$OH.HCl (0.66 g, 9.54 mmol) and pyridine (3.5 mL, 43.4 mmol) and the reaction was stirred for 2 hours. The MeOH was removed in vacuo and the residue was diluted with EtOAc and 1N HCl. The layers were separated and the aqueous solution was washed with EtOAc. The combined organic layers were dried over MgSO$_4$, filtered and concentrated in vacuo to afford the title compound of Step B (1.99 g). $^1$H NMR (400 MHz, CDCl$_3$) δ 8.07 (s, 1H), 7.23–7.28 (m, 2H), 7.12 (m, 1H), 6.93 (d, 1H), 4.51 (s, 2H), 1.46 (s, 9H).

Step C (3-Aminomethyl-phenoxy)-acetic acid tert-butyl ester. To a solution of (3-(hydroxyimino-methyl)-phenoxy)-acetic acid tert-butyl ester prepared of Preparation 20, Step B (2.25 g, 5.96 mmol) in EtOH (10 mL) was added Raney Nickel (about 1 g, washed with water followed by EtOH) in 100 mL EtOH. Additional EtOH (90 mL) was required for the transfer. Ammonium hydroxide (10 mL) was added and the mixture was shaken under 45 psi for H$_2$ for 4 hours. The catalyst was removed via filtration through Celite® and the solution was concentrated to a clear oil. Purification via flash chromatography on silica gel (96.5/3.5/0.1 to 9/1/0.1 CH$_2$Cl$_2$/MeOH/NH$_4$OH) afforded the title compound as a yellow oil. $^1$H NMR (400 MHz, CDCl$_3$) δ 7.23 (m, 1H), 6.92 (m, 2H), 6.72 (d, 1H), 4.50 (s, 2H), 3.82 (s, 2H), 1.96 (m, 2H), 1.46 (s, 9H); MS 238 (M+1).

Preparation 21

4-Pyrimidin-2-yl-benzaldehyde

A solution of 2-bromopyrimidine (1.00 g, 6.3 mmol) and tetrakistriphenylphosphine(O) palladium (0.218 g, 0.189 mmol) in ethylene glycol dimethyl ether (30 mL) was stirred at room temperature for 10 minutes. A solution of 4-formylbenzene boronic acid (1.14 g, 7.61 mmol) and sodium bicarbonate 1.58 g, 18.9 mmol) in 15 mL water was added and the reaction was hated at reflux for 16 h. The mixture was diluted with water and CH$_2$Cl$_2$. The layers were separated, and the aqueous solution was washed with CH$_2$Cl$_2$. The combined organic layers were dried over MgSO$_4$, filtered, and concentrated in vacuo. The residue was purified via flash chromatography on silica gel (10% to 30% hexanes in EtOAc) to afford the title compound (0.979 g). $^1$H NMR (400 MHz, CDCl$_3$) δ 10.11 (s, 1H), 8.83 (s, 2H), 8.82 (s, 1H), 7.98 (s, 2H), 7.23 (s, 2H).

Preparations 22–27

Preparations 22–27 were prepared from the appropriate starting materials in a manner analogous to the method of Preparation 21.

Preparation 22

4-Pyridin-2-yl-benzaldehyde $^1$H NMR (400 MHz, CDCl$_3$) δ 10.09 (s, 1H), 8.72 (s, 1H), 8.16 (s, 2H), 7.95 (s, 2H), 7.79 (s, 2H), 7.29 (m, 1H); MS 184 (M+1).

Preparation 23

4-Pyridin-3-yl-benzaldehyde $^1$H NMR (400 MHz, CDCl$_3$) δ 10.04 (s, 1H), 8.88 (s, 1H), 8.64 (s, 1H), 7.97 (s, 2H), 7.91 (m, 1H), 7.75 (m, 2H), 7.39 (m, 1H); MS 184 (M+1).

Preparation 24

4-Pyridin-4-yl-benzaldehyde $^1$H NMR (400 MHz, CDCl$_3$) δ 10.03 (s, 1H), 8.70 (s, 2H), 7.99 (s, 2H), 7.79 (s, 2H), 7.52 (s, 2H); MS 184 (M+1).

Preparation 25

4-Thiazol-2-yl-benzaldehyde

MS 189 (M+).

Preparation 26

4-Pyrimidin-5-yl-benzaldehyde $^1$H NMR (400 MHz, CDCl$_3$) δ 10.03 (s, 1H), 9.26 (s, 1H), 9.00 (s, 2H), 8.03 (m, 2H), 7.76 (m, 2H).

Preparation 27

4-Pyrazin-2-yl-benzaldehyde $^1$H NMR (400 MHz, CDCl$_3$) δ 10.03 (s, 1H), 9.10 (s, 1H), 8.69 (s, 1H), 8.59 (s, 1H), 8.21 (d, 2H), 8.03 (d, 2H).

Preparation 28

1-(2-Bromo-ethoxy)-3,5-dichloro-benzene. To a solution of NaOH (2.45 g, 61.3 mmol) in water (20 mL) was added 3,5-dichlorophenol (5 g, 30.7 mmol). The solution was heated at reflux for 1 h and was cooled to room temperature. 1,2-Dibromoethane (11.52 g, 61.3 mmol) was added and the reaction was heated at reflux for 24 h. The cooled solution was diluted with EtOAc and the organic solution was washed sequentially with HCl (1N, 1×), water (1×), and brine (1×). The organic solution was dried (MgSO$_4$), filtered, and concentrated. Purification by flash chromatography (hexanes to 5% EtOAc in hexanes) provided the title compound (3.79 g). $^1$H NMR (400 MHz, CDCl$_3$) δ 6.98 (m, 1H), 6.82 (m, 2H), 4.25 (t, 2H), 3.61 (t, 2H).

Preparation 29

1-(2-Bromo-ethoxy)-3-chlorobenzene. The compound of Preparation 29 was prepared from the appropriate starting materials in a manner analogous to the method of Preparation 28.

Preparation 30

4-[(1-Acetyloxy)-hexyl]-benzyl bromide

Step A: Grignard Reaction and Protection 4-((1-Acetyloxy)-hexyl)-toluene. Pentylmagnesium bromide (2.0 M in Et$_2$O, 25 mL, 50 mmol) was added slowly to p-tolylbenzaldehyde (5.0 mL, 42.4 mmol) in THF (50 mL) at 0° C. The reaction was warmed to room temperature and was stirred for 3 h. Aqueous 1N HCl was added and the aqueous solution was extracted with EtOAc. The organic solution was washed with brine, dried over MgSO$_4$, filtered, and concentrated. The residue was dissolved in pyridine (35 mL) and Ac$_2$O (10 mL) was added. The reaction was stirred for 24 h and was diluted with water. The product was extracted into EtOAc (3×) and the organic solution was washed with 1N HCl followed by brine, dried over MgSO$_4$, filtered, and concentrated. The product was purified by flash chromatography (10% EtOAc/hexanes) to afford 4-((1-acetyloxy)-hexyl)-toluene (2.082 g). $^1$H NMR (400 MHz, CDCl$_3$) δ 7.12–7.28 (m, 4H), 5.69 (t, 1H), 2.33 (s, 3H), 2.04 (s, 3H), 1.88 (m, 1H), 1.74 (m, 1H), 1.27 (m, 6H), 0.86 (m, 3H); MS 252 (M+18).

Step B: Benzylic Bromination

A mixture of 4-[(1-acetyloxy)-hexyl]-toluene prepared of Preparation 30, Step A (2.082 g, 8.89 mmol), N-bromosuccinimide (1.58 g, 8.89 mmol), and catalytic 2,2'-azobisisobutyronitrile in carbon tetrachloride (30 mL) was heated at reflux for 2 h. The reaction was cooled and was washed with aqueous NaHCO$_3$ (saturated), dried over MgSO$_4$, filtered, and concentrated. The product was purified by flash chromatography (5% EtOAc/hexanes) to afford the title compound of Preparation 30 (2.67 g). $^1$H NMR (400 MHz, CDCl$_3$) δ 7.34–7.40 (m, 4H), 5.70 (t, 1H), 4.47 (s, 2H), 2.06 (s, 3H), 1.86 (m, 1H), 1.73 (m, 1H), 1.27 (m, 6H), 0.85 (m, 3H).

Preparation 31

1-Methyl-1H-indole-2-carbaldehyde. The title compound can be prepared using the method described by Comins and coworkers in J. Org. Chem., 52, 1, 104–9, 1987.

Preparation 32

5-Phenyl-furan-2-carbaldehyde. The title compound can be prepared using the method described by D'Auria and coworkers in Heterocycles, 24, 6, 1575–1578, 1986.

Preparation 33

4-Phenethylsulfanyl-benzaldehyde. The title compound can be prepared using the method described in Clark and coworkers in EP 332331.

Preparation 34

3-Hydroxy-4-propoxy-benzaldehyde. The title compound can be prepared using the method described by Beke in Acta Chim. Acad. Sci. Hung., 14, 325–8, 1958.

Preparation 35

4-Formyl-N-methyl-benzenesulfonamide. The title compound can be prepared using the method described in Koetschet in Helv. Chim. Acta., 12, 682, 1929.

Preparation 36

4-Chloro-thiophene-2-carbaldehyde. The title compound can be prepared using the method described by Raggon and coworkers in Org. Prep. Proced. Int.; EN, 27, 2, 233–6, 1995.

Preparation 37

4-Cyclohexyl-benzylamine. The title compound can be prepared using the method described by Meglio and coworkers in Farmaco Ed. Sci.; IT; 35, 3, 191–202, 1980.

Preparation 38

4-Imidazol-1-yl-benzaldehyde. The title compound can be prepared using the method described by Sircar an coworkers in J. Med. Chem. 30, 6, 1023–9, 1987.

Preparation 39

4-(2-Oxo-pyrrolidin-1-yl)-benzaldehyde. The title compound can be prepared using the method described by Kukalenko in Chem. Heterocycl. Compd. (Engl. Transl.), 8, 43, 1972.

Preparation 40

2-(3-Chloro-phenylsulfanyl)-ethylamine. The title compound can be prepared using the method described by Elz and coworkers in Fed. Rep. Ger. Sci. Pharm., 56, 4, 22–234, 1988.

Preparation 41

Prop-2-ynyl-carbamic acid t-butyl ester. The title compound can be prepared using the method described in J. Chem. Soc. Perkin Trans. I, 1985, 2201–2208.

Preparation 42

4-Pyrazol-1-yl-benzaldehyde

Step A

4-Pyrazol-1-yl-benzonitrile. To a solution of 4-fluorobenzonitrile (1.5 g, 12.35 mmol) and pyrazole 0.843 g, 12.38 mmol) in DMF (10 mL) was added NaH (60% in oil, 0.644 g, 16.09 mmol). The reaction was heated to 145° C. for 20 h. The reaction was cooled to room temperature and was diluted with water and EtOAc. The aqueous layer was washed with EtOAc (3×) and the combined organic layers were washed with water (4×). The organic solution was dried (MgSO$_4$), filtered, and concentrated. Medium pressure chromatography (4:1 hexanes:EtOAc) provided 4-pyrazol-1-benzonitrile (1.6 g) as a white solid. $^1$H NMR (400 MHz, CDCl$_3$) δ 7.97 (d, 1H), 7.82 (d, 2H), 7.73 (m, 3H), 6.87 (d, 1H); MS 170 (M+1).

Step B

4-Pyrazol-1-yl-benzaldehyde. To a solution of 4-pyrazol-1-benzonitrile (1.6 g, 9.47 mmol), prepared in Step A of Preparation 42, in 75% aqueous formic acid (36 mL) was added Raney nickel alloy (1.6 g). The reaction was heated at reflux for 1.25 h and was cooled to room temperature. The solids were removed by filtration through Celite with the aid of hot EtOH. The solution was diluted with water and CHCl$_3$. The aqueous layer was washed with CHCl$_3$ (3×). To the organic solution was carefully added aqueous NaHCO$_3$ until a pH of about 8 was achieved. The organic layer was dried (MgSO$_4$), filtered, and concentrated. Purification by medium pressure chromatography (2:1 hexanes:EtOAc) provided the title compound (1.44 g) as a white solid. $^1$H NMR (400 MHz, CDCl$_3$) δ 9.99 (s, 1H), 8.01 (d, 1H), 7.96 (d, 2H), 7.87 (d, 2H), 7.76 (d, 1H), 6.51 (m, 1H); MS 173 (M+1).

Preparation 43

4-Imidazol-1-yl-benzaldehyde

4-Imidazol-1-yl-benzaldehyde. The title compound was prepared following the procedure described for Preparation 42. $^1$H NMR (400 MHz, CDCl$_3$) δ 10.04 (s, 1H), 8.10 (s, 1H), 8.02 (d, 2H), 7.38 (s, 1H), 7.28 (s, 1H); MS 173 (M+1).

Preparation 44

3-(3-Aminomethyl-phenyl)-propionic acid methyl ester hydrochloride Salt

Step A 3-(3-Bromo-phenyl)-acrylic acid methyl ester. A solution of 3-bromophenylacrylic acid (5.03 g), MeOH (75 mL), and concentrated HCl (1 mL) was heated at reflux for 3 h followed by stirring at room temperature for 20 h. Aqueous saturated NaHCO$_3$ was added and the aqueous solution was washed with CH$_2$Cl$_2$ (2×). The organic solution was dried (MgSO$_4$), filtered, and concentrated to provide the title ester of Step A (4.75 g). $^1$H NMR (400 MHz, CDCl$_3$) δ 7.63–7.20 (m, 5H), 6.40 (d, 1H), 3.78 (s, 3H).

Step B 3-(3-Cyano-phenyl)-acrylic acid methyl ester. The title compound was prepared from 3-(3-bromo-phenyl)-acrylic acid methyl ester of Step A (4.75 g, 19.72 mmol) following the procedure described for Preparation 13, Step A with a reaction time of 5 h. Purification by medium pressure chromatography (9:1 hexanes:EtOAc) provided the title compound of Step B (3.05 g). $^1$H NMR (400 MHz, CDCl$_3$) δ 7.75 (d, 1H), 7.70 (m, 1H), 7.64–7.60 (m, 2H), 7.49 (m, 1H), 6.46 (d, 1H), 3.80 (s, 3H).

Step C 3-(3-Aminomethyl-phenyl)-propionic acid methyl ester hydrochloride salt. A mixture of 3-(3-cyano-phenyl)-acrylic acid methyl ester of Step B (1.37 g, 7.32 mmol), 10% palladium on carbon (1.0 g), and HCl (4N in dioxane, 3 mL) in MeOH (50 mL) was hydrogenated on a Parr shaker at 50 psi for 65 h. The catalyst was removed by filtration through Celite and the solution was concentrated to provide the title compound (1.97 g). $^1$H NMR (400 MHz, CD$_3$OD) δ 7.25–7.24 (m, 4H), 4.06 (s, 2H), 3.60 (s, 3H), 2.92 (t, 2H), 2.64 (t, 2H).

Preparation 45

Thizole-2-sulfonyl chloride

To a solution of thiazole (2.5 g, 85 mmol) in THF (40 mL) at −78° C. was added n-BuLi (2.5 M in hexanes, 11.7 mL, 29.4 mmol) dropwise. The solution was stirred for 0.5 h, and SO$_2$ (g) was bubbled into the reaction for about 10 minutes. The ice bath was removed and the reaction was stirred at room temperature for 1.5 h. THF (about 30 mL) was removed in vacuo at room temperature and N-chlorosuccinimide (4.3 g, 32.3 mmol) in THF (50 mL) was added dropwise. The reaction was stirred for 45 minutes and water (80 mL) was added. The aqueous solution was washed with CH$_2$Cl$_2$ (3×) and the organic solution was washed with brine. The organic solution was dried (MgSO$_4$), filtered, and concentrated in vacuo at room temperature almost to dryness. The residue was purified by medium pressure chromatography (4:1 hexanes:EtOAc) to provide the title compound as an amber oil (1.6 g). $^1$H NMR (400 MHz, CDCl$_3$) δ 8.11 (d, 1H), 7.87 (d, 1H).

Preparation 46

3-[3-(Benzenesulfonylamino-methyl)-phenyl]-propionic Acid Methyl Ester

The title compound was prepared following the procedure described in Step B of Example 3 from benzenesulfonyl chloride and 3-(3-aminomethyl-phenyl)-propionic acid methyl ester hydrochloride salt, prepared of Preparation 44. $^1$H NMR (400 MHz, CDCl$_3$) δ 7.84 (d, 2H), 7.58–7.47 (m, 3H), 7.17 (m, 1H), 7.06 (m, 1H), 6.99 (m, 2H), 4.62 (m, 1H), 4.10 (d, 2H), 3.84 (s, 3H), 2.84 (t, 2H), 2.53 (t, 2H).

Preparation 47

1-(3-Bromo-propenyl)-3,5-dichloro-benzene

Step A: Grignard Reaction 1-(3,5-Dichloro-phenyl)-prop-2-en-1-ol. A solution of 3,5-dichlorobenzaldehyde (7.5 g, 43 mmol) in THF (75 mL) was cooled to 0° C. and vinylmagnesium bromide (1M in THF, 48 mL, 48 mmol) was added dropwise. The reaction was warmed to room temperature and was stirred overnight. Aqueous HCl (1N) and EtOAc were added. The aqueous solution was extracted with EtOAc and the organic solution was dried (MgSO$_4$), filtered, and concentrated. The residue was used in the next step without further purification.

Step B: Bromination 1-(3-Bromo-propenyl)-3,5-dichloro-benzene. The residue prepared in Step A was dissolved in Et$_2$O and HBr gas was slowly bubbled into the solution for about 15 minutes. The reaction was stirred at room temperature for 24 h and water and EtOAc were added. The aqueous solution was extracted with EtOAc and the organic solution was dried (MgSO$_4$), filtered, and concentrated. Purification by flash chromatography (hexanes) provided the title compound (6.91 g). $^1$H NMR (400 MHz, CDCl$_3$) δ 7.24 (s, 3H), 6.53 (d, 1H), 6.40 (m, 1H), 4.10 (m, 2H).

Preparation 47

Pyridine-2-sulfonyl chloride hydrochloride. The title compound can be prepared using the method described by Hanessian and coworkers in Heterocycles, 28, 1115–1120, 1989.

What is claimed is:

1. The compound (3-(((4-tert-butyl-benzyl)-(pyridine-3-sulfonyl)-amino)-methyl)-phenoxy)-acetic acid, or a pharmaceutically acceptable salt thereof.

2. The compound (3-(((4-tert-butyl-benzyl)-(pyridine-3-sulfonyl)-amino)-methyl)-phenoxy)-acetic acid sodium salt.

3. A method for treating a vertebrate having a condition which presents with low bone mass comprising administering to said vertebrate a therapeutically effective amount of (3-(((4-tert-butyl-benzyl)-(pyridine-3-sulfonyl)-amino)-methyl)-phenoxy)-acetic acid, or a pharmaceutically acceptable salt thereof.

4. The method of claim 3 wherein osteoporosis, osteotomy, childhood idiopathic bone loss or bone loss associated with periodontitis is treated.

5. The method of claim 4 wherein osteoporosis is treated in a human.

6. The method of claim 5 wherein glucocorticoid-induced osteoporosis, hyperthyroidism-induced osteoporosis, immobilization-induced osteoporosis, heparin-induced osteoporosis or immunosuppressive-induced osteoporosis is treated.

7. A method for augmenting and maintaining bone mass in a vertebrate comprising administering to said vertebrate a therapeutically effective amount of (3-(((4-tert-butyl-benzyl)-(pyridine-3-sulfonyl)-amino)-methyl)-phenoxy)-acetic acid, or a pharmaceutically acceptable salt thereof.

8. The method of claim 7 wherein bone healing following facial reconstruction, maxillary reconstruction or mandibular reconstruction is treated, vertebral synostosis is induced or long bone extension is enhanced, the healing rate of a bone graft is enhanced or prosthetic ingrowth is enhanced.

9. The method of claim 7 wherein a bone fracture is treated in a human.

10. A pharmaceutical composition which comprises an amount of (3-(((4-tert-butyl-benzyl)-(pyridine-3-sulfonyl)-amino)-methyl)-phenoxy)-acetic acid, or a pharmaceutically acceptable salt thereof, and a pharmaceutically acceptable carrier or diluent.

11. A method for treating glaucoma in a mammal suffering from glaucoma comprising administering to said mammal a therapeutically effective amount of (3-(((4-tert-butyl-benzyl)-(pyridine-3-sulfonyl)-amino)-methyl)-phenoxy)-acetic acid, or a pharmaceutically acceptable salt thereof.

12. A method for treating ocular hypertension in a mammal suffering from ocular hypertension comprising administering to said mammal a therapeutically effectivew amount of (3-(((4-tert-butyl-benzyl)-(pyridine-3-sulfonyl)-amino)-methyl)-phenoxy)-acetic acid, or a pharmaceutically acceptable salt thereof.

* * * * *